(12) United States Patent
van Niel et al.

(10) Patent No.: US 10,131,644 B2
(45) Date of Patent: *Nov. 20, 2018

(54) ARYL SULTAM DERIVATIVES AS RORC MODULATORS

(71) Applicant: Genentech, Inc., South San Francisco, CA (US)

(72) Inventors: Monique Bodil van Niel, Harlow (GB); Benjamin Fauber, Austin, TX (US); Emanuela Gancia, Harlow (GB); Simon Gaines, Harlow (GB); Alberto Gobbi, South San Francisco, CA (US); Christopher Hurley, Harlow (GB); Tammy Ladduwahetty, Harlow (GB); Olivier Rene, South San Francisco, CA (US); David Vesey, Harlow (GB); Stuart Ward, Harlow (GB); Paul Winship, Harlow (GB)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/199,447

(22) Filed: Jun. 30, 2016

(65) Prior Publication Data

US 2017/0137393 A1    May 18, 2017

Related U.S. Application Data

(63) Continuation of application No. PCT/EP2015/050292, filed on Jan. 9, 2015.

(60) Provisional application No. 61/925,845, filed on Jan. 10, 2014, provisional application No. 62/091,861, filed on Dec. 15, 2014.

(51) Int. Cl.
| | |
|---|---|
| *C07D 279/02* | (2006.01) |
| *C07D 417/10* | (2006.01) |
| *C07D 417/12* | (2006.01) |

(52) U.S. Cl.
CPC ......... *C07D 279/02* (2013.01); *C07D 417/10* (2013.01); *C07D 417/12* (2013.01)

(58) Field of Classification Search
None
See application file for complete search history.

(56) References Cited

U.S. PATENT DOCUMENTS

| | | | | |
|---|---|---|---|---|
| 2013/0190288 A1* | 7/2013 | Fauber | ................ | C07D 265/30 514/210.16 |
| 2014/0031330 A1* | 1/2014 | Bodil van Niel | .... | C07D 417/10 514/210.2 |
| 2014/0163024 A1* | 6/2014 | Fauber | ................ | C07D 211/46 514/231.2 |
| 2014/0163110 A1* | 6/2014 | Fauber | ................ | C07C 311/21 514/603 |
| 2014/0275032 A1* | 9/2014 | Fauber | ................ | C07D 417/12 514/211.08 |
| 2016/0311817 A1* | 10/2016 | Fauber | ................ | C07D 417/04 |

FOREIGN PATENT DOCUMENTS

| | | |
|---|---|---|
| WO | 2012/064744 A2 | 5/2012 |
| WO | 2013/092941 A1 | 6/2013 |
| WO | 2014/009447 A1 | 1/2014 |
| WO | 2014/202741 A1 | 12/2014 |

OTHER PUBLICATIONS

PCT ISR and Written Opinion of PCT/EP2015/050292.

* cited by examiner

*Primary Examiner* — Nyeemah A Grazier
(74) *Attorney, Agent, or Firm* — Robert C. Hall

(57) ABSTRACT

Compounds of the formula I:

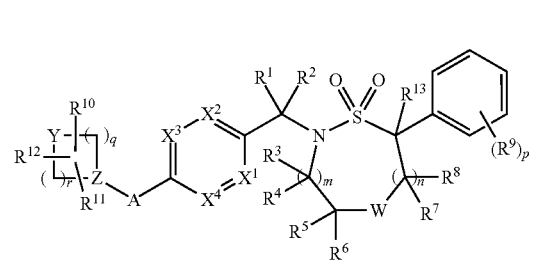

or pharmaceutically acceptable salts thereof, wherein m, n, p, q, r, $X^1$, $X^2$, $X^3$, $X^4$, Y, Z, A, $R^1$, $R^2$, $R^3$, $R^4$, $R^5$ $R^6$, $R^7$, $R^8$, $R^9$, $R^{10}$, $R^{11}$, $R^{12}$ and $R^{13}$ are as defined herein. Also disclosed are methods of making the compounds and using the compounds for treatment of inflammatory diseases such as arthritis, muscular sclerosis and psoriasis.

15 Claims, No Drawings

ARYL SULTAM DERIVATIVES AS RORC MODULATORS

RELATED APPLICATION DATA

This application is a Continuation of International Application No. PCT/EP2015/050292 filed on Jan. 9, 2015 which claims priority to Provisional Patent Application No. 61/925,845 filed on Jan. 10, 2014 and Provisional Patent Application No. 62/091,861 filed on Dec. 15, 2014, the disclosures of which are incorporated by reference in their entirety.

FIELD OF THE INVENTION

The invention pertains to compounds that modulate the function of retinoid-receptor related orphan receptor RORc (RORγ) and use of such compounds for treatment of autoimmune diseases

BACKGROUND OF THE INVENTION

T helper 17 cells (Th17) are interleukin (IL)-17 secreting CD4+ T cells involved in pathogenesis of autoimmune diseases such as rheumatoid arthritis, irritable bowel disease, psoriasis, psoriatic arthritis and spondyloarthridities. The retinoic acid-related orphan receptor γ (RORγ or RORc) is recognized as a transcription factor necessary for Th17 cell differentiation. RORc is an orphan member of the nuclear hormone receptor subfamily that includes RORα (RORa) and RORβ (RORb). RORc controls gene transcription by binding to DNA as a monomer. Selective modulation of RORc has been proposed as a route to discovery and development of Th17 cell-associated autoimmune diseases.

There is accordingly a need for compounds that inhibit RORc for use in treatment of autoimmune diseases such as rheumatoid arthritis, osteoarthritis, psoriatic arthritis, irritable bowel disease, asthma, COPD, psoriasis, lupus, Sjogren's disease, idiopathic pulmonary fibrosis, muscular sclerosis and spondyloarthridities.

SUMMARY OF THE INVENTION

The invention provides compounds of the formula I:

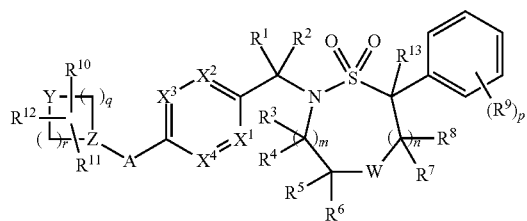

I or a pharmaceutically acceptable salt thereof,
wherein:
m is 0 or 1;
n is 0 or 1;
p is from 0 to 3;
q is 0, 1 or 2;
r is from 1 to 3;
A is:
a bond;
—$(CR_jR_k)_t$—;

—$C(O)$—$(CR_jR_k)_t$—;
—$(CR_jR_k)_t$—$C(O)$—;
—$NR^a$—$(CR_jR_k)_t$—;
—$(CR_jR_k)_t$—$NR^a$—;
—$C(O)NR^a$—$(CR_jR_k)_t$—;
—$(CR_jR_k)_t$—$NR^aC(O)$—;
—$O$—$(CR_jR_k)_t$—;
—$(CR_jR_k)_t$—$O$—;
—$S$—$(CR_jR_k)_t$—;
—$(CR_jR_k)_t$—$S$—;
—$SO_2$—$(CR_jR_k)_t$—;
—$(CR_jR_k)_t$—$SO_2$—; or
t is from 0 to 4;
W is:
—$CR^bR^c$—;
—O—;
—S—;
—$SO_2$—; or
—$NR^d$—;
one of $X^1$, $X^2$, $X^3$ and $X^4$ is N and the others are $CR^e$;
or two of $X^1$, $X^2$, $X^3$ and $X^4$ are N and the others are $CR^e$;
or three of $X^1$, $X^2$, $X^3$ and $X^4$ are N and the other is $CR^e$;
or each of $X^1$, $X^2$, $X^3$ and $X^4$ is $CR^e$;
Y is:
—O—;
—S—;
—$SO_2$—;
—$CR^fR^g$—; or
—$NR^h$—;
Z is: $CR^m$;
$R^1$, $R^2$, $R^3$, $R^4$, $R^5$, $R^6$, $R^7$ and $R^8$ each independently is:
hydrogen; or $C_{1-6}$alkyl which may be unsubstituted or substituted one or more times with halo;
or $R^3$ and $R^4$ together with the atom to which they are attached may form an ethylene group; or $R^3$ and $R^4$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or $R^5$ and $R^6$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or $R^7$ and $R^8$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^3$ and $R^4$ together with one of $R^5$ and $R^6$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^5$ and $R^6$ together with one of $R^7$ and $R^8$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;

each $R^9$ is independently:
$C_{1-6}$alkyl;
halo;
$C_{1-6}$alkoxy; or
cyano;
wherein the $C_{1-6}$alkyl moieties may be unsubstituted or substituted one or more times with halo;
$R^{10}$ is:
hydrogen;
carboxy;
$C_{1-6}$alkyl-carbonyl;
$C_{1-6}$alkoxy-carbonyl;
oxo;
hydroxy;
aminocarbonyl;
N—$C_{1-6}$alkyl-aminocarbonyl;
N,N-di-$C_{1-6}$alkyl-aminocarbonyl;
cyano;
hydroxy-$C_{1-6}$alkyl;
N—$C_{1-6}$alkoxy-$C_{1-6}$alkyl-aminocarbonyl;
N-hydroxy-$C_{1-6}$alkyl-aminocarbonyl;
N—$C_{1-6}$alkoxy-aminocarbonyl;
halo; or
$C_{1-6}$alkyl which may be unsubstituted or substituted one or more times with halo or oxo;
$R^{11}$ is:
hydrogen;
halo;
carboxy;
$C_{1-6}$alkyl-carbonyl;
$C_{1-6}$alkoxy-carbonyl;
oxo;
hydroxy;
aminocarbonyl;
N—$C_{1-6}$alkyl-aminocarbonyl;
N,N-di-$C_{1-6}$alkyl-aminocarbonyl;
$C_{1-6}$alkyl-sulfonylamino;
$C_{1-6}$alkyl-sulfonylamino-$C_{1-6}$alkyl;
cyano;
hydroxy-$C_{1-6}$alkyl;
N—$C_{1-6}$alkoxy-$C_{1-6}$alkyl-aminocarbonyl;
N-hydroxy-$C_{1-6}$alkyl-aminocarbonyl;
N—$C_{1-6}$alkoxy-aminocarbonyl; or
$C_{1-6}$alkyl which may be unsubstituted or substituted one or more times with halo or oxo;
or $R^{10}$ and $R^{11}$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or $R^{10}$ and $R^{11}$ together with the atoms to which they are attached may form a double bond;
$R^{12}$ is:
hydrogen;
halo;
carboxy;
$C_{1-6}$alkyl-carbonyl;
$C_{1-6}$alkoxy-carbonyl;
oxo;
hydroxy;
aminocarbonyl;
N—$C_{1-6}$alkyl-aminocarbonyl;
N,N-di-$C_{1-6}$alkyl-aminocarbonyl;
cyano;
hydroxy-$C_{1-6}$alkyl;
N—$C_{1-6}$alkoxy-$C_{1-6}$alkyl-aminocarbonyl;
N-hydroxy-$C_{1-6}$alkyl-aminocarbonyl;
N—$C_{1-6}$alkoxy-aminocarbonyl; or
$C_{1-6}$alkyl which may be unsubstituted or substituted one or more times with halo or oxo;
$R^{13}$ is:
hydrogen; or
$C_{1-6}$alkyl which may be unsubstituted or substituted one or more times with halo;
$R^a$, $R^b$, $R^c$ and $R^d$ each independent is:
hydrogen; or
$C_{1-6}$alkyl which may be unsubstituted or substituted one or more times with halo;
or $R^b$ and $R^c$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^b$ and $R^c$ together with one of $R^7$ and $R^8$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^b$ and $R^c$ together with one of $R^5$ and $R^6$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
each $R^e$ is independently:
hydrogen;
$C_{1-6}$alkyl;
halo;
$C_{1-6}$alkoxy; or
cyano;
wherein the $C_{1-6}$alkyl moieties may be unsubstituted or substituted one or more times with halo, hydroxy or $C_{1-6}$alkoxy;
$R^f$ is:
hydrogen;
halo;
$C_{1-6}$alkoxy; or
$C_{1-6}$alkyl which may be unsubstituted or substituted one or more times with halo, hydroxy, or $C_{1-6}$alkoxy;
$R^g$ is:
hydrogen;
$C_{1-6}$alkyl;
$C_{3-6}$cycloalkyl;
$C_{3-6}$cycloalkenyl;
$C_{3-6}$cycloalkyl-$C_{1-6}$alkyl;
halo;
$C_{1-6}$alkyl-carbonyl;
$C_{3-6}$cycloalkyl-carbonyl;
$C_{3-6}$cycloalkyl-$C_{1-6}$alkyl-carbonyl;
cyano-$C_{1-6}$alkyl-carbonyl;
hydroxy-$C_{1-6}$alkyl-carbonyl;
$C_{1-6}$alkoxy-$C_{1-6}$alkyl-carbonyl;
carboxy;
N-cyano-aminocarbonyl;
N-cyano-N—$C_{1-6}$alkyl-aminocarbonyl;
N—$C_{1-6}$alkyl-acetimidamidyl;
N,N'-di-$C_{1-6}$alkyl-acetimidamidyl;
N'-cyano-N—$C_{1-6}$alkyl-acetimidamidyl;
N'-hydroxy-acetimidamidyl;
N'—$C_{1-6}$alkoxy-acetimidamidyl;
N'-hydroxy-N—$C_{1-6}$alkyl-acetimidamidyl;

N'—C$_{1-6}$alkoxy-N—C$_{1-6}$alkyl-acetimidamidyl;
2-nitro-1-N—C$_{1-6}$alkylamino-vinyl; formyl;
C$_{1-6}$alkyl-sulfonyl;
C$_{3-6}$cycloalkyl-sulfonyl;
C$_{3-6}$cycloalkyl-C$_{1-6}$alkyl-sulfonyl;
C$_{1-6}$alkyl-sulfonyl-C$_{1-6}$alkyl;
aminocarbonyl;
carbonylamino;
N-hydroxy-aminocarbonyl;
N—C$_{1-6}$alkoxy-aminocarbonyl;
N—C$_{1-6}$alkyl-aminocarbonyl;
aminocarbonyl-C$_{1-6}$alkyl;
N—C$_{1-6}$alkyl-aminocarbonyl-C$_{1-6}$alkyl;
N,N-di-C$_{1-6}$alkyl-aminocarbonyl-C$_{1-6}$alkyl;
C$_{1-6}$alkoxy-carbonyl;
N-hydroxy-N—C$_{1-6}$alkyl-aminocarbonyl;
N—C$_{1-6}$alkoxy-N—C$_{1-6}$alkyl-aminocarbonyl;
N,N-di-C$_{1-6}$alkyl-aminocarbonyl;
aminosulfonyl;
N—C$_{1-6}$alkyl-aminosulfonyl;
N,N-di-C$_{1-6}$alkyl-aminosulfonyl;
cyano;
C$_{1-6}$alkoxy;
C$_{1-6}$alkyl-sulfonylamino;
N—C$_{1-6}$alkyl-sulfonylaminocarbonyl;
N—(C$_{1-6}$alkyl-sulfonyl)-N—C$_{1-6}$alkyl-aminocarbonyl;
N—(C$_{1-6}$alkyl-sulfonyl)-amino-C$_{1-6}$alkyl; amino;
N—C$_{1-6}$alkyl-amino;
N,N-di-C$_{1-6}$alkyl-amino;
halo-C$_{1-6}$alkyl;
phenyl;
heterocyclyl;
heteroaryl;
C$_{1-6}$alkyl-carbonylamino;
carbonylamino; or
hydroxy;
  wherein the C$_{1-6}$alkyl moieties may be unsubstituted or substituted one or more times with halo; and
  wherein the phenyl, heterocyclyl, heteroaryl, C$_{3-6}$cycloalkyl, C$_{3-6}$cycloalkenyl and C$_{3-6}$cycloalkyl-C$_{1-6}$alkyl moieties may be unsubstituted or substituted one or more times with R$^i$;
or R$^f$ and R$^g$ together may form oxo;
or R$^f$ and R$^g$ together with the atoms to which they are attached may form a four, five, six or seven membered saturated or partially saturated ring that may optionally include one or two heteroatoms selected from —O—, —NR$^a$— or —S—, and which may be optionally substituted one or more times with R$^i$;
  R$^h$ is:
  hydrogen;
  C$_{1-6}$alkyl;
  C$_{3-6}$cycloalkyl;
  C$_{3-6}$cycloalkenyl;
  C$_{3-6}$cycloalkyl-C$_{1-6}$alkyl;
  C$_{1-6}$alkyl-carbonyl;
  C$_{3-6}$cycloalkyl-carbonyl;
  C$_{3-6}$cycloalkyl-C$_{1-6}$alkyl-carbonyl;
  cyano-C$_{1-6}$alkyl-carbonyl;
  hydroxy-C$_{1-6}$alkyl-carbonyl;
  C$_{1-6}$alkoxy-C$_{1-6}$alkyl-carbonyl;
  N-cyano-aminocarbonyl;
  N-cyano-N—C$_{1-6}$alkyl-aminocarbonyl;
  N—C$_{1-6}$alkyl-acetimidamidyl;
  N,N'-di-C$_{1-6}$alkyl-acetimidamidyl;
  N'-cyano-N—C$_{1-6}$alkyl-acetimidamidyl;
  N'-hydroxy-acetimidamidyl;
  N'—C$_{1-6}$alkoxy-acetimidamidyl;
  N'-hydroxy-N—C$_{1-6}$alkyl-acetimidamidyl;
  N'—C$_{1-6}$alkoxy-N—C$_{1-6}$alkyl-acetimidamidyl;
  2-nitro-1-N—C$_{1-6}$alkylamino-vinyl;
  formyl;
  C$_{1-6}$alkyl-sulfonyl;
  C$_{3-6}$cycloalkyl-sulfonyl;
  C$_{3-6}$cycloalkyl-C$_{1-6}$alkyl-sulfonyl;
  C$_{1-6}$alkyl-sulfonyl-C$_{1-6}$alkyl;
  aminocarbonyl;
  N-hydroxy-aminocarbonyl;
  N—C$_{1-6}$alkoxy-aminocarbonyl;
  N—C$_{1-6}$alkyl-aminocarbonyl;
  N-hydroxy-N—C$_{1-6}$alkyl-aminocarbonyl;
  N—C$_{1-6}$alkoxy-N—C$_{1-6}$alkyl-aminocarbonyl;
  N,N-di-C$_{1-6}$alkyl-aminocarbonyl;
  aminosulfonyl;
  N—C$_{1-6}$alkyl-aminosulfonyl;
  N,N-di-C$_{1-6}$alkyl-aminosulfonyl;
  cyano;
  C$_{1-6}$alkyl-sulfonylamino;
  C$_{1-6}$alkyl-sulfonylamino-C$_{1-6}$alkyl;
  N—(C$_{1-6}$alkyl-sulfonyl)aminocarbonyl;
  N—(C$_{1-6}$alkyl-sulfonyl)-N—C$_{1-6}$alkyl-aminocarbonyl;
  N—(C$_{1-6}$alkyl-sulfonyl)-amino-C$_{1-6}$alkyl;
  aminocarbonyl-C$_{1-6}$alkyl;
  N—C$_{1-6}$alkyl-aminocarbonyl-C$_{1-6}$alkyl;
  N,N-di-C$_{1-6}$alkyl-aminocarbonyl-C$_{1-6}$alkyl;
  C$_{1-6}$alkoxy-carbonyl;
  phenyl;
  heterocyclyl; or
  heteroaryl;
    wherein the C$_{1-6}$alkyl moieties may be unsubstituted or substituted one or more times with halo; and
    wherein the phenyl, heterocyclyl, heteroaryl, C$_{3-6}$cycloalkyl, C$_{3-6}$cycloalkenyl and C$_{3-6}$cycloalkyl-C$_{1-6}$alkyl moieties may be unsubstituted or substituted one or more times with R$^i$;
  or R$^h$ and one of R$^{10}$ and R$^{11}$ together with the atoms to which they are attached may form a four, five, six or seven membered aromatic, partially saturated or unsaturated ring that may optionally include one or two additional heteroatom selected from —O—, —NR$^a$— or —S—, and which may be optionally substituted one or more times with R$^i$;
  or one of R$^f$ and R$^g$ and one of R$^{10}$ and R$^{11}$ together with the atoms to which they are attached may form a three, four, five, six or seven membered aromatic, partially saturated or unsaturated ring that may optionally include an additional heteroatom selected from —O—, —NR$^a$— or —S—, and which may be optionally substituted one or more times with R$^i$;
  R$^i$ is:
  C$_{1-6}$alkyl;
  halo-C$_{1-6}$alkyl;
  C$_{3-6}$cycloalkyl;
  halo;
  oxo;
  hydroxy;
  acetyl;
  C$_{1-6}$alkyl-carbonyl;
  amino-carbonyl;
  hydroxy-C$_{1-6}$alkyl;
  cyano;
  cyano-C$_{1-6}$alkyl;
  C$_{1-6}$alkoxy-C$_{1-6}$alkyl;
  carboxy; or
  C$_{1-6}$alkoxy;

$R^j$ and $R^k$ each independent is:
hydrogen; or
$C_{1-6}$alkyl which may be unsubstituted or substituted one or more times with halo; and
$R^m$ is: $C_{1-6}$alkyl;
hydroxy;
halo;
hydroxy-$C_{1-6}$alkyl;
$C_{1-6}$alkylsulfonyl-$C_{1-6}$alkyl;
cyano;
$C_{1-6}$alkylsulfonyl-amino-
$C_{1-6}$alkylsulfinyl-amino-
cyano-$C_{1-6}$alkyl;
cyano-$C_{2-6}$alkenyl;
amino-$C_{1-6}$alkyl;
$C_{1-6}$alkoxy-$C_{1-6}$alkyl;
$C_{1-6}$alkoxy-$C_{1-6}$alkoxy-$C_{1-6}$alkyl;
hydroxy-$C_{1-6}$alkoxy;
hydroxy-$C_{1-6}$alkoxy-$C_{1-6}$alkyl;
hydroxy-$C_{1-6}$alkyl-amino;
$C_{1-6}$alkoxy-$C_{1-6}$alkyl-amino;
N-hydroxy-carboxamidinyl;
$C_{1-6}$alkoxy-carbonyl-$C_{2-6}$alkenyl;
amino;
N—$C_{1-6}$alkylamino;
N,N-di-$C_{1-6}$alkylamino;
—$(CHR^t)_u$—C(O)—$NR^pR^q$;
—$(CHR^s)_u$—O—$(CHR^s)_v$—C(O)—$NR^pR^q$;
—$(CHR^s)_u$—$NR^n$—$(CHR^s)_v$—C(O)—$NR^pR^q$,
—$(CHR^t)_u$—C(O)—$R^u$;
—$(CHR^s)_u$—O—$(CHR^s)_v$—C(O)—$R^u$; or
—$(CHR^s)_u$—$NR^n$—$(CHR^s)_v$—C(O)—$R^u$;
u is from 0 to 2;
v is from 0 to 2;
each $R^n$ is independently:
hydrogen; or
$C_{1-6}$alkyl;
$R^p$ is:
hydrogen; or
$C_{1-6}$alkyl;
$R^q$ is:
hydrogen;
$C_{1-6}$alkyl;
hydroxy-$C_{1-6}$alkyl;
N—($C_{1-6}$alkylcarbonyl)-amino-$C_{1-6}$alkyl;
$C_{1-6}$alkylsulfonyl-$C_{1-6}$alkyl;
amino-$C_{1-6}$alkyl;
N—$C_{1-6}$alkylamino-$C_{1-6}$alkyl;
N,N-di-$C_{1-6}$alkylamino-$C_{1-6}$alkyl;
N,N-di-$C_{1-6}$alkylaminocarbonyl-$C_{1-6}$alkyl;
cyano-$C_{1-6}$alkyl;
carboxy-$C_{1-6}$alkyl;
aminocarbonyl-$C_{1-6}$alkyl;
N—$C_{1-6}$alkylaminocarbonyl-$C_{1-6}$alkyl;
N,N-di-$C_{1-6}$alkyl aminocarbonyl-$C_{1-6}$alkyl;
$C_{1-6}$alkylsulfonyl-$C_{1-6}$alkyl; or
$C_{1-6}$alkoxy-$C_{1-6}$alkyl;
each $R^s$ is independently:
hydrogen; or
$C_{1-6}$alkyl;
each $R^t$ is independently:
hydrogen;
$C_{1-6}$alkyl;
halo; or
hydroxy; and
$R^u$ is: $C_{1-6}$alkyl;
$C_{1-6}$alkoxy;
hydroxy; or
hydroxy-$C_{1-6}$alkyl.

The invention also provides and pharmaceutical compositions comprising the compounds, methods of using the compounds, and methods of preparing the compounds.

In the compounds of the invention, the group Z is a quaternary carbon with a substituent $R^m$. Surprisingly and unexpectedly, introduction of the group $R^m$ at group Z in accordance with the invention results in compounds having improved selectivity for RORc (RORγ) over other receptor subtypes RORa and RORb (RORα and RORβ) in comparison to analogous compounds that do not have the group $R^m$ substituent at group Z.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy' means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxyalkylcarbonyl" means a moiety of the formula —C(O)—R—R', wherein R is alkylene and R' is alkoxy as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —SO$_2$—R, wherein R is alkyl as defined herein.

"Alkylsulfonylalkyl means a moiety of the formula —R'—SO$_2$—R" where where R' is alkylene and R" is alkyl as defined herein.

"Alkylsulfonylalkoxy" means a group of the formula —O—R—SO$_2$—R' wherein R is alkylene and R' is alkyl as defined herein.

"Amino means a moiety of the formula —NRR' wherein R and R' each independently is hyrdogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"N-hydroxy-aminocarbonyl" means a group of the formula —C(O)—NR—OH wherein R is hydrogen or alkyl as defined herein.

"N-alkoxy-aminocarbonyl" means a group of the formula —C(O)—NR—R' wherein R is hydrogen or alkyl and R' is alkoxy as defined herein.

"N-alkyl-aminocarbonyl means a group of the formula —C(O)—NH—R wherein R is alkyl as defined herein.

"N-hydroxy-N-alkylaminocarbonyl means a group of the formula —C(O)—NRR' wherein R is alkyl as defined herein and R' is hydroxy.

"N-alkoxy-N-alkylaminocarbonyl" means a group of the formula —C(O)—NRR' wherein R is alkyl and R' is alkoxy as defined herein.

"N,N-di-C$_{1-6}$alkyl-aminocarbonyl" means a group of the formula —C(O)—NRR' wherein R and R' are alkyl as defined herein.

"Aminosulfonyl" means a group of the formula —SO$_2$—NH$_2$.

"N-alkylaminosulfonyl" means a group of the formula —SO$_2$—NHR wherein R is alkyl as defined herein.

"N,N-dialkylaminosulfonyl" means a group of the formula —SO$_2$—NRR' wherein R and R' are alkyl as defined herein.

"Alkylsulfonylamino" means a group of the formula —NR'—SO$_2$—R wherein R is alkyl and R' is hydrogen or alkyl as defined herein.

"N-(alkylsulfonyl)-aminoalkyl" means a group of the formula —R—NH—SO$_2$—R' wherein R is alkylene and R' is alkyl as defined herein.

"N-(Alkylsulfonyl)aminocarbonyl" means a group of the formula —C(O)—NH—SO$_2$—R wherein wherein R is alkyl as defined herein.

"N-(Alkylsulfonyl)-N-alkylaminocarbonyl" means a group of the formula —C(O)—NR—SO$_2$—R' wherein wherein R and R' are alkyl as defined herein.

"N-Alkoxyalkyl-aminocarbonyl" means a group of the formula —C(O)—NR—R'—OR" wherein R is hydrogen or alkyl, R' is alkylene, and R" is alkyl as defined herein.

"N-Hydroxyalkyl-aminocarbonyl" means a group of the formula —C(O)—NR—R'—OH" wherein R is hydrogen or alkyl and R' is alkylene as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein.

"Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" "means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substituted with one or more substituents, wherein each substituent is independently hydroxy, alkyl, alkoxy, halo, haloalkyl, amino, monoalkylamino, or dialkylamino. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkenyl" means a cycloalkyl as defined herein that includes at least one double bond or unsaturation. Exemplary cycloalkenyl include cyclohexenyl, cyclopentenyl, cyclobutenyl and the like.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Cycloalkylcarbonyl" means a moiety of the formula —C(O)—R, wherein R is cycloalkyl as defined herein.

"$C_{3-6}$cycloalkyl-$C_{1-6}$alkyl-carbonyl" means a moiety of the formula —C(O)—R, wherein R is cycloalkylalkyl as defined herein.

"Cyanoalkylcarbonyl" means a moiety of the formula —C(O)—R—R', wherein R is alkylene as defined herein and R' is cyano or nitrile.

"N-Cyano-aminocarbonyl" means a moiety of the formula —C(O)—NHR, wherein R is cyano or nitrile.

"N-Cyano-N-alkyl-aminocarbonyl" means a moiety of the formula —C(O)—NRR'—R, wherein R' is alkyl as defined herein and R is cyano or nitrile.

"Cycloalkylsulfonyl" means a group of the formula —SO$_2$—R wherein R is cycloalkyl as defined herein.

"Cycloalkylalkylsulfonyl" means a group of the formula —SO$_2$—R wherein R is cycloalkylalkyl as defined herein.

"Formyl" means a moiety of the formula —C(O)—H.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkylcarbonyl" means a moiety of the formula —C(O)—R—R', wherein R is alkylene as defined herein and R' is hydroxy.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Oxo" means a group of the formula =O (i.e., an oxygen with a double bond). Thus, for example, a 1-oxo-ethyl group is an acetyl group.

"Alkoxy hydroxyalkyl" and "hydroxy alkoxyalkyl", which may be used interchangeably, means an alkyl as defined herein that is substituted at least once with hydroxy and at least once with alkoxy.

"Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted" when used in association with an "aryl", phenyl", "heteroaryl" "cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate.

"Arthritis" means a disease or condition that causes damage to joints of the body and pain associated with such joint damage. Arthritis includes rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

"Respiratory disorder" refers to, without limitation, chronic obstructive pulmonary disease (COPD), asthma, bronchospasm, and the like.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature and chemical names used in this Application are based on ChembioOffice™ by CambridgeSoft™. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes. One or more carbon atom(s) of a compound of the invention may be replaced by a silicon atom(s), and it is contemplated that one or more oxygen atom(s) of a compound of the invention may be replaced by a sulfur or selenium atom(s).

Compounds of the Invention

The invention provides compounds of the formula I:

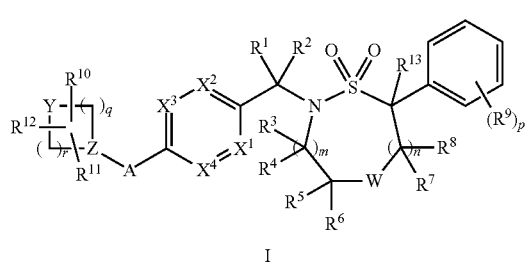

I or a pharmaceutically acceptable salt thereof, wherein:
m is 0 or 1;
n is 0 or 1;
p is from 0 to 3;
q is 0, 1 or 2;
r is from 1 to 3;
A is:
a bond;
—$(CR_jR_k)_t$—;
—C(O)—$(CR_jR_k)_t$—;
—$(CR_jR_k)_t$—C(O)—;
—$NR^a$—$(CR_jR_k)_t$—;
—$(CR_jR_k)_t$—$NR^a$—;
—C(O)$NR^a$—$(CR_jR_k)_t$—;
—$(CR_jR_k)_t$—$NR^aC(O)$—;
—O—$(CR_jR_k)_t$—;
—$(CR_jR_k)_t$—O—;
—S—$(CR_jR_k)_t$—;
—$(CR_jR_k)_t$—S—;
—$SO_2$—$(CR_jR_k)_t$—;
—$(CR_jR_k)_t$—$SO_2$—; or
t is from 0 to 4;
W is:
—$CR^bR^c$—;
—O—;
—S—;
—$SO_2$—; or
—$NR^d$—;
one of $X^1$, $X^2$, $X^3$ and $X^4$ is N and the others are $CR^e$;
or two of $X^1$, $X^2$, $X^3$ and $X^4$ are N and the others are $CR^e$;
or three of $X^1$, $X^2$, $X^3$ and $X^4$ are N and the other is $CR^e$;
or each of $X^1$, $X^2$, $X^3$ and $X^4$ is $CR^e$;
Y is:
—O—;
—S—;
—$SO_2$—;
—$CR^fR^g$—; or
—$NR^h$—;
Z is: $CR^m$;
$R^1$, $R^2$, $R^3$, $R^4$, $R^5$, $R^6$, $R^7$ and $R^8$ each independently is:
hydrogen; or $C_{1-6}$alkyl which may be unsubstituted or substituted one or more times with halo;
or $R^3$ and $R^4$ together with the atom to which they are attached may form an ethylene group; or $R^3$ and $R^4$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or $R^5$ and $R^6$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or $R^7$ and $R^8$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^3$ and $R^4$ together with one of $R^5$ and $R^6$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^5$ and $R^6$ together with one of $R^7$ and $R^8$ and the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

each R$^9$ is independently:
C$_{1-6}$alkyl;
halo;
C$_{1-6}$alkoxy; or
cyano;
wherein the C$_{1-6}$alkyl moieties may be unsubstituted or substituted one or more times with halo;

R$^{10}$ is:
hydrogen;
carboxy;
C$_{1-6}$alkyl-carbonyl;
C$_{1-6}$alkoxy-carbonyl;
oxo;
hydroxy;
aminocarbonyl;
N—C$_{1-6}$alkyl-aminocarbonyl;
N,N-di-C$_{1-6}$alkyl-aminocarbonyl;
cyano;
hydroxy-C$_{1-6}$alkyl;
N—C$_{1-6}$alkoxy-C$_{1-6}$alkyl-aminocarbonyl;
N-hydroxy-C$_{1-6}$alkyl-aminocarbonyl;
N—C$_{1-6}$alkoxy-aminocarbonyl;
halo; or
C$_{1-6}$alkyl which may be unsubstituted or substituted one or more times with halo or oxo;

R$^{11}$ is:
hydrogen;
halo;
carboxy;
C$_{1-6}$alkyl-carbonyl;
C$_{1-6}$alkoxy-carbonyl;
oxo;
hydroxy;
aminocarbonyl;
N—C$_{1-6}$alkyl-aminocarbonyl;
N,N-di-C$_{1-6}$alkyl-aminocarbonyl;
C$_{1-6}$alkyl-sulfonylamino;
C$_{1-6}$alkyl-sulfonylamino-C$_{1-6}$alkyl;
cyano;
hydroxy-C$_{1-6}$alkyl;
N—C$_{1-6}$alkoxy-C$_{1-6}$alkyl-aminocarbonyl;
N-hydroxy-C$_{1-6}$alkyl-aminocarbonyl;
N—C$_{1-6}$alkoxy-aminocarbonyl; or
C$_{1-6}$alkyl which may be unsubstituted or substituted one or more times with halo or oxo;

or R$^{10}$ and R$^{11}$ together with the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or R$^{10}$ and R$^{11}$ together with the atoms to which they are attached may form a double bond;

R$^{12}$ is:
hydrogen;
halo;
carboxy;
C$_{1-6}$alkyl-carbonyl;
C$_{1-6}$alkoxy-carbonyl;
oxo;
hydroxy;
aminocarbonyl;
N—C$_{1-6}$alkyl-aminocarbonyl;
N,N-di-C$_{1-6}$alkyl-aminocarbonyl;
cyano;
hydroxy-C$_{1-6}$alkyl;
N—C$_{1-6}$alkoxy-C$_{1-6}$alkyl-aminocarbonyl;
N-hydroxy-C$_{1-6}$alkyl-aminocarbonyl;
N—C$_{1-6}$alkoxy-aminocarbonyl; or
C$_{1-6}$alkyl which may be unsubstituted or substituted one or more times with halo or oxo;

R$^{13}$ is:
hydrogen; or
C$_{1-6}$alkyl which may be unsubstituted or substituted one or more times with halo;

R$^a$, R$^b$, R$^c$ and R$^d$ each independent is:
hydrogen; or
C$_{1-6}$alkyl which may be unsubstituted or substituted one or more times with halo;

or R$^b$ and R$^c$ together with the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or one of R$^b$ and R$^c$ together with one of R$^7$ and R$^8$ and the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or one of R$^b$ and R$^c$ together with one of R$^5$ and R$^6$ and the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

each R$^e$ is independently:
hydrogen;
C$_{1-6}$alkyl;
halo;
C$_{1-6}$alkoxy; or
cyano;
wherein the C$_{1-6}$alkyl moieties may be unsubstituted or substituted one or more times with halo, hydroxy or C$_{1-6}$alkoxy;

R$^f$ is:
hydrogen;
halo;
C$_{1-6}$alkoxy; or
C$_{1-6}$alkyl which may be unsubstituted or substituted one or more times with halo, hydroxy, or C$_{1-6}$alkoxy;

R$^g$ is:
hydrogen;
C$_{1-6}$alkyl;
C$_{3-6}$cycloalkyl;
C$_{3-6}$cycloalkenyl;
C$_{3-6}$cycloalkyl-C$_{1-6}$alkyl;
halo;
C$_{1-6}$alkyl-carbonyl;
C$_{3-6}$cycloalkyl-carbonyl;
C$_{3-6}$cycloalkyl-C$_{1-6}$alkyl-carbonyl;
cyano-C$_{1-6}$alkyl-carbonyl;
hydroxy-C$_{1-6}$alkyl-carbonyl;
C$_{1-6}$alkoxy-C$_{1-6}$alkyl-carbonyl;
carboxy;
N-cyano-aminocarbonyl;
N-cyano-N—C$_{1-6}$alkyl-aminocarbonyl;
N—C$_{1-6}$alkyl-acetimidamidyl;
N,N'-di-C$_{1-6}$alkyl-acetimidamidyl;

N'-cyano-N—$C_{1-6}$alkyl-acetimidamidyl;
N'-hydroxy-acetimidamidyl;
N'—$C_{1-6}$alkoxy-acetimidamidyl;
N'-hydroxy-N—$C_{1-6}$alkyl-acetimidamidyl;
N'—$C_{1-6}$alkoxy-N—$C_{1-6}$alkyl-acetimidamidyl;
2-nitro-1-N—$C_{1-6}$alkylamino-vinyl; formyl;
$C_{1-6}$alkyl-sulfonyl;
$C_{3-6}$cycloalkyl-sulfonyl;
$C_{3-6}$cycloalkyl-$C_{1-6}$alkyl-sulfonyl;
$C_{1-6}$alkyl-sulfonyl-$C_{1-6}$alkyl;
aminocarbonyl;
carbonylamino;
N-hydroxy-aminocarbonyl;
N—$C_{1-6}$alkoxy-aminocarbonyl;
N—$C_{1-6}$alkyl-aminocarbonyl;
aminocarbonyl-$C_{1-6}$alkyl;
N—$C_{1-6}$alkyl-aminocarbonyl-$C_{1-6}$alkyl;
N,N-di-$C_{1-6}$alkyl-aminocarbonyl-$C_{1-6}$alkyl;
$C_{1-6}$alkoxy-carbonyl;
N-hydroxy-N—$C_{1-6}$alkyl-aminocarbonyl;
N—$C_{1-6}$alkoxy-N—$C_{1-6}$alkyl-aminocarbonyl;
N,N-di-$C_{1-6}$alkyl-aminocarbonyl;
aminosulfonyl;
N—$C_{1-6}$alkyl-aminosulfonyl;
N,N-di-$C_{1-6}$alkyl-aminosulfonyl;
cyano;
$C_{1-6}$alkoxy;
$C_{1-6}$alkyl-sulfonylamino;
N—$C_{1-6}$alkyl-sulfonylaminocarbonyl;
N—($C_{1-6}$alkyl-sulfonyl)-N—$C_{1-6}$alkyl-aminocarbonyl;
N—($C_{1-6}$alkyl-sulfonyl)-amino-$C_{1-6}$alkyl; amino;
N—$C_{1-6}$alkyl-amino;
N,N-di-$C_{1-6}$alkyl-amino;
halo-$C_{1-6}$alkyl;
phenyl;
heterocyclyl;
heteroaryl;
$C_{1-6}$alkyl-carbonylamino;
carbonylamino; or
hydroxy;
wherein the $C_{1-6}$alkyl moieties may be unsubstituted or substituted one or more times with halo; and
wherein the phenyl, heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$;
or $R^f$ and $R^g$ together may form oxo;
or $R^f$ and $R^g$ together with the atoms to which they are attached may form a four, five, six or seven membered saturated or partially saturated ring that may optionally include one or two heteroatoms selected from —O—, —$NR^a$— or —S—, and which may be optionally substituted one or more times with $R^i$;
$R^h$ is:
hydrogen;
$C_{1-6}$alkyl;
$C_{3-6}$cycloalkyl;
$C_{3-6}$cycloalkenyl;
$C_{3-6}$cycloalkyl-$C_{1-6}$alkyl;
$C_{1-6}$alkyl-carbonyl;
$C_{3-6}$cycloalkyl-carbonyl;
$C_{3-6}$cycloalkyl-$C_{1-6}$alkyl-carbonyl;
cyano-$C_{1-6}$alkyl-carbonyl;
hydroxy-$C_{1-6}$alkyl-carbonyl;
$C_{1-6}$alkoxy-$C_{1-6}$alkyl-carbonyl;
N-cyano-aminocarbonyl;
N-cyano-N—$C_{1-6}$alkyl-aminocarbonyl;
N—$C_{1-6}$alkyl-acetimidamidyl;
N,N'-di-$C_{1-6}$alkyl-acetimidamidyl;
N'-cyano-N—$C_{1-6}$alkyl-acetimidamidyl;
N'-hydroxy-acetimidamidyl;
N'—$C_{1-6}$alkoxy-acetimidamidyl;
N'-hydroxy-N—$C_{1-6}$alkyl-acetimidamidyl;
N'—$C_{1-6}$alkoxy-N—$C_{1-6}$alkyl-acetimidamidyl;
2-nitro-1-N—$C_{1-6}$alkylamino-vinyl;
formyl;
$C_{1-6}$alkyl-sulfonyl;
$C_{3-6}$cycloalkyl-sulfonyl;
$C_{3-6}$cycloalkyl-$C_{1-6}$alkyl-sulfonyl;
$C_{1-6}$alkyl-sulfonyl-$C_{1-6}$alkyl;
aminocarbonyl;
N-hydroxy-aminocarbonyl;
N—$C_{1-6}$alkoxy-aminocarbonyl;
N—$C_{1-6}$alkyl-aminocarbonyl;
N-hydroxy-N—$C_{1-6}$alkyl-aminocarbonyl;
N—$C_{1-6}$alkoxy-N—$C_{1-6}$alkyl-aminocarbonyl;
N,N-di-$C_{1-6}$alkyl-aminocarbonyl;
aminosulfonyl;
N—$C_{1-6}$alkyl-aminosulfonyl;
N,N-di-$C_{1-6}$alkyl-aminosulfonyl;
cyano;
$C_{1-6}$alkyl-sulfonylamino;
$C_{1-6}$alkyl-sulfonylamino-$C_{1-6}$alkyl;
N—($C_{1-6}$alkyl-sulfonyl)aminocarbonyl;
N—($C_{1-6}$alkyl-sulfonyl)-N—$C_{1-6}$alkyl-aminocarbonyl;
N—($C_{1-6}$alkyl-sulfonyl)-amino-$C_{1-6}$alkyl;
aminocarbonyl-$C_{1-6}$alkyl;
N—$C_{1-6}$alkyl-aminocarbonyl-$C_{1-6}$alkyl;
N,N-di-$C_{1-6}$alkyl-aminocarbonyl-$C_{1-6}$alkyl;
$C_{1-6}$alkoxy-carbonyl;
phenyl;
heterocyclyl; or
heteroaryl;
wherein the $C_{1-6}$alkyl moieties may be unsubstituted or substituted one or more times with halo; and
wherein the phenyl, heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$;
or $R^h$ and one of $R^{10}$ and $R^{11}$ together with the atoms to which they are attached may form a four, five, six or seven membered aromatic, partially saturated or unsaturated ring that may optionally include one or two additional heteroatom selected from —O—, —$NR^a$— or —S—, and which may be optionally substituted one or more times with $R^i$—;
or one of $R^f$ and $R^g$ and one of $R^{10}$ and $R^{11}$ together with the atoms to which they are attached may form a three, four, five, six or seven membered aromatic, partially saturated or unsaturated ring that may optionally include an additional heteroatom selected from —O—, —$NR^a$— or —S—, and which may be optionally substituted one or more times with $R^i$;
$R^i$ is:
$C_{1-6}$alkyl;
halo-$C_{1-6}$alkyl;
$C_{3-6}$cycloalkyl;
halo;
oxo;
hydroxy;
acetyl;
$C_{1-6}$alkyl-carbonyl;
amino-carbonyl;
hydroxy-$C_{1-6}$alkyl;
cyano;

cyano-$C_{1-6}$alkyl;
$C_{1-6}$alkoxy-$C_{1-6}$alkyl;
carboxy; or
$C_{1-6}$alkoxy;
$R^j$ and $R^k$ each independent is:
hydrogen; or
$C_{1-6}$alkyl which may be unsubstituted or substituted one or more times with halo; and
$R^m$ is: $C_{1-6}$alkyl;
hydroxy;
halo;
hydroxy-$C_{1-6}$alkyl;
$C_{1-6}$alkylsulfonyl-$C_{1-6}$alkyl;
cyano;
$C_{1-6}$alkylsulfonyl-amino-
$C_{1-6}$alkylsulfinyl-amino-
cyano-$C_{1-6}$alkyl;
cyano-$C_{2-6}$alkenyl;
amino-$C_{1-6}$alkyl;
$C_{1-6}$alkoxy-$C_{1-6}$alkyl;
$C_{1-6}$alkoalkoxy-$C_{1-6}$alkoxy-$C_{1-6}$alkyl;
hydroxy-$C_{1-6}$alkoxy;
hydroxy-$C_{1-6}$alkoxy-$C_{1-6}$alkyl;
hydroxy-$C_{1-6}$alkyl-amino;
$C_{1-6}$alkoxy-$C_{1-6}$alkyl-amino;
N-hydroxy-carboxamidinyl;
$C_{1-6}$alkoxy-carbonyl-$C_{2-6}$alkenyl;
amino;
N—$C_{1-6}$alkylamino;
N,N-di-$C_{1-6}$alkylamino;
—(CHR$^t$)$_u$—C(O)—NR$^p$R$^q$;
—(CHR$^s$)$_u$—O—(CHR$^s$)$_v$—C(O)—NR$^p$R$^q$;
—(CHR$^s$)$_u$—NR$^n$—(CHR$^s$)$_v$—C(O)—NR$^p$R$^q$,
—(CHR$^t$)$_u$—C(O)—R$^u$;
—(CHR$^s$)$_u$—O—(CHR$^s$)$_v$—C(O)—R$^u$; or
—(CHR$^s$)$_u$—NR$^n$—(CHR$^s$)$_v$—C(O)—R$^u$;
u is from 0 to 2;
v is from 0 to 2;
each $R^n$ is independently:
hydrogen; or
$C_{1-6}$alkyl;
$R^p$ is:
hydrogen; or
$C_{1-6}$alkyl;
$R^g$ is:
hydrogen;
$C_{1-6}$alkyl;
hydroxy-$C_{1-6}$alkyl;
N—($C_{1-6}$alkylcarbonyl)-amino-$C_{1-6}$alkyl;
$C_{1-6}$alkylsulfonyl-$C_{1-6}$alkyl;
amino-$C_{1-6}$alkyl;
N—$C_{1-6}$alkylamino-$C_{1-6}$alkyl;
N,N-di-$C_{1-6}$alkylamino-$C_{1-6}$alkyl;
N,N-di-$C_{1-6}$alkylaminocarbonyl-$C_{1-6}$alkyl;
cyano-$C_{1-6}$alkyl;
carboxy-$C_{1-6}$alkyl;
aminocarbonyl-$C_{1-6}$alkyl;
N—$C_{1-6}$alkylaminocarbonyl-$C_{1-6}$alkyl;
N,N-di-$C_{1-6}$alkyl aminocarbonyl-$C_{1-6}$alkyl;
$C_{1-6}$alkylsulfonyl-$C_{1-6}$alkyl; or
$C_{1-6}$alkoxy-$C_{1-6}$alkyl;
each $R^s$ is independently:
hydrogen; or
$C_{1-6}$alkyl;
each $R^t$ is independently:
hydrogen;
$C_{1-6}$alkyl;
halo; or
hydroxy; and
$R^u$ is: $C_{1-6}$alkyl;
$C_{1-6}$alkoxy;
hydroxy; or
hydroxy-$C_{1-6}$alkyl.
In certain embodiments of formula I, m is 0.
In certain embodiments of formula I, m is 1.
In certain embodiments of formula I, n is 0.
In certain embodiments of formula I, n is 1.
In certain embodiments of formula I, p is from 0 to 2.
In certain embodiments of formula I, p is 0 or 1.
In certain embodiments of formula I, p is 0.
In certain embodiments of formula I, p is 1.
In certain embodiments of formula I, p is 2.
In certain embodiments of formula I, p is 3.
In certain embodiments of formula I, q is 0.
In certain embodiments of formula I, q is 1.
In certain embodiments of formula I, q is 2.
In certain embodiments of formula I, r is 1.
In certain embodiments of formula I, r is 2.
In certain embodiments of formula I, r is 3.
In certain embodiments of formula I, t is from 0 to 3.
In certain embodiments of formula I, t is 0.
In certain embodiments of formula I, t is 1.
In certain embodiments of formula I, t is 2.
In certain embodiments of formula I, t is 3.
In certain embodiments of formula I, A is: a bond; —CH$_2$—; —C(O)—; —NR$^a$—; —O—; —S—; or —SO$_2$—.
In certain embodiments of formula I, A is: a bond; —(CR$_j$R$_k$)$_t$—; —C(O)—(CR$_j$R$_k$)$_t$—; —(CR$_j$R$_k$)$_t$—C(O)—; —(CR$_j$R$_k$)$_t$—NR$^a$—; —C(O)NR$^a$—(CR$_j$R$_k$)$_t$—; —(CR$_j$R$_k$)$_t$—NR$^a$C(O)—; —(CR$_j$R$_k$)$_t$—O—; —(CR$_j$R$_k$)$_t$—S—; —or —(CR$_j$R$_k$)$_t$—SO$_2$—.
In certain embodiments of formula I, A is: a bond; —C(O)—(CR$_j$R$_k$)$_t$—; —(CR$_j$R$_k$)$_t$—C(O)—; —(CR$_j$R$_k$)$_t$—NR$^a$—; —C(O)NR$^a$—(CR$_j$R$_k$)$_t$—; (CR$_j$R$_k$)$_t$—NR$^a$C(O)—; or —(CR$_j$R$_k$)$_t$—O—.
In certain embodiments of formula I, A is: a bond; —NR$^a$—; —O—; or —S—.
In certain embodiments of formula I, A is: a bond; —NR$^a$—; or —O—.
In certain embodiments of formula I, A is: a bond; or —(CR$_j$R$_k$)$_t$—O—.
In certain embodiments of formula I, A is a bond.
In certain embodiments of formula I, A is —CH$_2$—.
In certain embodiments of formula I, A is —C(O)—.
In certain embodiments of formula I, A is —NR$^a$—.
In certain embodiments of formula I, A is —O—.
In certain embodiments of formula I, A is —S—.
In certain embodiments of formula I, A is —SO$_2$—.
In certain embodiments of formula I, A is —C(O)NR$^a$—(CH$_2$)$_t$.
In certain embodiments of formula I, A is —(CH$_2$)$_t$—NR$^a$C(O)—.
In certain embodiments of formula I, A is —(CR$_j$R$_k$)$_t$—.
In certain embodiments of formula I, A is —CR$_j$R$_k$—.
In certain embodiments of formula I, A is —C(O)—(CR$_j$R$_k$)$_t$—.
In certain embodiments of formula I, A is —(CR$_j$R$_k$)$_t$—C(O)—.
In certain embodiments of formula I, A is —NR$^a$—(CR$_j$R$_k$)$_t$—.
In certain embodiments of formula I, A is —(CR$_j$R$_k$)$_t$—NR$^a$—.

In certain embodiments of formula I, A is —C(O)NR$^a$—(CR$_j$R$_k$)$_t$—.

In certain embodiments of formula I, A is (CR$_j$R$_k$)$_t$—NR$^a$C(O)—.

In certain embodiments of formula I, A is —O—(CR$_j$R$_k$)$_t$—.

In certain embodiments of formula I, A is —(CR$_j$R$_k$)$_t$—O—.

In certain embodiments of formula I, A is —S—(CR$_j$R$_k$)$_t$—.

In certain embodiments of formula I, A is —(CR$_j$R$_k$)$_t$—S—.

In certain embodiments of formula I, A is —SO$_2$—(CR$_j$R$_k$)$_t$—.

In certain embodiments of formula I, A is —(CR$_j$R$_k$)$_t$—SO$_2$—.

In certain embodiments of formula I, A is —(CH$_2$)$_2$—O—.

In certain embodiments of formula I, A is —(CH$_2$)—O—.

In certain embodiments of formula I, A is —O—(CH$_2$)$_2$—.

In certain embodiments of formula I, A is —O—(CH$_2$)—.

In certain embodiments of formula I, A is —(CH$_2$)$_2$—C(O)—.

In certain embodiments of formula I, A is —(CH$_2$)—C(O)—.

In certain embodiments of formula I, A is —C(O)—(CH$_2$)$_2$—.

In certain embodiments of formula I, A is —C(O)—(CH$_2$)—.

In certain embodiments of formula I, A is —C(O)—NH—.

In certain embodiments of formula I, A is —CH$_2$—C(O)—NH—.

In certain embodiments of formula I, A is —NH—.

In certain embodiments of formula I, A is —(CH$_2$)$_2$—NH—.

In certain embodiments of formula I, A is —CH$_2$—NH—.

In certain embodiments of formula I, A is —NH—(CH$_2$)$_2$—.

In certain embodiments of formula I, A is —NH—CH$_2$—.

In certain embodiments of formula I, A is —NH—C(O)—.

In certain embodiments of formula I, t is from 0 to 3.
In certain embodiments of formula I, t is from 1 to 3.
In certain embodiments of formula I, t is from 0 to 2.
In certain embodiments of formula I, t is 0
In certain embodiments of formula I, t is 1.
In certain embodiments of formula I, t is 2.
In certain embodiments of formula I, t is 3.
In certain embodiments of formula I, t is 4.
In certain embodiments of formula I, W is —CR$^b$R$^c$— or —O—.
In certain embodiments of formula I, W is —CR$^b$R$^c$—.
In certain embodiments of formula I, W is —O—.
In certain embodiments of formula I, W is —NR$^d$—.
In certain embodiments of formula I, W is —S—.
In certain embodiments of formula I, W is —SO$_2$—.
In certain embodiments of formula I, W is —CH$_2$—.
In certain embodiments of formula I, one or two of X$^1$, X$^2$, X$^3$ and X$^4$ is N and the others are CR$^e$.
In certain embodiments of formula I, three of X$^1$, X$^2$, X$^3$ and X$^4$ are CR$^e$ and the other is N.
In certain embodiments of formula I, X$^1$, X$^2$, X$^3$ and X$^4$ are CR$^e$.
In certain embodiments of formula I, X$^1$ is N and X$^2$, X$^3$ and X$^4$ are CR$^e$.
In certain embodiments of formula I, X$^2$ is N and X$^1$, X$^3$ and X$^4$ are CR$^e$.
In certain embodiments of formula I, X$^1$ and X$^4$ are N, and X$^2$ and X$^3$ are CR$^a$.
In certain embodiments of formula I, X$^2$ and X$^3$ are N, and X$^1$ and X$^4$ are CR$^e$.
In certain embodiments of formula I, X$^1$ and X$^2$ are N, and X$^3$ and X$^4$ are CR$^e$.
In certain embodiments of formula I, Y is —O—, —CR$^f$R$^g$— or —NR$^h$—.
In certain embodiments of formula I, Y is —CR$^f$R$^g$— or —NR$^h$—.
In certain embodiments of formula I, Y is —O—.
In certain embodiments of formula I, Y is —S—.
In certain embodiments of formula I, Y is —SO$_2$—.
In certain embodiments of formula I, Y is —CR$^f$R$^g$—.
In certain embodiments of formula I, Y is —NR$^h$—.
In certain embodiments of formula I, R$^1$ is hydrogen.
In certain embodiments of formula I, R$^1$ is C$_{1-6}$alkyl.
In certain embodiments of formula I, R$^2$ is hydrogen.
In certain embodiments of formula I, R$^2$ is C$_{1-6}$alkyl.
In certain embodiments of formula I, R$^3$ is hydrogen.
In certain embodiments of formula I, R$^3$ is C$_{1-6}$alkyl.
In certain embodiments of formula I, R$^3$ is halo-C$_{1-6}$alkyl.
In certain embodiments of formula I, R$^3$ is difluoromethyl.
In certain embodiments of formula I, R$^3$ is trifluoromethyl.
In certain embodiments of formula I, R$^4$ is hydrogen.
In certain embodiments of formula I, R$^4$ is C$_{1-6}$alkyl.
In certain embodiments of formula I, R$^5$ is hydrogen.
In certain embodiments of formula I, R$^5$ is C$_{1-6}$alkyl.
In certain embodiments of formula I, R$^6$ is hydrogen.
In certain embodiments of formula I, R$^6$ is C$_{1-6}$alkyl.
In certain embodiments of formula I, R$^7$ is hydrogen.
In certain embodiments of formula I, R$^7$ is C$_{1-6}$alkyl.
In certain embodiments of formula I, R$^8$ is hydrogen.
In certain embodiments of formula I, R$^8$ is C$_{1-6}$alkyl.
In certain embodiments of formula I, R$^3$ and R$^4$ together with the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, R$^3$ and R$^4$ together with the atoms to which they are attached form a three, four or five membered saturated ring.

In certain embodiments of formula I, R$^5$ and R$^6$ together with the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, R$^5$ and R$^6$ together with the atoms to which they are attached form a three, four or five membered saturated ring.

In certain embodiments of formula I, R$^7$ and R$^8$ together with the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, R$^7$ and R$^8$ together with the atoms to which they are attached form a three, four or five membered saturated ring.

In certain embodiments of formula I, one of R$^3$ and R$^4$ together with one of R$^5$ and R$^6$ and the atoms to which they are attached form a three, four, five, six or seven membered ring that may optionally include one or two heteroatoms selected from —O—, —NR$^a$— or —S—, and which may be optionally substituted one or more times with R$^i$.

In certain embodiments of formula I, one of R$^5$ and R$^6$ together with one of R$^7$ and R$^8$ and the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, each R$^9$ is independently: C$_{1-6}$alkyl; halo; or halo-C$_{1-6}$alkyl.

In certain embodiments of formula I, R$^9$ is C$_{1-6}$alkyl.
In certain embodiments of formula I, R$^9$ is halo.
In certain embodiments of formula I, R$^9$ is C$_{1-6}$alkoxy.
In certain embodiments of formula I, R$^9$ is cyano.
In certain embodiments of formula I, R$^9$ is halo-C$_{1-6}$alkyl.
In certain embodiments of formula I, each R$^9$ is independently: fluoro; chloro; or trifluoromethyl.

In certain embodiments of formula I, R$^{10}$ is: hydrogen; halo; or C$_{1-6}$alkyl which may be unsubstituted or substituted one or more times with halo or oxo.

In certain embodiments of formula I, R$^{10}$ is: hydrogen or C$_{1-6}$alkyl.
In certain embodiments of formula I, R$^{10}$ is hydrogen.
In certain embodiments of formula I, R$^{10}$ is C$_{1-6}$alkyl.
In certain embodiments of formula I, R$^{10}$ is methyl.
In certain embodiments of formula I, R$^{10}$ is halo.
In certain embodiments of formula I, R$^{10}$ is carboxy.
In certain embodiments of formula I, R$^{10}$ is C$_{1-6}$alkyl-carbonyl.
In certain embodiments of formula I, R$^{10}$ is C$_{1-6}$alkoxy-carbonyl. In certain embodiments of formula I, R$^{10}$ is oxo.
In certain embodiments of formula I, R$^{10}$ is hydroxy.
In certain embodiments of formula I, R$^{10}$ is aminocarbonyl.
In certain embodiments of formula I, R$^{10}$ is N—C$_{1-6}$alkyl-aminocarbonyl.
In certain embodiments of formula I, R$^{10}$ is N,N-di-C$_{1-6}$alkyl-aminocarbonyl.
In certain embodiments of formula I, R$^{10}$ is cyano
In certain embodiments of formula I, R$^{10}$ is hydroxy-C$_{1-6}$alkyl.
In certain embodiments of formula I, R$^{10}$ is N—C$_{1-6}$alkoxy-C$_{1-6}$alkyl-aminocarbonyl.
In certain embodiments of formula I, R$^{10}$ is N-hydroxy-C$_{1-6}$alkyl-aminocarbonyl.
In certain embodiments of formula I, R$^{10}$ is N—C$_{1-6}$alkoxy-aminocarbonyl.

In certain embodiments of formula I, R$^{11}$ is: hydrogen; halo; oxo; hydroxy; or C$_{1-6}$alkyl which may be unsubstituted or substituted one or more times with halo; or oxo.

In certain embodiments of formula I, R$^{11}$ is: hydrogen; halo; carboxy; C$_{1-6}$alkyl-carbonyl; C$_{1-6}$alkoxy-carbonyl; oxo; hydroxy; aminocarbonyl; N—C$_{1-6}$alkyl-aminocarbonyl; N,N-di-C$_{1-6}$alkyl-aminocarbonyl; or C$_{1-6}$alkyl which may be unsubstituted or substituted one or more times with halo or oxo.

In certain embodiments of formula I, R$^{11}$ is: hydrogen; halo; or C$_{1-6}$alkyl.

In certain embodiments of formula I, R$^{11}$ is: hydrogen; C$_{1-6}$alkyl; or halo.

In certain embodiments of formula I, R$^{11}$ is: hydrogen; or C$_{1-6}$alkyl.

In certain embodiments of formula I, R$^{11}$ is hydrogen.
In certain embodiments of formula I, R$^{11}$ is C$_{1-6}$alkyl
In certain embodiments of formula I, R$^{101}$ is methyl.
In certain embodiments of formula I, R$^{11}$ is halo.
In certain embodiments of formula I, R$^{11}$ is oxo.
In certain embodiments of formula I, R$^{11}$ is C$_{1-6}$alkyl-sulfonylamino.
In certain embodiments of formula I, R$^{11}$ is C$_{1-6}$alkyl-sulfonylamino-C$_{1-6}$alkyl.
In certain embodiments of formula I, R$^{11}$ is cyano.
In certain embodiments of formula I, R$^{11}$ is hydroxy-C$_{1-6}$alkyl.
In certain embodiments of formula I, R$^{11}$ is N—C$_{1-6}$alkoxy-C$_{1-6}$alkyl-aminocarbonyl.
In certain embodiments of formula I, R$^{11}$ is N-hydroxy-C$_{1-6}$alkyl-aminocarbonyl.
In certain embodiments of formula I, R$^{11}$ is N—C$_{1-6}$alkoxy-aminocarbonyl.

In certain embodiments of formula I, R$^{12}$ is: hydrogen; or C$_{1-6}$alkyl.
In certain embodiments of formula I, R$^{12}$ is hydrogen.
In certain embodiments of formula I, R$^{12}$ is halo.
In certain embodiments of formula I, R$^{12}$ is carboxy.
In certain embodiments of formula I, R$^{12}$ is C$_{1-6}$alkyl-carbonyl.
In certain embodiments of formula I, R$^{12}$ is C$_{1-6}$alkoxy-carbonyl.
In certain embodiments of formula I, R$^{12}$ is oxo.
In certain embodiments of formula I, R$^{12}$ is hydroxy.
In certain embodiments of formula I, R$^{12}$ is aminocarbonyl.
In certain embodiments of formula I, R$^{12}$ is N—C$_{1-6}$alkyl-aminocarbonyl.
In certain embodiments of formula I, R$^{12}$ is N,N-di-C$_{1-6}$alkyl-aminocarbonyl.
In certain embodiments of formula I, R$^{12}$ is cyano.
In certain embodiments of formula I, R$^{12}$ is hydroxy-C$_{1-6}$alkyl.
In certain embodiments of formula I, R$^{12}$ is N—C$_{1-6}$alkoxy-C$_{1-6}$alkyl-aminocarbonyl.
In certain embodiments of formula I, R$^{12}$ is N-hydroxy-C$_{1-6}$alkyl-aminocarbonyl.
In certain embodiments of formula I, R$^{12}$ is N—C$_{1-6}$alkoxy-aminocarbonyl.
In certain embodiments of formula I, R$^{12}$ is C$_{1-6}$alkyl.
In certain embodiments of formula I, R$^{12}$ is methyl.

In certain embodiments of formula I, R$^{10}$ and R$^{11}$ together with the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, R$^{10}$ and R$^{11}$ together with the atoms to which they are attached form a four, five, six or seven membered ring.

In certain embodiments of formula I, R$^{10}$ and R$^{11}$ together with the atoms to which they are attached form a double bond.

In certain embodiments of formula I, R$^{13}$ is hydrogen.
In certain embodiments of formula I, R$^{13}$ is C$_{1-6}$alkyl.
In certain embodiments of formula I, R$^a$, R$^b$, R$^c$ and R$^d$ each independent is: hydrogen; or C$_{1-6}$alkyl.
In certain embodiments of formula I, R$^a$ is hydrogen.
In certain embodiments of formula I, R$^a$ is C$_{1-6}$alkyl.
In certain embodiments of formula I, R$^b$ is hydrogen.
In certain embodiments of formula I, R$^b$ is C$_{1-6}$alkyl.
In certain embodiments of formula I, R is hydrogen.
In certain embodiments of formula I, R is C$_{1-6}$alkyl.
In certain embodiments of formula I, R$^b$ and R$^c$ together with the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, one of R$^b$ and R$^c$ together with one of R$^7$ and R$^8$ and the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, one of R$^b$ and R$^c$ together with one of R$^5$ and R$^6$ and the atoms to which they are attached form a three, four, five, six or seven membered saturated or partially saturated ring that may optionally include one or two heteroatoms selected from —O—, —NR$^a$— or —S—, and which may be optionally substituted one or more times with R$^i$.

In certain embodiments of formula I, R$^d$ is hydrogen.
In certain embodiments of formula I, R$^d$ is C$_{1-6}$alkyl.
In certain embodiments of formula I, each R$^e$ is independently: hydrogen; C$_{1-6}$alkyl; halo; or halo-C$_{1-6}$alkyl.
In certain embodiments of formula I, each R$^e$ is independently: hydrogen; C$_{1-6}$alkyl; or halo.
In certain embodiments of formula I, each R$^e$ is independently: hydrogen; or halo.
In certain embodiments of formula I, each R$^e$ is independently: hydrogen; or fluoro.
In certain embodiments of formula I, R$^e$ is hydrogen.
In certain embodiments of formula I, R$^e$ is C$_{1-6}$alkyl.
In certain embodiments of formula I, R$^e$ is halo.
In certain embodiments of formula I, R$^e$ is C$_{1-6}$alkoxy.
In certain embodiments of formula I, R$^e$ is cyano.
In certain embodiments of formula I, R$^e$ is halo-C$_{1-6}$alkyl.
In certain embodiments of formula I, each R$^f$ is independently: hydrogen; or C$_{1-6}$alkyl.
In certain embodiments of formula I, R$^f$ is hydrogen.
In certain embodiments of formula I, R$^f$ is C$_{1-6}$alkyl.
In certain embodiments of formula I, R$^f$ is halo.
In certain embodiments of formula I, R$^f$ is C$_{1-6}$alkoxy.
In certain embodiments of formula I, R$^g$ is: C$_{1-6}$alkyl; C$_{3-6}$cycloalkyl; C$_{3-6}$cycloalkenyl; C$_{3-6}$cycloalkyl-C$_{1-6}$alkyl; halo; C$_{1-6}$alkyl-carbonyl; C$_{3-6}$cycloalkyl-carbonyl; C$_{3-6}$cycloalkyl-C$_{1-6}$alkyl-carbonyl; cyano-C$_{1-6}$alkyl-carbonyl; hydroxy-C$_{1-6}$alkyl-carbonyl; C$_{1-6}$alkoxy-C$_{1-6}$alkyl-carbonyl; carboxy; N-cyano-aminocarbonyl; N-cyano-N—C$_{1-6}$alkyl-aminocarbonyl; N—C$_{1-6}$alkyl-acetimidamidyl; N,N'-di-C$_{1-6}$alkyl-acetimidamidyl; N'-cyano-N—C$_{1-6}$alkyl-acetimidamidyl; N'-hydroxy-acetimidamidyl; N'—C$_{1-6}$alkoxy-acetimidamidyl; N'-hydroxy-N—C$_{1-6}$alkyl-acetimidamidyl; N'—C$_{1-6}$alkoxy-N—C$_{1-6}$alkyl-acetimidamidyl; 2-nitro-1-N—C$_{1-6}$alkylamino-vinyl; formyl; C$_{1-6}$alkyl-sulfonyl; C$_{3-6}$cycloalkyl-sulfonyl; C$_{3-6}$cycloalkyl-C$_{1-6}$alkyl-sulfonyl; C$_{1-6}$alkyl-sulfonyl-C$_{1-6}$alkyl; aminocarbonyl; N-hydroxy-aminocarbonyl; N—C$_{1-6}$alkoxy-aminocarbonyl; N—C$_{1-6}$alkyl-aminocarbonyl; N-hydroxy-N—C$_{1-6}$alkyl-aminocarbonyl; N—C$_{1-6}$alkoxy-N—C$_{1-6}$alkyl-aminocarbonyl; N,N-di-C$_{1-6}$alkyl-aminocarbonyl; aminosulfonyl; N—C$_{1-6}$alkyl-aminosulfonyl; N,N-di-C$_{1-6}$alkyl-aminosulfonyl; cyano; C$_{1-6}$alkoxy; C$_{1-6}$alkyl-sulfonylamino; N—C$_{1-6}$alkyl-sulfonylaminocarbonyl; N—(C$_{1-6}$alkyl-sulfonyl)-N—C$_{1-6}$alkyl-aminocarbonyl; N—(C$_{1-6}$alkyl-sulfonyl)-amino-C$_{1-6}$alkyl; amino; N—C$_{1-6}$alkyl-amino; N,N-di-C$_{1-6}$alkyl-amino; halo-C$_{1-6}$alkyl; heterocyclyl; heteroaryl; or hydroxyl; wherein the C$_{1-6}$alkyl moieties may be unsubstituted or substituted one or more times with halo; and wherein the heterocyclyl, heteroaryl, C$_{3-6}$cycloalkyl, C$_{3-6}$cycloalkenyl and C$_{3-6}$cycloalkyl-C$_{1-6}$alkyl moieties may be unsubstituted or substituted one or more times with R$^i$.

In certain embodiments of formula I, R$^g$ is: hydrogen; C$_{1-6}$alkyl; C$_{3-6}$cycloalkyl; C$_{3-6}$cycloalkyl-C$_{1-6}$alkyl; halo; C$_{1-6}$alkyl-carbonyl; C$_{3-6}$cycloalkyl-carbonyl; C$_{3-6}$cycloalkyl-C$_{1-6}$alkyl-carbonyl; C$_{1-6}$alkyl-sulfonyl; C$_{3-6}$cycloalkyl-sulfonyl; C$_{3-6}$cycloalkyl-C$_{1-6}$alkyl-sulfonyl; aminocarbonyl; N—C$_{1-6}$alkyl-aminocarbonyl; N,N-di-C$_{1-6}$alkyl-aminocarbonyl; aminosulfonyl; N—C$_{1-6}$alkyl-aminosulfonyl; N,N-di-C$_{1-6}$alkyl-aminosulfonyl; cyano; C$_{1-6}$alkoxy; C$_{1-6}$alkyl-sulfonylamino; amino; N—C$_{1-6}$alkyl-amino; N,N-di-C$_{1-6}$alkyl-amino; halo-C$_{1-6}$alkyl; or hydroxyl; wherein the C$_{1-6}$alkyl moieties may be unsubstituted or substituted one or more times with halo; and wherein the C$_{3-6}$cycloalkyl, and C$_{3-6}$cycloalkyl-C$_{1-6}$alkyl moieties may be unsubstituted or substituted one or more times with R$^i$.

In certain embodiments of formula I, R$^g$ is: hydrogen; C$_{1-6}$alkyl; halo; carbonylamino; C$_{1-6}$alkoxy; heteroaryl; C$_{1-6}$alkyl-carbonylamino; carbonylamino; or hydroxyl.

In certain embodiments of formula I, R$^g$ is hydrogen.
In certain embodiments of formula I, R$^g$ is C$_{1-6}$alkyl.
In certain embodiments of formula I, R$^g$ is C$_{3-6}$cycloalkyl which may be unsubstituted or substituted one or more times with R$^i$.
In certain embodiments of formula I, R$^g$ is C$_{3-6}$cycloalkyl-C$_{1-6}$alkyl which may be unsubstituted or substituted one or more times with R$^i$.
In certain embodiments of formula I, R$^g$ is halo.
In certain embodiments of formula I, R$^g$ is C$_{1-6}$alkyl-carbonyl.
In certain embodiments of formula I, R$^g$ is C$_{3-6}$cycloalkyl-carbonyl wherein the C$_{3-6}$cycloalkyl moeity may be unsubstituted or substituted one or more times with R$^i$.
In certain embodiments of formula I, R$^g$ is C$_{3-6}$cycloalkyl-C$_{1-6}$alkyl-carbonyl wherein the C$_{3-6}$cycloalkyl-C$_{1-6}$alkyl moiety may be unsubstituted or substituted one or more times with R$^i$.
In certain embodiments of formula I, R$^g$ is C$_{1-6}$alkyl-sulfonyl.
In certain embodiments of formula I, R$^g$ is C$_{3-6}$cycloalkyl-sulfonyl.
In certain embodiments of formula I, R$^g$ is C$_{3-6}$cycloalkyl-C$_{1-6}$alkyl-sulfonyl.
In certain embodiments of formula I, R$^g$ is aminocarbonyl.
In certain embodiments of formula I, R$^g$ is N—C$_{1-6}$alkyl-aminocarbonyl.
In certain embodiments of formula I, R$^g$ is N,N-di-C$_{1-6}$alkyl-aminocarbonyl.
In certain embodiments of formula I, R$^g$ is aminosulfonyl.
In certain embodiments of formula I, R$^g$ is N—C$_{1-6}$alkyl-aminosulfonyl.
In certain embodiments of formula I, R$^g$ is N,N-di-C$_{1-6}$alkyl-aminosulfonyl.
In certain embodiments of formula I, R$^g$ is cyano.
In certain embodiments of formula I, R$^g$ is C$_{1-6}$alkoxy.
In certain embodiments of formula I, R$^g$ is C$_{1-6}$alkyl-sulfonylamino.
In certain embodiments of formula I, R$^g$ is amino.
In certain embodiments of formula I, R$^g$ is N—C$_{1-6}$alkyl-amino.
In certain embodiments of formula I, R$^g$ is N,N-di-C$_{1-6}$alkyl-amino.
In certain embodiments of formula I, R$^g$ is halo-C$_{1-6}$alkyl.
In certain embodiments of formula I, R$^g$ is hydroxy.

In certain embodiments of formula I, $R^g$ is $C_{3-6}$cycloalkeny which may be unsubstituted or substituted one or more times with $R^i$.

In certain embodiments of formula I, $R^g$ is cyano-$C_{1-6}$alkyl-carbonyl.

In certain embodiments of formula I, $R^g$ is hydroxy-$C_{1-6}$alkyl-carbonyl.

In certain embodiments of formula I, $R^g$ is $C_{1-6}$alkoxy-$C_{1-6}$alkyl-carbonyl.

In certain embodiments of formula I, $R^g$ is carboxy.

In certain embodiments of formula I, $R^g$ is N-cyano-aminocarbonyl.

In certain embodiments of formula I, $R^g$ is N-cyano-N—$C_{1-6}$alkyl-aminocarbonyl.

In certain embodiments of formula I, $R^g$ is N—$C_{1-6}$alkyl-acetimidamidyl.

In certain embodiments of formula I, $R^g$ is N,N'-di-$C_{1-6}$alkyl-acetimidamidyl.

In certain embodiments of formula I, $R^g$ N'-cyano-N—$C_{1-6}$alkyl-acetimidamidyl.

In certain embodiments of formula I, $R^g$ N'-hydroxy-acetimidamidyl.

In certain embodiments of formula I, $R^g$ N'—$C_{1-6}$alkoxy-acetimidamidyl.

In certain embodiments of formula I, $R^g$ N'-hydroxy-N—$C_{1-6}$alkyl-acetimidamide; N'—$C_{1-6}$alkoxy-N—$C_{1-6}$alkyl-acetimidamidyl.

In certain embodiments of formula I, $R^g$ is 2-nitro-1-N—$C_{1-6}$alkylamino-vinyl.

In certain embodiments of formula I, $R^g$ is $C_{1-6}$alkyl-sulfonyl-$C_{1-6}$alkyl.

In certain embodiments of formula I, $R^g$ is N-hydroxy-aminocarbonyl.

In certain embodiments of formula I, $R^g$ is N—$C_{1-6}$alkoxy-aminocarbonyl.

In certain embodiments of formula I, $R^g$ is N-hydroxy-N—$C_{1-6}$alkyl-aminocarbonyl.

In certain embodiments of formula I, $R^g$ is N—$C_{1-6}$alkoxy-N—$C_{1-6}$alkyl-aminocarbonyl.

In certain embodiments of formula I, $R^g$ is N—$C_{1-6}$alkyl-sulfonylaminocarbonyl.

In certain embodiments of formula I, $R^g$ is N—($C_{1-6}$alkyl-sulfonyl)-N—$C_{1-6}$alkyl-aminocarbonyl.

In certain embodiments of formula I, $R^g$ is aminocarbonyl-$C_{1-6}$alkyl.

In certain embodiments of formula I, $R^g$ is N—$C_{1-6}$alkyl-aminocarbonyl-$C_{1-6}$alkyl In certain embodiments of formula I, $R^g$ is N,N-di-$C_{1-6}$alkyl-aminocarbonyl-$C_{1-6}$alkyl.

In certain embodiments of formula I, $R^g$ is $C_{1-6}$alkoxy-carbonyl.

In certain embodiments of formula I, $R^g$ is carbonylamino.

In certain embodiments of formula I, $R^g$ is heterocyclyl which may be unsubstituted or substituted one or more times with $R^i$.

In embodiments of formula I wherein $R^g$ is heterocyclyl, such heterocyclyl may be oxetanyl, tetrahydrofuranyl, tetrahydropyranyl, azetidinyl, pyrrolidinyl, piperidinyl, azepinyl or piperazinyl, each of which may be unsubstituted or substituted one or more times with $R^i$.

In certain embodiments of formula I, $R^g$ is heteroaryl which may be unsubstituted or substituted one or more times with $R^i$.

In embodiments of formula I wherein $R^g$ is heteroaryl, such heteroaryl may be be pyridinyl, pyrimidinyl, triazinyl, pyrrolyl, imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In embodiments of formula I wherein $R^g$ is heteroaryl, such heteroaryl may be be imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In certain embodiments of formula I, $R^g$ is triazolyl.

In certain embodiments of formula I, $R^g$ is [1,2,4]triazol-4-yl.

In certain embodiments of formula I, $R^g$ is [1,2,4]triazol-3-yl.

In certain embodiments of formula I, $R^g$ is 4-methyl-[1,2,4]triazol-3-yl.

In certain embodiments of formula I, $R^g$ is [1,2,4]triazol-1-yl.

In certain embodiments of formula I, $R^g$ is [1,2,3]triazol-1-yl.

In certain embodiments of formula I, $R^g$ is [1,2,3]triazol-4-yl.

In certain embodiments of formula I, $R^g$ is 4-methyl-[1,2,4]triazol-3-yl.

In certain embodiments of formula I, $R^g$ is pyrazolyl.

In certain embodiments of formula I, $R^g$ is pyrazol-3-yl.

In certain embodiments of formula I, $R^g$ is pyrazol-1-yl.

In certain embodiments of formula I, $R^g$ is pyrazol-4-yl.

In certain embodiments of formula I, $R^g$ is imidazolyl.

In certain embodiments of formula I, $R^g$ is imidazol-1-yl.

In certain embodiments of formula I, $R^g$ is 1-methyl-imidazol-2-yl.

In certain embodiments of formula I, $R^g$ is isoxazolyl.

In certain embodiments of formula I, $R^g$ is 3-hydroxy-isoxazol-5-yl.

In certain embodiments of formula I, $R^g$ is oxdiazolyl.

In certain embodiments of formula I, $R^g$ is [1,2,4]oxadiazol-5-yl.

In certain embodiments of formula I, $R^g$ is [1,2,4]oxadiazol-3-yl.

In certain embodiments of formula I, $R^g$ is [1,2,3]oxadiazol-2-yl.

In certain embodiments of formula I, $R^g$ is [1,2,3]oxadiazol-2-one-5-yl.

In certain embodiments of formula I, $R^g$ is tetrazolyl.

In certain embodiments of formula I, $R^g$ is tetrazol-5-yl.

In certain embodiments of formula I, $R^g$ is tetrazol-1-yl.

In certain embodiments of formula I, $R^g$ is tetrazol-2-yl.

In certain embodiments of formula I, $R^g$ is pyrazolyl.

In certain embodiments of formula I, $R^g$ is pyridazinyl.

In certain embodiments of formula I, $R^g$ is triazinyl.

In certain embodiments of formula I, $R^f$ and $R^g$ together with the atoms to which they are attached form a three, four, five, six or seven membered saturated or partially saturated ring.

In certain embodiments of formula I, $R^f$ and $R^g$ together with the atoms to which they are attached form a three membered ring.

In certain embodiments of formula I, $R^f$ and $R^g$ together with the atoms to which they are attached form a four membered ring.

In certain embodiments of formula I, $R^f$ and $R^g$ together with the atoms to which they are attached form a five membered ring.

In certain embodiments of formula I, $R^f$ and $R^g$ together with the atoms to which they are attached form a six membered ring.

In certain embodiments of formula I, $R^f$ and $R^g$ together with the atoms to which they are attached form a seven membered ring.

In certain embodiments of formula I, $R^f$ and $R^g$ together with the atoms to which they are attached form oxo.

In certain embodiments of formula I, $R^h$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; N-cyano-aminocarbonyl; N-cyano-N—$C_{1-6}$alkyl-aminocarbonyl; N—$C_{1-6}$alkyl-acetimidamidyl; N,N'-di-$C_{1-6}$alkyl-acetimidamidyl; N'-cyano-N—$C_{1-6}$alkyl-acetimidamidyl; N'-hydroxy-acetimidamidyl; N'—$C_{1-6}$alkoxy-acetimidamidyl; N'-hydroxy-N—$C_{1-6}$alkyl-acetimidamidyl; N'—$C_{1-6}$alkoxy-N—$C_{1-6}$alkyl-acetimidamidyl; 2-nitro-1-N—$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N—$C_{1-6}$alkoxy-aminocarbonyl; N—$C_{1-6}$alkyl-aminocarbonyl; N-hydroxy-N—$C_{1-6}$alkyl-aminocarbonyl; N—$C_{1-6}$alkoxy-N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkyl-sulfonylamino; $C_{1-6}$alkyl-sulfonylamino-$C_{1-6}$alkyl; N—($C_{1-6}$alkyl-sulfonyl)aminocarbonyl; N—($C_{1-6}$alkyl-sulfonyl)-N—$C_{1-6}$alkyl-aminocarbonyl; N—($C_{1-6}$alkyl-sulfonyl)-amino-$C_{1-6}$alkyl; halo-$C_{1-6}$alkyl; heterocyclyl; or heteroaryl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$.

In certain embodiments of formula I, $R^h$ is: hydrogen; $C_{1-6}$alkyl; $C_{3-6}$cycloalkyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-aminocarbonyl; N,N-di-$C_{1-6}$alkyl-aminocarbonyl; aminosulfonyl; N—$C_{1-6}$alkyl-aminosulfonyl; or N,N-di-$C_{1-6}$alkyl-aminosulfonyl; wherein the $C_{1-6}$alkyl moieties may be unsubstituted or substituted one or more times with halo; and wherein the $C_{3-6}$cycloalkyl, and $C_{3-6}$cycloalkyl-$C_{1-6}$alkyl moieties may be unsubstituted or substituted one or more times with $R^i$.

In certain embodiments of formula I, $R^h$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-aminocarbonyl; or N,N-di-$C_{1-6}$alkyl-aminocarbonyl; aminosulfonyl; N—$C_{1-6}$alkyl-aminosulfonyl; or N,N-di-$C_{1-6}$alkyl-aminosulfonyl; wherein the $C_{3-6}$cycloalkyl, and $C_{3-6}$cycloalkyl-$C_{1-6}$alkyl moieties each may be unsubstituted or substituted one or more times with $R^i$.

In certain embodiments of formula I, $R^h$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; or $C_{3-6}$cycloalkyl-$C_{1-6}$alkyl-sulfonyl; wherein the $C_{3-6}$cycloalkyl, and $C_{3-6}$cycloalkyl-$C_{1-6}$alkyl moieties each may be unsubstituted or substituted one or more times with $R^i$.

In certain embodiments of formula I, $R^h$ is: $C_{1-6}$alkyl-carbonyl; $C_{3-6}$cycloalkyl-carbonyl; or $C_{3-6}$cycloalkyl-$C_{1-6}$alkyl-carbonyl; wherein the $C_{3-6}$cycloalkyl, and $C_{3-6}$cycloalkyl-$C_{1-6}$alkyl moieties each may be unsubstituted or substituted one or more times with $R^i$.

In certain embodiments of formula I, $R^h$ is hydrogen.

In certain embodiments of formula I, $R^h$ is $C_{1-6}$alkyl.

In certain embodiments of formula I, $R^h$ is $C_{3-6}$cycloalkyl which may be unsubstituted or substituted one or more times with $R^i$.

In certain embodiments of formula I, $R^h$ is $C_{3-6}$cycloalkyl-$C_{1-6}$alkyl.

In certain embodiments of formula I, $R^h$ is $C_{1-6}$alkyl-carbonyl.

In certain embodiments of formula I, $R^h$ is $C_{3-6}$cycloalkyl-carbonyl.

In certain embodiments of formula I, $R^h$ is $C_{3-6}$cycloalkyl-$C_{1-6}$alkyl-carbonyl.

In certain embodiments of formula I, $R^h$ is $C_{1-6}$alkyl-sulfonyl.

In certain embodiments of formula I, $R^h$ is $C_{3-6}$cycloalkyl-sulfonyl.

In certain embodiments of formula I, $R^h$ is $C_{3-6}$cycloalkyl-$C_{1-6}$alkyl-sulfonyl.

In certain embodiments of formula I, $R^h$ is aminocarbonyl.

In certain embodiments of formula I, $R^h$ is N—$C_{1-6}$alkyl-aminocarbonyl.

In certain embodiments of formula I, $R^h$ is N,N-di-$C_{1-6}$alkyl-aminocarbonyl.

In certain embodiments of formula I, $R^h$ is aminosulfonyl.

In certain embodiments of formula I, $R^h$ is N—$C_{1-6}$alkyl-aminosulfonyl.

In certain embodiments of formula I, $R^h$ is or N,N-di-$C_{1-6}$alkyl-aminosulfonyl.

In certain embodiments of formula I, $R^h$ is $C_{3-6}$cycloalkenyl.

In certain embodiments of formula I, $R^h$ is cyano-$C_{1-6}$alkyl-carbonyl.

In certain embodiments of formula I, $R^h$ is hydroxy-$C_{1-6}$alkyl-carbonyl.

In certain embodiments of formula I, $R^h$ is $C_{1-6}$alkoxy-$C_{1-6}$alkyl-carbonyl.

In certain embodiments of formula I, $R^h$ is N-cyano-aminocarbonyl.

In certain embodiments of formula I, $R^h$ is N-cyano-N—$C_{1-6}$alkyl-aminocarbonyl.

In certain embodiments of formula I, $R^h$ is N—$C_{1-6}$alkyl-acetimidamidyl.

In certain embodiments of formula I, $R^h$ is N,N'-di-$C_{1-6}$alkyl-acetimidamidyl.

In certain embodiments of formula I, $R^h$ is N'-cyano-N—$C_{1-6}$alkyl-acetimidamidyl.

In certain embodiments of formula I, $R^h$ is N'-hydroxy-acetimidamidyl.

In certain embodiments of formula I, $R^h$ is N'—$C_{1-6}$alkoxy-acetimidamidyl.

In certain embodiments of formula I, $R^h$ is N'-hydroxy-N—$C_{1-6}$alkyl-acetimidamidyl.

In certain embodiments of formula I, $R^h$ is N'—$C_{1-6}$alkoxy-N—$C_{1-6}$alkyl-acetimidamidyl.

In certain embodiments of formula I, $R^h$ is 2-nitro-1-N—$C_{1-6}$alkylamino-vinyl.

In certain embodiments of formula I, $R^h$ is $C_{1-6}$alkyl-sulfonyl-$C_{1-6}$alkyl.

In certain embodiments of formula I, $R^h$ is N-hydroxy-aminocarbonyl.

In certain embodiments of formula I, $R^h$ is N—$C_{1-6}$alkoxy-aminocarbonyl.

In certain embodiments of formula I, $R^h$ is N-hydroxy-N—$C_{1-6}$alkyl-aminocarbonyl.

In certain embodiments of formula I, $R^h$ is N—$C_{1-6}$alkoxy-N—$C_{1-6}$alkyl-aminocarbonyl.

In certain embodiments of formula I, $R^h$ is $C_{1-6}$alkyl-sulfonylamino-$C_{1-6}$alkyl.

In certain embodiments of formula I, $R^h$ is N—($C_{1-6}$alkylsulfonyl)aminocarbonyl.

In certain embodiments of formula I, $R^h$ is N—($C_{1-6}$alkylsulfonyl)-N—$C_{1-6}$alkyl-aminocarbonyl.

In certain embodiments of formula I, $R^h$ is aminocarbonyl-$C_{1-6}$alkyl.

In certain embodiments of formula I, $R^h$ is N—$C_{1-6}$alkyl-aminocarbonyl-$C_{1-6}$alkyl In certain embodiments of formula I, $R^h$ is N,N-di-$C_{1-6}$alkyl-aminocarbonyl-$C_{1-6}$alkyl.

In certain embodiments of formula I, $R^h$ is $C_{1-6}$alkoxycarbonyl.

In certain embodiments of formula I, $R^h$ is heterocyclyl which may be unsubstituted or substituted one or more times with $R^i$.

In certain embodiments of formula I, $R^h$ is heteroaryl which may be unsubstituted or substituted one or more times with $R^i$.

In embodiments of formula I wherein $R^h$ is heteroaryl, such heteroaryl may be be pyridinyl, pyrimidinyl, pyrolyl, imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In embodiments of formula I wherein $R^h$ is heteroaryl, such heteroaryl may be be imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In certain embodiments of formula I, $R^h$ is acetyl.

In certain embodiments of formula I, $R^h$ is methanesulfonyl.

In certain embodiments of formula I, $R^h$ is cyclopropylcarbonyl.

In certain embodiments of formula I, $R^h$ and one of $R^{10}$ and $R^{11}$ together with the atoms to which they are attached form a four, five, six or seven membered aromatic, partially saturated or unsaturated ring.

In certain embodiments of formula I, $R^h$ and one of $R^{10}$ and $R^{11}$ together with the atoms to which they are attached form a four membered ring.

In certain embodiments of formula I, $R^h$ and one of $R^{10}$ and $R^{11}$ together with the atoms to which they are attached form a five membered ring.

In certain embodiments of formula I, $R^h$ and one of $R^{10}$ and $R^{11}$ together with the atoms to which they are attached form a six membered ring.

In certain embodiments of formula I, $R^h$ and one of $R^{10}$ and $R^{11}$ together with the atoms to which they are attached form a seven membered ring.

In certain embodiments of formula I, one of $R^f$ and $R^g$ and one of $R^{10}$ and $R^{11}$ together with the atoms to which they are attached form a four, five, six or seven membered aromatic, partially saturated or unsaturated ring.

In certain embodiments of formula I, one of $R^f$ and $R^g$ and one of $R^{10}$ and $R^{11}$ together with the atoms to which they are attached form a five or six membered aromatic ring.

In certain embodiments of formula I, one of $R^f$ and $R^g$ and one of $R^{10}$ and $R^{11}$ together with the atoms to which they are attached form a five membered aromatic ring.

In certain embodiments of formula I, one of $R^f$ and $R^g$ and one of $R^{10}$ and $R^{11}$ together with the atoms to which they are attached form a six membered aromatic ring.

In certain embodiments of formula I, one of $R^f$ and $R^g$ and one of $R^{10}$ and $R^{11}$ together with the atoms to which they are attached form a five or six membered saturated ring.

In certain embodiments of formula I, one of $R^f$ and $R^g$ and one of $R^{10}$ and $R^{11}$ together with the atoms to which they are attached form a five membered saturated ring.

In certain embodiments of formula I, one of $R^f$ and $R^g$ and one of $R^{10}$ and $R^{11}$ together with the atoms to which they are attached form a six membered saturated ring.

In certain embodiments of formula I, one of $R^f$ and $R^g$ and one of $R^{10}$ and $R^{11}$ together with the atoms to which they are attached form a four membered ring.

In certain embodiments of formula I, one of $R^f$ and $R^g$ and one of $R^{10}$ and $R^{11}$ together with the atoms to which they are attached form a five membered ring.

In certain embodiments of formula I, one of $R^f$ and $R^g$ and one of $R^{10}$ and $R^{11}$ together with the atoms to which they are attached form a six membered ring.

In certain embodiments of formula I, one of $R^f$ and $R^g$ and one of $R^{10}$ and $R^{11}$ together with the atoms to which they are attached form a seven membered ring.

In certain embodiments of formula I, $R^i$ is: $C_{1-6}$alkyl; halo; oxo; hydroxy; acetyl; or $C_{1-6}$alkoxy.

In certain embodiments of formula I, $R^i$ is $C_{1-6}$alky.

In certain embodiments of formula I, $R^i$ is halo.

In certain embodiments of formula I, $R^i$ is $C_{1-6}$alkoxy.

In certain embodiments of formula I, $R^i$ is halo-$C_{1-6}$alkyl.

In certain embodiments of formula I, $R^i$ is oxo.

In certain embodiments of formula I, $R^i$ is hydroxy.

In certain embodiments of formula I, $R^i$ is acetyl.

In certain embodiments of formula I, $R^i$ is $C_{1-6}$alkylcarbonyl.

In certain embodiments of formula I, $R^i$ is amino-carbonyl.

In certain embodiments of formula I, $R^i$ is hydroxy-$C_{1-6}$alkyl.

In certain embodiments of formula I, $R^i$ is cyano.

In certain embodiments of formula I, $R^i$ is halo-$C_{1-6}$alkyl.

In certain embodiments of formula I, $R^i$ is $C_{3-6}$cycloalkyl.

In certain embodiments of formula I, $R^j$ and $R^k$ each independent is: hydrogen; or methyl.

In certain embodiments of formula I, $R^j$ is hydrogen.

In certain embodiments of formula I, $R^k$ is hydrogen.

In certain embodiments of formula I, $R^m$ is: $C_{1-6}$alkyl; hydroxy; halo; hydroxy-$C_{1-6}$alkyl; $C_{1-6}$alkylsulfonyl-$C_{1-6}$alkyl; cyano; aminocarbonyloxy; $C_{1-6}$alkoxycarbonyl; carboxy; aminocarbonyl; N—$C_{1-6}$alkylaminocarbonyl; or N,N-di-$C_{1-6}$alkylaminocarbonyl.

In certain embodiments of formula I, $R^m$ is $C_{1-6}$alkyl.

In certain embodiments of formula I, $R^m$ is hydroxy.

In certain embodiments of formula I, $R^m$ is halo;

In certain embodiments of formula I, $R^m$ is amino.

In certain embodiments of formula I, $R^m$ is N—$C_{1-6}$alkylamino.

In certain embodiments of formula I, $R^m$ is N,N-di-$C_{1-6}$alkylamino.

In certain embodiments of formula I, $R^m$ is hydroxy-$C_{1-6}$alkyl.

In certain embodiments of formula I, $R^m$ is $C_{1-6}$alkylsulfonyl-$C_{1-6}$alkyl.

In certain embodiments of formula I, $R^m$ is cyano.

In certain embodiments of formula I, $R^m$ is N—($C_{1-6}$alkylsulfonyl)-amino-$C_{1-6}$alkyl.

In certain embodiments of formula I, $R^m$ is cyano-$C_{1-6}$alkyl.

In certain embodiments of formula I, $R^m$ is cyano-$C_{2-6}$alkenyl.

In certain embodiments of formula I, $R^m$ is $C_{1-6}$alkoxy-$C_{1-6}$alkyl.

In certain embodiments of formula I, $R^m$ is $C_{1-6}$alkoxy-$C_{1-6}$alkoxy-$C_{1-6}$alkyl.

In certain embodiments of formula I, $R^m$ is hydroxy-$C_{1-6}$alkoxy.

In certain embodiments of formula I, $R^m$ is hydroxy-$C_{1-6}$alkoxy-$C_{1-6}$alkyl.

In certain embodiments of formula I, $R^m$ is N-hydroxycarboxamidinyl.

In certain embodiments of formula I, $R^m$ is N-(hydroxy-$C_{1-6}$alkyl)-amino.

In certain embodiments of formula I, $R^m$ is N-(hydroxy-$C_{1-6}$alkyl)-N—$C_{1-6}$alkyl-amino.

In certain embodiments of formula I, $R^m$ is N—($C_{1-6}$alkoxy—$C_{1-6}$alkyl)-amino.

In certain embodiments of formula I, $R^m$ is N—($C_{1-6}$alkoxy—$C_{1-6}$alkyl)-N—$C_{1-6}$alkyl-amino.

In certain embodiments of formula I, $R^m$ is carboxy.

In certain embodiments of formula I, $R^m$ is carboxy-$C_{1-6}$alkyl.

In certain embodiments of formula I, $R^m$ is $C_{1-6}$alkylcarbonyl.

In certain embodiments of formula I, $R^m$ is $C_{1-6}$alkylcarbonyl-$C_{1-6}$alkyl.

In certain embodiments of formula I, $R^m$ is hydroxy-$C_{1-6}$alkyl-amino.

In certain embodiments of formula I, $R^m$ is —(CHR$^t$)$_u$—C(O)—NR$^p$R$^q$;

In certain embodiments of formula I, $R^m$ is —(CHR$^s$)$_u$—O—(CHR$^s$)$_v$—C(O)—NR$^p$R$^q$;

In certain embodiments of formula I, $R^m$ is —(CHR$^s$)$_u$—NR$^n$—(CHR$^s$)$_v$—C(O)—NR$^p$R$^q$;

In certain embodiments of formula I, $R^m$ is —(CHR$^t$)$_u$—C(O)—R$^u$;

In certain embodiments of formula I, $R^m$ is —(CHR$^s$)$_u$—O—(CHR$^s$)$_v$—C(O)—R$^u$; or In certain embodiments of formula I, $R^m$ is —(CHR$^s$)$_u$—NR$^n$—(CHR$^s$)$_v$—C(O)—R$^u$;

In certain embodiments of formula I, u is 0.
In certain embodiments of formula I, u is 1.
In certain embodiments of formula I, u is 0 or 1.
In certain embodiments of formula I, u is 2.
In certain embodiments of formula I, v is 0.
In certain embodiments of formula I, v is 1.
In certain embodiments of formula I, v is 0 or 1.
In certain embodiments of formula I, v is 2.
In certain embodiments of formula I, $R^n$ is hydrogen.
In certain embodiments of formula I, $R^n$ is $C_{1-6}$alkyl.
In certain embodiments of formula I, $R^p$ is hydrogen.
In certain embodiments of formula I, $R^p$ is $C_{1-6}$alkyl.
In certain embodiments of formula I, $R^q$ is hydrogen.
In certain embodiments of formula I, $R^q$ is $C_{1-6}$alkyl.
In certain embodiments of formula I, $R^q$ is hydroxy-$C_{1-6}$alkyl.
In certain embodiments of formula I, $R^q$ is N—($C_{1-6}$alkylcarbonylamino)-$C_{1-6}$alkyl.
In certain embodiments of formula I, $R^q$ is amino-$C_{1-6}$alkyl.
In certain embodiments of formula I, $R^q$ is N—$C_{1-6}$alkylamino-$C_{1-6}$alkyl.
In certain embodiments of formula I, $R^q$ is N,N-di-$C_{1-6}$alkylamino-$C_{1-6}$alkyl.

In certain embodiments of formula I, $R^q$ is N,N-di-$C_{1-6}$alkylaminocarbonyl-$C_{1-6}$alkyl.

In certain embodiments of formula I, $R^q$ is cyano-$C_{1-6}$alkyl.

In certain embodiments of formula I, $R^q$ is carboxy-$C_{1-6}$alkyl.

In certain embodiments of formula I, $R^q$ is aminocarbonyl-$C_{1-6}$alkyl.

In certain embodiments of formula I, $R^q$ is N—$C_{1-6}$alkylaminocarbonyl-$C_{1-6}$alkyl.

In certain embodiments of formula I, $R^q$ is N,N-di-$C_{1-6}$alkyl aminocarbonyl-$C_{1-6}$alkyl.

In certain embodiments of formula I, $R^q$ is $C_{1-6}$alkylsulfonyl-$C_{1-6}$alkyl.

In certain embodiments of formula I, $R^q$ is $C_{1-6}$alkoxy-$C_{1-6}$alkyl.

In certain embodiments of formula I, $R^s$ is hydrogen.
In certain embodiments of formula I, $R^s$ is $C_{1-6}$alkyl.
In certain embodiments of formula I, $R^t$ is hydrogen;
In certain embodiments of formula I, $R^t$ is $C_{1-6}$alkyl.
In certain embodiments of formula I, $R^t$ is halo.
In certain embodiments of formula I, $R^t$ is hydroxyl.
In certain embodiments of formula I, $R^u$ is $C_{1-6}$alkyl.
In certain embodiments of formula I, $R^u$ is $C_{1-6}$alkoxy.
In certain embodiments of formula I, $R^u$ is hydroxyl.
In certain embodiments of formula I, $R^u$ is hydroxy-$C_{1-6}$alkyl.

In certain embodiments of formula I, $R^m$ is selected from:

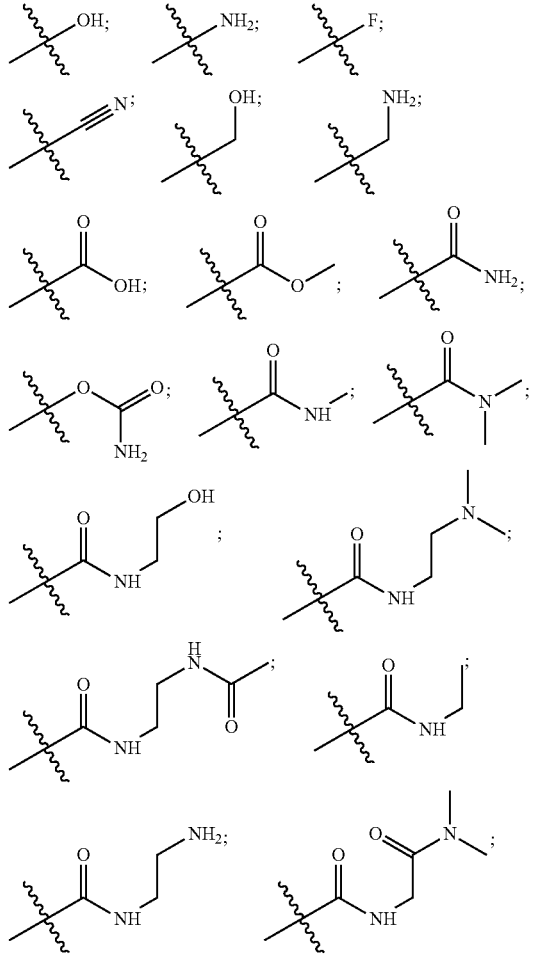

-continued
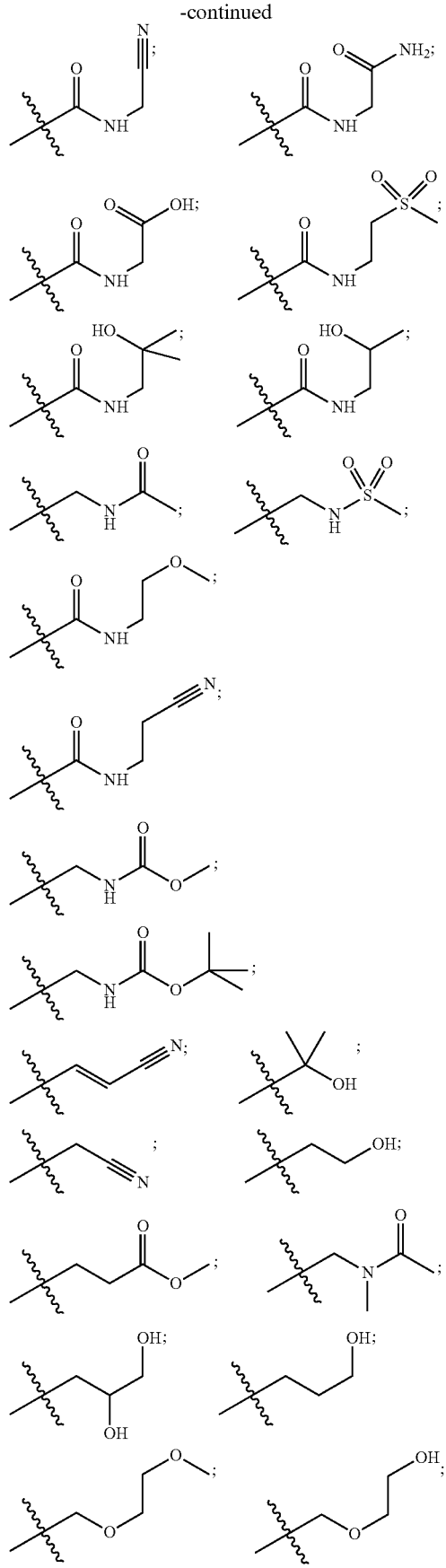
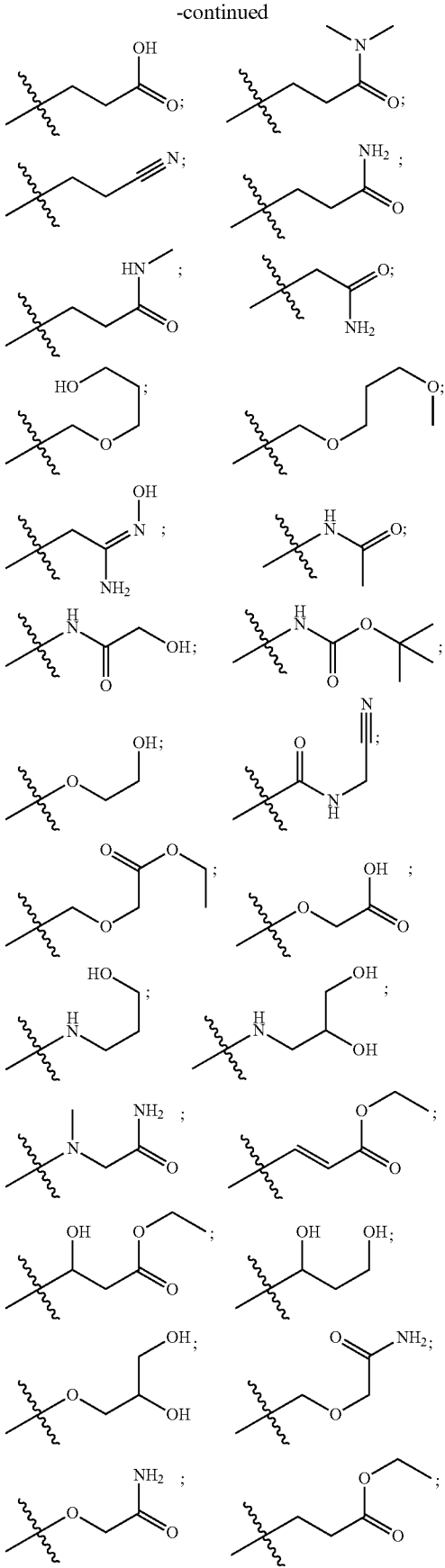

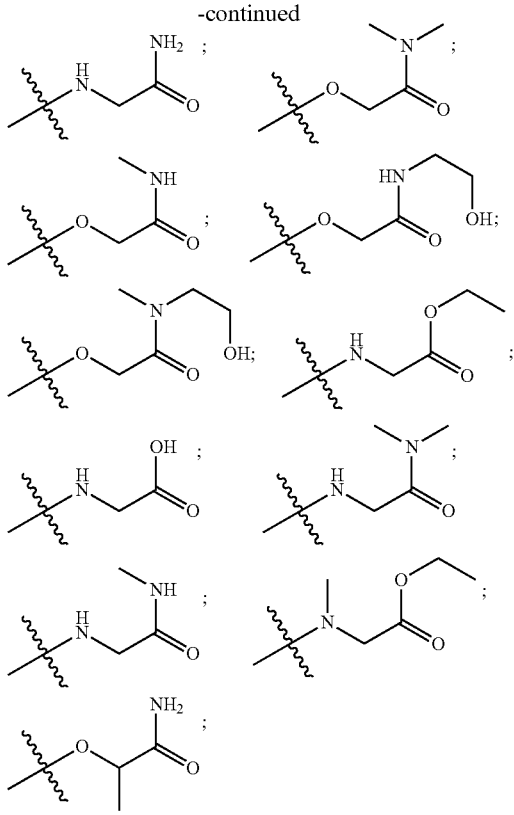

In certain embodiments, the subject compounds may be of formula II:

II wherein s is from 0 to 3 and $R^e$ is: $C_{1-6}$alkyl; $C_{1-6}$alkoxy; hydroxy; halo; hydroxy-$C_{1-6}$alkyl; or cyano; and p, q, r, A, Y, Z, $R^1$, $R^2$, $R^3$, $R^9$, $R^{10}$, $R^{11}$, and $R^m$ are as defined herein.

In certain embodiments, the subject compounds may be of formula III:

III wherein p, q, r, s, Y, $R^1$, $R^2$, $R^3$, $R^9$, $R^{10}$, $R^{11}$, $R^e$ and $R^m$ are as defined herein.

In certain embodiments, the subject compounds may be of formula IV:

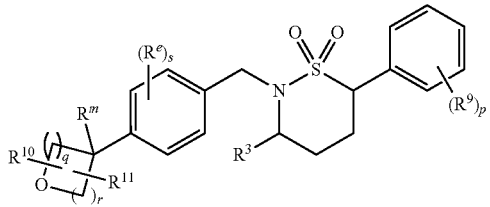

IV wherein p, q, r, s, $R^3$, $R^9$, $R^{10}$, $R^{11}$, $R^e$ and $R^m$ are as defined herein.

In certain embodiments, the subject compounds may be of formula V:

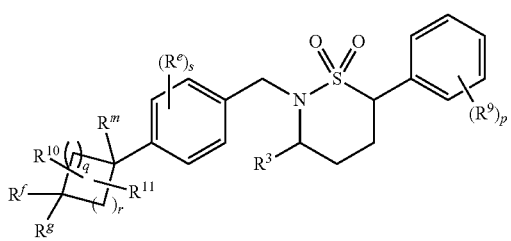

V wherein p, q, r, s, $R^3$, $R^9$, $R^{10}$, $R^{11}$, $R^e$, $R^f$, $R^g$, and $R^m$ are as defined herein.

In certain embodiments, the subject compounds may be of formula VI:

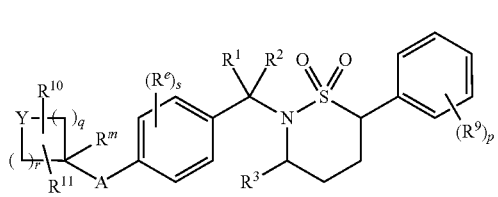

VI wherein p, q, r, s, $R^3$, $R^9$, $R^{10}$, $R^u$, $R^e$, $R^h$ and $R^m$ are as defined herein.

In certain embodiments, the subject compounds may be of formula VII:

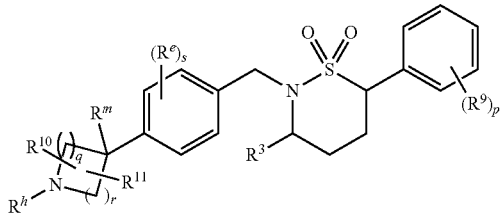

VII wherein p, q, r, s, $R^3$, $R^9$, $R^{10}$, $R^{11}$, $R^e$ and $R^m$ are as defined herein.

In certain embodiments, the subject compounds may be of formula VIII:

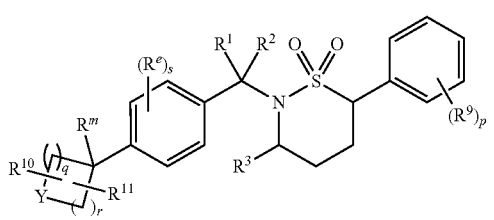
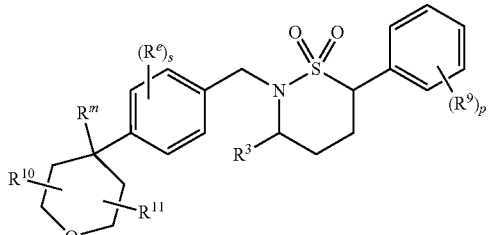

VIII

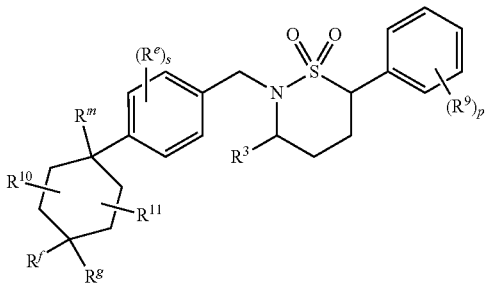

wherein p, q, r, s, $R^3$, $R^9$, $R^{10}$, $R^{11}$, $R^e$, $R^f$, $R^g$, and $R^m$ are as defined herein.

In certain embodiments, the subject compounds may be of formula IX:

IX

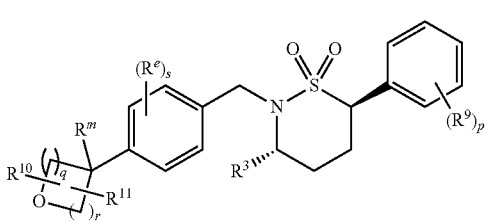

wherein p, q, r, s, $R^3$, $R^9$, $R^{10}$, $R^{11}$, $R^e$ and $R^m$ are as defined herein.

In certain embodiments, the subject compounds may be of formula X:

X

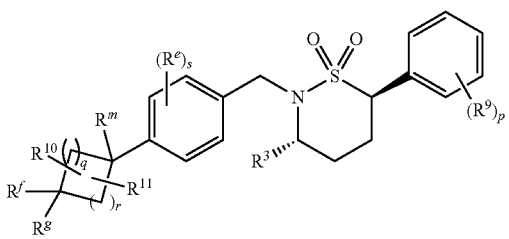

wherein p, q, r, s, $R^3$, $R^9$, $R^{10}$, $R^{11}$, $R^e$, $R^f$, $R^g$, and $R^m$ are as defined herein.

In certain embodiments, the subject compounds may be of formula XI:

VI

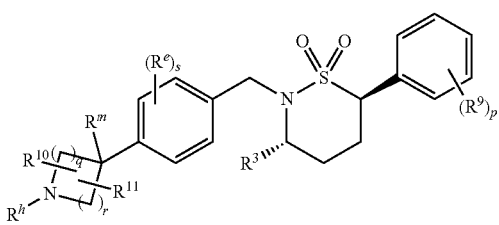

wherein p, q, r, s, $R^3$, $R^9$, $R^{10}$, $R^{11}$, $R^e$, $R^h$ and $R^m$ are as defined herein.

In certain embodiments, the subject compounds may be of formula XII:

XII

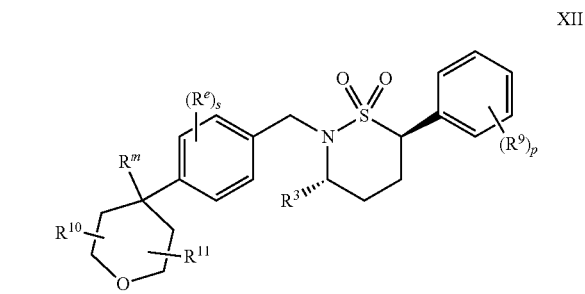

wherein p, q, r, s, $R^3$, $R^9$, $R^{10}$, $R^{11}$, $R^e$ and $R^m$ are as defined herein.

In certain embodiments, the subject compounds may be of formula XIII:

XIII

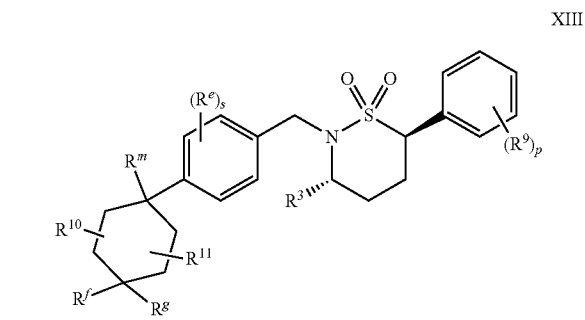

wherein p, q, r, s, $R^3$, $R^9$, $R^{10}$, $R^{11}$, $R^e$, $R^f$, $R^g$, and $R^m$ are as defined herein.

Methods

The invention also provides a method for treating a disease or condition mediated by or otherwise associated with the RORc receptor, the method comprising administering to a subject in need thereof an effective amount of a compound of the invention.

The disease may be arthritis such as rheumatoid arthritis or osteoarthritis.

The disease may be asthma or COPD.

The disease may be psoriasis, lupus, Sjogren's disease, irritable bowel disease or idiopathic pulmonary fibrosis.

The disease may be muscular sclerosis.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I, wherein LG is a leaving group such as halo, sulfonate, or the like, and m, n, p, q, A, $X^1$, $X^2$, $X^3$, $X^4$, Y, $R^1$, $R^2$, $R^3$, $R^4$, $R^5$, $R^6$, $R^7$, $R^8$, $R^9$, $R^{10}$, $R^b$ and $R^c$ are as defined herein.

SCHEME A

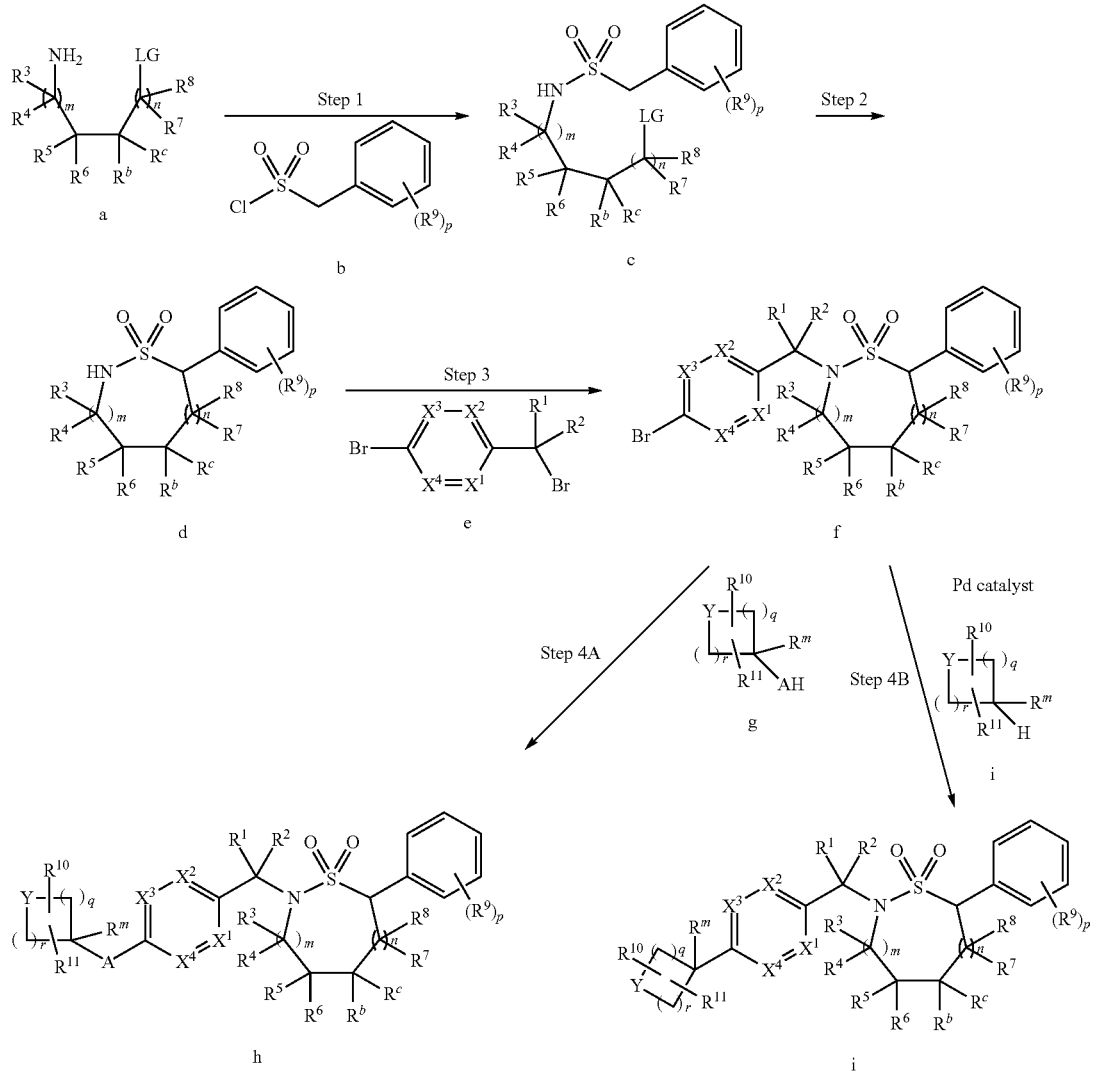

In step 1 of Scheme A, alkyl amine a is reacted with benzyl sulfonyl chloride b to form sulfonamide compound c. The reaction of step 1 may be carried out in a polar aprotic solvent such as THF or methylene chloride, and in the presence of a tertiary amine base or weak base such as potassium carbonate. The leaving group of compound a may be bromo in certain embodiments. Similarly, the chloro group of compound b may in certain embodiments be replaced by other halo or leaving group.

A cyclization reaction is carried out in step 2 to afford thiazinane compound d. The cyclization may be achieved in the presence of a strong base such as an alkyl lithium reagent, using polar aprotic solvent under anhydrous conditions.

In step 3, thiazinane compound c is reacted with aryalkyl halide compound e to yield aralkyl thiazinane f. The reaction of step 3 may be carried out in the presence of a strong base such as sodium hydride under anhydrous polar aprotic solvent conditions. The bromo groups of compound e may be replaced by other suitable leaving groups used in the art.

Thiazinane compound f may be treated with reagent g in step 4A to provide sultam compound h, which is a compound of formula I in accordance with the invention. In embodiments wherein A is oxygen such that reagent g is a cyclic alcohol, the reaction of step 4A may utilize a copper catalyst with hydrophobic solvent, in the presence of cesium carbonate or like base.

Alternatively, step 4B may be carried out wherein Thiazinane compound f undergoes an alkylation reaction with compound i to afford sultam compound j, which is a compound of formula I in accordance with the invention. The reaction of step may utilize a suitable palladium catalyst under Buchwald reaction conditions.

Scheme B below shows another synthetic procedure usable to prepare specific compounds of formula I, wherein TBS is tri-(tert-butyl)-silyl, and m, n, p, q, A, $X^1$, $X^2$, $X^3$, $X^4$, Y, $R^1$, $R^2$, $R^3$, $R^4$, $R^5$, $R^6$, $R^9$ and $R^{10}$ are as defined herein.

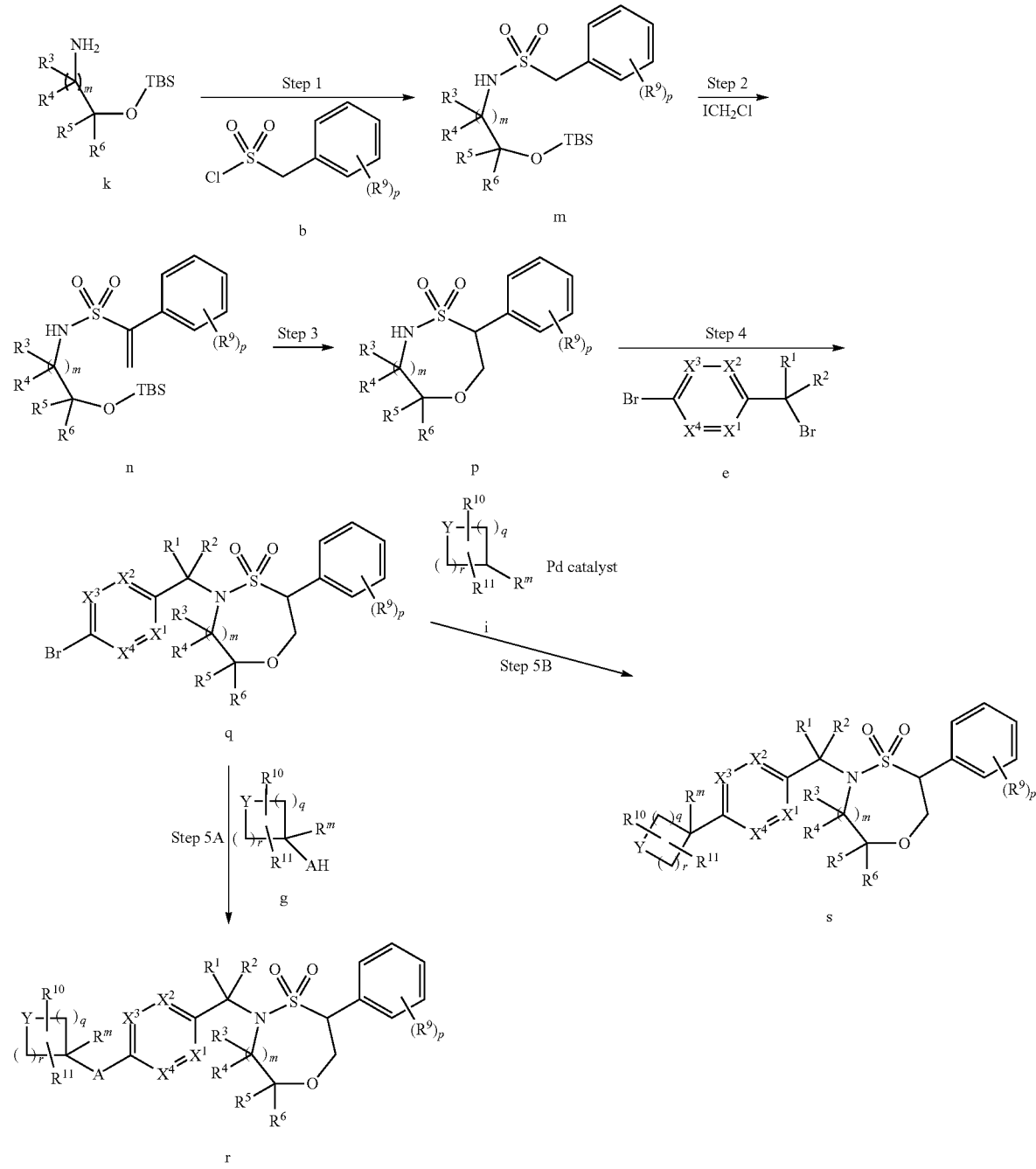

SCHEME B

In step 1 of Scheme B, tri-(tert-butyl)-slilyloxy amine k is reacted with benzyl sulfonyl chloride b, as described above with reference to Scheme A, to form sulfonamide compound m. In certain embodiments the tri-(tert-butyl)-slilyloxy group may be replaced with other leaving groups.

In step 2, sulfonamide compound m is reacted with iodochloromethane to provide an alkenylsulfonamide compound n. This reaction may be achieved in the presence of a strong base such as an alkyl lithium reagent, using polar aprotic solvent such as THF under anhydrous conditions. In certain embodiments iodochloromethane may be replaced with other methylene reagents.

In step 3, a cyclization reaction is affected to provide oxathiazepane compound p. The cyclization may be carried out in the presence of an amine base under polar aprotic solvent conditions.

In step 4, oxathiazepane compound p is reacted with aryalkyl halide compound e to yield aralkyl oxathiazepane compound q, in the manner described above with reference to Scheme A.

Steps 5A or 5B may then be carried out by reaction of oxathiazepane compound q with reagents g and i respectively, in the manner described above with reference to Scheme A, to afford sultam compounds r and s respectively, which are compounds of formula I in accordance with the invention.

Many variations on the procedures of Scheme A and Scheme B are possible and will suggest themselves to those skilled in the art. Specific details for producing compounds of the invention are described in the Examples below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of immune disorders generally. The compounds may be used for treatment of arthritis, including rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

The compounds may be used for treatment of respiratory disorders such as chronic obstructive pulmonary disease (COPD), asthma, bronchospasm, and the like.

The compounds may be used for treatment of gastrointestinal disorder ("GI disorder") such as Irritable Bowel Syndrome (IBS), Inflammatory Bowel Disease (IBD), biliary colic and other biliary disorders, renal colic, diarrhea-dominant IBS, pain associated with GI distension, and the like.

The compounds may be used for treatment of pain conditions such as inflammatory pain; arthritic pain, surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

LIST OF ABBREVIATIONS

AcOH Acetic acid
AIBN 2,2'-Azobis(2-methylpropionitrile)
Atm. Atmosphere
(BOC)$_2$O di-tert-Butyl dicarbonate
DCM Dichloromethane/Methylene chloride
DIAD Diisopropyl azodicarboxylate
DIPEA Diisopropylethylamine
DMAP 4-Dimethylaminopyridine
DME 1,2-Dimethoxyethane
DMF N,N-Dimethylformamide
DMSO Dimethyl sulfoxide
DPPF 1,1'-Bis(diphenylphosphino)ferrocene
Et$_2$O Diethyl ether
EtOH Ethanol/Ethyl alcohol
EtOAc Ethyl acetate
HATU 2-(1H-7-Azabenzotriazol-1-yl)-1,1,3,3-tetramethyl uronium hexafluorophosphate Methanaminium
HBTU O-Benzotriazol-1-yl-N,N,N',N'-tetramethyluronium hexafluorophosphate
HOBT 1-Hydroxybenzotriazole
HPLC High pressure liquid chromatography
RP HPLC Reverse phase high pressure liquid chromatography
i-PrOH Isopropanol/isopropyl alcohol
LCMS Liquid Chromatograph/Mass Spectroscopy
MDAP Mass directed auto purification
MeOH Methanol/Methyl alcohol
MW Microwaves
NBS N-Bromosuccinimide
NMP 1-Methyl-2-pyrrolidinone
PSI Pound per square inch
r.t. Room temperature
TBDMS tert-Butyldimethylsilyl
TFA Trifluoroacetic acid
THF Tetrahydrofuran
TLC Thin layer chromatography Preparations 1 and 2: (3R)-3-Aminobutan-1-ol and (3S)-3-Aminobutan-1-ol

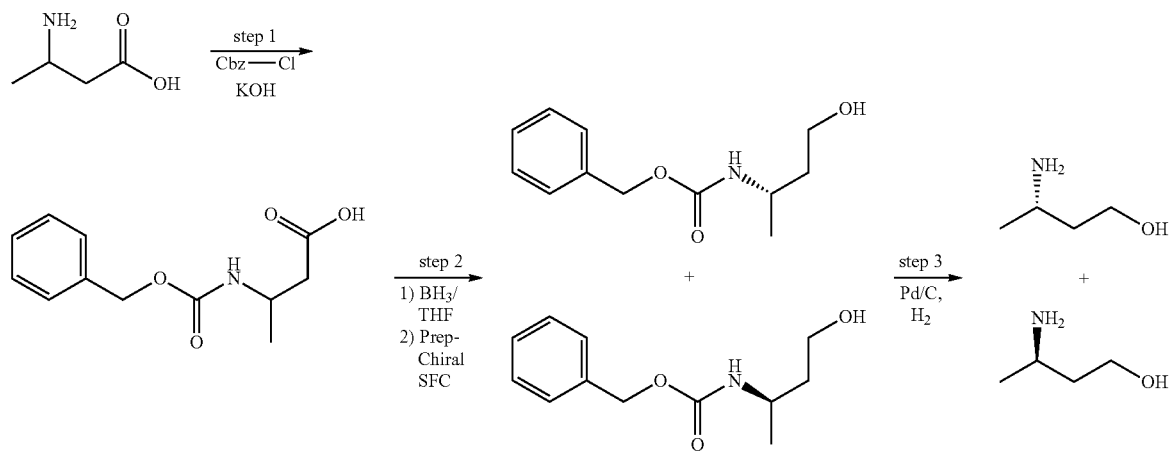

Step 1 3-[[(Benzyloxy)carbonyl]amino]butanoic acid

Into a 2000-mL 4-necked round-bottom flask was placed a solution of 3-aminobutanoic acid (100 g, 969.75 mmol, 1.00 equiv) in water (1000 mL), followed by the addition of potassium hydroxide (136 g, 2.42 mol, 2.50 equiv) in several batches. To this was added benzyl chloroformate (247 g, 1.45 mol, 1.50 equiv) dropwise with stirring at 0-5° C. The resulting solution was stirred at 25° C. for 5 h. The reaction progress was monitored by LCMS. The resulting solution was extracted with dichloromethane and the aqueous layers were combined. The pH value of the water phase was adjusted to 3 with hydrogen chloride (2 mol/L). The precipitates were collected by filtration and dried to afford 102 g (44%) of 3-[[(benzyloxy)carbonyl]amino]butanoic acid as a white solid.

Step 2: Benzyl N-[(2S)-4-hydroxybutan-2-yl]carbamate and Benzyl N-[(2R)-4-hydroxybutan-2-yl] carbamate Into a 2000-mL 3-necked round-bottom flask purged and maintained with an inert atmosphere of nitrogen was placed a solution of 3-[[(benzyloxy)carbonyl]amino]butanoic acid (102 g, 429.92 mmol, 1.00 equiv) in THF (300 mL), followed by the addition of BH$_3$/THF (1N) (645 mL, 1.50 equiv) dropwise with stirring at 0-5° C. The resulting solution was stirred at 40° C. for 2 h, quenched by the addition of 200 mL of methanol and concentrated under vacuum. The residue was purified on a silica gel column eluting with ethyl acetate:petroleum ether (1:2). The crude product (70 g) was purified by Prep-SFC with the following conditions (prep SFC): Column, Phenomenex Lux 5 u Cellulose-4, 2.12*25.5 um; mobile phase, $CO_2$ (85%), ethanol (15%); Detector, UV 254 nm. This resulted in 30 g (31.5%) of benzyl N-[(2R)-4-hydroxybutan-2-yl]carbamate as an off-white solid and 30 g (31.5%) of benzyl N-[(2S)-4-hydroxybutan-2-yl]carbamate as an off-white solid.

Step 3: (3R)-3-Aminobutan-1-ol and (3S)-3-Aminobutan-1-ol

Into a 1000-mL round-bottom flask was placed a solution of benzyl N-[(2S)-4-hydroxybutan-2-yl]carbamate (30 g, 134.4 mmol, 1.00 equiv) in methanol (500 mL) and palladium carbon (3 g, 0.10 equiv). The resulting solution was stirred at 25° C. for 12 h under an atmosphere of hydrogen. The solids were filtered out and the filtrate was concentrated under vacuum to afford 11.7 g (92%) of (3S)-3-aminobutan-1-ol as an oil. $^1$H NMR (300 MHz, DMSO, ppm): δ 4.48 (3H, s), 3.47 (2H, s), 2.96 (1H, s), 1.47-1.41 (2H, q), 1.02-0.99 (3H, d); LCMS (ESI), m/z, 90 [M+H]+; measured $[\alpha]_D^{20.2}$+11.65° (C=1.22 g/100 mL in EtOH), lit. $[\alpha]_D^{20}$+16.3° (c=4.5 in EtOH) (*J. Org. Chem.* 1996, 61, 2293-2304.).

Using the above procedure, 12.0 g 12 g (94%) of (3R)-3-aminobutan-1-ol was isolated as an oil. $^1$H NMR (300 MHz, DMSO, ppm): δ 4.48 (3H, s), 3.47 (2H, s), 2.96 (1H, s), 1.47-1.41 (2H, q), 1.02-0.99 (3H, d); LCMS (ESI), m/z, 90 [M+H]+; measured $[\alpha]_D^{20.2}$−11.1° (C=0.32 g/100 mL in EtOH), lit. $[\alpha]_D^{25}$−25° (c=1.25 in EtOH) (*Tetrahedron: Asymmetry* 1999, 10, 2213-2224.).

Preparation 3: (R)—N-(4-Chlorobutan-2-yl)-1-phenylmethanesulfonamide

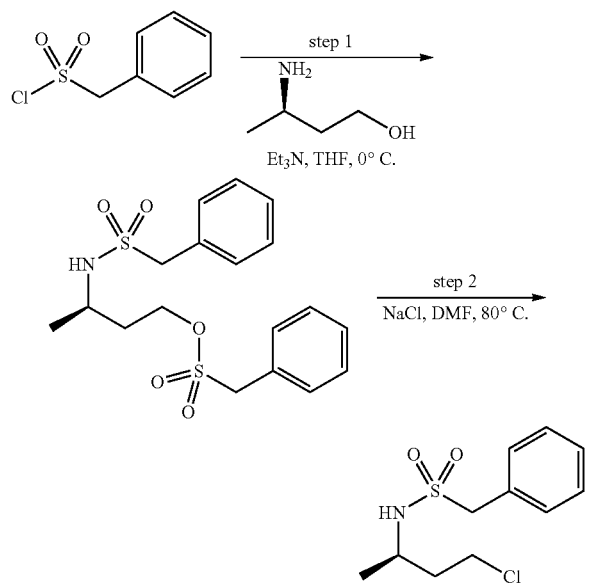

Step 1: (R)-3-(Phenylmethylsulfonamido)butyl phenylmethanesulfonate

To a solution of (3R)-3-aminobutan-1-ol (1.0 g, 11.2 mmol) and triethylamine (3.3 mL, 23.6 mmol) in tetrahydrofuran (37 mL) at 0° C. was slowly added phenylmethanesulfonyl chloride (4.49 g, 23.6 mmol) and the reaction was stirred at room temperature for 16 hours. MTBE (100 mL) was then added and the Et$_3$N HCl salt was removed by filtration. The filtrate was then concentrated to give crude (R)-3-(phenylmethylsulfonamido)butyl phenylmethanesulfonate which was used without purification. LCMS (ESI), m/z, 398 [M+H]+.

Step 2: (R)—N-(4-Chlorobutan-2-yl)-1-phenylmethanesulfonamide

To the crude (R)-3-(phenylmethylsulfonamido)butyl phenylmethanesulfonate (23.6 mmol) was added sodium chloride (984 mg, 16.8 mmol) and dimethylformamide (37 mL) and the reaction was stirred at 80° C. for 16 hours. The reaction was then diluted with EtOAc, washed with water (×2) and brine, dried with MgSO$_4$, concentrated and purified by silica gel column chromatography (0-50% Acetone in Heptane, 216 nM) to give (R)—N-(4-chlorobutan-2-yl)-1-phenylmethanesulfonamide (1.71 g, 6.53 mmol, 58% yield over 2 steps). LCMS (ESI), m/z, 261 [M+H]+.

Additional compounds made using the above procedure are shown in Table 1.

TABLE 1

| | Structure | Name | LCMS (ESI), m/z, [M + H]+ |
|---|---|---|---|
| 4 | 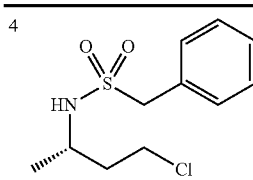 | (S)-N-(4-chlorobutan-2-yl)-1-phenylmethanesulfonamide | 261 |
| 5 | 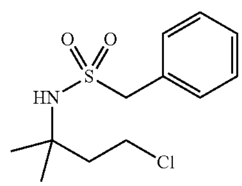 [SMILES: CC(C)(CCCl)NS(=O)(=O)Cc1ccccc1] | N-(4-chloro-2-methylbutan-2-yl)-1-phenylmethanesulfonamide | 275 |
| 6 | 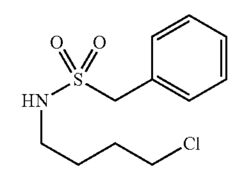 [SMILES: O=S(=O)(Cc1ccccc1)NCCCCCl] | N-(4-chlorobutyl)-1-phenylmethanesulfonamide | 261 |

Preparation 7: N-(2-bromoethyl)(phenyl)methanesulfonamide

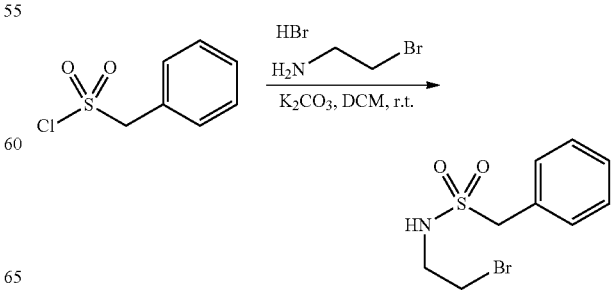

K$_2$CO$_3$ (8.7 g, 62 mmol) was added into a mixture of phenylmethanesulfonyl chloride (6 g, 31 mmol) and 2-bromoethanamine hydrobromide (6.4 g, 31 mmol) in DCM (100 mL) at 0° C. And the resulting mixture was stirred at r.t. for 4 hours and left standing overnight. Upon the completion of reaction, water (100 mL) was added in and DCM phase was separated. The aqueous phase was extracted with DCM. The combined organic phase was dried over Na$_2$SO$_4$, filtered and concentrated in vacuo to provide a crude which was separated with column chromatography (silica gel with 200-300 mesh, 0 to 50% of EtOAc in petroleum ether) to provide compound N-(2-bromoethyl)(phenyl)methanesulfonamide (7.0 g, 80%) as a pale yellow solid. $^1$H NMR (300 MHz, CDCl$_3$) δ 7.40 (m, 5H), 4.58 (m, 1H), 4.29 (s, 2H), 3.34-3.29 (m, 4H). LCMS (ESI), 300, 302 [M+Na]$^+$, Br pattern found.

Preparation 8
N-(2-bromoethyl)(4-fluorophenyl)methanesulfonamide

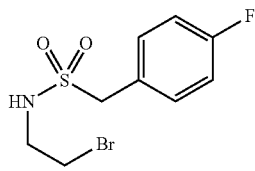 [SMILES: O=S(=O)(Cc1ccc(F)cc1)NCCBr]

N-(2-bromoethyl)(4-fluorophenyl)methanesulfonamide was also made using the above procedure, replacing phenylmethanesulfonyl chloride with 4-fluoro-phenylmethanesulfonyl chloride. $^1$H NMR (300 MHz, CDCl$_3$) δ 7.43-7.38 (m, 2H), 7.13-7.07 (m, 2H), 4.62 (br s, 1H), 4.26 (s, 2H), 3.41-3.32 (m, 4H).

Preparation 9:
N-(3-bromopropyl)(phenyl)methanesulfonamide

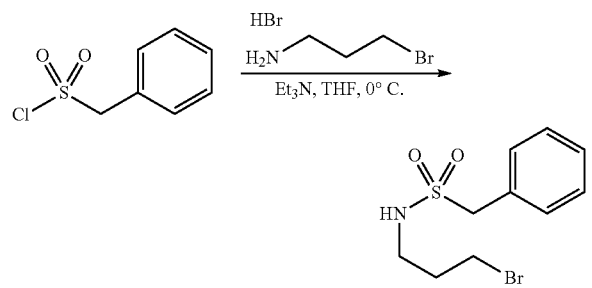

A solution of phenylmethanesulfonyl chloride (2.19 g, 10 mmol) was added into a suspension of 3-bromopropan-1-amine hydrobromide (2.19 g, 10 mmol) and Et$_3$N (2.02 g, 20 mmol) in THF (50 mL) at 0° C. The mixture was stirred at 0° C. for 5 min. TLC confirmed the completion of reaction. Solid was filtered out with suction, and the filtrate was concentrated to provide compound N-(3-bromopropyl)(phenyl)methanesulfonamide (2.7 g, quant.) as a pale yellow solid which was used in the next step without further purification. $^1$H NMR (300 MHz, CDCl$_3$) δ 7.40 (m, 5H), 4.48 (m, 1H), 4.27 (s, 2H), 3.41 (t, J=6.6 Hz, 2H), 3.16 (q, 2H), 2.01 (m, 2H). LCMS (ESI), m/z, 314 and 316 [M+Na]$^+$, Br pattern found.

Preparation 10: N-(3-bromopropyl)(4-fluorophenyl)methanesulfonamide

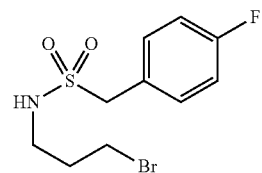 [SMILES: O=S(=O)(Cc1ccc(F)cc1)NCCCBr]

N-(3-bromopropyl)(4-fluorophenyl)methanesulfonamide was prepared using the above procedure. $^1$H NMR (300 MHz, CDCl$_3$) δ 7.42-7.37 (m, 2H), 7.13-7.07 (m, 2H), 4.26 (m, 1H), 4.24 (s, 2H), 3.46-3.42 (m, 2H), 3.20-3.16 (m, 2H), 2.05-2.00 (m, 2H).

Preparation 11: 6-Phenyl-1,2-thiazinane 1,1-dioxide

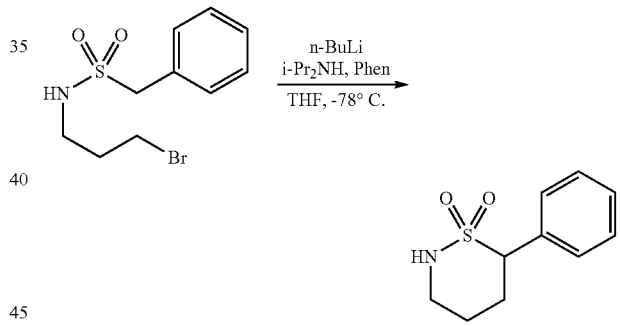

To a solution of N-(3-bromopropyl)-1-phenylmethanesulfonamide (2.3 g, 7.9 mmol), diisopropylamine (0.28 mL, 2.0 mmol) and 1,10-phenanthroline (3.6 mg, 0.02 mmol) in tetrahydrofuran (26 mL) at −78° C. was added n-BuLi (6.8 mL, 2.5M in hexanes) dropwise and the reaction was stirred for 16 hours. Saturated NH$_4$Cl was then added and the reaction was diluted with EtOAc, washed with water and brine, dried with MgSO$_4$, concentrated and purified by silica gel column chromatography (0-50% EtOAc/heptane) to 6-Phenyl-1,2-thiazinane 1,1-dioxide (1.3 g, 80% yield). $^1$H NMR (300 MHz, DMSO-d$_6$) δ 7.40-7.35 (m, 5H), 6.98 (m, 1H), 4.12 (dd, 1H), 3.26-3.20 (m, 2H), 2.40-2.30 (m, 1H), 2.16-2.12 (m, 1H), 1.77-1.65 (m, 2H). LCMS (ESI), m/z, 234 [M+Na]$^+$. (Reference: D. Askin, et al. *Org. Lett.* 2003, 4175.)

Additional compounds made using the above procedure are shown in Table 2.

TABLE 2
| | Structure | Name | LCMS (ESI), m/z, [M + H]+ |
|---|---|---|---|
| 12 | 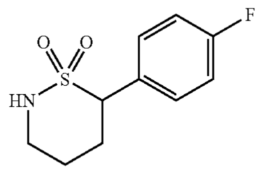 [SMILES: O=S1(=O)NCCCC1c1ccc(F)cc1] | 6-(4-fluorophenyl)-1,2-thiazinane 1,1-dioxide | 230 |
| 13 | 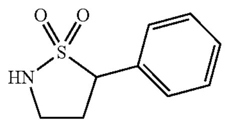 [SMILES: O=S1(=O)NCCC1c1ccccc1] | 5-phenylisothiazolidine 1,1-dioxide | 198 |
| 14 | 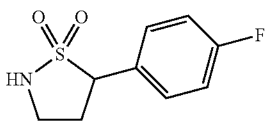 [SMILES: O=S1(=O)NCCC1c1ccc(F)cc1] | 5-(4-fluorophenyl)isothiazolidine 1,1-dioxide | 216 |
| 15 | 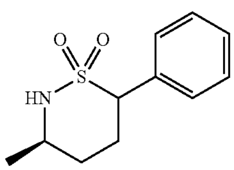 | (3R)-3-methyl-6-phenyl-1,2-thiazinane 1,1-dioxide | 226 |
| 16 | 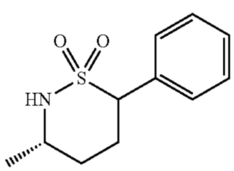 | (3S)-3-methyl-6-phenyl-1,2-thiazinane 1,1-dioxide | 226 |
| 17 | 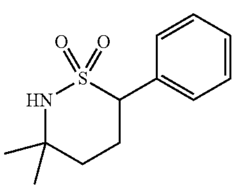 [SMILES: CC1(C)CCC(c2ccccc2)S(=O)(=O)N1] | 3,3-dimethyl-6-phenyl-1,2-thiazinane 1,1-dioxide | 240 |
| 18 | 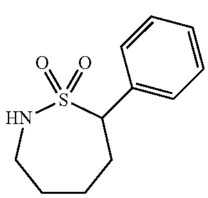 [SMILES: O=S1(=O)NCCCCC1c1ccccc1] | 7-phenyl-1,2-thiazepane 1,1-dioxide | 226 |
Preparation 19: 3-Phenyl-1,4,5-oxathiazepane 4,4-dioxide
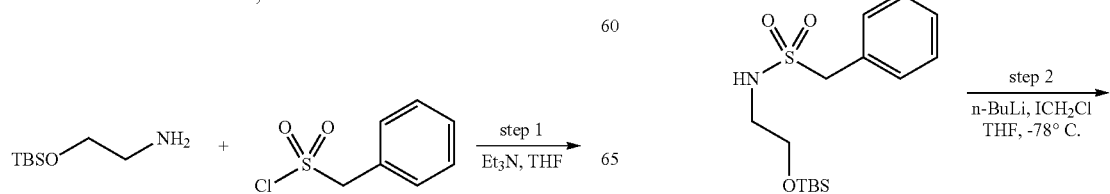

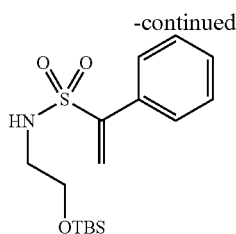

step 3
TBAF, THF
→

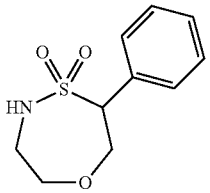

Step 1: N-(2-((Tert-butyldimethylsilyl)oxy)ethyl)-1-phenylmethanesulfonamide

To a solution of 2-((tert-butyldimethylsilyl)oxy)ethanamine (11.7 g, 66.6 mmol) and triethylamine (11.2 mL, 79.9 mmol) in tetrahydrofuran (222 mL) at 0° C. was slowly added phenylmethanesulfonyl chloride (12.7 g, 66.6 mmol) portion wise and the reaction was stirred at room temperature for 16 hours. MTBE was then added and the Et$_3$N—HCl salt was removed by filtration. The filtrate was then concentrated and purified by silica gel column chromatography (0-30% Acetone in heptane, 216 nM) to N-(2-((tert-butyldimethylsilyl)oxy)ethyl)-1-phenylmethanesulfonamide (17.8 g, 81% yield). LCMS (ESI), m/z, 330. [M+H]+.

Step 2: N-(2-((Tert-butyldimethylsilyl)oxy)ethyl)-1-phenylethenesulfonamid

To a solution of N-[2-[tert-butyl(dimethyl)silyl]oxyethyl]-1-phenyl-methanesulfonamide (33 g, 100.2 mmol) in tetrahydrofuran (334 mL) at −78° C. was slowly added n-BuLi (2.5M in hexanes) (100 mL, 250 mmol) via cannula and the reaction was stirred at −78° C. was 2 hours. Chloroiodomethane (8.3 mL, 110 mmol) was then slowly added and the reaction was stirred at −78° C. for one hour, then allowed to warm to room temperature and aged for 16 hours. The reaction was then quenched with saturated NH$_4$Cl and extracted with dichloromethane, dried with MgSO$_4$, concentrated and purified by silica gel column chromatography (0-60% EtOAc in heptane) to give N-[2-[tert-butyl(dimethyl)silyl]oxyethyl]-1-phenyl-ethenesulfonamide (24 g, 70% yield). LCMS (ESI), m/z, 342. [M+H]+.

Step 3: 3-Phenyl-1,4,5-oxathiazepane 4,4-dioxide

To a solution of N-(2-((Tert-butyldimethylsilyl)oxy)ethyl)-1-phenylethenesulfonamide (717 mg, 2.1 mmol) in tetrahydrofuran (7 mL) at 0° C. was added tetrabutylammonium fluoride (1.0M in THF) (2.2 mL, 2.2 mmol) dropwise and the reaction was stirred at room temperature for 16 hours. Saturated NH$_4$Cl was then added and the product was extracted with dichloromethane (×2), dried with MgSO$_4$, concentrated and purified by silica gel column chromatography (0-100% EtOAc in heptane) to give 3-phenyl-1,4,5-oxathiazepane 4,4-dioxide (401 mg, 84% yield). (24 g, 70% yield). LCMS (ESI), m/z, 228. [M+H]+. (Reference: P. Hansen, et al. *Org. Lett.* 2008, 2951).

Additional compounds made using the above procedure are shown in Table 3.

TABLE 3

| | Structure | Name | LCMS (ESI), m/z, [M + H]+ |
|---|---|---|---|
| 20 | 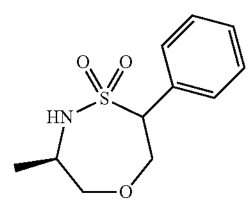 [SMILES: C[C@@H]1COCC(c2ccccc2)S(=O)(=O)N1] | (6R)-6-methyl-3-phenyl-1,4,5-oxathiazepane 4,4-dioxide | 242 |
| 21 | 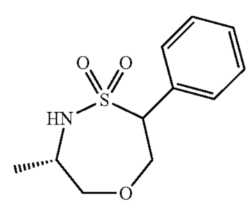 [SMILES: C[C@H]1COCC(c2ccccc2)S(=O)(=O)N1] | (6S)-6-methyl-3-phenyl-1,4,5-oxathiazepane 4,4-dioxide | 242 |
| 22 | 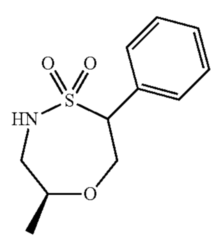 [SMILES: C[C@H]1CNS(=O)(=O)C(c2ccccc2)CO1] | (7S)-7-methyl-3-phenyl-1,4,5-oxathiazepane 4,4-dioxide | 242 |

TABLE 3-continued

| | Structure | Name | LCMS (ESI), m/z, [M + H]+ |
|---|---|---|---|
| 23 | 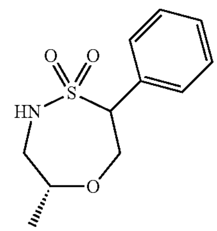 [SMILES: C[C@@H]1CNS(=O)(=O)C(c2ccccc2)CO1] | (7R)-7-methyl-3-phenyl-1,4,5-oxathiazepane 4,4-dioxide | 242 |

Example 1: 1-[4-(3-fluoro-4-{[(3S,6R)-3-methyl-1,1-dioxido-6-phenyl-1,2-thiazinan-2-yl]methyl}phenyl)-4-hydroxypiperidin-1-yl]ethanone

Step 1: 4-(4-Ethoxycarbonyl-3-fluoro-phenyl)-4-hydroxy-piperidine-1-carboxylic acid tert-butyl ester

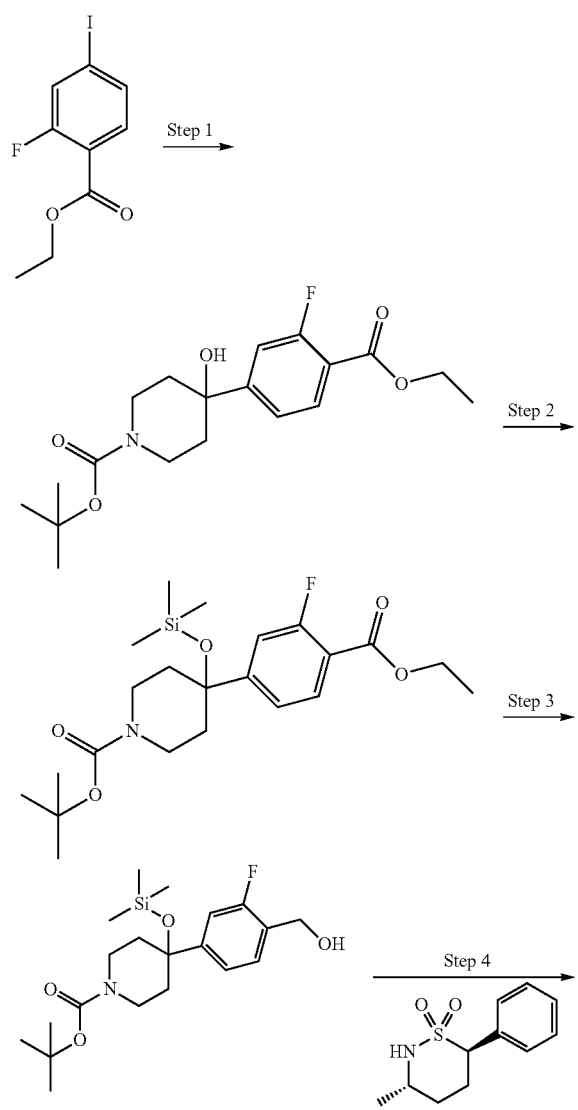

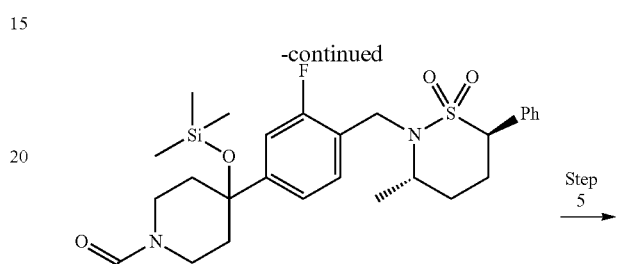

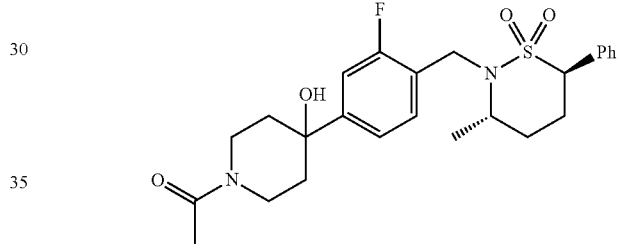

Ethyl-2-fluoro-4-iodobenzoate (2.0 g, 6.8 mmol) was dissolved in anhydrous THF (20 mL), placed under N$_2$, and cooled to −30° C. (isopropanol/dry ice). Isopropylmagnesium chloride (2M in THF, 4.1 mL, 8.2 mmol, 1.2 eq) was added and the reaction stirred at −30° C. for 3 h. 4-Oxo-piperidine-1-carboxylic acid-tert-butyl ester (1.3 g, 6.8 mmol) was dissolved in anhydrous THF (5 mL) and added to the reaction mixture which was stirred for 30 minutes at −30° C. and 15 minutes at room temperature. The contents were then poured into a 1:1 mixture of EtOAc and water. The aqueous layer was extracted with EtOAc and the organic layers were combined, washed with brine, dried over MgSO$_4$, filtered and concentrated in vacuo. Purification by chromatography on silica (2-40% EtOAc in cyclohexanes) gave the title compound as an oil (0.782 g, 32%). $^1$H NMR (300 MHz, CHCl$_3$-d): ☐ 7.92 (1H, t, J=7.77 Hz), 7.30 (1H, m), 7.26 (1H, m), 4.39 (2H, q, J=7.13 Hz), 4.08 (2H, m), 3.21 (2H, m), 1.98 (2H, m), 1.66-1.70 (2H, m), 1.43 (9H, s), 1.42 (3H, t, J=7.14 Hz).

Step 2: 4-(4-Ethoxycarbonyl-3-fluoro-phenyl)-4-trimethylsilanyloxy-piperidine-1-carboxylic acid tert-butyl ester The product from Step 1 (0.782 g, 2.14 mmol) was dissolved in DMA (4 mL) and imidazole (0.37 g, 5.4 mmol, 2.5 eq) added, followed by TMSCl (0.52 mL, 4.3 mmol, 2 eq). The reaction was stirred at room temperature for 16 h.

The reaction mixture was poured into water and the aqueous layer was extracted with EtOAc. The organic layers were combined, washed with water, brine, dried over MgSO$_4$, filtered and concentrated in vacuo. Purification by chromatography on silica (2 to 20% EtOAc in cyclohexane) gave the title compound as a colourless oil (0.66 g, 70%). $^1$H NMR (300 MHz, CHCl$_3$-d): □ 7.92 (1H, t, J=7.90 Hz), 7.26 (2H, m), 4.40 (2H, q, J=7.13 Hz), 3.99 (2H, br m), 3.20 (2H, br m), 1.78-1.91 (4H, m), 1.47 (9H, s), 1.40 (3H, t, J=7.13 Hz), −0.06 (9H, s).

Step 3: 4-(3-Fluoro-4-hydroxymethyl-phenyl)-4-trimethylsilanyloxy-piperidine-1-carboxylic acid tert-butyl ester The product from Step 2 (1.05 g, 2.4 mmol) was dissolved in DCM (10 mL) and cooled to 0° C. under nitrogen. Diisobutylaluminium hydride (1M in DCM, 6 mL) was added and the reaction stirred at 0° C. for 1 h. The reaction was quenched with MeOH (1 mL) and poured into a saturated solution of sodium potassium tartrate (Rochelle's salt). The product was extracted into EtOAc, the organic layer washed with ice-cold 0.5M HCl, brine, dried over MgSO$_4$, filtered and concentrated in vacuo. Purification by chromatography on silica (5 to 40% EtOAc in cyclohexane) gave the title compound as a colourless oil (0.529 g, 58%). $^1$H NMR (300 MHz, CHCl$_3$-d): δ 7.40 (1H, t, J=7.85 Hz), 7.24 (1H, m), 7.11 (1H, m), (4.76 (2H, br s), 3.97 (2H, m), 3.21 (2H, t, J=12.33 Hz), 1.78-1.92 (4H, m), 1.83 (9H, s), −0.09 (9H, s).

Step 4: 4-[3-Fluoro-4-((3S,6R)-3-methyl-1,1-dioxo-6-phenyl-1lambda*6*-[1,2]thiazinan-2-ylmethyl)-phenyl]-4-trimethylsilanyloxy-piperidine-1-carboxylic acid tert-butyl ester The product from Step 3 (0.529 g, 1.4 mmol) was dissolved in anhydrous THF (10 mL) and (3S,6R)-3-methyl-6-phenyl-[1,2]thiazine-1,1-dioxide (0.306 g, 1.4 mmol) was added, followed by N,N,N',N'-tetramethylazodicarboxamide (0.361 g, 2.1 mmol (1.5 eq) and n-butylphosphine (0.7 mL, 2.8 mmol, 2 eq). The reaction was stirred under nitrogen for 16 h. The contents were then poured into a mixture of EtOAc and water. The aqueous layer was extracted with EtOAc and the organic layers were combined, washed with brine, dried over MgSO$_4$, filtered and concentrated in vacuo. Purification by chromatography on silica (2-40% EtOAc in cyclohexanes) gave the title compound as an oil (0.352 g, 42%). $^1$H NMR (300 MHz, CHCl$_3$-d): δ 7.65 (1H, t, J=8.09 Hz), 7.31-7.50 (5H, m), 7.21 (1H, dd, J=7.89, 1.60 Hz), 7.06 (1H, dd, J=11.98, 1.79 Hz), 4.49 (2H, dd, J=39, 17 Hz), 4.23 (1H, m), 3.98 (2H, dd, J=12.84, 3.79 Hz), 3.20 (2H, br s), 2.57-2.66 (1H, m), 2.22 (1H, dd, J=14.12, 3.70 Hz), 1.79-1.87 (7H, m), 1.46 (9H, s), 1.11 (3H, d, J=6.92 Hz), −0.12 (9H, s). LCMS RT 5.30 min, m/z 627 [M+23]$^+$.

Step 5: 1-[4-(3-fluoro-4-{[(3S,6R)-3-methyl-1,1-dioxido-6-phenyl-1,2-thiazinan-2-yl]methyl}phenyl)-4-hydroxypiperidin-1-yl]ethanone The product from Step 4 (0.225 g, 0.37 mmol) was suspended in MeOH (10 mL) and HCl (4N dioxane, 4 mL) was added and the reaction was stirred at room temperature for 2 h. The solvent was evaporated in vacuo and the residue was dissolved in DCM (5 mL), cooled to 0° C. under nitrogen and triethylamine (0.08 mL, 0.55 mmol) added, followed by acetyl chloride (0.03 mL, 0.48 mmol). The reaction was stirred at 0° C. for 0.5 h and then diluted with DCM (30 mL) and K$_2$CO$_3$ (2M, 10 mL). The contents stirred for 10 minutes and poured into a phase separator cartridge. The aqueous layers were washed with DCM and the combined organic layers concentrated in vacuo. Purification by chromatography on silica (0-6% MeOH in DCM) gave the title compound as a white solid (0.114 g, 65%). $^1$H NMR (400 MHz, DMSO-d$_6$): δ 7.23-7.48 (8H, m), 5.22 (1H, s), 4.54 (2H, m), 4.34 (2H, m), 4.13 (1H, dd, J=11.96, 6.88 Hz), 3.69 (1H, d, J=13.22 Hz), 3.41 (1H, t, J=12.83 Hz), 2.89 (1H, t, J=12.46 Hz), 2.43 (2H, dd, J=14.64, 13.17 Hz), 2.10 (2H, dd, J=13.93, 3.80 Hz), 2.02 (3H, s), 1.52-1.95 (4H, m), 1.09 (3H, d, J=6.90 Hz). LCMS 4.16 min, m/z 475 [M+1]$^+$.

Example 2: Cis-1-(2,5-difluoro-4-{[(3S,6R)-3-methyl-1,1-dioxido-6-phenyl-1,2-thiazinan-2-yl]methyl}phenyl)-4-(4H-1,2,4-triazol-4-yl)cyclohexanol (5a)

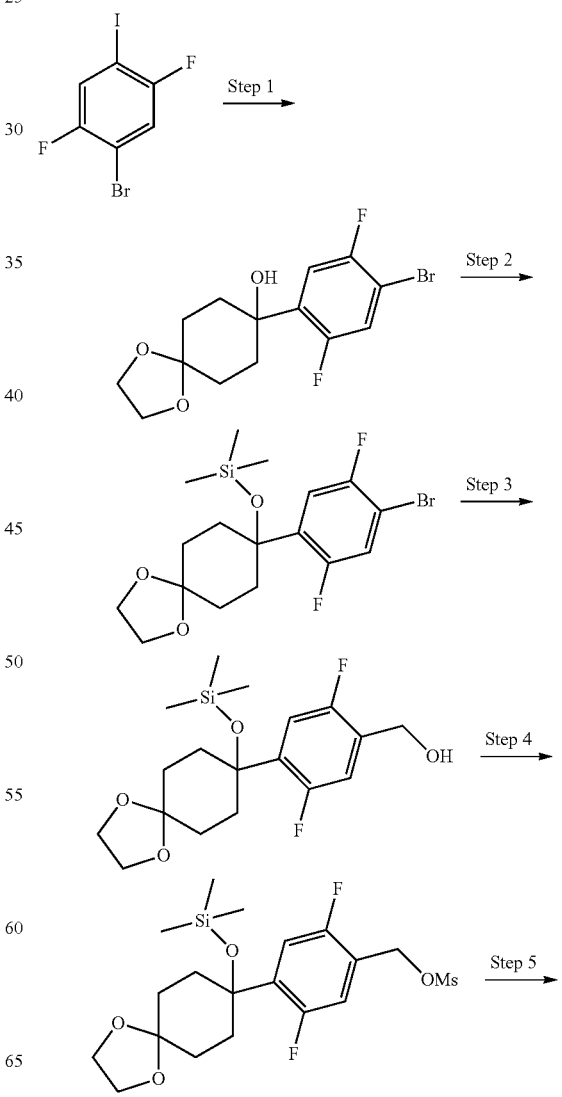

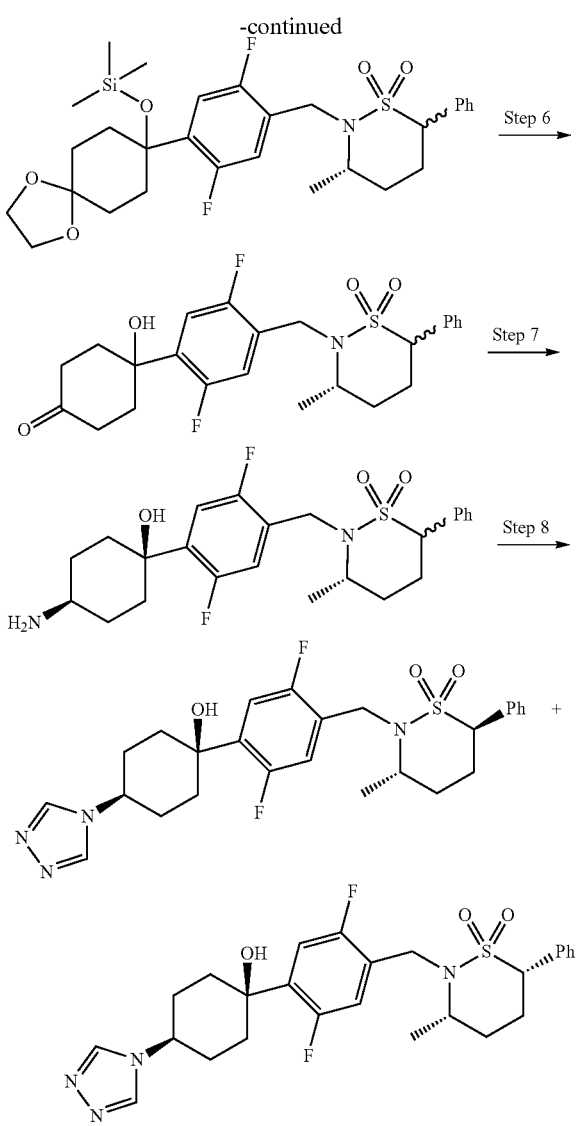

Step 1: 8-(4-Bromo-2,5-difluoro-phenyl)-1,4-dioxa-spiro[4.5]decan-8-ol

4-Bromo-2,5-difluoroiodobenzene (0.77 g, 2.4 mmol) was dissolved in anhydrous THF (6 mL) and cooled to −40° C. (isopropanol/dry ice). Isopropylmagnesium chloride (2M in THF, 1.4 mL, 2.87 mmol) was added and the reaction stirred at −40° C. for 1 h. The reaction mixture was then cooled to −60° C. and cyclohexananedione monoketal (0.374 g, 2.4 mmol) dissolved in THF (2 mL) was then added. The reaction was stirred at −60° C. for 0.5 h and at room temperature for another 0.5 h. The reaction mixture was poured into 1:1 NH$_4$Cl (sat) and EtOAc. The aqueous layer was extracted with EtOAc and the organic layers were combined, washed with brine, dried over MgSO$_4$, filtered and concentrated in vacuo. Purification by chromatography on silica (7-60% EtOAc in cyclohexanes) gave the title compound as a white solid (0.84 g, 44%). $^1$H NMR (300 MHz, CHCl$_3$-d): ☐ 7.36 (1H, dd, J=9.68, 6.87 Hz), 7.25 (1H, s), 3.98 (4H, m), 2.34 (2H, td, J=13.60, 3.97 Hz), 2.04-2.07 (2H, m), 1.94 (2H, d, J=3.22 Hz), 1.80 (2H, d, J=13.71 Hz).

Step 2: [8-(4-Bromo-2,5-difluoro-phenyl)-1,4-dioxa-spiro[4.5]dec-8-yloxy]-trimethyl-silane The product from Step 1 (0.32 g, 0.91 mmol) was dissolved in DCM (20 mL) and cooled to 0° C. under nitrogen. Lutidine (0.25 mL, 2.2 eq) was added, followed by trimethylsilyl trifluoromethanesulfonate (0.37 mL, 2.2 eq). The reaction was stirred at 0° C. for 1 h, allowed to warm to room temperature and EtOAc:water (2:1) added. The aqueous layer was extracted with EtOAc and the organic layers were combined, washed with brine, dried over MgSO$_4$, filtered and concentrated in vacuo. Purification by chromatography on silica (2 to 20% EtOAc in cyclohexane) gave the title compound as a colourless oil which crystallised on standing (0.26 g, 68%). $^1$H NMR (300 MHz, CHCl$_3$-d): ☐ 7.12-7.26 (2H, m), 3.96 (4H, m), 2.15 (1H, m), 2.04-2.08 (5H, m), 1.65 (2H, d, J=8.94 Hz), −0.03 (9H, s).

Step 3: [2,5-Difluoro-4-(8-trimethylsilanyloxy-1,4-dioxa-spiro[4.5]dec-8-yl)-phenyl]-methanol The product from Step 2 (0.256 g, 0.6 mmol) was dissolved in THF (10 mL) and cooled to −78° C. under nitrogen. nBuLi (2.5M solution, 1.7 mL, 14.3 mmol) was added and the reaction stirred at −78° C. for 0.5 h. DMF (0.14 mL, 1.7 mmol) was added and the reaction was stirred for a further 0.5 h, and then warmed to room temperature. The contents were poured into a saturated NH$_4$Cl solution and the aqueous layer was extracted with EtOAc. The combined organic layers were washed with brine, dried over MgSO$_4$, filtered, and concentrated in vacuo. The resulting oil was dissolved in MeOH (20 mL) and cooled to 0° C. Sodium borohydride (0.040 g, 1.1 mmol) was added and the reaction stirred for 20 minutes. The reaction was quenched with water (50 mL) and the aqueous layer was extracted with EtOAc. The organic layers were combined, washed with brine, dried over MgSO$_4$, filtered, and concentrated in vacuo. Purification by chromatography on silica (5 to 60% EtOAc in cyclohexane) gave the title compound as a colourless oil (0.165 g, 55%). $^1$H NMR (300 MHz, CHCl$_3$-d): ☐ 7.04-7.15 (2H, m), 4.73 (2H, br s), 3.97 (4H, dd, J=6.29, 3.82 Hz), 2.10-2.14 (6H, m), 1.65 (2H, m), −0.04 (9H, s).

Step 4: Methanesulfonic acid 2,5-difluoro-4-(8-trimethylsilanyloxy-1,4-dioxa-spiro[4.5]dec-8-yl)-benzyl ester The product from Step 3 (0.107 g, 0.29 mmol) was dissolved in DCM cooled to 0° C. and triethylamine (0.06 mL, 0.43 mmol) added, followed by methanesulfonyl chloride (0.03 mL, 0.377 mmol). The reaction was stirred at 0° C. for 0.5 h and poured into EtOAc and water. The aqueous layer was extracted with EtOAc, the organic layers then combined, washed with brine, dried over MgSO$_4$, filtered, and concentrated in vacuo. Purification by chromatography on silica (5-60% EtOAc in cyclohexane) gave the title compound as an oil (0.097 g, 74%). $^1$H NMR (300 MHz, CHCl$_3$-d): ☐ 7.07-7.19 (2H, m), 5.24 (2H, br s), 3.97 (4H, dd, J=6.69, 3.93 Hz), 3.03 (3H, s), 2.00-2.19 (6H, m), 1.66 (2H, d, J=8.03 Hz), −0.04 (9H, s).

Step 5: (3S,6R)-2-[2,5-Difluoro-4-(8-trimethylsilanyloxy-1,4-dioxa-spiro[4.5]dec-8-yl)-benzyl]-3-methyl-6-phenyl-[1,2]thiazinane 1,1-dioxide The product from Step 4 (0.9 g, 2 mmol) was dissolved in DMA (15 mL) and cooled to 0° C. under nitrogen. (3S,6R)-

3-methyl-6-phenyl-[1,2]thiazine-1,1-dioxide (0.585 g, 2.6 mmol, 1.3 eq) was added followed by sodium hydride (60% dispersion in oil, 0.122 g, 3.0 mmol, 1.5 eq). The reaction was stirred at 0° C. for 15 minutes and then the ice bath removed and stirred for a further 10 minutes. The reaction was poured into 250 mL of ice/water and the product extracted with EtOAc. The combined organic layers were washed with water, brine, dried over MgSO$_4$ and filtered and concentrated in vacuo. The residue was recrystalised from EtOAc and cyclohexane to give a white solid that contained a mixture of the title compound (approx. 70:30 mixture of sultam isomers) and (3S,6R)-3-methyl-6-phenyl-[1,2]thiazine-1,1-dioxide (0.600 g). LCMS title compound RT 5.03 min, m/z 602 [M+23]+; (3S)-2-[(4-bromo-2-fluoro-phenyl)methyl]-3-methyl-6-phenyl-thiazinane 1,1-dioxide RT 3.24 min, m/z 224 [M−1]. The filtrate was concentrated and recrystallized once more to give a further 0.210 g of the mixture.

Step 6: 4-[2,5-Difluoro-4-((3S,6R)-3-methyl-1,1-dioxo-6-phenyl-1lambda*6*-[1,2]thiazinan-2-ylmethyl)-phenyl]-4-hydroxy-cyclohexanone The product from Step 5 (0.6 g) was dissolved in acetone (12 mL) and 1M HCl (12 mL) and heated to 50° C. for 3 h. The reaction mixture was cooled and the acetone evaporated. The aqueous layer was extracted with EtOAc and the combined organic layers washed with saturated NaHCO$_3$, brine, dried over MgSO$_4$ and evaporated in vacuo. Purification by chromatography on silica (12-100% EtOAc in cyclohexane) gave the title compound (approx. 70:30 mixture of sultam isomers) as a solid (0.249 g, 52%). $^1$H NMR (300 MHz, CHCl$_3$-d): □ 7.42-7.44 (5H, m), 7.26 (2H, s), 4.45-4.47 (2H, m), 4.26-4.29 (1H, m), 4.00 (1H, dd, J=12.87, 3.55 Hz), 2.86-2.89 (2H, m), 2.62-2.67 (1H, m), 2.28-2.34 (8H, m), 1.76-1.79 (2H, m), 1.16 (2H, d, J=6.90 Hz). LCMS RT 3.92 min, m/z 486 [M+23]+, 400 [M−17]+.

Step 7: Cis-4-Amino-1-[2,5-difluoro-4-((3S,6R)-3-methyl-1,1-dioxo-6-phenyl-1lambda*6*-[1,2]thiazinan-2-ylmethyl)-phenyl]-cyclohexanol The product from Step 6 (0.200 g, 0.43 mmol) was suspended in MeOH (4 mL) and DCM (2 mL) and a solution of ammonia in MeOH (2M, 0.9 mL, 1.72 mmol, 4 eq) was added, followed by titanium isopropoxide (0.24 mL, 0.86 mmol, 2 eq). The reaction was stirred at room temperature for 16 h. The reaction was then cooled to −10° C. and sodium borohydride (0.033 g, 0.86 mmol, 2 eq) added and the reaction stirred for 0.5 h. Water (10 mL) and ammonium hydroxide (10 mL) was added and the product extracted into EtOAc. The combined organic layers were washed with water, brine, dried over MgSO$_4$ and evaporated in vacuo. The residue was purified on an SCX (cation exchange) to give the title compound (approx. 70:30 mixture of sultam isomers) as an oil (0.154 g, 53%). LCMS RT 2.86 min, m/z 488 [M+23]+, 447 [M−17]+).

Step 8: Cis-1-(2,5-difluoro-4-{[(3S,6R)-3-methyl-1,1-dioxido-6-phenyl-1,2-thiazinan-2-yl]methyl}phenyl)-4-(4H-1,2,4-triazol-4-yl)cyclohexanol and cis-1-(2,5-difluoro-4-{[(3S,6S)-3-methyl-1,1-dioxido-6-phenyl-1,2-thiazinan-2-yl]methyl}phenyl)-4-(4H-1,2,4-triazol-4-yl)cyclohexanol The product from Step 6 (0.154 g, 0.33 mmol) was dissolved in toluene and N,N'-bis(dimethylaminomethylene) hydrazine (0.236 g, 1.66 mmol, 5 eq) added, along with p-toluenesulfonic acid monohydrate (20 mg). The contents then heated to 100° C. under nitrogen for 16 h. The reaction mixture was cooled, and the solvent evaporated in vacuo. The residue was diluted with 10% MeOH/EtOAc and washed with 5% AcOH solution. The organic layer was then washed with saturated NaHCO$_3$ solution, brine, then dried over MgSO$_4$ and evaporated. Purification by chromatography on silica (0-10% MeOH/DCM) gave the title compound (approx. 70:30 mixture of isomers) as a white solid (0.070 g, 42%). The individual isomers were obtained by purification using chiral SFC. Cis-1-(2,5-difluoro-4-{[(3S,6R)-3-methyl-1,1-dioxido-6-phenyl-1,2-thiazinan-2-yl]methyl}phenyl)-4-(4H-1,2,4-triazol-4-yl)cyclohexanol: 1H NMR (400 MHz, DMSO-d$_6$□□): 8.63 (2H, s), 7.33-7.49 (6H, m), 7.20 (1H, dd, J=11.92, 6.06 Hz), 5.43 (1H, s), 4.56 (1H, m), 4.43 (2H, dd, J=15 Hz), 4.30 (1H, br s), 4.12 (1H, m), 3.65 (1H, t, J=6.60 Hz), 2.44 (1H, m), 2.10-2.18 (4H, m), 1.92 (2H, s), 1.74-1.83 (2H, m), 1.66 (1H, m), 1.13 (3H, d, J=7.11 Hz). LCMS RT 4.14 min, m/z 517 [M+1]+. Cis-1-(2,5-difluoro-4-{[(3S,6S)-3-methyl-1,1-dioxido-6-phenyl-1,2-thiazinan-2-yl]methyl}phenyl)-4-(4H-1,2,4-triazol-4-yl)cyclohexanol: 1H NMR (400 MHz, DMSO-d$_6$□□): 8.63 (2H, s), 7.42-7.44 (6H, m), 7.22 (1H, dd, J=11.92, 6.06 Hz), 5.46 (1H, s), 4.50-4.52 (3H, m), 4.32 (1H, br s), 3.65 (1H, t, J=6.60 Hz), 2.74 (1H, d, J=13.34 Hz), 2.0-2.23 (5H, t, J=9.11 Hz), 1.93 (2H, s), 1.77 (2H, d, J=8.89 Hz), 1.65 (1H, d, J=14.03 Hz), 1.41 (3H, d, J=7.11 Hz). LCMS RT 4.10 min, m/z 517 [M+1]+.

Example 3: Cis-1-(3-fluoro-4-{[(3S,6R)-3-methyl-1,1-dioxido-6-phenyl-1,2-thiazinan-2-yl]methyl}phenyl)-4-(4H-1,2,4-triazol-4-yl)cyclohexanecarbonitrile

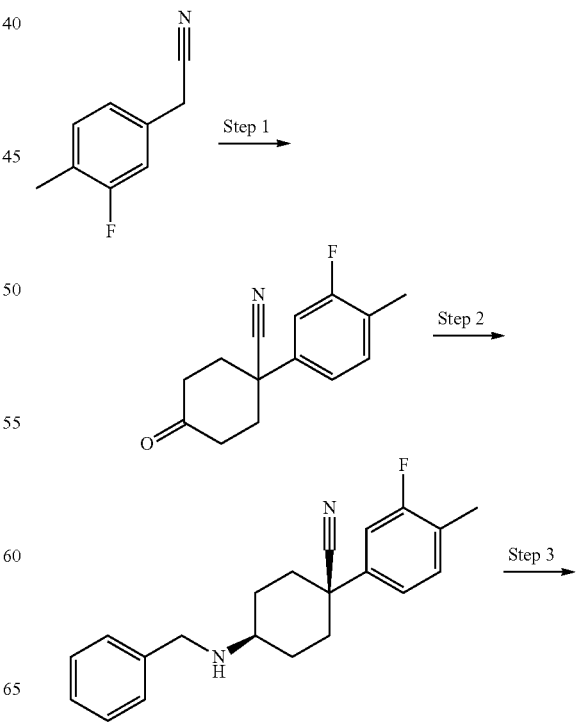

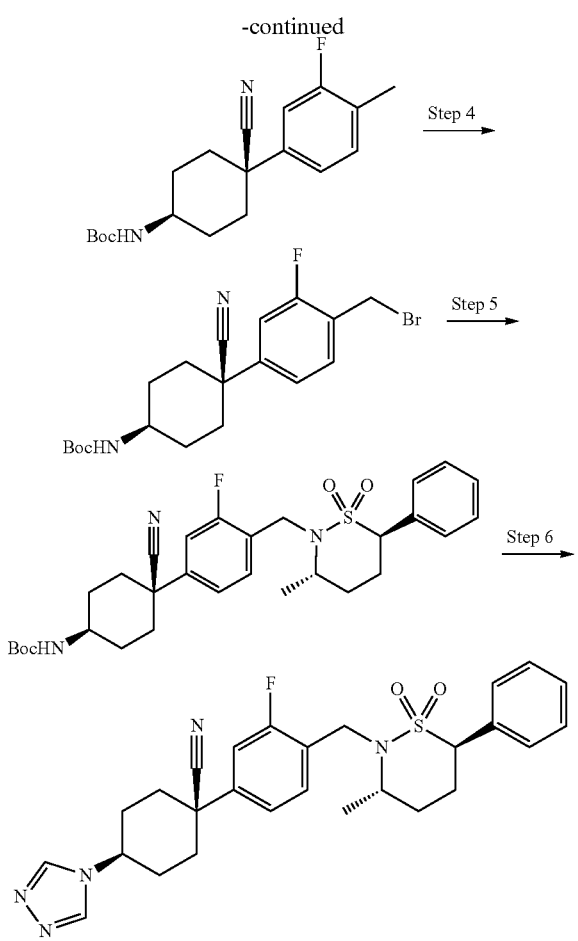

Step 1: 1-(3-Fluoro-4-methyl-phenyl)-4-oxo-cyclohexanecarbonitrile

To a stirred solution of (3-fluoro-4-methyl-phenyl)-acetonitrile (1.28 g, 8.58 mmol) and methyl acrylate (1.54 mL, 17.10 mmol) in anhydrous THF (30 mL) was added potassium tert-butoxide (1.68 g, 14.97 mmol). Water was added after 20 min (150 mL) and the resultant mixture was heated at reflux for 2 h. The mixture was allowed to cool to room temperature, diluted with water and then extracted with EtOAc (3×150 mL). The extracts were combined, washed with water and then brine and finally dried and evaporated in vacuo to give a pale brown oil. This material was crystallised from cyclohexane to give the title compound (0.55 g, 28%) as a pale yellow solid. The mother liquors were evaporated to give a further batch (1.58 g) as yellow brown crystals. LCMS: RT 3.75 min, no molecular ion.

Step 2: 4-Benzylamino-1-(3-fluoro-4-methyl-phenyl)-cyclohexanecarbonitrile

To a stirred solution of the product from Step 1 (1.58 g, 6.83 mmol) in anhydrous DCM (80 mL) was added benzylamine (0.85 mL, 7.78 mmol) followed by sodium triacetoxyborohydride (2.25 g, 10.60 mmol), acetic acid (0.61 mL, 10.60 mmol) and 4A molecular sieves (2 g). This mixture was allowed to stand at room temperature for 2 h and was then diluted with DCM and the resultant mixture was washed with saturated aqueous NaHCO$_3$ (×2). The organic phase was separated off and evaporated to dryness to leave crude product as a brown oil. Purification by chromatography on silica (60-100% EtOAC/cyclohexane) gave the title compound as a pale yellow oil which crystallised on standing (0.84 g). $^1$H NMR (300 MHz, CHCl$_3$-d): ☐ 7.34 (4H, d, J=4.19 Hz), 7.11-7.35 (4H, m), 3.87 (2H, s), 2.60 (1H, s), 2.21 (8H, d, J=27.76 Hz), 1.69-1.79 (4H, m). LCMS: RT 2.64 min, m/z 323=[M+1]$^+$.

Step 3: [4-Cyano-4-(3-fluoro-4-methyl-phenyl)-cyclohexyl]-carbamic acid tert-butyl ester The product from Step 2 (3.81 g, 11.81 mmol), ammonium formate (2.17 g, 34.43 mmol), palladium hydroxide (20% on carbon, 0.82 g) and IMS (165 mL) was heated at reflux with stirring under nitrogen for 20 mins. The reaction was allowed to cool to room temperature and was then filtered through a pad of Celite. The filtrate was concentrated by evaporation and then purified using an SCX cartridge to give a pale yellow solid (2.79 g, 99%). The solid was dissolved in DCM (100 mL) and triethylamine (3.86 mL, 27.72 mmol) followed by di-tert-butyldicarbonate (4.54 g, 20.79 mmol) was added and the resultant solution was allowed to stand at room temperature for 20 h. The reaction was diluted with DCM washed with saturated NaHCO$_3$ and then water. The organic phase was separated and evaporated to dryness to give a colourless oil which crystallised on standing. This material was triturated with cyclohexane and then the solid was collected by filtration, washed with cyclohexane and dried in vacuo at 40° C. to give the title compound (2.57 g, 56%) as a white solid. The mother liquors were evaporated to give (3.0 g) as an off white crystalline solid. $^1$H NMR (300 MHz, CHCl$_3$-d): ☐ 7.14-7.16 (1H, m), 2.12-2.23 (2H, m), 4.51 (1H, br s), 2.26 (3H, s), 1.84-1.87 (4H, m), 1.67-1.71 (4H, m), 1.46 (9H, s). LCMS: RT 4.42 min, m/z 333 [M+1]$^+$.

Step 4: [4-(4-Bromomethyl-3-fluoro-phenyl)-4-cyano-cyclohexyl]-carbamic acid tert-butyl ester The product from Step 3 (4.48 g, 13.48 mmol), N-bromosuccinimide (2.64 g, 14.82 mmol) and benzoyl peroxide (0.32 g, 1.35 mmol) in chloroform (250 mL) was heated at reflux for 40 min. More N-bromosuccinimide (1.20 g, 6.75 mmol) and benzoyl peroxide (0.090 g, 0.37 mmol) were added and the mixture reheated to reflux for a further 40 min. The reaction mixture was allowed to cool to room temperature and the resultant partial solution was evaporated to dryness. The residue was dissolved in EtOAc and the resultant solution was washed with sat. NaHCO$_3$ and then dried over MgSO$_4$ and evaporated to give a pale yellow oil (7.22 g). Purification by chromatography on silica (5-30% EtOAC/cyclohexane) gave the title compound as a white crystalline solid (1.34 g, 24%). Mixed fractions were re-purified to give second batch of title compound (0.90 g, 16%) as a white crystalline solid. $^1$H NMR (300 MHz, CHCl$_3$-d): ☐ 7.43 (1H, t, J=7.93 Hz), 7.19-7.21 (2H, m), 4.49 (2H, s), 3.53 (1H, br s), 2.19 (4H, d, J=12.15 Hz), 1.83-1.88 (2H, m), 1.66-1.71 (2H, m), 1.44 (9H, s).

Step 5: {4-Cyano-4-[3-fluoro-4-((3S,6R)-3-methyl-1,1-dioxo-6-phenyl-1lambda*6*-[1,2]thiazinan-2-ylmethyl)-phenyl]-cyclohexyl}-carbamic acid tert-butyl ester To a stirred solution of the product from Step 4 (1.58 g, 3.84 mmol) and (3S,6R)-3-methyl-6-phenyl-[1,2]thiazine-1, 1-dioxide (0.86 g. 3.84 mmol) in DMA (12 ml) was added cesium carbonate (1.87 g, 5.76 mmol). The resultant mixture was allowed to stir at room temperature for 20 h and was then partitioned between EtOAc and water. The aqueous phase was separated and was re-extracted with EtOAc. The organic phases were combined, washed with water and brine, dried over MgSO$_4$ and evaporated to leave a brown oil (3.78 g). Purification by chromatography on silica (5-40% EtOAC/cyclohexane) gave the title compound as a white crystalline solid (0.50 g, 23%). $^1$H NMR (300 MHz, CHCl$_3$-d): ☐☐ 7.73 (1H, d, J=8.11 Hz), 7.41-7.43 (5H, m), 7.26 (1H, s), 7.13 (1H, dd, J=11.43, 1.95 Hz), 4.47-4.50 (2H, m), 4.25-4.29 (1H, m), 4.00 (1H, dd, J=12.86, 3.57 Hz), 3.53 (1H, br s), 2.61-2.68 (4H, m), 2.05-2.29 (4H, m), 1.6-1.94 (5H, m), 1.44 (9H, d, J=8.65 Hz), 1.14 (3H, d, J=6.90 Hz). LCMS: RT 4.59 min, m/z 578 [M+Na]$^+$.

Step 6: Cis-1-(3-fluoro-4-{[(3S,6R)-3-methyl-1,1-dioxido-6-phenyl-1,2-thiazinan-2-yl]methyl}phenyl)-4-(4H-1,2,4-triazol-4-yl)cyclohexanecarbonitrile A solution of the product from Step 5 (0.50 g, 0.90 mmol) in HCl (4N dioxane, 10 mL) was stirred at room temperature for 2 h. The reaction mixture was evaporated to dryness and the residue was partitioned between DCM and saturated aqueous NaHCO$_3$. The aqueous phase was separated and was re-extracted with DCM. The organic phases were combined, passed through a hydrophobic frit (Phase separator) and then evaporated to leave a pale yellow solid (0.38 g). This material was combined with N,N'-bis(dimethylaminomethylene)hydrazine (0.59 g, 4.15 mmol), p-toluenesulphonic acid monohydrate (0.017 g, 0.089 mmol) and dry toluene (6 mL) and the mixture was heated at reflux for 20 h. The reaction mixture was allowed to cool to room temperature and was then partitioned between EtOAc and 5% aqueous acetic acid. The organic phase was separated and was washed with 5% aqueous acetic acid and dried over MgSO$_4$ and evaporated to dryness leave a yellow brown crystalline solid. Purification by chromatography on silica (5-20% EtOAC/cyclohexane) gave the title compound as a white solid (0.15 g, 36%). $^1$H NMR (300 MHz, CHCl$_3$-d): ☐☐ 8.27 (2H, s), 7.76 (1H, t, J=8.07 Hz), 7.15-7.48 (7H, s), 4.49-4.51 (2H, m), 4.28 (1H, m), 4.18 (1H, m), 4.00 (1H, m), 2.68 (3H, m), 2.30-2.36 (5H, m), 2.01 (2H, d, J=16.80 Hz), 1.77-1.79 (2H, m), 1.15 (3H, d, J=6.91 Hz). LCMS: RT 3.69 min, m/z 508=[M+H]+.

Example 4: Methyl cis-1-(4-{[(3S,6R)-3-methyl-1,1-dioxido-6-phenyl-1,2-thiazinan-2-yl]methyl}phenyl)-4-(4H-1,2,4-triazol-4-yl)cyclohexanecarboxylate

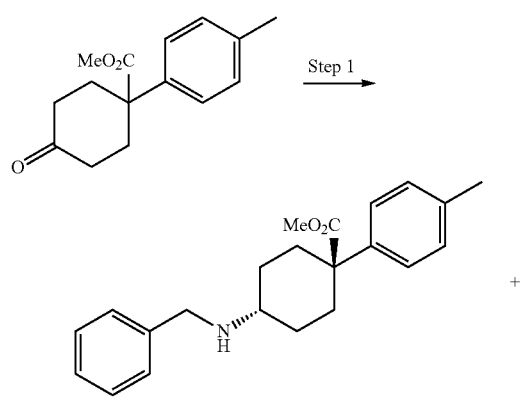

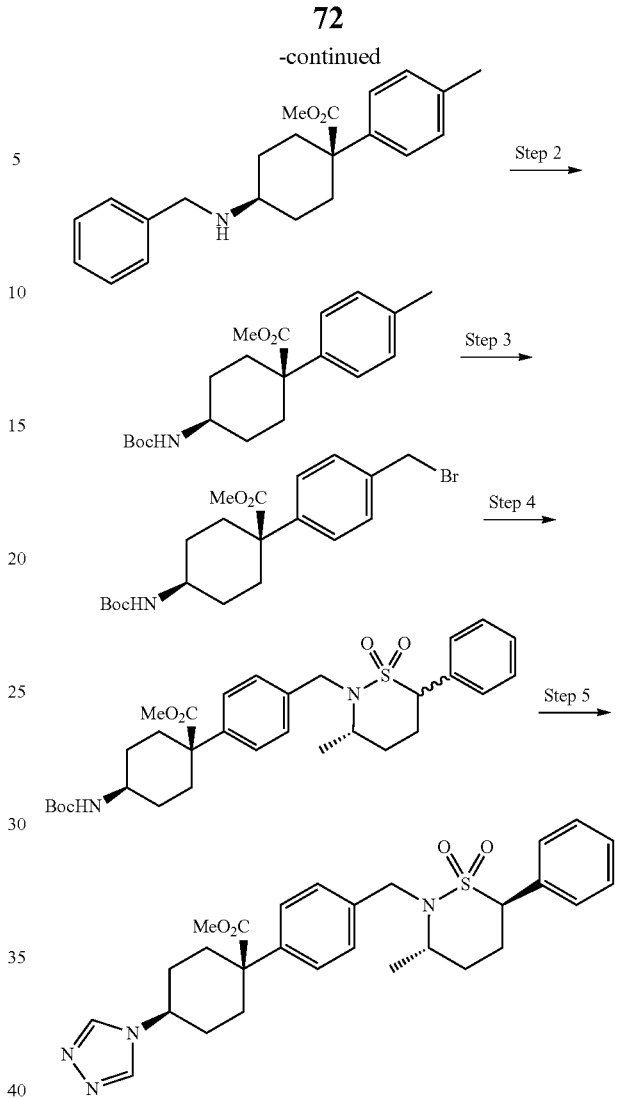

Step 1: Cis-4-benzylamino-1-p-tolyl-cyclohexanecarboxylic acid methyl ester and trans-4-benzylamino-1-p-tolyl-cyclohexanecarboxylic acid methyl ester To a stirring mixture of 4-oxo-1-p-tolyl-cyclohexanecarboxylic acid methyl ester (prepared according to *J. Org. Chem.*, 2007, 7455; 1.42 g, 5.8 mmol), benzylamine (0.720 mL, 6.6 mmol), sodium triacetoxyborohydride (1.9 g, 9.0 mmol) and DCM (50 mL) was added glacial acetic acid (0.51 mL, 9.0 mmol). The reaction mixture was stirred at RT for 20 minutes. DCM (100 mL) added and the organic layer was washed with sat. NaHCO$_3$ (140 mL), dried over MgSO$_4$, evaporated in vacuo and purified using flash chromatography (EtOAc/cyclohexane 2:1-EtOAc) to give the less polar trans isomer as a white solid (1.5 g) and the more polar cis isomer as a white solid (0.40 g). (trans isomer): $^1$H NMR (400 MHz, DMSO-d$_6$ ☐☐☐☐ 7.26-7.27 (m, 6H); 7.16-7.18 (m, 3H); 3.64 (s, 2H); 3.51 (s, 3H); 2.58 (t, J=5.1 Hz, 1H); 2.27 (m, 5H); 1.93 (t, J=10.7 Hz, 3H); 1.59-1.64 (m, 2H); 1.35 (br s, 2H). LCMS RT 2.64 min, m/z 338 [M+1]. (cis isomer): $^1$H NMR (400 MHz, DMSO-d$_6$): ☐☐ 7.29-7.30 (m, 4H); 7.19-7.20 (m, 3H); 7.12 (d, J=8.1 Hz, 2H); 3.71 (s, 2H); 3.59 (s, 3H); 2.49-2.50 (m, 4H); 2.39-2.44

(m, 3H); 1.91 (d, J=13.5 Hz, 2H); 1.52 (td, J=13.2, 3.2 Hz, 2H); 1.15 (q, J=12.3 Hz, 2H). LCMS RT 2.71 min, m/z 338 [M+1].

Steps 2-5: Methyl cis-1-(4-{[(3S,6R)-3-methyl-1,1-dioxido-6-phenyl-1,2-thiazinan-2-yl]methyl}phenyl)-4-(4H-1,2,4-triazol-4-yl)cyclohexanecarboxylate Methyl cis-1-(4-{[(3S,6R)-3-methyl-1,1-dioxido-6-phenyl-1,2-thiazinan-2-yl]methyl}phenyl)-4-(4H-1,2,4-triazol-4-yl)cyclohexanecarboxylate was prepared according to the method described for cis-1-(3-fluoro-4-{[(3S,6R)-3-methyl-1,1-dioxido-6-phenyl-1,2-thiazinan-2-yl]methyl}phenyl)-4-(4H-1,2,4-triazol-4-yl)cyclohexanecarbonitrile in Example 3, using the product from from Step 1. $^1$H NMR (400 MHz, DMSO-d$_6$): □□ 8.62 (s, 2H); 7.40-7.41 (m, 9H); 4.29-4.31 (m, 5H); 3.67 (s, 3H); 2.64 (d, J=9.2 Hz, 2H); 2.44 (dd, J=13.2, 3.5 Hz, 1H); 2.10-2.17 (m, 3H); 1.71-1.75 (m, 6H); 1.09 (d, J=6.9 Hz, 3H). LCMS RT 4.30 min, 523[M+1]$^+$.

Example 5: Methyl trans-1-(4-{[(3S,6R)-3-methyl-1,1-dioxido-6-phenyl-1,2-thiazinan-2-yl]methyl}phenyl)-4-(4H-1,2,4-triazol-4-yl)cyclohexanecarboxylate

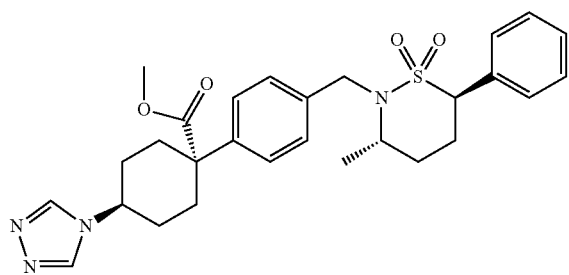 [SMILES: COC(=O)[C@]1(c2ccc(CN3[C@@H](C)CC[C@H](c4ccccc4)S3(=O)=O)cc2)CC[C@@H](n2cnnc2)CC1]

Methyl trans-1-(4-{[(3S,6R)-3-methyl-1,1-dioxido-6-phenyl-1,2-thiazinan-2-yl]methyl}phenyl)-4-(4H-1,2,4-triazol-4-yl)cyclohexanecarboxylate was prepared according to the method described for cis-1-(3-fluoro-4-{[(3S,6R)-3-methyl-1,1-dioxido-6-phenyl-1,2-thiazinan-2-yl]methyl}phenyl)-4-(4H-1,2,4-triazol-4-yl)cyclohexanecarbonitrile in Example 13, using the trans-4-benzylamino-1-p-tolyl-cyclohexanecarboxylic acid methyl ester prepared as described above. $^1$H NMR (400 MHz, DMSO-d$_6$ □□□□ 8.50 (s, 2H); 7.41-7.43 (m, 9H); 4.36-4.38 (m, 5H); 3.54 (s, 3H); 2.43 (m, 3H); 2.09 (t, J=13.2 Hz, 5H); 1.66-1.79 (m, 4H); 1.09 (d, J=6.9 Hz, 3H). LCMS RT 4.12 min, 523[M+1]$^+$.

Example 6: methyl 4-(4-{[(3S,6R)-3-methyl-1,1-dioxido-6-phenyl-1,2-thiazinan-2-yl]methyl}phenyl)tetrahydro-2H-pyran-4-carboxylate

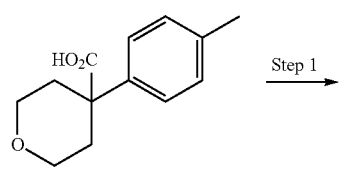

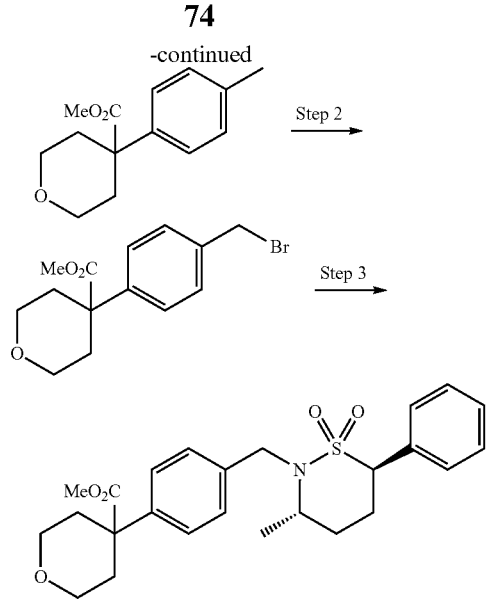

Step 1: 4-p-Tolyl-tetrahydro-pyran-4-carboxylic acid methyl ester

To a mixture of 4-p-tolyl-tetrahydro-pyran-4-carboxylic acid (0.250 g, 1.14 mmol) and MeOH (15 mL) was added thionyl chloride (0.5 mL) drop wise. The resultant mixture was refluxed for 2 h, evaporated to dryness and re-evaporated with chloroform to give the title compound as a white waxy solid (0.260 g). $^1$H NMR (300 MHz, CHCl$_3$-d): □□ 07.25-7.26 (m, 2H); 7.15 (d, J=8.1 Hz, 2H); 3.92 (dt, J=12.0, 3.7 Hz, 2H); 3.66 (s, 3H); 3.55 (td, J=11.5, 2.0 Hz, 2H); 2.50 (d, J=13.6 Hz, 2H); 2.33 (s, 3H); 1.97-1.99 (m, 2H). LCMS: RT 3.80 min. No molecular ion.

Step 2: 4-(4-Bromomethyl-phenyl)-tetrahydro-pyran-4-carboxylic acid methyl ester 4-(4-Bromomethyl-phenyl)-tetrahydro-pyran-4-carboxylic acid methyl ester was prepared as described above for [4-(4-bromomethyl-3-fluoro-phenyl)-4-cyano-cyclohexyl]-carbamic acid tert-butyl ester. The residue obtained after work up was purified using flash chromatography (EtOAc/cyclohexane 1:5-1:3) to give the title compound as a white waxy solid (0.280 g). $^1$H NMR (300 MHz, CHCl$_3$-d): □ 7.36 (d, J=3.0 Hz, 4H); 4.48 (s, 2H); 3.93 (dt, J=12.0, 3.6 Hz, 2H); 3.68 (s, 3H); 3.55 (td, J=11.6, 2.0 Hz, 2H); 2.48-2.52 (m, 2H); 1.97 (ddd, J=13.5, 11.2, 4.3 Hz, 2H). LCMS: RT 3.87 min. No molecular ion.

Step 3: Methyl 4-(4-{[(3S,6R)-3-methyl-1,1-dioxido-6-phenyl-1,2-thiazinan-2-yl]methyl}phenyl)tetrahydro-2H-pyran-4-carboxylate Methyl 4-(4-{[(3S,6R)-3-methyl-1,1-dioxido-6-phenyl-1,2-thiazinan-2-yl]methyl}phenyl)tetrahydro-2H-pyran-4-carboxylate was prepared as described above for [4-(4-bromomethyl-3-fluoro-phenyl)-4-cyano-cyclohexyl]-carbamic acid tert-butyl ester in Example 12 step 5. The residue obtained after work up was purified using flash chromatography (EtOAc/cyclohexane 1:5-1:3) to give the title compound as a white solid (0.215 g). $^1$H NMR (400 MHz, DMSO-d$_6$ □□□□ 7.43 (dd, J=7.5, 1.8 Hz, 2H); 7.33-7.34 (m, 7H); 4.42-4.44 (m, 2H); 4.26-4.28 (m, 1H);

4.06 (dd, J=11.9, 6.8 Hz, 1H); 3.78 (dt, J=11.9, 3.7 Hz, 2H); 3.58 (s, 3H); 3.38 (t, J=11.3 Hz, 2H); 2.33-2.37 (m, 3H); 2.06-2.08 (m, 1H); 1.80-1.84 (m, 3H); 1.62 (dd, J=14.2, 3.1 Hz, 1H); 1.03-1.04 (m, 3H). LCMS: RT 4.90 min, m/z 458 [M+1].

Example 7: 4-(4-{[(3S,6R)-3-methyl-1,1-dioxido-6-phenyl-1,2-thiazinan-2-yl]methyl}phenyl)tetrahydro-2H-pyran-4-carbonitrile

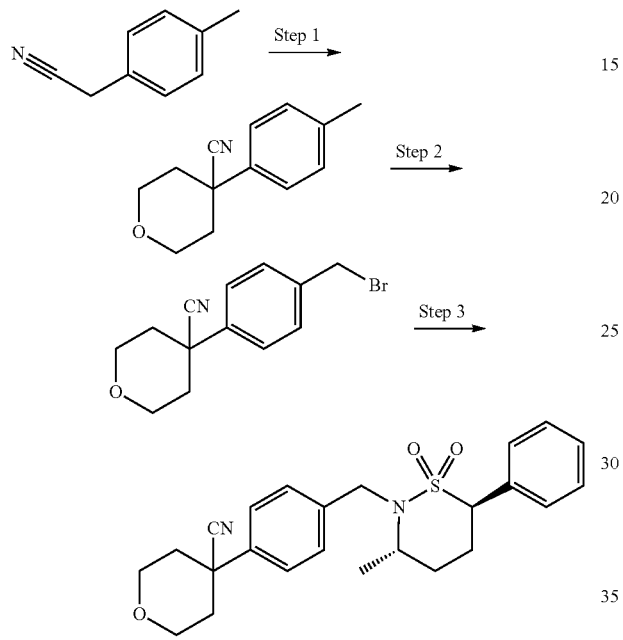

Step 1: 4-p-Tolyl-tetrahydro-pyran-4-carbonitrile

A mixture of p-tolyl-acetonitrile (0.66 g, 5.0 mmol), chloro-2-(2-chloroethoxy)ethane (0.586 ml, 5.0 mmol), hexadecyltributylphosphonium bromide (0.130 g, 0.25 mmol) and 50% aqueous NaOH (8 mL) was heated a 100° C. with vigorous stirring. The reaction mixture was cooled, water added (20 mL) and the product extracted into Et$_2$O (40 mL), dried over MgSO$_4$ and evaporated to dryness. The residue was purified using flash chromatography (EtOAc/cyclohexane 1:8-1:4) to give the title compound as a yellow oil (0.400 g). $^1$H NMR (300 MHz, CHCl$_3$-d): □ 7.36-7.37 (m, 2H); 7.23 (d, J=7.8 Hz, 2H); 4.07-4.10 (m, 2H); 3.90 (td, J=11.8, 2.5 Hz, 2H); 2.36 (s, 3H); 2.07-2.09 (m, 4H).

Step 2: 4-(4-Bromomethyl-phenyl)-tetrahydro-pyran-4-carbonitrile 4-(4-Bromomethyl-phenyl)-tetrahydro-pyran-4-carbonitrile was prepared as described for [4-(4-bromomethyl-3-fluoro-phenyl)-4-cyano-cyclohexyl]-carbamic acid tert-butyl ester in Example 12, Step 4. The residue obtained after work up was purified using flash chromatography (EtOAc/cyclohexane 1:4) to give a pale yellow oil (0.270 g). $^1$H NMR (300 MHz, CHCl$_3$-d): □ 7.46 (d, J=1.2 Hz, 4H); 4.49 (s, 2H); 4.09 (dd, J=12.3, 4.2 Hz, 2H); 3.91 (td, J=11.9, 2.4 Hz, 2H); 2.09-2.12 (m, 4H).

Step 3: 4-(4-{[(3S,6R)-3-methyl-1,1-dioxido-6-phenyl-1,2-thiazinan-2-yl]methyl}phenyl)tetrahydro-2H-pyran-4-carbonitrile A mixture of (3S,6R)-3-methyl-6-phenyl-[1,2]thiazine-1,1-dioxide (0.191 g, 0.85 mmol), the product from Step 2 (0.252 g, 0.90 mmol), cesium carbonate (0.417 g, 1.28 mmol) and DMA (3 mL) was stirred at room temperature for 16 h. EtOAc (70 mL) was added and the organic layer washed with water, dried over MgSO$_4$ and concentrated in vacuo. The residue was purified using flash chromatography (EtOAc/cyclohexane 1:3) to obtain a white solid which was filtered off and washed with cyclohexane to obtain the title compound (0.120 g). $^1$H NMR (400 MHz, DMSO-d$_6$) □□□ 7.42-7.43 (m, 9H); 4.52 (d, J=17.1 Hz, 1H); 4.41 (dd, J=12.7, 3.5 Hz, 1H); 4.32 (d, J=17.1 Hz, 1H); 4.08 (dd, J=12.0, 6.9 Hz, 1H); 3.98 (dd, J=11.9, 3.5 Hz, 2H); 3.63 (td, J=11.6, 2.8 Hz, 2H); 2.40 (td, J=13.2, 3.7 Hz, 1H); 2.03-2.07 (m, 5H); 1.77-1.81 (m, 1H); 1.62-1.66 (m, 1H); 1.06 (d, J=6.9 Hz, 3H). LCMS: RT 4.79 min, m/z 425[M+1].

Example 8: 4-(4-{[(3S,6R)-3-methyl-1,1-dioxido-6-phenyl-1,2-thiazinan-2-yl]methyl}phenyl)tetrahydro-2H-pyran-4-carboxamide

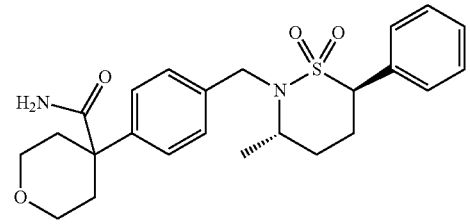 [SMILES: C[C@H]1CC[C@H](c2ccccc2)S(=O)(=O)N1Cc1ccc(C2(C(N)=O)CCOCC2)cc1]

A mixture of 4-[4-((3S,6R)-3-methyl-1,1-dioxo-6-phenyl-1lambda*6*-[1,2]thiazinan-2-ylmethyl)-phenyl]-tetrahydro-pyran-4-carbonitrile (0.080 g, 0.19 mmol), hydrido (dimethylphosphinous acid-kP) [hydrogen bis (dimethylphosphinito-kP)]platinum (II) (4 mg), ethanol (10 mL) and water (3 drops) was heated to reflux for 24 h. The solvent was partially evaporated the, and the resulting precipitate filtered off and dried to give the title compound as a white solid (0.063 g). $^1$H NMR (400 MHz, DMSO-d$_6$ □□□ 7.40-7.42 (m, 5H); 7.32 (s, 4H); 7.14 (s, 1H); 6.94 (s, 1H); 4.48 (d, J=17.0 Hz, 1H); 4.39 (dd, J=12.7, 3.6 Hz, 1H); 4.26 (d, J=17.0 Hz, 1H); 4.06 (dd, J=11.9, 6.9 Hz, 1H); 3.71 (d, J=11.4 Hz, 2H); 3.44 (t, J=11.0 Hz, 2H); 2.39-2.43 (m, 3H); 2.07 (dd, J=13.9, 3.8 Hz, 1H); 1.76 (t, J=12.6 Hz, 3H); 1.62 (d, J=14.2 Hz, 1H); 1.06 (d, J=6.9 Hz, 3H). LCMS RT 4.02 min, m/z 443 [M+1].

Example 18: 8-(3-fluoro-4-{[(3S,6R)-3-methyl-1,1-dioxido-6-phenyl-1,2-thiazinan-2-yl]methyl}phenyl)-1,4-dioxaspiro[4.5]decane-8-carbonitrile

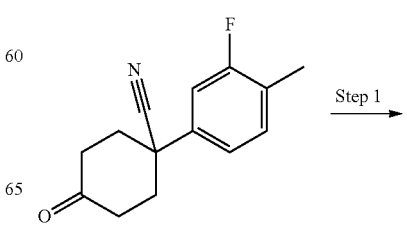

Step 1

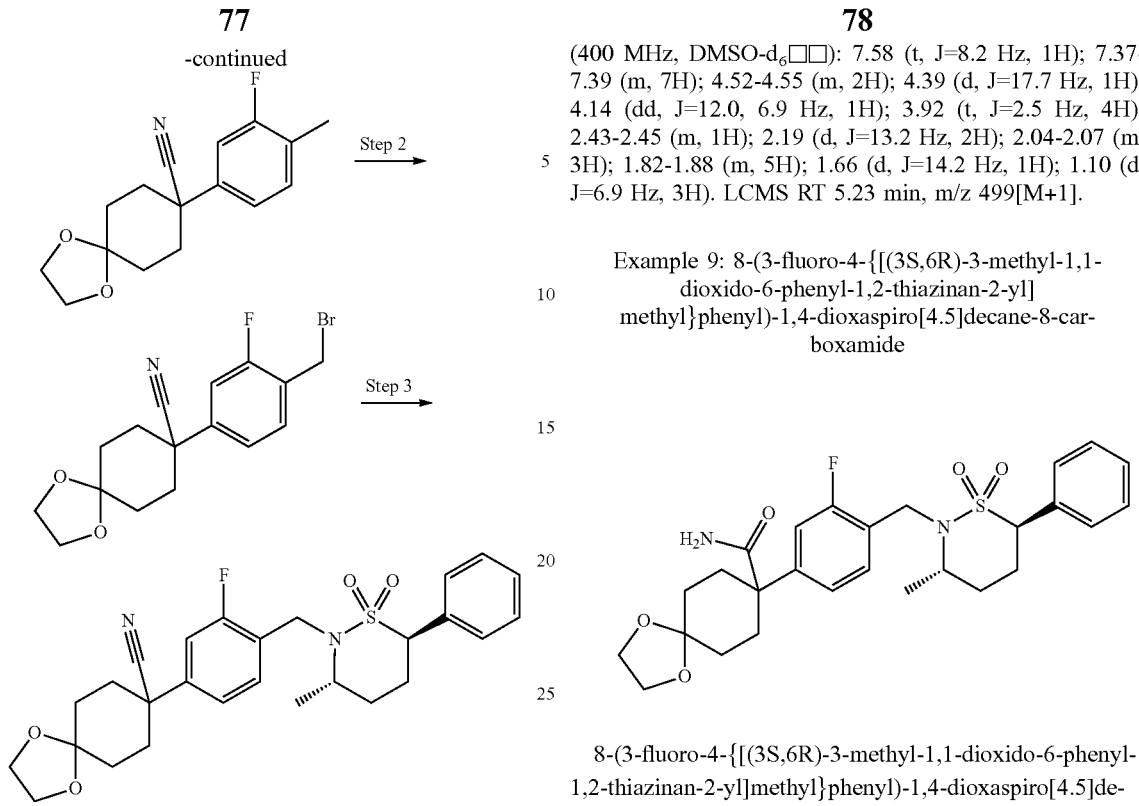

Step 1: 8-(3-fluoro-4-methyl-phenyl)-1,4-dioxaspiro[4.5]decane-8-carbonitrile A mixture of 1-(3-fluoro-4-methyl-phenyl)-4-oxo-cyclohexanecarbonitrile (1.16 g, 5.0 mmol), ethylene glycol (0.36 mL), p-TsOH (0.016 g) and toluene (10 mL) was heated to reflux using a Dean-Stark trap for 1.5 h. EtOAc (10 mL) was added and the organic layer washed with sat. NaHCO$_3$ (30 mL), then dried over MgSO$_4$ and most of the solvent evaporated. Heptane was then added and the resulting solid filtered off to give the title compound (1.0 g). $^1$H NMR (300 MHz, CHCl$_3$-d): ☐☐ 7.16-7.18 (m, 3H); 3.98-3.99 (m, 4H); 2.27 (d, J=1.9 Hz, 3H); 2.12 (m, 6H); 1.83-1.87 (m, 2H). LCMS RT 4.11 min, 276 [M+1].

Step 2: 8-(4-Bromomethyl-3-fluoro-phenyl)-1,4-dioxa-spiro[4.5]decane-8-carbonitrile 8-(4-Bromomethyl-3-fluoro-phenyl)-1,4-dioxa-spiro[4.5]decane-8-carbonitrile was prepared as described in Example 12 step 4, using the product from Step 1 above. The residue obtained after work up was purified using flash chromatography (EtOAc/cyclohexane 1:5-1:3) to give the title compound as a white solid (0.25 g). $^1$H NMR (300 MHz, CHCl$_3$-d): ☐ 7.31 (dd, J=8.1, 2.0 Hz, 1H); 7.18-7.20 (m, 2H); 4.50 (s, 2H); 3.97-3.99 (m, 4H); 2.13 (s, 6H); 1.87 (d, J=9.7 Hz, 2H). LCMS RT 4.12 min. No molecular ion.

Step 3: 8-(3-fluoro-4-{[(3S,6R)-3-methyl-1,1-dioxido-6-phenyl-1,2-thiazinan-2-yl]methyl}phenyl)-1,4-dioxaspiro[4.5]decane-8-carbonitrile 8-(3-fluoro-4-{[(3S,6R)-3-methyl-1,1-dioxido-6-phenyl-1,2-thiazinan-2-yl]methyl}phenyl)-1,4-dioxaspiro[4.5]decane-8-carbonitrile was prepared as described in Example 15 Step 3 using the product from Step 2 above. $^1$H NMR (400 MHz, DMSO-d$_6$☐☐): 7.58 (t, J=8.2 Hz, 1H); 7.37-7.39 (m, 7H); 4.52-4.55 (m, 2H); 4.39 (d, J=17.7 Hz, 1H); 4.14 (dd, J=12.0, 6.9 Hz, 1H); 3.92 (t, J=2.5 Hz, 4H); 2.43-2.45 (m, 1H); 2.19 (d, J=13.2 Hz, 2H); 2.04-2.07 (m, 3H); 1.82-1.88 (m, 5H); 1.66 (d, J=14.2 Hz, 1H); 1.10 (d, J=6.9 Hz, 3H). LCMS RT 5.23 min, m/z 499[M+1].

Example 9: 8-(3-fluoro-4-{[(3S,6R)-3-methyl-1,1-dioxido-6-phenyl-1,2-thiazinan-2-yl]methyl}phenyl)-1,4-dioxaspiro[4.5]decane-8-carboxamide

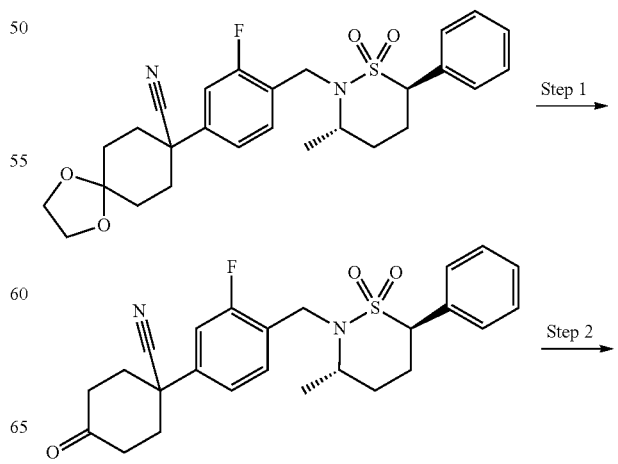

8-(3-fluoro-4-{[(3S,6R)-3-methyl-1,1-dioxido-6-phenyl-1,2-thiazinan-2-yl]methyl}phenyl)-1,4-dioxaspiro[4.5]decane-8-carboxamide was prepared as described in Example 17 using 8-(3-fluoro-4-{[(3S,6R)-3-methyl-1,1-dioxido-6-phenyl-1,2-thiazinan-2-yl]methyl}phenyl)-1,4-dioxaspiro[4.5]decane-8-carbonitrile. $^1$H NMR (400 MHz, DMSO-d$_6$): ☐☐ 7.58 (t, J=8.2 Hz, 1H); 7.37-7.39 (m, 7H); 4.52-4.55 (m, 2H); 4.39 (d, J=17.7 Hz, 1H); 4.14 (dd, J=12.0, 6.9 Hz, 1H); 3.92 (t, J=2.5 Hz, 4H); 2.43-2.45 (m, 1H); 2.19 (d, J=13.2 Hz, 2H); 2.04-2.07 (m, 3H); 1.82-1.88 (m, 5H); 1.66 (d, J=14.2 Hz, 1H); 1.10 (d, J=6.9 Hz, 3H). LCMS RT 5.23 min, m/z 499 [M+1].

Example 10: 1-{3-fluoro-4-[(3-methyl-1,1-dioxido-6-phenyl-1,2-thiazinan-2-yl)methyl]phenyl}-4-hydroxycyclohexanecarbonitrile

Step 1: 1-[3-Fluoro-4-((3S,6R)-3-methyl-1,1-dioxo-6-phenyl-1lambda*6*-[1,2]thiazinan-2-ylmethyl)-phenyl]-4-oxo-cyclohexanecarbonitrile

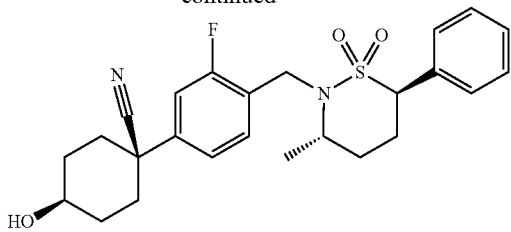

A mixture of 8-(3-fluoro-4-{[(3S,6R)-3-methyl-1,1-dioxido-6-phenyl-1,2-thiazinan-2-yl]methyl}phenyl)-1,4-dioxaspiro[4.5]decane-8-carbonitrile (Example 18, 0.10 g, 0.20 mmol), acetone (5 ml) and 1N HCl solution was heated at 50° C. for 5 h. The reaction was evaporated to dryness, EtOAc (40 mL) added and the organic layer washed with water (20 mL), dried over MgSO$_4$ and evaporated in vacuo. The residue was purified on silica, eluting with (EtOAc/cyclohexane 1:2-1:1) followed by trituration with cyclohexane to give the title compound as a white solid (0.070 g). LCMS RT 4.15 min, m/z 477[M+Na]$^+$.

Step 2: 1-{3-fluoro-4-[(3-methyl-1,1-dioxido-6-phenyl-1,2-thiazinan-2-yl)methyl]phenyl}-4-hydroxycyclohexanecarbonitrile To a solution of the product from Step 1 (0.70 g, 0.15 mmol) in dry THF (5 mL) at −78° C. was added sodium borohydride (0.010 g, 0.26 mmol) and the mixture stirred at −78° C. for 1.5 h. The mixture was allowed to warm to RT and 1N HCl solution (1 mL) added followed by water (20 mL). The product was extracted into EtOAc (30 mL) and dried over MgSO$_4$. The solvent was evaporated in vacuo and purified using preparative HPLC and freeze dried to give the title compound as a white solid as a mixture of cis/trans sultam (0.038 g). LCMS RT 4.60 min, 457 [M+1]. $^1$H NMR (400 MHz, DMSO-d$_6$): □ 7.54-7.56 (m, 1H); 7.39-7.40 (m, 7H); 4.81 (t, J=4.1 Hz, 1H); 4.51-4.53 (m, 2H); 4.38 (d, J=17.7 Hz, 1H); 4.13 (d, J=9.3 Hz, 1H); 3.49-3.58 (m, 2H); 2.38 (d, J=42.0 Hz, 1H); 2.10 (d, J=13.3 Hz, 3H); 1.94 (t, J=12.0 Hz, 4H); 1.57-1.62 (m, 3H); 1.40 (d, J=7.1 Hz, 1H); 1.10 (d, J=6.9 Hz, 2H).

Example 11: 4-{4-[(3-methyl-1,1-dioxido-6-phenyl-1,2-thiazinan-2-yl)methyl]phenyl}tetrahydro-2H-pyran-4-carboxylic acid

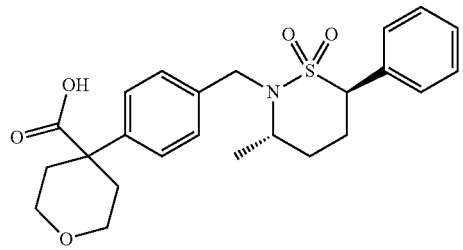 [SMILES: C[C@H]1CC[C@H](c2ccccc2)S(=O)(=O)N1Cc1ccc(C2(C(=O)O)CCOCC2)cc1]

A mixture of methyl 4-(4-{[(3S,6R)-3-methyl-1,1-dioxido-6-phenyl-1,2-thiazinan-2-yl]methyl}phenyl)tetrahydro-2H-pyran-4-carboxylate (0.070 g, 0.15 mmol), 1N NaOH (3 mL) and MeOH (10 ml) was heated to reflux for 3 h. Water (5 mL) was added and the reaction heated to reflux for a further 16 h. The solvent was partially evaporated and the mixture acidified with glacial acetic acid. The resulting white precipitate was filtered off, washed with water and dried to give the title compound as a white solid as a mixture of cis/trans sultam (0.050 g). LCMS RT 4.35 min, m/z 444 [M+1]. $^1$H NMR (400 MHz, DMSO-d$_6$): □ 7.42-7.45 (m, 2H); 7.34-7.36 (m, 7H); 4.37-4.39 (m, 4H); 3.76 (d, J=11.5 Hz, 2H); 3.43 (t, J=11.9 Hz, 4H); 2.31-2.37 (m, 2H); 2.05-2.10 (m, 1H); 1.67-1.73 (m, 4H); 1.33 (d, J=7.1 Hz, 1H); 1.06 (d, J=6.9 Hz, 2H).

Example 12: [4-(4-{[(3S,6R)-3-methyl-1,1-dioxido-6-phenyl-1,2-thiazinan-2-yl]methyl}phenyl)tetrahydro-2H-pyran-4-yl]methanol

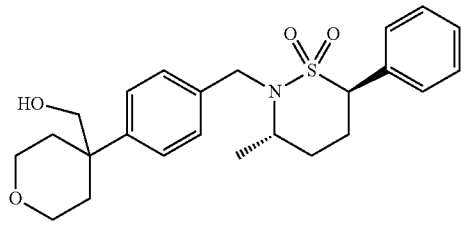 [SMILES: C[C@H]1CC[C@H](c2ccccc2)S(=O)(=O)N1Cc1ccc(C2(CO)CCOCC2)cc1]

To a solution of methyl 4-(4-{[(3S,6R)-3-methyl-1,1-dioxido-6-phenyl-1,2-thiazinan-2-yl]methyl}phenyl)tetrahydro-2H-pyran-4-carboxylate (0.100 g, 0.22 mmol) in dry THF (10 ml) was added LiAlH$_4$ (2M in THF) (0.15 mL, 0.30 mmol) dropwise. The reaction was stirred at RT for 10 minutes then water added dropwise until fizzing stopped. 1N NaOH (0.5 ml) was added, the reaction stirred for 5 minutes then filtered through Celite, and the Celite washed with 5% MeOH/DCM. The filtrate was evaporated to dryness and the residue purified using flash chromatography (EtOAc/cyclohexane 2:1-EtOAc) to give the title compound as a white solid (0.025 g). $^1$H NMR (400 MHz, DMSO-d$_6$ □□□□ 7.37-7.39 (m, 9H); 4.60 (t, J=5.4 Hz, 1H); 4.51 (d, J=16.9 Hz, 1H); 4.41 (dd, J=12.6, 3.6 Hz, 1H); 4.28 (d, J=16.9 Hz, 1H); 4.06-4.10 (m, 1H); 3.65-3.69 (m, 2H); 3.35 (d, J=6.3 Hz, 4H); 2.42-2.44 (m, 1H); 2.10 (dd, J=13.9, 3.9 Hz, 1H); 1.84-1.89 (m, 5H); 1.65 (d, J=14.1 Hz, 1H); 1.10 (d, J=6.9 Hz, 3H). LCMS RT 4.27 min, m/z 430 [M+1].

Example 13: N,N-dimethyl-4-(4-{[(3S,6R)-3-methyl-1,1-dioxido-6-phenyl-1,2-thiazinan-2-yl]methyl}phenyl)tetrahydro-2H-pyran-4-carboxamide

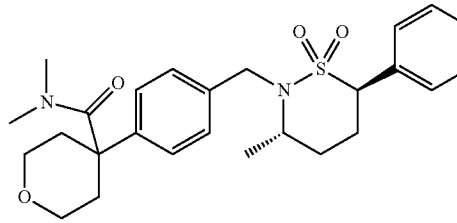

A mixture of 4-{4-[(3-methyl-1,1-dioxido-6-phenyl-1,2-thiazinan-2-yl)methyl]phenyl}tetrahydro-2H-pyran-4-carboxylic acid (0.81 g, 0.18 mmol), dimethylamine solution (2M in THF) (0.30 mL, 0.60 mmol), HATU (0.081 g, 0.21 mmol) DIPEA (0.051 mL, 0.30 mmol) in DCM (15 mL) was stirred at room temperature for 16 h. DCM (30 mL) was added and the organic layer washed with sat. NaHCO₃ dried over MgSO₄ and evaporated in vacuo. The residue obtained was purified on silica eluting with (EtOAc/cyclohexane 2:1-5:1) to give the title compound as a white solid (0.030 g). $^1$H NMR (400 MHz, DMSO-d$_6$) ☐☐☐☐ 7.46 (dd, J=7.5, 1.8 Hz, 2H); 7.39 (d, J=8.0 Hz, 5H); 7.21 (d, J=8.2 Hz, 2H); 4.52 (d, J=16.8 Hz, 1H); 4.41 (dd, J=12.6, 3.6 Hz, 1H); 4.29 (d, J=16.9 Hz, 1 H); 4.05-4.08 (m, 1H); 3.74 (d, J=11.3 Hz, 2H); 3.59 (t, J=11.2 Hz, 2H); 2.63 (br s, 6H); 2.40-2.43 (m, 1H); 2.10-2.14 (m, 3H); 1.82-1.89 (m, 3H); 1.63-1.67 (m, 1H); 1.06 (d, J=6.9 Hz, 3H). LCMS RT 4.5 min, m/z 471 [M+1].

Example 14: N-methyl-4-{4-[(3-methyl-1,1-dioxido-6-phenyl-1,2-thiazinan-2-yl)methyl]phenyl}tetrahydro-2H-pyran-4-carboxamide

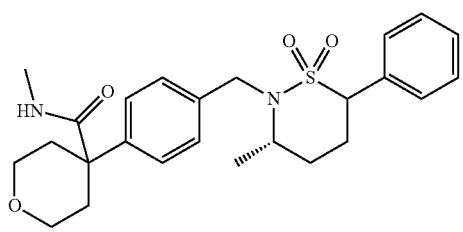 [SMILES: CNC(=O)C1(c2ccc(CN3[C@@H](C)CCC(c4ccccc4)S3(=O)=O)cc2)CCOCC1]

A mixture of 4-{4-[(3-methyl-1,1-dioxido-6-phenyl-1,2-thiazinan-2-yl)methyl]phenyl}tetrahydro-2H-pyran-4-carboxylic acid (0.081 g, 0.18 mmol), methylamine solution (2M in THF) (0.30 mL, 0.60 mmol), HATU (0.081 g, 0.21 mmol) and DIPEA (0.051 mL, 0.30 mmol) was stirred at RT for 16 h in DCM (15 mL). Additional HATU (0.081 g, 0.21 mmol) and methylamine solution (2M in THF, 0.30 mL, 0.60 mmol) was added and the reaction stirred for a further 24 h. DCM (30 mL) was added and the organic layer washed with sat. NaHCO₃ (30 mL), dried over MgSO₄ and evaporated in vacuo. The residue was purified on silica, eluting with (EtOAc/cyclohexane 4:1-EtOAc) to give the title compound as a white solid (0.032 g). LCMS RT 4.16 min, m/z 457 [M+1]. $^1$H NMR (400 MHz, DMSO-d$_6$): ☐ 7.36-7.37 (m, 9H); 4.43-4.45 (m, 3H); 4.28 (d, J=17.0 Hz, 1H); 4.07-4.12 (m, 1H); 3.69-3.74 (m, 3H); 3.42-3.47 (m, 3H); 2.54-2.55 (m, 2H); 2.40-2.43 (m, 2H); 2.10 (dd, J=14.2, 3.8 Hz, 1H); 1.77-1.85 (m, 3H); 1.36-1.40 (m, 1H); 1.10 (d, J=6.9 Hz, 3H).

Example 15 4-(3-Fluoro-4-(((3S,6R)-3-methyl-1,1-dioxido-6-phenyl-1,2-thiazinan-2-yl)methyl)phenyl)tetrahydro-2H-pyran-4-carboxylic acid

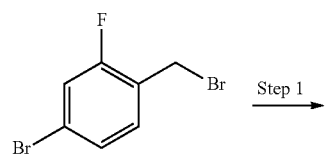

Step 1

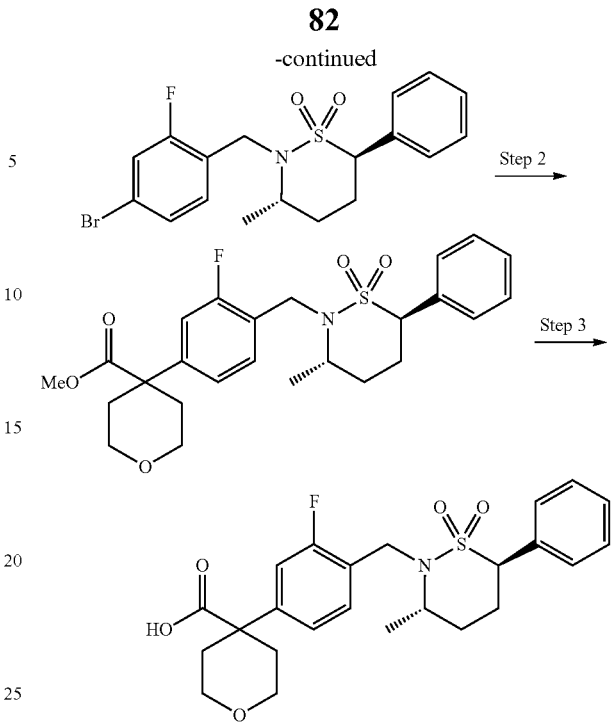

Step 1: (3S,6R)-2-(4-Bromo-2-fluorobenzyl)-3-methyl-6-phenyl-1,2-thiazinane 1,1-dioxide To a solution of (3S,6R)-3-methyl-6-phenyl-thiazinane 1,1-dioxide (22.9 g, 102 mmol) and 4-bromo-1-(bromomethyl)-2-fluoro-benzene (28.6 g, 107 mmol) in N,N-dimethylformamide (300 mL) at 0° C. was added sodium hydride (60% in mineral oil, 4.27 g, 107 mmol) in small portions. The reaction was then stirred at 0° C. for 1 hour before warming to room temperature and stirred at that temperature for an additional 4 hours. Water (500 mL) was then added and the precipitate was collected by filtration and dried under vacuum for 3 hours to give crude material. To the crude solid was added 750 mL of heptane and the suspension was heated to reflux. Under reflux conditions, EtOAc was slowly added until complete dissolution of the material occurred (~250 mL of EtOAc). The solution was then subjected to a hot filtration to remove solid impurities and then cooled to room temperature and subsequently stored at 4° C. for 16 hours. Crystallization occurred an the crystals were collected by filtration to give (3S,6R)-2-[(4-bromo-2-fluoro-phenyl)methyl]-3-methyl-6-phenyl-thiazinane 1,1-dioxide (34 g, 82.5 mmol, 81% yield). $^1$H NMR (300 MHz, DMSO) δ 7.55-7.31 (m, 8H), 4.61-4.43 (m, 2H), 4.41-4.29 (m, 1H), 4.23-4.00 (m, 1H), 2.48-2.34 (m, 1H), 2.18-2.03 (m, 1H), 1.92-1.72 (m, 1H), 1.72-1.58 (m, 1H), 1.12-1.03 (d, J=6.8 Hz, 3H).

Step 2: Methyl 4-(3-fluoro-4-(((3S,6R)-3-methyl-1,1-dioxido-6-phenyl-1,2-thiazinan-2-yl)methyl)phenyl)tetrahydro-2H-pyran-4-carboxylate A flask was charged with (3S,6R)-2-[(4-bromo-2-fluoro-phenyl)methyl]-3-methyl-6-phenyl-thiazinane 1,1-dioxide (10.0 g, 24.3 mmol), bis(dibenzylideneacetone)palladium (1.39 g, 2.43 mmol) and 2-dicyclohexylphosphino-2',6'-di-i-propoxy-1,1'-biphenyl (1.15 g, 2.43 mmol) and purged with nitrogen for 2 minutes. Tetrahydrofuran (120 mL), methyl tetrahydropyran-4-carboxylate (B, 2.5 equiv., 60.6 mmol, 100 mass %) and zinc chloro 2,2,6,6-retramethylpi-peridide lithium chloride complex (0.65M in THF, 93 mL, 60.6 mmol) were subsequently added and the reaction was stirred at 60° C. for 2 hours. The reaction was then cooled to room temperature and quenched with a saturated aqueous solution of NH$_4$Cl (100 mL) and extracted with ethyl acetate (3×100 mL). The combines extracted were dried with MgSO$_4$, concentrated and purified by silica gel column chromatography (0% to 100% EtOAc in heptane) to give methyl 4-[3-fluoro-4-[[(3S,6R)-3-methyl-1,1-dioxo-6-phenyl-thiazinan-2-yl]methyl]phenyl]tetrahydropyran-4-carboxylate (6.5 g, 14 mmol, 56% yield). $^1$H NMR (400 MHz, DMSO) δ 7.55-7.48 (m, 1H), 7.48-7.43 (m, 2H), 7.43-7.33 (m, 3H), 7.26-7.20 (m, 1H), 7.18-7.12 (m, 1H), 4.58-4.47 (m, 2H), 4.41-4.32 (m, 1H), 4.20-4.06 (m, 1H), 3.85-3.75 (m, 2H), 3.66-3.60 (s, 3H), 3.47-3.36 (m, 2H), 2.47-2.31 (m, 3H), 2.15-2.05 (m, 1H), 1.96-1.74 (m, 3H), 1.71-1.61 (m, 1H), 1.15-1.07 (d, J=6.9 Hz, 3H).

Step 3: 4-(3-Fluoro-4-(((3S,6R)-3-methyl-1,1-dioxido-6-phenyl-1,2-thiazinan-2-yl)methyl)phenyl)tetrahydro-2H-pyran-4-carboxylic acid To a solution of methyl 4-[3-fluoro-4-[[(3S,6R)-3-methyl-1,1-dioxo-6-phenyl-thiazinan-2-yl]methyl]phenyl]tetrahydropyran-4-carboxylate (5.67 g, 11.9 mmol) in tetrahydrofuran (60 mL) and water (20 mL) was added lithium hydroxide hydrate (5.0 g, 119 mmol) and the reaction was stirred at room temperature for 72 hours. The reaction was then diluted with water (50 mL) and the pH was adjusted to ~1 using 1N HCl. The product was extracted with EtOAc (3×75 mL), dried with MgSO$_4$, concentrated and purified by silica gel chromatography (0% to 100% EtOAc in heptane) to give 4-[3-fluoro-4-[[(3S, 6R)-3-methyl-1,1-dioxo-6-phenyl-thiazinan-2-yl]methyl]phenyl]tetrahydropyran-4-carboxylic acid (4.0 g, 8.7 mmol, 73% yield). $^1$H NMR (400 MHz, DMSO) δ 7.54-7.43 (m, 3H), 7.43-7.33 (m, 3H), 7.28-7.23 (m, 1H), 7.18-7.12 (m, 1H), 4.58-4.46 (m, 2H), 4.42-4.32 (m, 1H), 4.19-4.05 (m, 1H), 3.84-3.74 (m, 2H), 3.51-3.38 (m, 2H), 2.47-2.41 (m, 1H), 2.38-2.30 (m, 2H), 2.16-2.06 (m, 1H), 1.88-1.74 (m, 3H), 1.72-1.61 (m, 1H), 1.15-1.05 (d, J=6.8 Hz, 3H).

Example 16 2-{[4-(2,5-difluoro-4-{[(3S,6R)-3-methyl-1,1-dioxido-6-phenyl-1,2-thiazinan-2-yl]methyl}phenyl)tetrahydro-2H-pyran-4-yl]oxy}acetamide

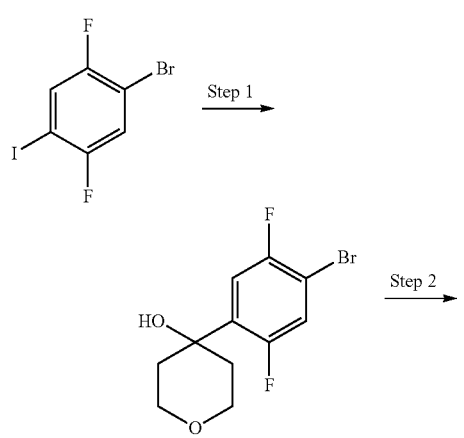

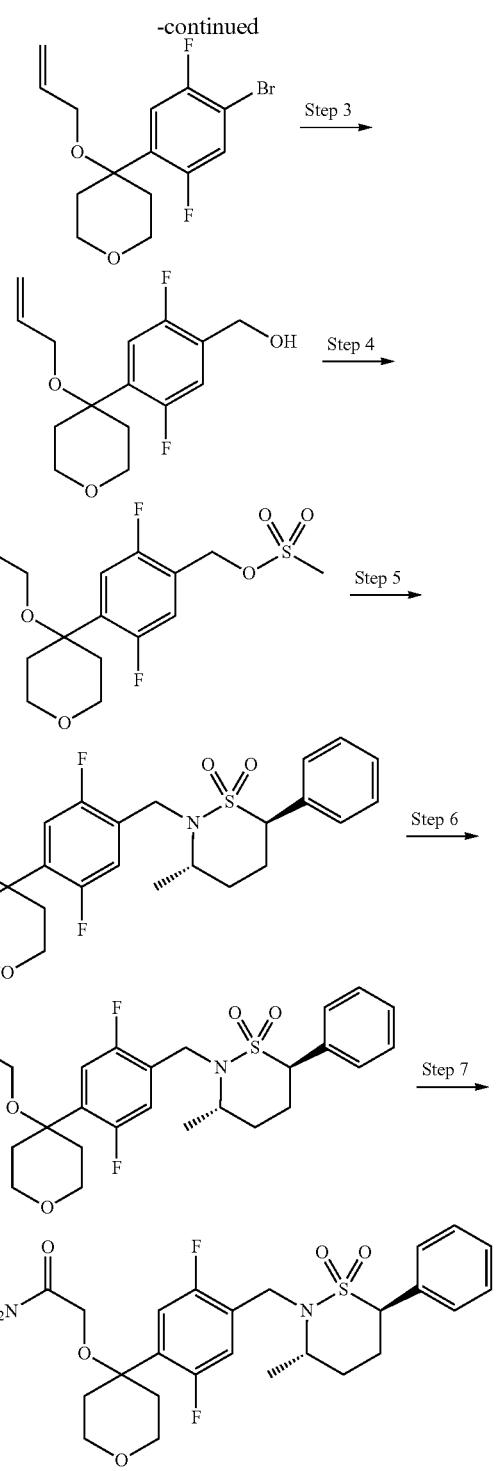

Step 1: 4-(4-Bromo-2,5-difluoro-phenyl)-tetrahydropyran-4-ol

To a stirred solution of 2,5-difluoro-4-bromoiodobenzene (5.0 g, 15.7 mmol) in THF (50 mL) at −30° C. was added iPrMgCl (8.65 mL, 17.3 mmol, 2.0M in THF). A solution of tetrahydropyran-4-one (1.73 mL, 18.8 mmol) in THF (20 mL) was added after 1 h and the reaction stirred for 0.5 h before warming to RT. After 16 h, the reaction was quenched with NH$_4$Cl (30 mL), extracted with EtOAc, dried over Na₂SO₄ and concentrated in vacuo. Purification by flash chromatography (0-80% EtOAc/cyclohexane) gave the title compound as an orange oil (740 mg). ¹H NMR (300 MHz, CDCl₃) □□ 7.31 (2H, dt, J=7.0, 12.9 Hz), 3.90 (4H, ddd, J=5.0, 5.0, 3.4 Hz), 3.49 (1H, d, J=8.3 Hz), 2.36 (4H, qd, J=6.7, 11.5 Hz).

Step 2: 4-Allyloxy-4-(4-bromo-2,5-difluoro-phenyl)-tetrahydro-pyran

To a stirred solution of the product from step 1 (1.16 g, 3.96 mmol) in DME (12 mL) at 0° C. was added NaH (238 mg, 5.94 mmol of a 60% disp. in mineral oil). The reaction was stirred for 0.5 h before allyl bromide (0.51 mL, 5.94 mmol) was added and the reaction stirred at RT for 1 h. The reaction was quenched with brine (30 mL), extracted with EtOAc, dried over Na₂SO₄ and concentrated in vacuo. Purification by flash chromatography (0-80% EtOAc/cyclohexane) gave the title compound as an oil (1.19 g). ¹H NMR (300 MHz, CDCl₃) □□ 7.26 (1H, s), 7.21 (1H, dq, J=6.0, 16.5 Hz), 5.97-5.83 (1H, m), 5.31 (1H, ddd, J=1.6, 3.3, 17.1 Hz), 5.17 (1H, dd, J=1.6, 10.3 Hz), 3.95-3.77 (4H, m), 3.72-3.68 (2H, m), 2.23-2.00 (4H, m).

Step 3: [4-(4-Allyloxy-tetrahydro-pyran-4-yl)-2,5-difluoro-phenyl]-methanol

To a stirred solution of the product from step 2 (1.19 g, 3.57 mmol) in THF (32 mL) at −78° C. was added nBuLi (2.14 mL, 5.36 mmol of a 2.5M solution in hexanes). The reaction was stirred for 0.5 h before DMF (1.16 mL, 14.28 mmol) was added and the reaction was allowed to warm to RT after 0.5 h. The reaction was quenched with NH₄Cl (30 mL) after 1 h at RT, extracted with EtOAc, dried over Na₂SO₄ and concentrated in vacuo. The residue was dissolved in MeOH (20 mL), cooled to 0° C. and NaBH₄ (542 mg, 14.28 mmol) added portionwise. The reaction was quenched with H₂O (20 mL) after 1 h, extracted with EtOAc and the combined extracts were washed with brine, dried over Na₂SO₄ and concentrated in vacuo. Purification by flash chromatography (0-80% EtOAc/cyclohexane) gave the title compound as an oil (968 mg). ¹H NMR (300 MHz, CDCl₃) □ 7.20-7.01 (2H, m), 5.98-5.84 (1H, m), 5.31 (1H, dd, J=1.7, 17.2 Hz), 5.18-5.13 (1H, m), 4.74 (2H, d, J=5.3 Hz), 3.97-3.76 (4H, m), 3.69 (2H, dd, J=1.5, 3.8 Hz), 2.14 (4H, ddd, J=7.3, 18.5, 24.8 Hz).

Step 4: Methanesulfonic acid 4-(4-allyloxy-tetrahydro-pyran-4-yl)-2,5-difluoro-benzyl ester To a stirred solution of the product from step 3 (968 mg, 3.41 mmol) in DCM (34 mL) at 0° C. was added methanesulfonyl chloride (0.33 mL, 4.43 mmol) followed by triethylamine (0.71 mL, 5.12 mmol). After 1 h, the reaction was concentrated in vacuo and the residue was filtered through a phase separator and purified using flash chromatography (0-70% EtOAc/cyclohexane) to give the title compound as an oil (1.05 mg). ¹H NMR (300 MHz, CDCl₃) □ 7.20-7.10 (2H, m), 5.98-5.84 (1H, m), 5.36-5.15 (4H, m), 3.94-3.69 (6H, m), 3.06 (3H, s), 2.21-2.00 (4H, m);

Step 5: (3S,6R)-2-[4-(4-Allyloxy-tetrahydro-pyran-4-yl)-2,5-difluoro-benzyl]-3-methyl-6-phenyl-[1,2]thiazinane 1,1-dioxide To a stirred solution of the product from step 4 (1.05 g, 2.90 mmol) in DMA (6 mL) was added (3S,6R)-3-methyl-6-phenyl-[1,2]thiazine-1,1-dioxide (587 mg, 2.61 mmol) followed by Cs₂CO₃ (1.42 g, 4.35 mmol) and the reaction stirred for 16 h. The reaction was quenched with brine (20 mL), extracted with EtOAc, dried over Na₂SO₄ and concentrated in vacuo. Purification by flash chromatography (0-80% EtOAc/cyclohexane) gave the title compound as a foam (1.26 g). ¹H NMR (300 MHz, CDCl₃) □□ 7.50-7.34 (6H, m), 7.01 (1H, dd, J=6.1, 11.2 Hz), 5.98-5.84 (1H, m), 5.30 (1H, ddd, J=1.7, 3.4, 17.2 Hz), 5.15 (1H, dd, J=1.7, 10.3 Hz), 4.45 (2H, dd, J=18.0, 40.4 Hz), 4.04-3.76 (5H, m), 3.72-3.66 (2H, m), 2.74-2.57 (1H, m), 2.27-2.01 (6H, m), 1.83-1.73 (2H, m), 1.43 (3H, s).

Step 6: {4-[2,5-Difluoro-4-((3S,6R)-3-methyl-1,1-dioxo-6-phenyl-1lambda*6*-[1,2]thiazinan-2-ylmethyl)-phenyl]-tetrahydro-pyran-4-yloxy}-acetic acid To a stirred solution of the product from step 5 (0.3 g, 0.611 mmol) in EtOAc (3 mL), CH₃CN (3 mL) and H₂O (4.5 mL) was added sodium metaperiodate (915 mg, 4.28 mmol) followed by RuCl₃.2H₂O (2.7 mg, 0.012 mmol) and the reaction stirred for 1 h. The reaction was quenched with 1N HCl (10 mL), extracted with EtOAc, and the combined extracts washed with sodium metabisulfite (30 mL), brine, dried over Na₂SO₄ and concentrated in vacuo to give the title compound as a white solid. LCMS RT 3.79 min, m/z 532[M+Na].

Step 7: 2-{[4-(2,5-difluoro-4-{[(3S,6R)-3-methyl-1,1-dioxido-6-phenyl-1,2-thiazinan-2-yl]methyl}phenyl)tetrahydro-2H-pyran-4-yl]oxy}acetamide To a stirred solution of the product from step 6 (250 mg, 0.491 mmol) in DCM (10 mL) was added DMF (2 drops) followed by oxalyl chloride (50 uL, 0.589 mmol). The reaction stirred for 1 h, concentrated in vacuo and the residue taken up in DCM (5 mL) and 2M NH₃/MeOH (5 mL) was added. After 1.5 h the reaction was concentrated in vacuo and purified by MDAP to give the title compound as a white solid (155 mg). ¹H NMR (400 MHz, DMSO) □ 7.46-7.15 (7H, m), 4.58-4.48 (1H, m), 4.37 (1H, d, J=17.8 Hz), 4.17-4.06 (1H, m), 3.80-3.63 (6H, m), 3.47 (2H, s), 2.46-2.37 (1H, m), 2.14-1.98 (6H, m), 1.85-1.73 (1H, m), 1.65 (1H, dd, J=2.1, 14.1 Hz), 1.11 (3H, d, J=6.9 Hz). LCMS RT 3.66 min, m/z 531[M+Na].

Example 18 Ethyl 3-[4-(3-fluoro-4-{[(3S,6R)-3-methyl-1,1-dioxido-6-phenyl-1,2-thiazinan-2-yl]methyl}phenyl)tetrahydro-2H-pyran-4-yl]propanoate

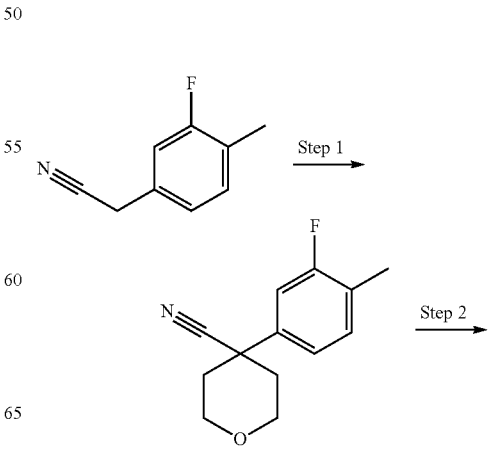

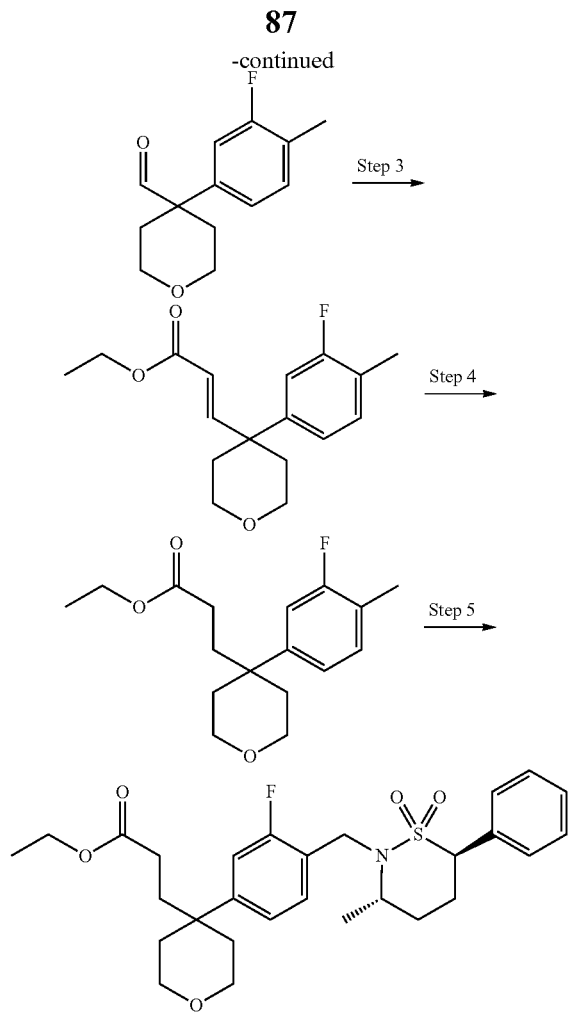

Step 3: (E)-3-[4-(3-Fluoro-4-methyl-phenyl)-tetra-hydro-pyran-4-yl]-acrylic acid ethyl ester To a solution of the product from step 2 (650 mg, 2.9 mmol) in anhydrous THF (25 mL) was added diisopropylamine (4.5 mL, 26 mmol) and lithium bromide (750 mg, 8.67 mmol) followed after 20 minutes by triethylphosphonoacetate (1.72 mL, 8.67 mmol). After standing at RT overnight, further diisopropylamine (2 mL), lithium bromide (300 mg) and triethylphosphonoacetate (0.6 mL, 8.67 mmol) was added and the reaction allowed to stand for 24 h. The reaction was partitioned between 1N HCl/EtOAc, washed with 1N HCl, $H_2O$ then dried over $MgSO_4$ and concentrated in vacuo. Purification by flash chromatography (0-25% EtOAc/cyclohexane) gave the title compound as a colourless oil (750 mg). LCMS RT 4.19 min, no molecular ion.

Step 4: 3-[4-(3-Fluoro-4-methyl-phenyl)-tetrahydro-pyran-4-yl]-propionic acid ethyl ester A mixture of the product from step 3 (750 mg), 10% Pd—C (300 mg) and ammonium formate (1.6 g, 26 mmol) in EtOH (40 mL) was heated at reflux for 10 minutes. The cooled reaction was filtered through a pad of HyFlo and the filter cake washed with EtOH. The filtrate was concentrated in vacuo and partitioned between $EtOAc/H_2O$ dried over $MgSO_4$ and concentrated in vacuo. Purification by flash chromatography (0-10% $EtOAc/CH_2Cl_2$) gave the title compound as a colourless oil (550 mg). $^1$H NMR (300 MHz, $CDCl_3$) □ 7.15 (1H, dd, J=8.2, 8.2 Hz), 4.06-3.99 (2H, m), 3.78 (2H, ddd, J=3.9, 5.3, 11.7 Hz), 3.58-3.48 (2H, m), 2.25 (3H, d, J=1.6 Hz), 2.13-2.03 (2H, m), 2.04 (2H, s), 1.99-1.89 (4H, m), 1.87-1.75 (2H, m), 1.19 (3H, t, J=7.5 Hz). LCMS RT 4.18 min, no molecular ion.

Step 5: Ethyl 3-[4-(3-fluoro-4-{[(3S,6R)-3-methyl-1,1-dioxido-6-phenyl-1,2-thiazinan-2-yl]methyl}phenyl)tetrahydro-2H-pyran-4-yl]propanoate The product from step 4 (550 mg, 1.87 mmol) was reacted as described in example 9 to give the title compound as a white solid (220 mg). $^1$H NMR (400 MHz, DMSO) □ 7.49-7.33 (6H, m), 7.18-7.09 (2H, m), 4.52-4.45 (2H, m), 4.35 (1H, d, J=17.5 Hz), 4.14-4.04 (1H, m), 3.89 (2H, q, J=7.1 Hz), 3.64-3.62 (2H, m), 3.37-3.30 (2H, m), 2.45-2.35 (1H, m), 2.11-1.98 (2H, m), 1.85-1.70 (9H, m), 1.09-1.04 (6H, m). LCMS RT 5.27 min, m/z 518.1[M+].

Example 19 1-[4-(3-fluoro-4-{[(3S,6R)-3-methyl-1,1-dioxido-6-phenyl-1,2-thiazinan-2-yl]methyl}phenyl)tetrahydro-2H-pyran-4-yl]methanamine hydrogen chloride

Step 1: 4-(3-Fluoro-4-methyl-phenyl)-tetrahydro-pyran-4-carbonitrile

A mixture of (3-fluoro-4-methylphenyl)acetonitrile, (745 mg, 5 mmol), chloro-2-(2-chloroethoxy)ethane (586 uL, 5.0 mmol) and hexadexyl tributylphosphonium bromide (130 mg, 0.25 mmol) in 50% NaOH (w/w, 8 mL) was heated at 100° C. for 1.5 h. The cooled reaction was quenched with $H_2O$ (30 mL), extracted with EtOAc, dried over $MgSO_4$ and concentrated in vacuo. Purification by flash chromatography (10-20% EtOAc/cyclohexane) gave the title compound as a yellow solid (600 mg). LCMS RT 3.78 min, no molecular ion.

Step 2: 4-(3-Fluoro-4-methyl-phenyl)-tetrahydro-pyran-4-carbaldehyde

To a stirred solution of the product from step 1 (929 mg, 4.2 mmol) in $CH_2Cl_2$ (10 mL) at −78° C. was added over 3 minutes DIBAL-H (4.4 mL, 4.4 mmol of 1M solution in $CH_2Cl_2$). After 2.5 h, EtOH (5 drops) was added followed by 1N HCl (4 mL) and the reaction allowed to stir whilst warming to RT over 0.5 h. The organic phase and extracts were dried over $MgSO_4$ and concentrated in vacuo. Purification by flash chromatography (20-33% EtOAc/cyclohexane) gave the title compound as a colourless oil (650 mg). LCMS RT 3.79 min, m/z 223.2[M+1].

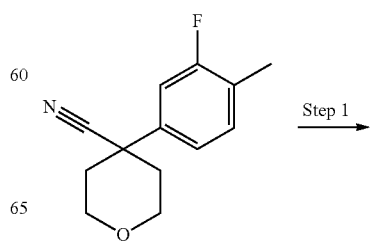

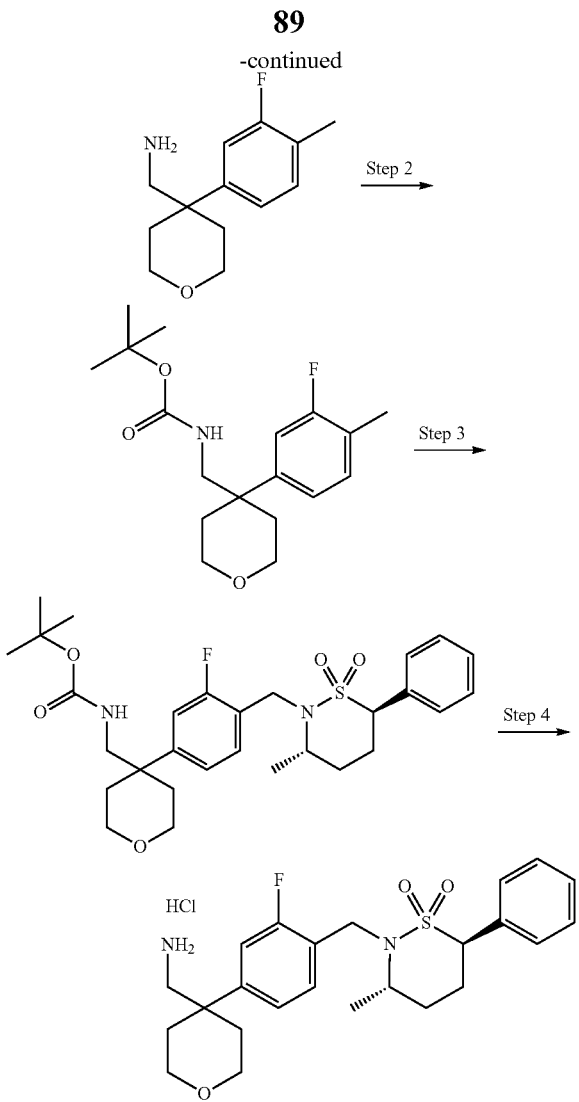

Step 3: {4-[3-Fluoro-4-((3S,6R)-3-methyl-1,1-dioxo-6-phenyl-1lambda*6*-[1,2]thiazinan-2-ylmethyl)-phenyl]-tetrahydro-pyran-4-ylmethyl}-carbamic acid tert-butyl ester The product from step 2 (600 mg, 1.85 mmol) was reacted as described in example 9 to give the title compound as a white solid (270 mg). $^1$H NMR (400 MHz, DMSO) □□ 7.46-7.33 (6H, m), 7.16-7.03 (2H, m), 6.66 (1H, dd, J=6.2, 6.2 Hz), 4.51-4.43 (2H, m), 4.33 (1H, d, J=17.4 Hz), 4.09 (1H, dd, J=6.8, 10.7 Hz), 3.69-3.65 (2H, m), 3.06 (2H, d, J=6.3 Hz), 2.46-2.36 (1H, m), 2.08 (1H, dd, J=3.2, 13.8 Hz), 1.94 (2H, d, J=13.7 Hz), 1.84-1.62 (4H, m), 1.25 (9H, s), 1.15 (1H, s), 1.06 (3H, d, J=6.8 Hz). LCMS RT 5.21 min, m/z 547.2[M+1].

Step 4: 1-[4-(3-fluoro-4-{[(3S,6R)-3-methyl-1,1-dioxido-6-phenyl-1,2-thiazinan-2-yl]methyl}phenyl)tetrahydro-2H-pyran-4-yl]methanamine hydrogen chloride The product from step 3 (950 mg, 1.7 mmol) was dissolved in 4N HCl/dioxane (10 mL) and allowed to stand for 1 h. The solid was collected by filtration and washed with Et$_2$O to give the title compound as a white solid (750 mg). $^1$H NMR (400 MHz, DMSO) □ 7.49-7.34 (6H, m), 7.18-7.06 (2H, m), 4.52-4.45 (2H, m), 4.35 (1H, d, J=17.4 Hz), 4.14-4.06 (1H, m), 3.68-3.60 (2H, m), 3.38-3.32 (2H, m), 3.33 (2H, d, J=9.1 Hz), 2.61 (2H, s), 2.46-2.36 (1H, m), 2.11-1.90 (3H, m), 1.82-1.71 (3H, m), 1.64 (1H, dd, J=2.2, 14.2 Hz), 1.27-1.27 (2H, m), 1.07 (3H, d, J=6.9 Hz). LCMS RT 3.23 min, m/z 447.1[M+1].

Example 20 3-[4-(3-fluoro-4-{[(3S,6R)-3-methyl-1,1-dioxido-6-phenyl-1,2-thiazinan-2-yl]methyl}phenyl)tetrahydro-2H-pyran-4-yl]propanenitrile

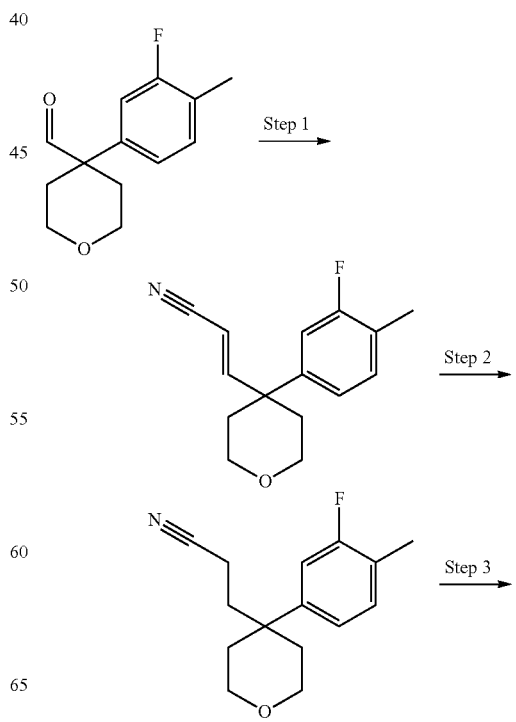

Step 1: C-[4-(3-Fluoro-4-methyl-phenyl)-tetrahydro-pyran-4-yl]-methylamine

To a solution of 4-(3-fluoro-4-methyl-phenyl)-tetrahydro-pyran-4-carbonitrile (700 mg, 3.2 mmol) in anhydrous THF (30 mL) was added dropwise LiAlH$_4$ (2.5 ml, 5 mmol of a 2M solution in THF) and the reaction stirred for 18 h. The reaction was carefully quenched with H$_2$O, stirred with 1N NaOH (1 mL) for 10 minutes, filtered and the filtrate concentrated in vacuo to give the title compound as an oil (720 mg).

Step 2: [4-(3-Fluoro-4-methyl-phenyl)-tetrahydro-pyran-4-ylmethyl]-carbamic acid tert-butyl ester The product from step 1 (720 mg, 3.2 mmol) was dissolved in DCM (50 mL) and triethylamine (0.55 mL, 4 mmol) followed by di-tert-butyldicarbonate (0.76 g, 3.5 mmol) and the reaction allowed to stand at room temperature for 1.5 h. The reaction was concentrated in vacuo and the residue was purified using flash chromatography (0-25% EtOAc/cyclohexane) to give the title compound as a colourless oil (600 mg).

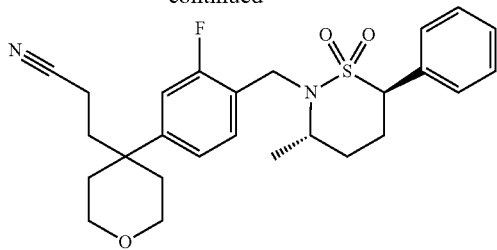

Step 1: 4-(3-Fluoro-4-methyl-phenyl)-tetrahydro-pyran-4-carbaldehyde

A solution of 4-(3-fluoro-4-methyl-phenyl)-tetrahydro-pyran-4-carbaldehyde (700 mg, 3.15 mmol), (triphenylphosphoranylidene)acetonitrile (1.05 g, 3.5 mmol) in PhCH₃ (15 mL) was heated to 90° C. for 1 h. The reaction was concentrated in vacuo and the residue was purified using flash chromatography (20-33% EtOAc/cyclohexane) to give the title compound as a colourless oil (580 mg). LCMS RT 3.85 min, m/z 246.2 [M+1].

Step 2: (E)-3-[4-(3-Fluoro-4-methyl-phenyl)-tetrahydro-pyran-4-yl]-acrylonitrile A mixture of the product from step 1 (580 mg, 2.4 mmol), 10% Pd—C (250 mg) and ammonium formate (1.5 g, 24 mmol) in EtOH (30 mL) was heated at reflux for 5 minutes. The cooled reaction was filtered through a pad of HyFlo and the filter cake washed with EtOH. The filtrate was concentrated in vacuo and the residue was purified using flash chromatography (10-20% EtOAc/cyclohexanes) to give the title compound as a colourless oil (550 mg). LCMS RT 3.75 min, m/z 248.2 [M+1].

Step 3: 3-[4-(3-fluoro-4-{[(3S,6R)-3-methyl-1,1-dioxido-6-phenyl-1,2-thiazinan-2-yl]methyl}phenyl)tetrahydro-2H-pyran-4-yl]propanenitrile The product from step 2 (550 mg, 2.23 mmol) was reacted as described in example 9 to give the title compound as a white solid (350 mg). ¹H NMR (400 MHz, DMSO) □ 7.51-7.34 (6H, m), 7.20-7.12 (2H, m), 4.52-4.45 (2H, m), 4.35 (1H, d, J=17.4 Hz), 4.14-3.99 (1H, m), 3.69-3.63 (2H, m), 3.38-3.30 (2H, m), 2.45-2.30 (1H, m), 2.12-1.63 (12H, m). LCMS RT 4.87 min, m/z 471.1[M+1].

Example 21 3-[4-(3-fluoro-4-{[(3S,6R)-3-methyl-1,1-dioxido-6-phenyl-1,2-thiazinan-2-yl]methyl}phenyl)tetrahydro-2H-pyran-4-yl]propanamide

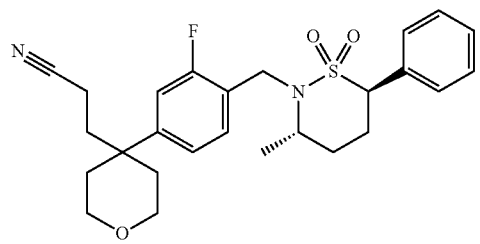

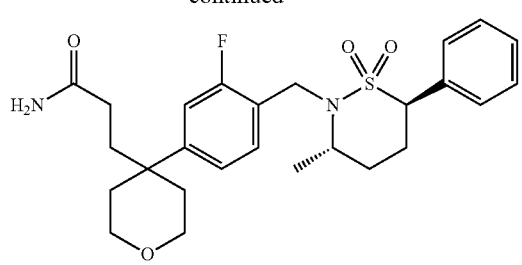

Step 1: 3-[4-(3-fluoro-4-{[(3S,6R)-3-methyl-1,1-dioxido-6-phenyl-1,2-thiazinan-2-yl]methyl}phenyl)tetrahydro-2H-pyran-4-yl]propanamide A mixture of 3-[4-(3-fluoro-4-{[(3S,6R)-3-methyl-1,1-dioxido-6-phenyl-1,2-thiazinan-2-yl]methyl}phenyl)tetrahydro-2H-pyran-4-yl]propanenitrile (80 mg, 0.169 mmol) and hydrido(dimethylphosphinous acid-kP) [hydrogen bis(dimethylphosphinito-kP)]platinum (II) (4 mg) in EtOH (10 mL) was heated at reflux for 8 h. The reaction was allowed to stand at RT overnight, heated to reflux and 4 mL H₂O was added and the EtOH allowed to evaporate. A white solid which formed on cooling was collected to give the title compound 978 mg). ¹H NMR (400 MHz, DMSO) □□ 7.49-7.33 (6H, m), 7.18-7.07 (3H, m), 6.58 (1H, s), 4.52-4.45 (2H, m), 4.35 (1H, d, J=17.4 Hz), 4.15-4.04 (1H, m), 3.69-3.60 (2H, m), 3.41-3.33 (2H, m), 2.45-2.36 (1H, m), 2.12-2.03 (1H, m), 1.98 (2H, dd, J=3.0, 13.1 Hz), 1.84-1.57 (8H, m), 1.07 (3H, d, J=6.9 Hz). LCMS RT 4.87 min, m/z 489.1[M+1].

Example 22 4-(3-fluoro-4-{[(3S,6R)-3-methyl-1,1-dioxido-6-phenyl-1,2-thiazinan-2-yl]methyl}phenyl)tetrahydro-2H-pyran-4-amine

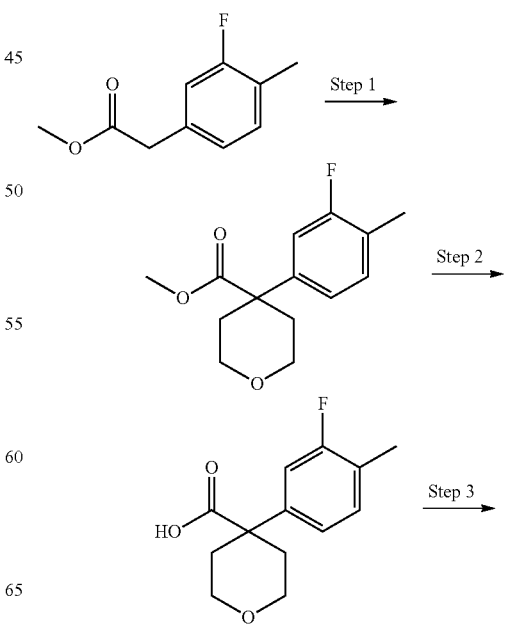

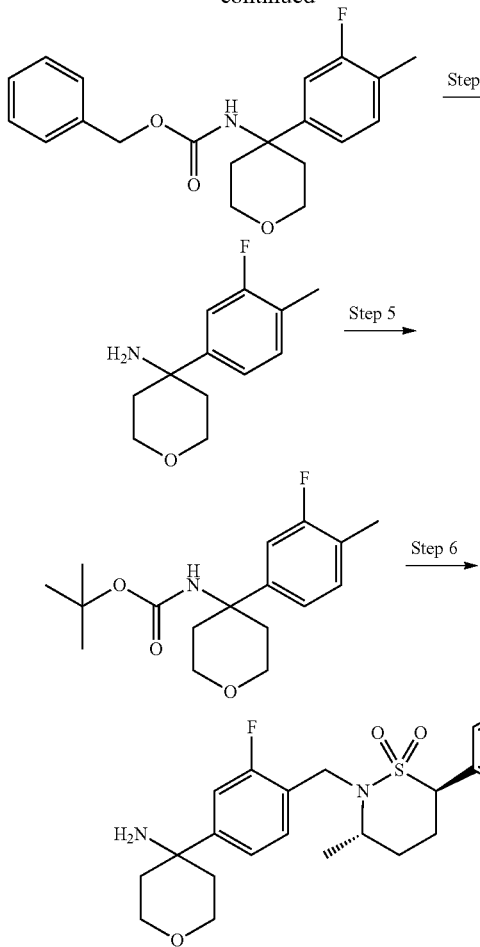

Step 1: 4-(3-Fluoro-4-methyl-phenyl)-tetrahydropyran-4-carboxylic acid methyl ester A mixture of bromo-2-(2-bromoethoxy)ethane (21.4 g, 92.2 mmol) and NaH (7.7 g, 192 mmol of a 60% dispersion in mineral oil) in NMP (100 mL) at 0° C. was treated with a solution of (3-fluoro-4-methyl-phenyl)-acetic acid methyl ester, (14 g, 76.8 mmol) in NMP (50 mL) whilst keeping the internal temperature below 25° C. On complete addition, the cooling bath was removed and stirring continued for 18 h. The reaction was partitioned between EtOAc/H₂O, extracted with EtOAc and the combined extracts washed with H₂O, brine, dried over MgSO₄ and concentrated in vacuo. Purification by flash chromatography (0-20% EtOAc/cyclohexane) gave the title compound as a colourless oil which solidified on standing (11.35 g). $^1$H NMR (300 MHz, CDCl₃) □ 7.18-7.11 (1H, m), 7.05-7.00 (2H, m), 3.96-3.87 (2H, m), 3.67 (3H, s), 3.66-3.49 (2H, m), 2.48 (2H, dd, J=2.9, 13.6 Hz), 2.25 (3H, d, J=1.8 Hz), 1.99-1.90 (2H, m).

Step 2: 4-(3-Fluoro-4-methyl-phenyl)-tetrahydropyran-4-carboxylic acid

A solution of the product from step 1 (4.69 g, 18.5 mmol) in MeOH (40 mL) was treated with NaOH (2.23 g, 55.7 mmol) in H₂O (10 mL) and the reaction heated to 50° C. for 2 h. The cooled reaction was evaporated in vacuo and the residue dissolved in H₂O and washed with Et₂O. The aqueous phase was acidified with 2N HCl and extracted into CH₂Cl₂, dried over Na₂SO₄ and concentrated in vacuo to give the title compound as a white solid (4.05 g). $^1$H NMR (300 MHz, CDCl₃) □ 7.18-7.03 (3H, m), 3.96-3.87 (2H, m), 3.66-3.56 (2H, m), 2.47 (2H, d, J=13.3 Hz), 2.25 (3H, d, J=1.7 Hz), 2.01-1.90 (2H, m).

Step 3: [4-(3-Fluoro-4-methyl-phenyl)-tetrahydro-pyran-4-yl]-carbamic acid benzyl ester A solution of the product from step 2 (4.05 g, 16.9 mmol), diphenylphosphoryl azide (5.15 g, 18.6 mmol), n-butanol (2.2 g, 20.3 mmol) and Et₃N (2.06 g, 20.3 mmol) in PhCH₃ (40 mL) was heated to 90° C. for 18 h. The cooled reaction was evaporated in vacuo and the residue dissolved in EtOAc and washed with 0.5M citric acid. The organic phase was washed with H₂O, NaHCO₃, H₂O, brine, dried over Na₂SO₄ and concentrated in vacuo. The residue was purified using flash chromatography (0-40% EtOAc/cyclohexane) to give the title compound as a colourless gum (5.8 g). $^1$H NMR (300 MHz, CDCl₃) □ 7.40-7.28 (6H, m), 7.19-6.98 (3H, m), 5.11 (1H, s), 5.01 (2H, s), 3.89-3.68 (4H, m), 2.24 (3H, d, J=1.7 Hz), 2.21-2.05 (3H, m).

Step 4: 4-(3-Fluoro-4-methyl-phenyl)-tetrahydropyran-4-ylamine

To a solution of the product from step 2 (5.8 g, 16.8 mmol) in IMS (60 mL) was added 10% Pd—C (600 mg) and the flask evacuated, purged with hydrogen from a balloon and left to stir for 18 h. The reaction was filtered through a PTFE filter and the filtrate evaporated in vacuo to give the title compound as a sticky solid (3.5 g). $^1$H NMR (300 MHz, DMSO) □□ 7.33-7.22 (3H, m), 3.90-3.78 (2H, m), 3.57-3.50 (2H, m), 2.21 (3H, d, J=1.8 Hz), 2.07-1.95 (2H, m), 1.61 (2H, d, J=13.3 Hz).

Step 5: [4-(3-Fluoro-4-methyl-phenyl)-tetrahydropyran-4-yl]-carbamic acid tert-butyl ester A mixture of the product from step 4 (3.5 g, 16.7 mmol), di-tert-butyldicarbonate (4.02 g, 18.3 mmol) and Et₃N (2.54 g, 25 mmol) in DCE (35 mL) was heated to 70° C. for 18 h. The cooled reaction was partitioned between EtOAc/0.5M citric acid and the organic phase was washed with NaHCO₃, H₂O, brine, dried over Na₂SO₄ and concentrated in vacuo. The residue was purified using flash chromatography (0-40% EtOAc/cyclohexane) to give the title compound as a colourless gum which solidified on standing (4.53 g). $^1$H NMR (300 MHz, CDCl₃) □ 7.18-7.00 (3H, m), 4.85 (1H, s), 3.90-3.70 (4H, m), 2.24 (3H, d, J=1.6 Hz), 2.17-2.06 (4H, m), 1.44-1.27 (9H, m).

Step 6: 4-(3-fluoro-4-{[(3S,6R)-3-methyl-1,1-dioxido-6-phenyl-1,2-thiazinan-2-yl]methyl}phenyl)tetrahydro-2H-pyran-4-amine The product from step 5 (5.5 g, 14.5 mmol) was reacted as described in example 9 and then example 4, step 4 before being purified by SCX column to give the title compound as a white solid (2.68 g). $^1$H NMR (400 MHz, CDCl₃) □□ 7.66 (1H, dd, J=8.1, 8.1 Hz), 7.46 (2H, dd, J=1.7, 7.7 Hz), 7.40-7.35 (3H, m), 7.25 (1H, s), 7.24 (1H, dd, J=2.0, 6.1 Hz), 7.11 (1H, dd, J=1.8, 12.3 Hz), 4.49 (2H, dd, J=14.8, 51.3 Hz), 4.30-4.22 (1H, m), 4.02-3.86 (3H, m), 3.81-3.74 (2H, m), 2.70-2.58 (1H, m), 2.26-2.08 (3H, m), 1.82-1.73 (2H, m), 1.61 (2H, dd, J=1.2, 11.6 Hz), 1.14 (3H, d, J=6.9 Hz). LCMS RT 3.34 min, m/z 416.1[M+1].

Example 23 [4-(3-fluoro-4-{[(3S,6R)-3-methyl-1,1-dioxido-6-phenyl-1,2-thiazinan-2-yl]methyl}phenyl) tetrahydro-2H-pyran-4-yl]acetonitrile

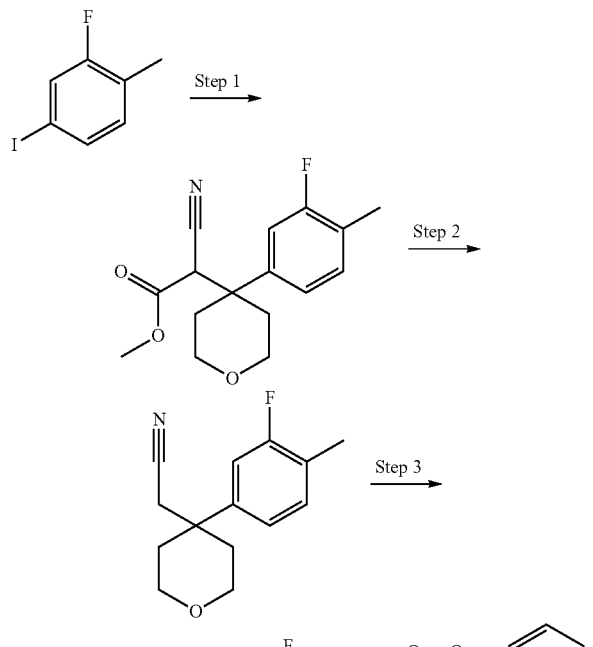

Step 1: Cyano-[4-(3-fluoro-4-methyl-phenyl)-tetra-hydro-pyran-4-yl]-acetic acid methyl ester A solution of 2-fluoro-4-iodotoluene (1.6 g, 6.65 mmol) in THF (15 mL) was cooled to −30° C. under an Argon atmosphere. iPrMgCl (2M in THF, 3.6 mL, 7.2 mmol) was added. The reaction was stirred at −30° C. for 1 h and copper (I) bromide dimethyl sulfide complex (30 mg) was added followed by cyano-(tetrahydro-pyran-4-ylidene)-acetic acid ethyl ester (1.1 g, 5.64 mmol) dissolved in THF (5 mL). The reaction was stirred for 0.25 h and at room temperature for 16 h. The reaction was partitioned between EtOAc/NH$_4$Cl and the organic phase was washed with brine, dried over MgSO$_4$ and concentrated in vacuo.

Step 2: [4-(3-Fluoro-4-methyl-phenyl)-tetrahydro-pyran-4-yl]-acetonitrile

A mixture of the product from step 1 and KOH (0.63 g) in ethylene glycol (10 mL) were heated at 190° C. for 0.5 h. The cooled reaction was partitioned between EtOAc/NH$_4$Cl and the organic phase was washed with brine, dried over MgSO$_4$ and concentrated in vacuo. Purification by flash chromatography (10-60% EtOAc/cyclohexane) gave the title compound as a pale yellow oil (1.31 g). $^1$H NMR (300 MHz, CDCl$_3$) ☐☐ 7.22 (1H, t, J=7.8 Hz), 7.06-6.96 (2H, m), 3.83-3.74 (2H, m), 3.62-3.52 (2H, m), 2.57 (2H, s), 2.27 (4H, d, J=1.6 Hz), 2.22-2.19 (1H, m), 2.05-1.91 (2H, m).

Step 3: [4-(3-fluoro-4-{[(3S,6R)-3-methyl-1,1-dioxido-6-phenyl-1,2-thiazinan-2-yl]methyl}phenyl) tetrahydro-2H-pyran-4-yl]acetonitrile A solution of the product from step 2 (162 mg, 0.52 mmol) was reacted as described in example 9 to give the title compound as a solid (125 mg). $^1$H NMR (400 MHz, DMSO) ☐☐ 7.54-7.22 (8H, m), 4.54-4.48 (2H, m), 4.37 (1H, d, J=17.5 Hz), 4.15-4.07 (1H, m), 3.72-3.66 (2H, m), 3.66 (2H, d, J=3.6 Hz), 2.91 (2H, s), 2.46-2.36 (1H, m), 2.13-2.05 (3H, m), 1.88-1.75 (3H, m), 1.64 (1H, dd, J=2.2, 14.2 Hz), 1.08 (3H, d, J=6.9 Hz). LCMS RT 4.74 min, m/z 457.1[M+1].

The above compounds, together with additional compounds made by the same procedures above, are shown below in Table 4, together with IC$_{50}$ values for RORc.

TABLE 4

| | Structure | name | IC$_{50}$ |
|---|---|---|---|
| 1 | 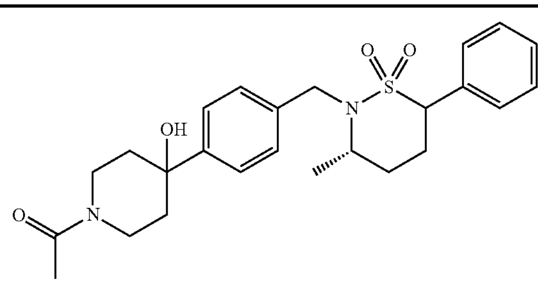 | 1-{4-Hydroxy-4-[4-((S)-3-methyl-1,1-dioxo-6-phenyl-[1,2]thiazinan-2-ylmethyl)-phenyl]-piperidin-1-yl}-ethanone | 0.120 |
| 2 | 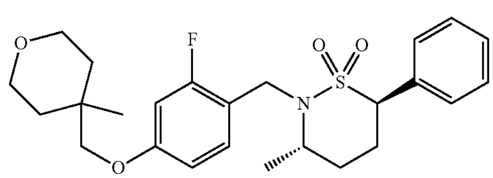 [SMILES: C[C@H]1CC[C@H](c2ccccc2)S(=O)(=O)N1Cc1ccc(OCC2(C)CCOCC2)cc1F] | (3S,6R)-2-[2-Fluoro-4-(4-methyl-tetrahydro-pyran-4-ylmethoxy)-benzyl]-3-methyl-6-phenyl-[1,2]thiazinane 1,1-dioxide | 0.067 |

TABLE 4-continued

| | Structure | name | IC$_{50}$ |
|---|---|---|---|
| 3 | 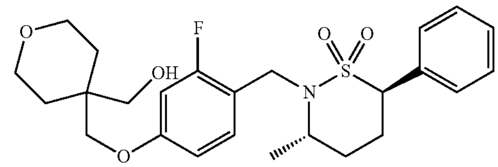 [SMILES: C[C@H]1CC[C@H](c2ccccc2)S(=O)(=O)N1Cc1ccc(OCC2(CO)CCOCC2)cc1F] | {4-{3-Fluoro-4-((3S,6R)-3-methyl-1,1-dioxo-6-phenyl-[1,2]thiazinan-2-ylmethyl)-phenoxymethyl}-tetrahydro-pyran-4-yl}-methanol | 0.082 |
| 4 | 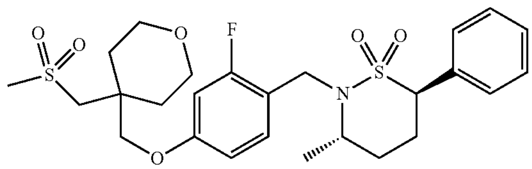 [SMILES: C[C@H]1CC[C@H](c2ccccc2)S(=O)(=O)N1Cc1ccc(OCC2(CS(C)(=O)=O)CCOCC2)cc1F] | (3S,6R)-2-[2-Fluoro-4-(4-methanesulfonylmethyl-tetrahydro-pyran-4-ylmethoxy)-benzyl]-3-methyl-6-phenyl-[1,2]thiazinane 1,1-dioxide | 0.046 |
| 5 | 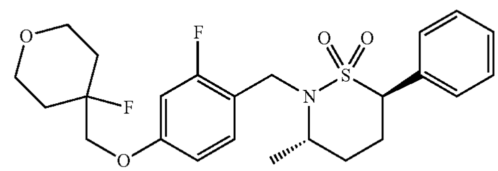 [SMILES: C[C@H]1CC[C@H](c2ccccc2)S(=O)(=O)N1Cc1ccc(OCC2(F)CCOCC2)cc1F] | (3S,6R)-2-[2-Fluoro-4-(4-fluoro-tetrahydro-pyran-4-ylmethoxy)-benzyl]-3-methyl-6-phenyl-[1,2]thiazinane 1,1-dioxide | 0.160 |
| 6 | 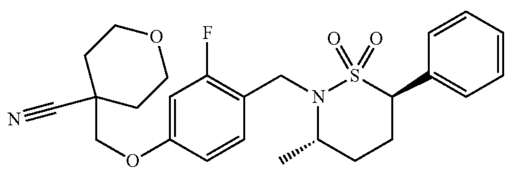 [SMILES: C[C@H]1CC[C@H](c2ccccc2)S(=O)(=O)N1Cc1ccc(OCC2(C#N)CCOCC2)cc1F] | 4-{3-Fluoro-4-((3S,6R)-3-methyl-1,1-dioxo-6-phenyl-[1,2]thiazinan-2-ylmethyl)-phenoxymethyl}-tetrahydro-pyran-4-carbonitrile | 0.220 |
| 7 | 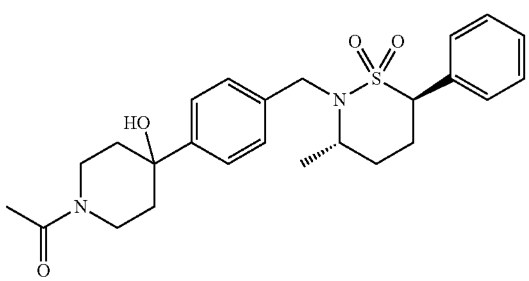 [SMILES: CC(=O)N1CCC(O)(c2ccc(CN3[C@@H](C)CC[C@H](c4ccccc4)S3(=O)=O)cc2)CC1] | 1-{4-Hydroxy-4-[4-((3S,6R)-3-methyl-1,1-dioxo-6-phenyl-[1,2]thiazinan-2-ylmethyl)-phenyl]-piperidin-1-yl}-ethanone | 0.330 |
| 8 | 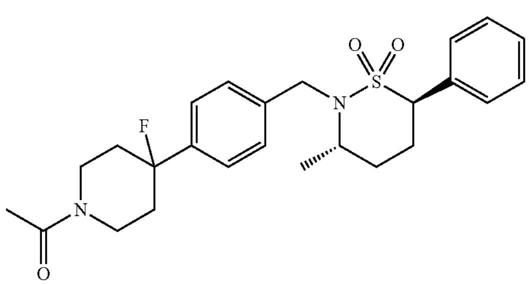 [SMILES: CC(=O)N1CCC(F)(c2ccc(CN3[C@@H](C)CC[C@H](c4ccccc4)S3(=O)=O)cc2)CC1] | 1-{4-Fluoro-4-[4-((3S,6R)-3-methyl-1,1-dioxo-6-phenyl-[1,2]thiazinan-2-ylmethyl)-phenyl]-piperidin-1-yl}-ethanone | 0.200 |
| 9 | 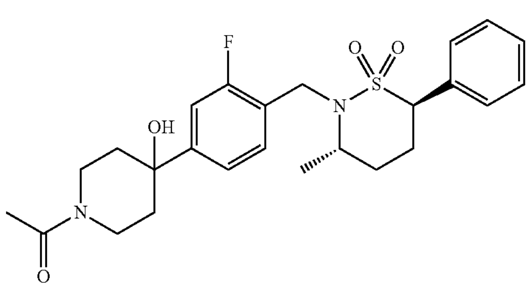 [SMILES: CC(=O)N1CCC(O)(c2ccc(CN3[C@@H](C)CC[C@H](c4ccccc4)S3(=O)=O)c(F)c2)CC1] | 1-{4-[3-Fluoro-4-((3S,6R)-3-methyl-1,1-dioxo-6-phenyl-[1,2]thiazinan-2-ylmethyl)-phenyl]-4-hydroxy-piperidin-1-yl}-ethanone | 0.130 |

TABLE 4-continued

| | Structure | name | IC$_{50}$ |
|---|---|---|---|
| 10 | 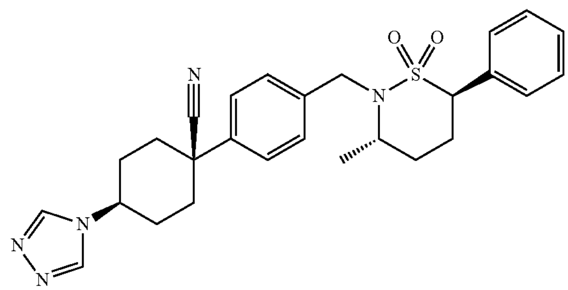 [SMILES: C[C@H]1CC[C@H](c2ccccc2)S(=O)(=O)N1Cc1ccc([C@]2(C#N)CC[C@@H](n3cnnc3)CC2)cc1] | 1-[4-((3S,6R)-3-Methyl-1,1-dioxo-6-phenyl-[1,2]thiazinan-2-ylmethyl)-phenyl]-4-[1,2,4]triazol-4-yl-cyclohexanecarbonitrile | 0.150 |
| 11 | 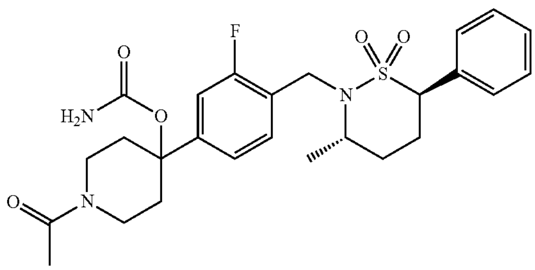 [SMILES: CC(=O)N1CCC(OC(N)=O)(c2ccc(CN3[C@@H](C)CC[C@H](c4ccccc4)S3(=O)=O)c(F)c2)CC1] | Carbamic acid 1-acetyl-4-[3-fluoro-4-((3S,6R)-3-methyl-1,1-dioxo-6-phenyl-[1,2]thiazinan-2-ylmethyl)-phenyl]-piperidin-4-yl ester | 0.410 |
| 12 | 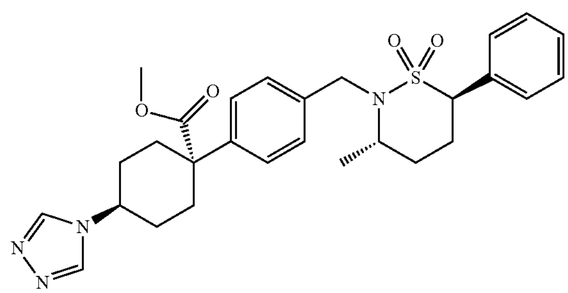 [SMILES: COC(=O)[C@]1(c2ccc(CN3[C@@H](C)CC[C@H](c4ccccc4)S3(=O)=O)cc2)CC[C@@H](n2cnnc2)CC1] | 1-[4-((3S,6R)-3-Methyl-1,1-dioxo-6-phenyl-[1,2]thiazinan-2-ylmethyl)-phenyl]-4-[1,2,4]triazol-4-yl-cyclohexanecarboxylic acid methyl ester | 0.630 |
| 13 | 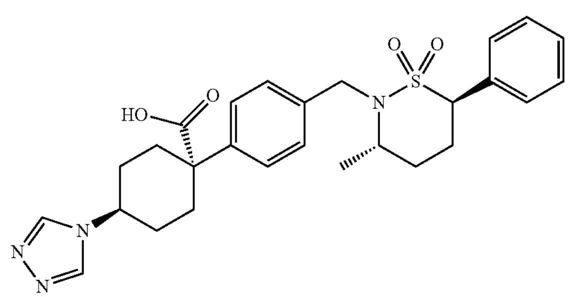 [SMILES: C[C@H]1CC[C@H](c2ccccc2)S(=O)(=O)N1Cc1ccc([C@]2(C(=O)O)CC[C@H](n3cnnc3)CC2)cc1] | 1-[4-((3S,6R)-3-Methyl-1,1-dioxo-6-phenyl-[1,2]thiazinan-2-ylmethyl)-phenyl]-4-[1,2,4]triazol-4-yl-cyclohexane-carboxylic acid | 2.700 |
| 14 | 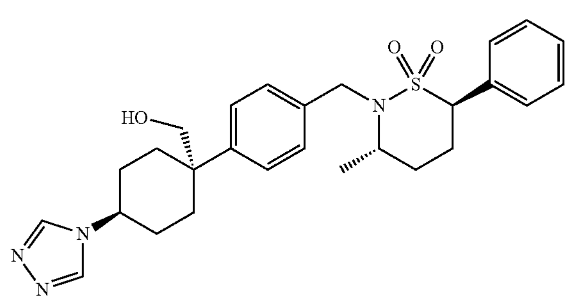 [SMILES: C[C@H]1CC[C@H](c2ccccc2)S(=O)(=O)N1Cc1ccc([C@]2(CO)CC[C@H](n3cnnc3)CC2)cc1] | {1-[4-((3S,6R)-3-Methyl-1,1-dioxo-6-phenyl-[1,2]thiazinan-2-ylmethyl)-phenyl]-4-[1,2,4]triazol-4-yl-cyclohexyl}-methanol | 1.800 |

TABLE 4-continued

| | Structure | name | IC$_{50}$ |
|---|---|---|---|
| 15 | 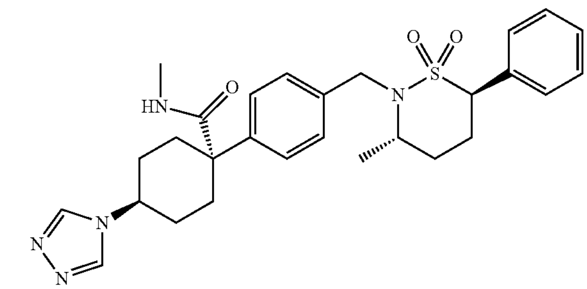 [SMILES: CNC(=O)[C@]1(c2ccc(CN3[C@@H](C)CC[C@H](c4ccccc4)S3(=O)=O)cc2)CC[C@@H](n2cnnc2)CC1] | 1-[4-((3S,6R)-3-Methyl-1,1-dioxo-6-phenyl-[1,2]thiazinan-2-ylmethyl)-phenyl]-4-[1,2,4]triazol-4-yl-cyclohexanecarboxylic acid methylamide | |
| 16 | 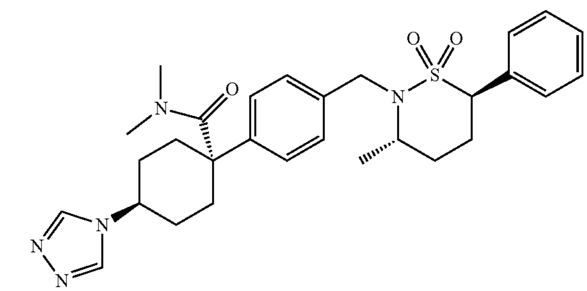 [SMILES: C[C@H]1CC[C@H](c2ccccc2)S(=O)(=O)N1Cc1ccc([C@]2(C(=O)N(C)C)CC[C@H](n3cnnc3)CC2)cc1] | 1-[4-((3S,6R)-3-Methyl-1,1-dioxo-6-phenyl-[1,2]thiazinan-2-ylmethyl)-phenyl]-4-[1,2,4]triazol-4-yl-cyclohexanecarboxylic acid dimethylamide | 2.400 |
| 17 | 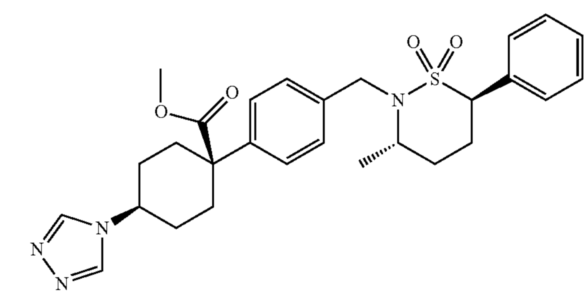 [SMILES: COC(=O)[C@]1(c2ccc(CN3[C@@H](C)CC[C@H](c4ccccc4)S3(=O)=O)cc2)CC[C@H](n2cnnc2)CC1] | 1-[4-((3S,6R)-3-Methyl-1,1-dioxo-6-phenyl-[1,2]thiazinan-2-ylmethyl)-phenyl]-4-[1,2,4]triazol-4-yl-cyclohexanecarboxylic acid methyl ester | 0.360 |
| 18 | 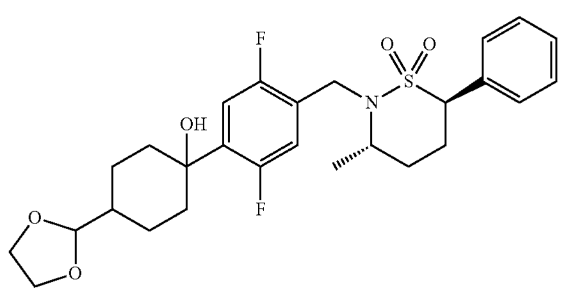 [SMILES: C[C@H]1CC[C@H](c2ccccc2)S(=O)(=O)N1Cc1cc(F)c(C2(O)CCC(C3OCCO3)CC2)cc1F] | 8-[2,5-Difluoro-4-((3S,6R)-3-methyl-1,1-dioxo-6-phenyl-[1,2]thiazinan-2-ylmethyl)-phenyl]-1,4-dioxa-spiro[4.5]decan-8-ol | 0.120 |
| 19 | 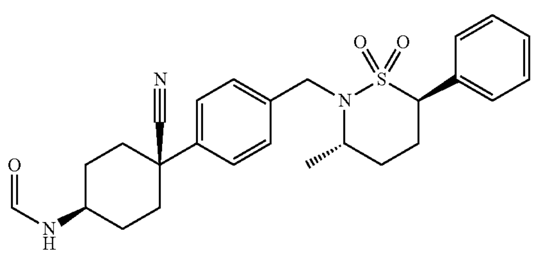 [SMILES: C[C@H]1CC[C@H](c2ccccc2)S(=O)(=O)N1Cc1ccc([C@]2(C#N)CC[C@@H](NC=O)CC2)cc1] | N-{4-Cyano-4-[4-((3S,6R)-3-methyl-1,1-dioxo-6-phenyl-[1,2]thiazinan-2-ylmethyl)-phenyl]-cyclohexyl}-formamide | 0.310 |

TABLE 4-continued

| | Structure | name | IC$_{50}$ |
|---|---|---|---|
| 20 | 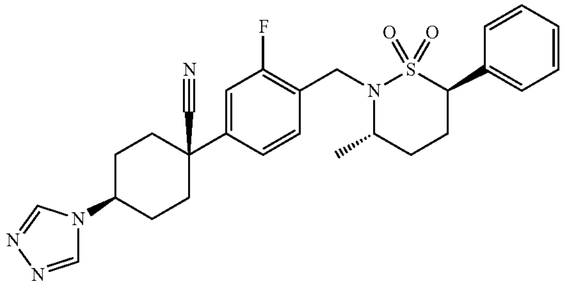 [SMILES: C[C@H]1CC[C@H](c2ccccc2)S(=O)(=O)N1Cc1ccc([C@]2(C#N)CC[C@@H](n3cnnc3)CC2)cc1F] | 1-[3-Fluoro-4-((3S,6R)-3-methyl-1,1-dioxo-6-phenyl-[1,2]thiazinan-2-ylmethyl)-phenyl]-4-[1,2,4]triazol-4-yl-cyclohexanecarbonitrile | 0.110 |
| 21 | 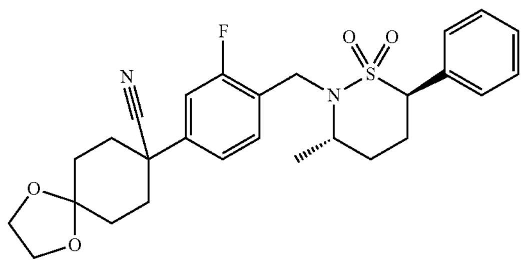 [SMILES: C[C@H]1CC[C@H](c2ccccc2)S(=O)(=O)N1Cc1ccc(C2(C#N)CCC3(CC2)OCCO3)cc1F] | 8-[3-Fluoro-4-((3S,6R)-3-methyl-1,1-dioxo-6-phenyl-[1,2]thiazinan-2-ylmethyl)-phenyl]-1,4-dioxa-spiro[4.5]decane-8-carbonitrile | 0.035 |
| 22 | 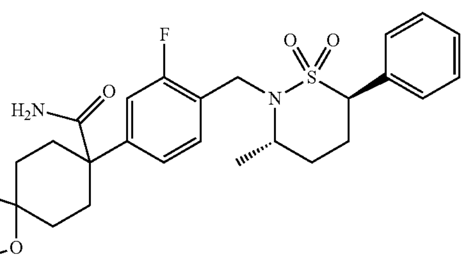 | 8-[3-Fluoro-4-((3S,6R)-3-methyl-1,1-dioxo-6-phenyl-[1,2]thiazinan-2-ylmethyl)-phenyl]-1,4-dioxa-spiro[4.5]decane-8-carboxylic acid amide | 0.030 |
| 23 | 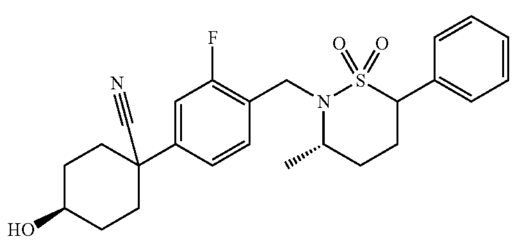 | 1-[3-Fluoro-4-((S)-3-methyl-1,1-dioxo-6-phenyl-[1,2]thiazinan-2-ylmethyl)-phenyl]-4-hydroxy-cyclohexanecarbonitrile | 0.260 |
| 24 | 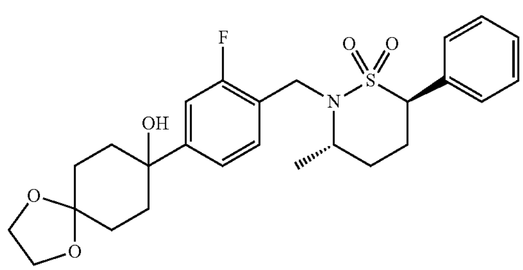 [SMILES: C[C@H]1CC[C@H](c2ccccc2)S(=O)(=O)N1Cc1ccc(C2(O)CCC3(CC2)OCCO3)cc1F] | 8-[3-Fluoro-4-((3S,6R)-3-methyl-1,1-dioxo-6-phenyl-[1,2]thiazinan-2-ylmethyl)-phenyl]-1,4-dioxa-spiro[4.5]decan-8-ol | 0.180 |

TABLE 4-continued

| | Structure | name | IC$_{50}$ |
|---|---|---|---|
| 25 | 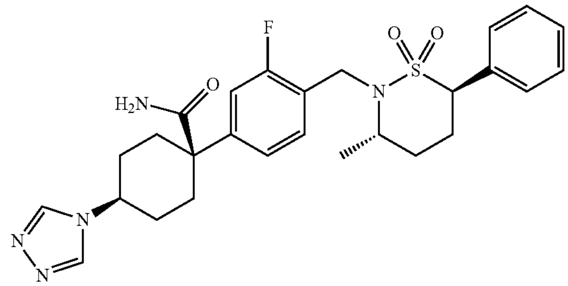 | 1-[3-Fluoro-4-((3S,6R)-3-methyl-1,1-dioxo-6-phenyl-[1,2]thiazinan-2-ylmethyl)-phenyl]-4-[1,2,4]triazol-4-yl-cyclohexanecarboxylic acid amide | 0.022 |
| 26 | 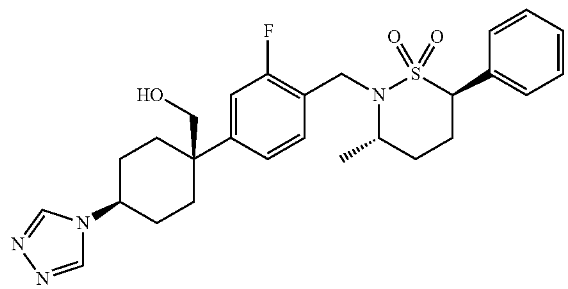 [SMILES: C[C@H]1CC[C@H](c2ccccc2)S(=O)(=O)N1Cc1ccc([C@]2(CO)CC[C@@H](n3cnnc3)CC2)cc1F] | {1-[3-Fluoro-4-((3S,6R)-3-methyl-1,1-dioxo-6-phenyl-[1,2]thiazinan-2-ylmethyl)-phenyl]-4-[1,2,4]triazol-4-yl-cyclohexyl}-methanol | 0.032 |
| 27 | 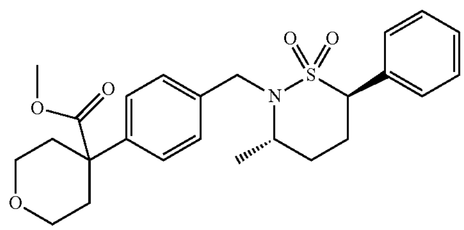 [SMILES: COC(=O)C1(c2ccc(CN3[C@@H](C)CC[C@H](c4ccccc4)S3(=O)=O)cc2)CCOCC1] | 4-[4-((3S,6R)-3-Methyl-1,1-dioxo-6-phenyl-[1,2]thiazinan-2-ylmethyl)-phenyl]-tetrahydro-pyran-4-carboxylic acid methyl ester | 0.500 |
| 28 | 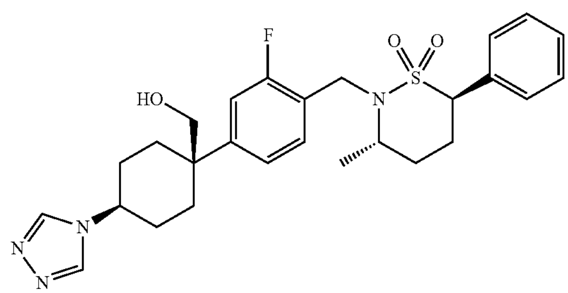 [SMILES: C[C@H]1CC[C@H](c2ccccc2)S(=O)(=O)N1Cc1ccc([C@]2(CO)CC[C@@H](n3cnnc3)CC2)cc1F] | (3S,6R)-2-(2-fluoro-4-((1s,4R)-1-(hydroxymethyl)-4-(4H-1,2,4-triazol-4-yl)cyclohexyl)benzyl)-3-methyl-6-phenyl-1,2-thiazinane 1,1-dioxide | |
| 29 | 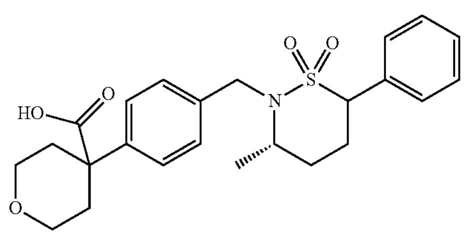 [SMILES: C[C@H]1CCC(c2ccccc2)S(=O)(=O)N1Cc1ccc(C2(C(=O)O)CCOCC2)cc1] | 4-[4-((S)-3-Methyl-1,1-dioxo-6-phenyl-[1,2]thiazinan-2-ylmethyl)-phenyl]-tetrahydro-pyran-4-carboxylic acid | 4.400 |
| 30 | 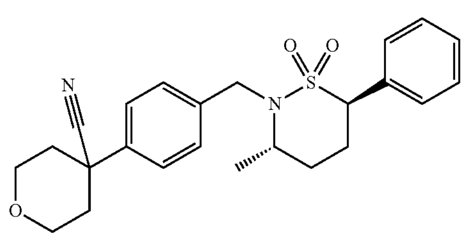 [SMILES: C[C@H]1CC[C@H](c2ccccc2)S(=O)(=O)N1Cc1ccc(C2(C#N)CCOCC2)cc1] | 4-[4-((3S,6R)-3-Methyl-1,1-dioxo-6-phenyl-[1,2]thiazinan-2-ylmethyl)-phenyl]-tetrahydro-pyran-4-carbonitrile | 0.680 |

TABLE 4-continued

| | Structure | name | IC$_{50}$ |
|---|---|---|---|
| 31 | 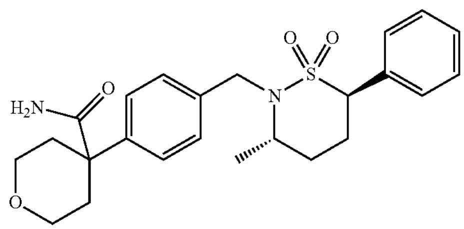 [SMILES: C[C@H]1CC[C@H](c2ccccc2)S(=O)(=O)N1Cc1ccc(C2(C(N)=O)CCOCC2)cc1] | 4-[4-((3S,6R)-3-Methyl-1,1-dioxo-6-phenyl-[1,2]thiazinan-2-ylmethyl)-phenyl]-tetrahydro-pyran-4-carboxylic acid amide | 0.420 |
| 32 | 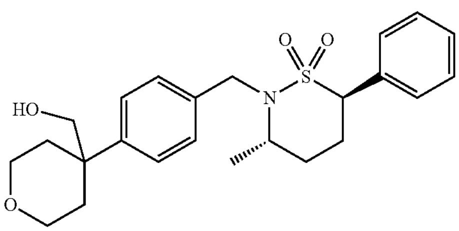 [SMILES: C[C@H]1CC[C@H](c2ccccc2)S(=O)(=O)N1Cc1ccc(C2(CO)CCOCC2)cc1] | {4-[4-((3S,6R)-3-Methyl-1,1-dioxo-6-phenyl-[1,2]thiazinan-2-ylmethyl)-phenyl]-tetrahydro-pyran-4-yl}-methanol | 0.310 |
| 33 | 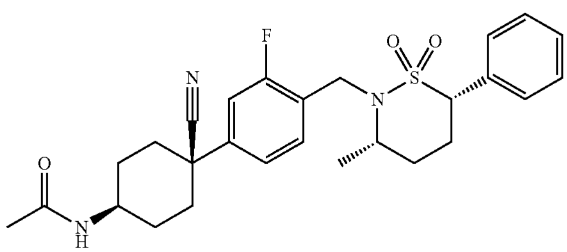 [SMILES: CC(=O)N[C@H]1CC[C@](C#N)(c2ccc(CN3[C@@H](C)CC[C@@H](c4ccccc4)S3(=O)=O)c(F)c2)CC1] | N-{4-Cyano-4-[3-fluoro-4-((3S,6S)-3-methyl-1,1-dioxo-6-phenyl-[1,2]thiazinan-2-ylmethyl)-phenyl]-cyclohexyl}-acetamide | 1.800 |
| 34 | 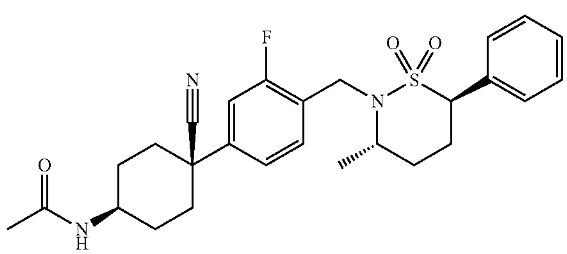 [SMILES: CC(=O)N[C@H]1CC[C@](C#N)(c2ccc(CN3[C@@H](C)CC[C@H](c4ccccc4)S3(=O)=O)c(F)c2)CC1] | N-{4-Cyano-4-[3-fluoro-4-((3S,6R)-3-methyl-1,1-dioxo-6-phenyl-[1,2]thiazinan-2-ylmethyl)-phenyl]-cyclohexyl}-acetamide | 2.300 |
| 35 | 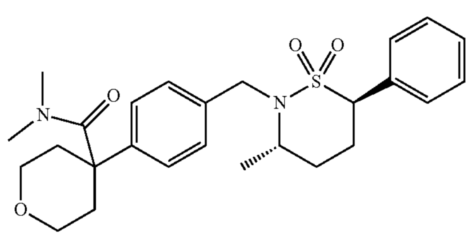 [SMILES: C[C@H]1CC[C@H](c2ccccc2)S(=O)(=O)N1Cc1ccc(C2(C(=O)N(C)C)CCOCC2)cc1] | 4-[4-((3S,6R)-3-Methyl-1,1-dioxo-6-phenyl-[1,2]thiazinan-2-ylmethyl)-phenyl]-tetrahydro-pyran-4-carboxylic acid dimethylamide | 0.820 |
| 36 | 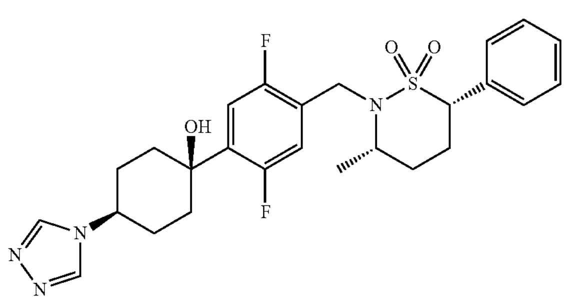 [SMILES: C[C@H]1CC[C@@H](c2ccccc2)S(=O)(=O)N1Cc1cc(F)c([C@]2(O)CC[C@@H](n3cnnc3)CC2)cc1F] | 1-[2,5-Difluoro-4-((3S,6S)-3-methyl-1,1-dioxo-6-phenyl-[1,2]thiazinan-2-ylmethyl)-phenyl]-4-[1,2,4]triazol-4-yl-cyclohexanol | 0.013 |

TABLE 4-continued

| | Structure | name | IC$_{50}$ |
|---|---|---|---|
| 37 | 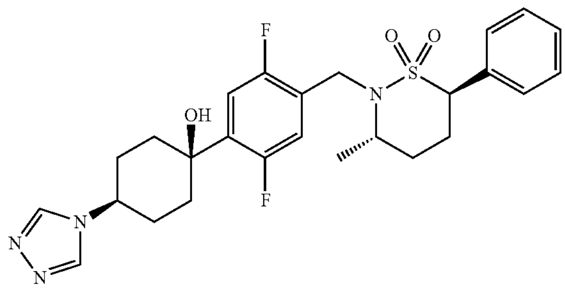 [SMILES: C[C@H]1CC[C@H](c2ccccc2)S(=O)(=O)N1Cc1cc(F)c([C@]2(O)CC[C@@H](n3cnnc3)CC2)cc1F] | 1-[2,5-Difluoro-4-((3S,6R)-3-methyl-1,1-dioxo-6-phenyl-[1,2]thiazinan-2-ylmethyl)-phenyl]-4-[1,2,4]triazol-4-yl-cyclohexanol | 0.020 |
| 38 | 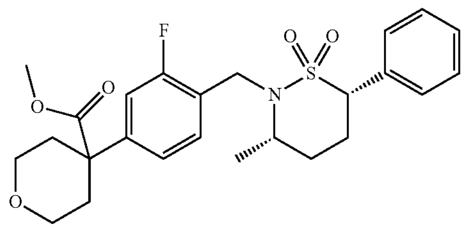 [SMILES: COC(=O)C1(c2ccc(CN3[C@@H](C)CC[C@@H](c4ccccc4)S3(=O)=O)c(F)c2)CCOCC1] | 4-[3-Fluoro-4-((3S,6S)-3-methyl-1,1-dioxo-6-phenyl-[1,2]thiazinan-2-ylmethyl)-phenyl]-tetrahydro-pyran-4-carboxylic acid methyl ester | 0.480 |
| 39 | 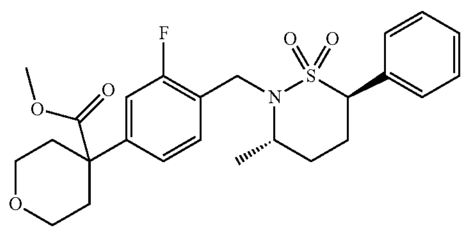 [SMILES: COC(=O)C1(c2ccc(CN3[C@@H](C)CC[C@H](c4ccccc4)S3(=O)=O)c(F)c2)CCOCC1] | 4-[3-Fluoro-4-((3S,6R)-3-methyl-1,1-dioxo-6-phenyl-[1,2]thiazinan-2-ylmethyl)-phenyl]-tetrahydro-pyran-4-carboxylic acid methyl ester | 0.190 |
| 40 | 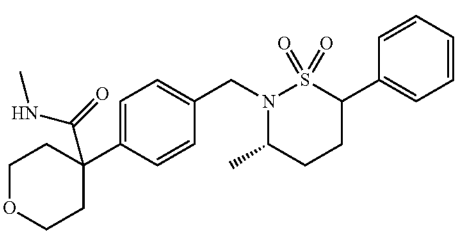 [SMILES: CNC(=O)C1(c2ccc(CN3[C@@H](C)CCC(c4ccccc4)S3(=O)=O)cc2)CCOCC1] | 4-[4-((S)-3-Methyl-1,1-dioxo-6-phenyl-[1,2]thiazinan-2-ylmethyl)-phenyl]-tetrahydro-pyran-4-carboxylic acid methylamide | 0.570 |
| 41 | 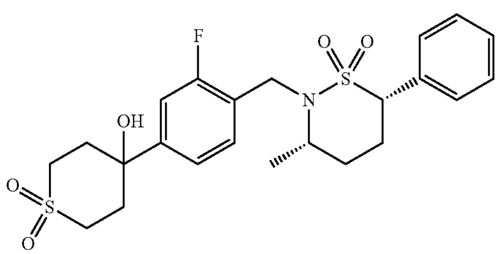 [SMILES: C[C@H]1CC[C@@H](c2ccccc2)S(=O)(=O)N1Cc1ccc(C2(O)CCS(=O)(=O)CC2)cc1F] | (3S,6S)-2-(2-fluoro-4-(4-hydroxy-1,1-dioxidotetrahydro-2H-thiopyran-4-yl)benzyl)-3-methyl-6-phenyl-1,2-thiazinane 1,1-dioxide | 1.200 |
| 42 | 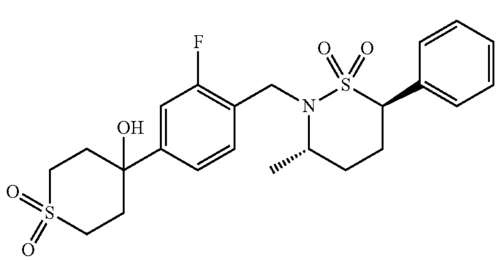 [SMILES: C[C@H]1CC[C@H](c2ccccc2)S(=O)(=O)N1Cc1ccc(C2(O)CCS(=O)(=O)CC2)cc1F] | (3S,6R)-2-(2-fluoro-4-(4-hydroxy-1,1-dioxidotetrahydro-2H-thiopyran-4-yl)benzyl)-3-methyl-6-phenyl-1,2-thiazinane 1,1-dioxide | 0.190 |

TABLE 4-continued

| | Structure | name | IC$_{50}$ |
|---|---|---|---|
| 43 | 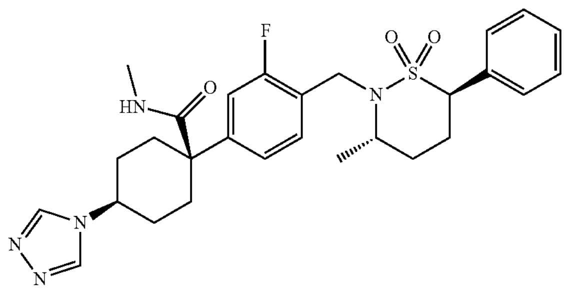 [SMILES: CNC(=O)[C@]1(c2ccc(CN3[C@@H](C)CC[C@H](c4ccccc4)S3(=O)=O)c(F)c2)CC[C@H](n2cnnc2)CC1] | 1-[3-Fluoro-4-(((3S,6R)-3-methyl-1,1-dioxo-6-phenyl[1,2]thiazinan-2-ylmethyl)-phenyl]-4-[1,2,4]triazol-4-yl-cyclohexanecarboxylic acid methylamide | 0.096 |
| 44 | 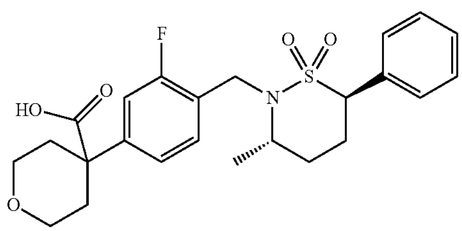 [SMILES: C[C@H]1CC[C@H](c2ccccc2)S(=O)(=O)N1Cc1ccc(C2(C(=O)O)CCOCC2)cc1F] | 4-[3-Fluoro-4-((3S,6R)-3-methyl-1,1-dioxo-6-phenyl-[1,2]thiazinan-2-ylmethyl)-phenyl]-tetrahydro-pyran-4-carboxylic acid | 1.100 |
| 45 | 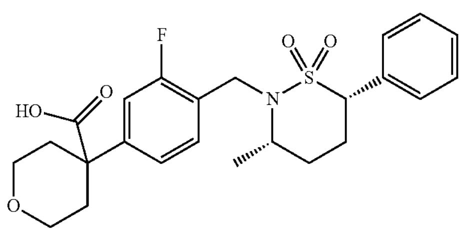 [SMILES: C[C@H]1CC[C@@H](c2ccccc2)S(=O)(=O)N1Cc1ccc(C2(C(=O)O)CCOCC2)cc1F] | 4-[3-Fluoro-4-((3S,6S)-3-methyl-1,1-dioxo-6-phenyl-[1,2]thiazinan-2-ylmethyl)-phenyl]-tetrahydro-pyran-4-carboxylic acid | 6.100 |
| 46 | 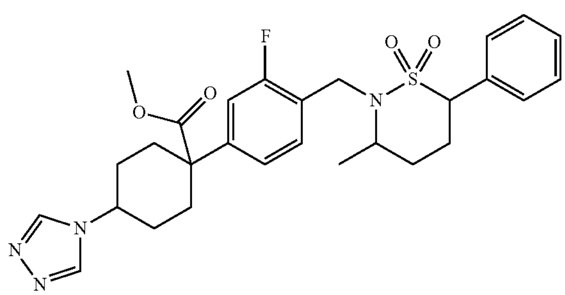 [SMILES: COC(=O)C1(c2ccc(CN3C(C)CCC(c4ccccc4)S3(=O)=O)c(F)c2)CCC(n2cnnc2)CC1] | methyl 1-(3-fluoro-4-((3-methyl-1,1-dioxido-6-phenyl-1,2-thiazinan-2-yl)methyl)phenyl)-4-(4H-1,2,4-triazol-4-yl)cyclohexanecarboxylate | 0.054 |
| 47 | 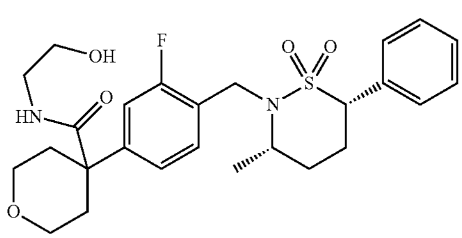 [SMILES: C[C@H]1CC[C@@H](c2ccccc2)S(=O)(=O)N1Cc1ccc(C2(C(=O)NCCO)CCOCC2)cc1F] | 4-(3-fluoro-4-(((3S,6S)-3-methyl-1,1-dioxido-6-phenyl-1,2-thiazinan-2-yl)methyl)phenyl)-N-(2-hydroxyethyl)tetrahydro-2H-pyran-4-carboxamide | 0.991 |
| 48 | 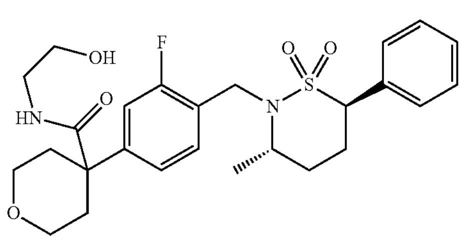 [SMILES: C[C@H]1CC[C@H](c2ccccc2)S(=O)(=O)N1Cc1ccc(C2(C(=O)NCCO)CCOCC2)cc1F] | 4-(3-fluoro-4-(((3S,6R)-3-methyl-1,1-dioxido-6-phenyl-1,2-thiazinan-2-yl)methyl)phenyl)-N-(2-hydroxyethyl)tetrahydro-2H-pyran-4-carboxamide | 0.337 |

TABLE 4-continued

| | Structure | name | IC$_{50}$ |
|---|---|---|---|
| 49 | 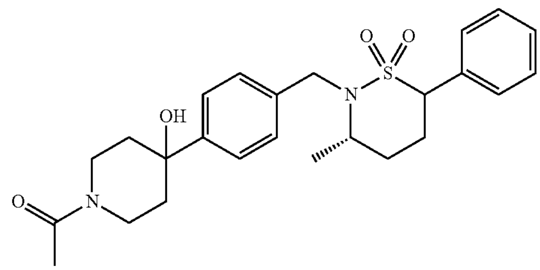 [SMILES: CC(=O)N1CCC(O)(c2ccc(CN3[C@@H](C)CCC(c4ccccc4)S3(=O)=O)cc2)CC1] | 1-{4-Hydroxy-4-[4-((S)-3-methyl-1,1-dioxo-6-phenyl-[1,2]thiazinan-2-ylmethyl)-phenyl]-piperidin-1-yl}-ethanone | 0.120 |
| 50 | 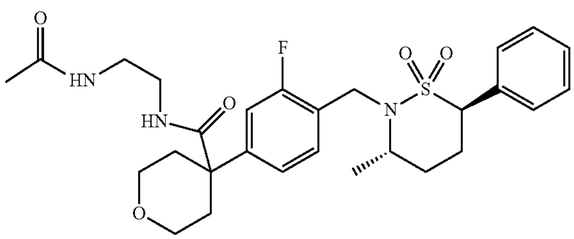 [SMILES: CC(=O)NCCNC(=O)C1(c2ccc(CN3[C@@H](C)CC[C@H](c4ccccc4)S3(=O)=O)c(F)c2)CCOCC1] | N-(2-acetamidoethyl)-4-[3-fluoro-4-[[(3S,6R)-3-methyl-1,1-dioxo-6-phenyl-thiazinan-2-yl]methyl]phenyl]tetrahydropyran-4-carboxamide | 0.25 |
| 51 | 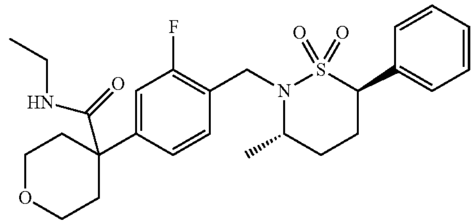 [SMILES: CCNC(=O)C1(c2ccc(CN3[C@@H](C)CC[C@H](c4ccccc4)S3(=O)=O)c(F)c2)CCOCC1] | N-ethyl-4-[3-fluoro-4-[[(3S,6R)-3-methyl-1,1-dioxo-6-phenyl-thiazinan-2-yl]methyl]phenyl]tetrahydropyran-4-carboxamide | 0.147 |
| 52 | 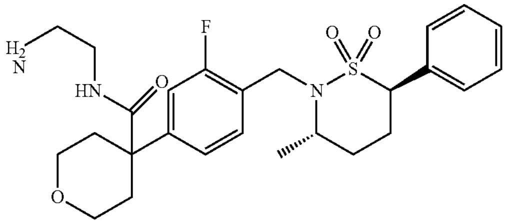 [SMILES: C[C@H]1CC[C@H](c2ccccc2)S(=O)(=O)N1Cc1ccc(C2(C(=O)NCCN)CCOCC2)cc1F] | N-(2-aminoethyl)-4-[3-fluoro-4-[[(3S,6R)-3-methyl-1,1-dioxo-6-phenyl-thiazinan-2-yl]methyl]phenyl]tetrahydropyran-4-carboxamide | 0.48 |
| 53 | 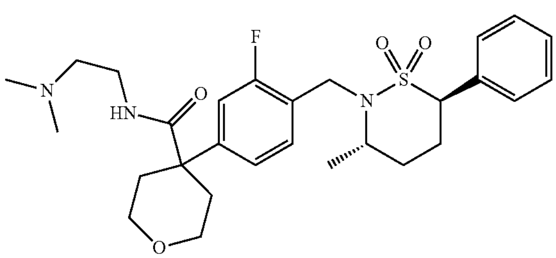 [SMILES: C[C@H]1CC[C@H](c2ccccc2)S(=O)(=O)N1Cc1ccc(C2(C(=O)NCCN(C)C)CCOCC2)cc1F] | N-[2-(dimethylamino)ethyl]-4-[3-fluoro-4-[[(3S,6R)-3-methyl-1,1-dioxo-6-phenyl-thiazinan-2-yl]methyl]phenyl]tetrahydropyran-4-carboxamide | 0.845 |
| 54 | 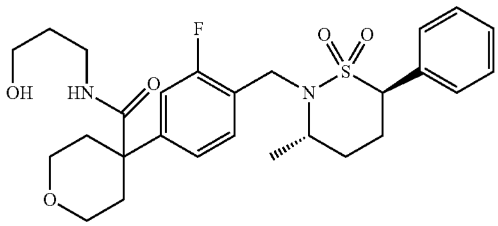 [SMILES: C[C@H]1CC[C@H](c2ccccc2)S(=O)(=O)N1Cc1ccc(C2(C(=O)NCCCN)CCOCC2)cc1F] | 4-[3-fluoro-4-[[(3S,6R)-3-methyl-1,1-dioxo-6-phenyl-thiazinan-2-yl]methyl]phenyl]-N-(3-hydroxypropyl)tetrahydropyran-4-carboxamide | 0.0798 |

TABLE 4-continued

| | Structure | name | IC$_{50}$ |
|---|---|---|---|
| 55 | 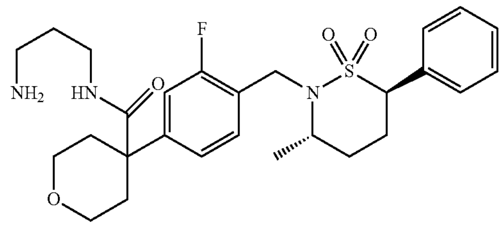 | N-(3-aminopropyl)-4-[3-fluoro-4-[[(3S,6R)-3-methyl-1,1-dioxo-6-phenyl-thiazinan-2-yl]methyl]phenyl]tetrahydropyran-4-carboxamide | 0.913 |
| 56 | 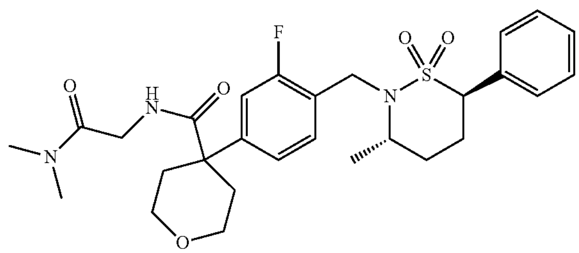 [SMILES: C[C@H]1CC[C@H](c2ccccc2)S(=O)(=O)N1Cc1ccc(C2(C(=O)NCC(=O)N(C)C)CCOCC2)cc1F] | N-[2-(dimethylamino)-2-oxo-ethyl]-4-[3-fluoro-4-[[(3S,6R)-3-methyl-1,1-dioxo-6-phenyl-thiazinan-2-yl]methyl]phenyl]tetrahydropyran-4-carboxamide | 0.403 |
| 57 | 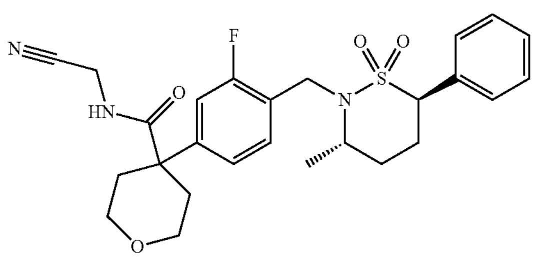 [SMILES: C[C@H]1CC[C@H](c2ccccc2)S(=O)(=O)N1Cc1ccc(C2(C(=O)NCC#N)CCOCC2)cc1F] | N-(cyanomethyl)-4-[3-fluoro-4-[[(3S,6R)-3-methyl-1,1-dioxo-6-phenyl-thiazinan-2-yl]methyl]phenyl]tetrahydropyran-4-carboxamide | 0.0802 |
| 58 | 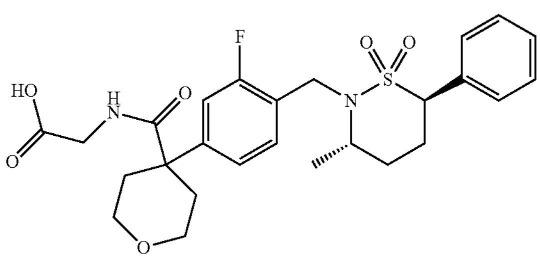 [SMILES: C[C@H]1CC[C@H](c2ccccc2)S(=O)(=O)N1Cc1ccc(C2(C(=O)NCC(=O)O)CCOCC2)cc1F] | 2-[[4-[3-fluoro-4-[[(3S,6R)-3-methyl-1,1-dioxo-6-phenyl-thiazinan-2-yl]methyl]phenyl]tetrahydropyran-4-carbonyl]amino]acetic acid | 0.228 |
| 59 | 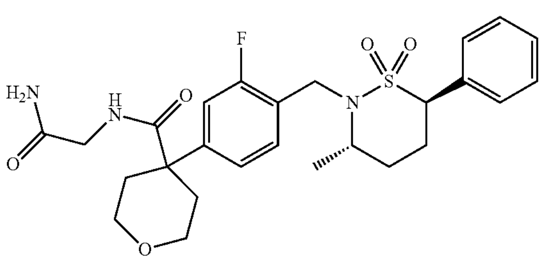 [SMILES: C[C@H]1CC[C@H](c2ccccc2)S(=O)(=O)N1Cc1ccc(C2(C(=O)NCC(N)=O)CCOCC2)cc1F] | N-(2-amino-2-oxo-ethyl)-4-[3-fluoro-4-[[(3S,6R)-3-methyl-1,1-dioxo-6-phenyl-thiazinan-2-yl]methyl]phenyl]tetrahydropyran-4-carboxamide | 0.268 |
| 60 | 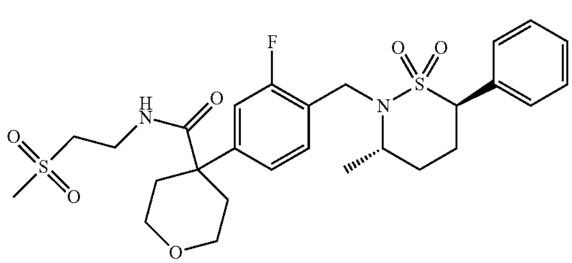 [SMILES: C[C@H]1CC[C@H](c2ccccc2)S(=O)(=O)N1Cc1ccc(C2(C(=O)NCCS(C)(=O)=O)CCOCC2)cc1F] | 4-[3-fluoro-4-[[(3S,6R)-3-methyl-1,1-dioxo-6-phenyl-thiazinan-2-yl]methyl]phenyl]-N-(2-methylsulfonylethyl)tetrahydropyran-4-carboxamide | 0.111 |

TABLE 4-continued

| | Structure | name | IC$_{50}$ |
|---|---|---|---|
| 61 | 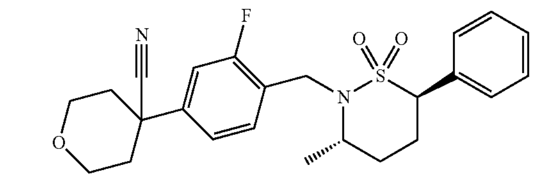 [SMILES: C[C@H]1CC[C@H](c2ccccc2)S(=O)(=O)N1Cc1ccc(C2(C#N)CCOCC2)cc1F] | 4-[3-fluoro-4-[[(3S,6R)-3-methyl-1,1-dioxo-6-phenyl-thiazinan-2-yl]methyl]phenyl]tetrahydropyran-4-carbonitrile | 0.186 |
| 62 | 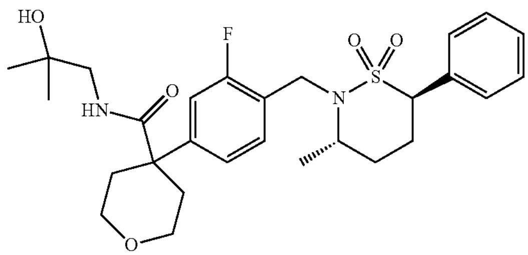 [SMILES: C[C@H]1CC[C@H](c2ccccc2)S(=O)(=O)N1Cc1ccc(C2(C(=O)NCC(C)(C)O)CCOCC2)cc1F] | 4-[3-fluoro-4-[[(3S,6R)-3-methyl-1,1-dioxo-6-phenyl-thiazinan-2-yl]methyl]phenyl]-N-(2-hydroxy-2-methyl-propyl)tetrahydropyran-4-carboxamide | 0.149 |
| 63 | 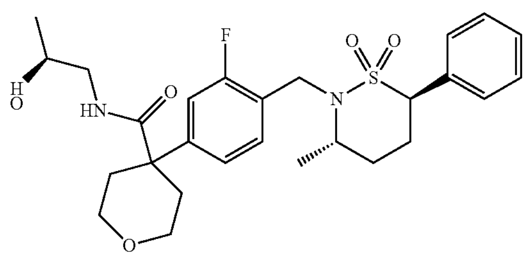 [SMILES: C[C@H](O)CNC(=O)C1(c2ccc(CN3[C@@H](C)CC[C@H](c4ccccc4)S3(=O)=O)c(F)c2)CCOCC1] | 4-[3-fluoro-4-[[(3S,6R)-3-methyl-1,1-dioxo-6-phenyl-thiazinan-2-yl]methyl]phenyl]-N-[(2S)-2-hydroxypropyl]tetrahydropyran-4-carboxamide | 0.036 |
| 64 | 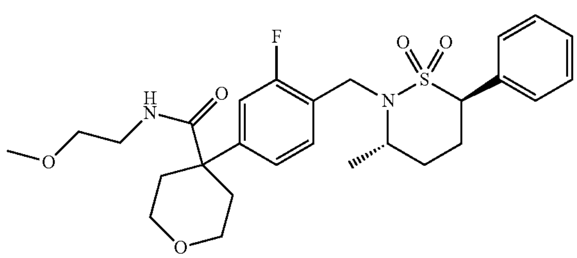 [SMILES: COCCNC(=O)C1(c2ccc(CN3[C@@H](C)CC[C@H](c4ccccc4)S3(=O)=O)c(F)c2)CCOCC1] | 4-[3-fluoro-4-[[(3S,6R)-3-methyl-1,1-dioxo-6-phenyl-thiazinan-2-yl]methyl]phenyl]-N-(2-methoxyethyl)tetrahydropyran-4-carboxamide | 0.089 |
| 65 | 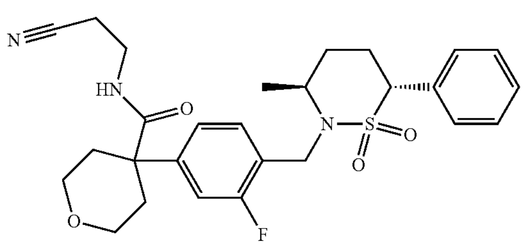 [SMILES: C[C@H]1CC[C@H](c2ccccc2)S(=O)(=O)N1Cc1ccc(C2(C(=O)NCCC#N)CCOCC2)cc1F] | N-(2-cyanoethyl)-4-[3-fluoro-4-[[(3S,6R)-3-methyl-1,1-dioxo-6-phenyl-thiazinan-2-yl]methyl]phenyl]tetrahydropyran-4-carboxamide | 0.0529 |
| 66 | 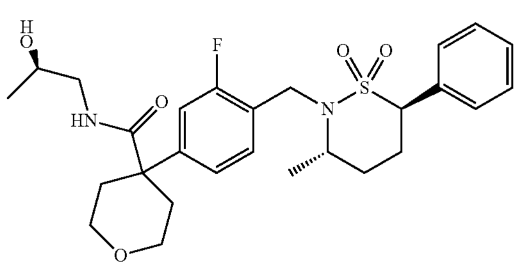 [SMILES: C[C@@H](O)CNC(=O)C1(c2ccc(CN3[C@@H](C)CC[C@H](c4ccccc4)S3(=O)=O)c(F)c2)CCOCC1] | 4-[3-fluoro-4-[[(3S,6R)-3-methyl-1,1-dioxo-6-phenyl-thiazinan-2-yl]methyl]phenyl]-N-(2R)-2-hydroxypropyl]tetrahydropyran-4-carboxamide | 0.0474 |

TABLE 4-continued

| | Structure | name | IC$_{50}$ |
|---|---|---|---|
| 67 | 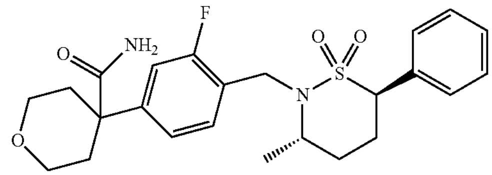 [SMILES: C[C@H]1CC[C@H](c2ccccc2)S(=O)(=O)N1Cc1ccc(C2(C(N)=O)CCOCC2)cc1F] | 4-[3-fluoro-4-[[(3S,6R)-3-methyl-1,1-dioxo-6-phenyl-thiazinan-2-yl]methyl]phenyl]tetrahydropyran-4-carboxamide | 0.018 |
| 68 | 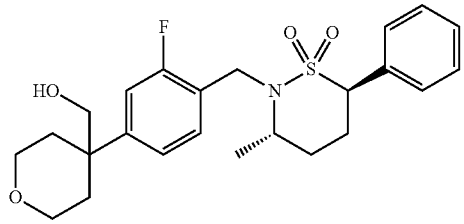 [SMILES: C[C@H]1CC[C@H](c2ccccc2)S(=O)(=O)N1Cc1ccc(C2(CO)CCOCC2)cc1F] | [4-[3-fluoro-4-[[(3S,6R)-3-methyl-1,1-dioxo-6-phenyl-thiazinan-2-yl]methyl]phenyl]tetrahydropyran-4-yl]methanol | 0.0385 |
| 69 | 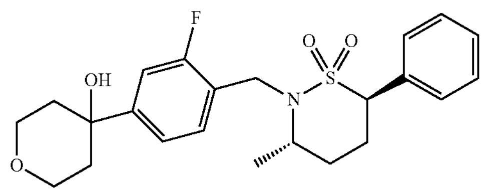 [SMILES: C[C@H]1CC[C@H](c2ccccc2)S(=O)(=O)N1Cc1ccc(C2(O)CCOCC2)cc1F] | 4-[3-fluoro-4-[[(3S,6R)-3-methyl-1,1-dioxo-6-phenyl-thiazinan-2-yl]methyl]phenyl]tetrahydropyran-4-ol | 0.093 |
| 70 | 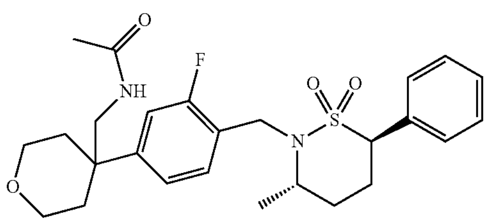 [SMILES: CC(=O)NCC1(c2ccc(CN3[C@@H](C)CC[C@H](c4ccccc4)S3(=O)=O)c(F)c2)CCOCC1] | N-[[4-[3-fluoro-4-[[(3S,6R)-3-methyl-1,1-dioxo-6-phenyl-thiazinan-2-yl]methyl]phenyl]tetrahydropyran-4-yl]methyl]acetamide | 0.148 |
| 71 | 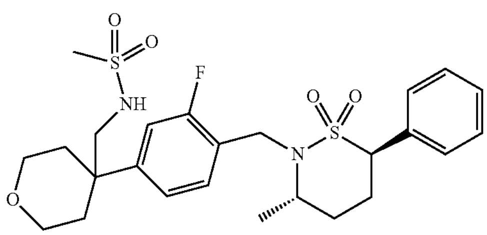 [SMILES: C[C@H]1CC[C@H](c2ccccc2)S(=O)(=O)N1Cc1ccc(C2(CNS(C)(=O)=O)CCOCC2)cc1F] | N-[[4-[3-fluoro-4-[[(3S,6R)-3-methyl-1,1-dioxo-6-phenyl-thiazinan-2-yl]methyl]phenyl]tetrahydropyran-4-yl]methyl]methanesulfonamide | 0.0767 |
| 72 | 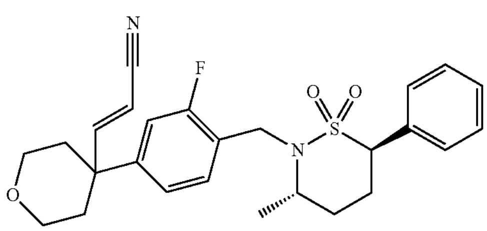 [SMILES: C[C@H]1CC[C@H](c2ccccc2)S(=O)(=O)N1Cc1ccc(C2(/C=C/C#N)CCOCC2)cc1F] | (E)-3-[4-[3-fluoro-4-[[(3S,6R)-3-methyl-1,1-dioxo-6-phenyl-thiazinan-2-yl]methyl]phenyl]tetrahydropyran-4-yl]prop-2-enenitrile | 0.0087 |
| 73 | 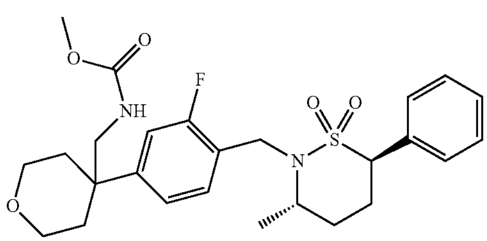 [SMILES: COC(=O)NCC1(c2ccc(CN3[C@@H](C)CC[C@H](c4ccccc4)S3(=O)=O)c(F)c2)CCOCC1] | methyl N-[[4-[3-fluoro-4-[[(3S,6R)-3-methyl-1,1-dioxo-6-phenyl-thiazinan-2-yl]methyl]phenyl]tetrahydropyran-4-yl]methyl]carbamate | 0.0532 |

TABLE 4-continued

| | Structure | name | IC$_{50}$ |
|---|---|---|---|
| 74 | 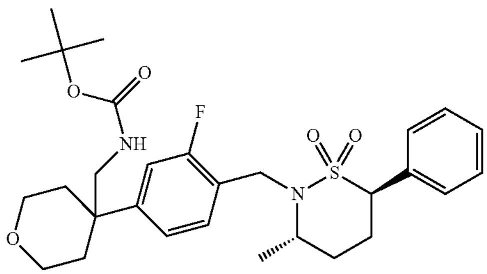 [SMILES: C[C@H]1CC[C@H](c2ccccc2)S(=O)(=O)N1Cc1ccc(C2(CNC(=O)OC(C)(C)C)CCOCC2)cc1F] | tert-butyl N-[[4-[3-fluoro-4-[[(3S,6R)-3-methyl-1,1-dioxo-6-phenyl-thiazinan-2-yl]methyl]phenyl]tetrahydropyran-4-yl]methyl]carbamate | 0.141 |
| 75 | 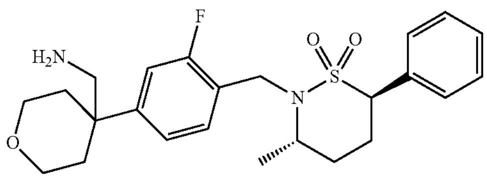 [SMILES: C[C@H]1CC[C@H](c2ccccc2)S(=O)(=O)N1Cc1ccc(C2(CN)CCOCC2)cc1F] | [4-[3-fluoro-4-[[(3S,6R)-3-methyl-1,1-dioxo-6-phenyl-thiazinan-2-yl]methyl]phenyl]tetrahydropyran-4-yl]methanamine | 0.639 |
| 76 | 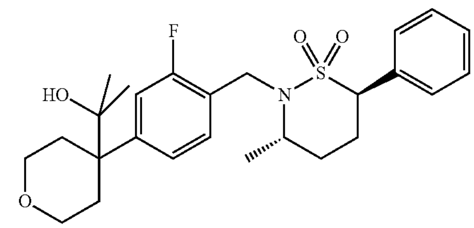 [SMILES: C[C@H]1CC[C@H](c2ccccc2)S(=O)(=O)N1Cc1ccc(C2(C(C)(C)O)CCOCC2)cc1F] | 2-[4-[3-fluoro-4-[[(3S,6R)-3-methyl-1,1-dioxo-6-phenyl-thiazinan-2-yl]methyl]phenyl]tetrahydropyran-4-yl]propan-2-ol | 0.0321 |
| 77 | 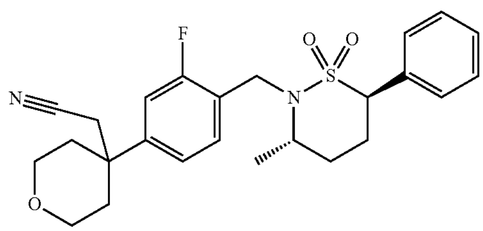 [SMILES: C[C@H]1CC[C@H](c2ccccc2)S(=O)(=O)N1Cc1ccc(C2(CC#N)CCOCC2)cc1F] | 2-[4-[3-fluoro-4-[[(3S,6R)-3-methyl-1,1-dioxo-6-phenyl-thiazinan-2-yl]methyl]phenyl]tetrahydropyran-4-yl]acetonitrile | 0.0312 |
| 78 | 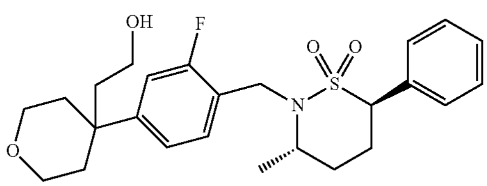 [SMILES: C[C@H]1CC[C@H](c2ccccc2)S(=O)(=O)N1Cc1ccc(C2(CCO)CCOCC2)cc1F] | 2-[4-[3-fluoro-4-[[(3S,6R)-3-methyl-1,1-dioxo-6-phenyl-thiazinan-2-yl]methyl]phenyl]tetrahydropyran-4-yl]ethanol | 0.0137 |
| 79 | 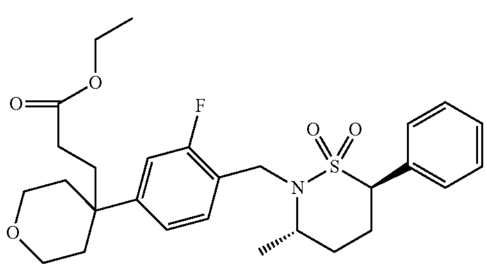 [SMILES: CCOC(=O)CCC1(c2ccc(CN3[C@@H](C)CC[C@H](c4ccccc4)S3(=O)=O)c(F)c2)CCOCC1] | ethyl 3-[4-[3-fluoro-4-[[(3S,6R)-3-methyl-1,1-dioxo-6-phenyl-thiazinan-2-yl]methyl]phenyl]tetrahydropyran-4-yl]propanoate | 0.0049 |
| 80 | 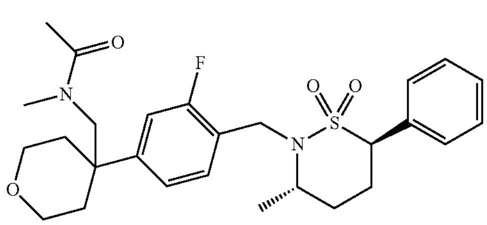 [SMILES: CC(=O)N(C)CC1(c2ccc(CN3[C@@H](C)CC[C@H](c4ccccc4)S3(=O)=O)c(F)c2)CCOCC1] | N-[[4-[3-fluoro-4-[[(3S,6R)-3-methyl-1,1-dioxo-6-phenyl-thiazinan-2-yl]methyl]phenyl]tetrahydropyran-4-yl]methyl]-N-methyl-acetamide | 0.104 |

TABLE 4-continued

| | Structure | name | IC$_{50}$ |
|---|---|---|---|
| 81 | 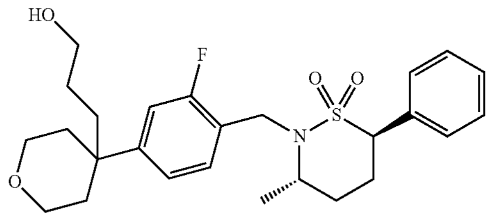 [SMILES: C[C@H]1CC[C@H](c2ccccc2)S(=O)(=O)N1Cc1ccc(C2(CCCO)CCOCC2)cc1F] | 3-[4-[3-fluoro-4-[[(3S,6R)-3-methyl-1,1-dioxo-6-phenyl-thiazinan-2-yl]methyl]phenyl]tetrahydropyran-4-yl]propan-1-ol | 0.0062 |
| 82 | 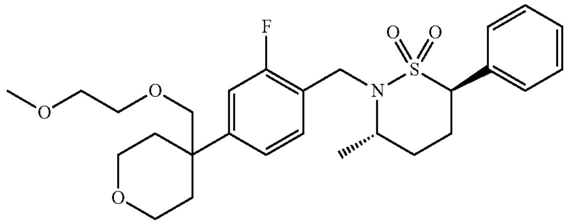 [SMILES: COCCOCC1(c2ccc(CN3[C@@H](C)CC[C@H](c4ccccc4)S3(=O)=O)c(F)c2)CCOCC1] | (3S,6R)-2-[[2-fluoro-4-[4-(2-methoxyethoxymethyl)tetrahydropyran-4-yl]phenyl]methyl]-3-methyl-6-phenyl-thiazinane 1,1-dioxide | 0.0705 |
| 83 | 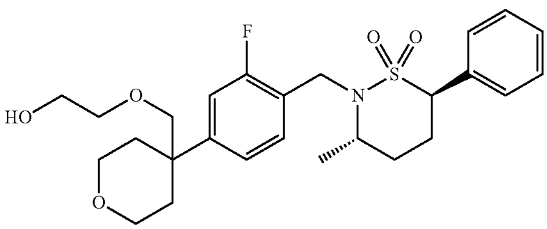 [SMILES: C[C@H]1CC[C@H](c2ccccc2)S(=O)(=O)N1Cc1ccc(C2(COCCO)CCOCC2)cc1F] | 2-[[4-[3-fluoro-4-[[(3S,6R)-3-methyl-1,1-dioxo-6-phenyl-thiazinan-2-yl]methyl]phenyl]tetrahydropyran-4-yl]methoxy]ethanol | 0.046 |
| 84 | 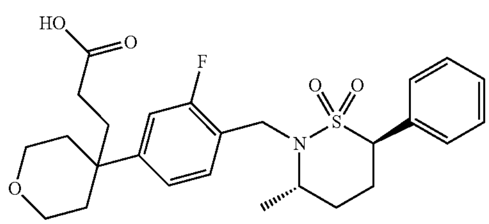 [SMILES: C[C@H]1CC[C@H](c2ccccc2)S(=O)(=O)N1Cc1ccc(C2(CCC(=O)O)CCOCC2)cc1F] | 3-[4-[3-fluoro-4-[[(3S,6R)-3-methyl-1,1-dioxo-6-phenyl-thiazinan-2-yl]methyl]phenyl]tetrahydropyran-4-yl]propanoic acid | 0.0492 |
| 85 | 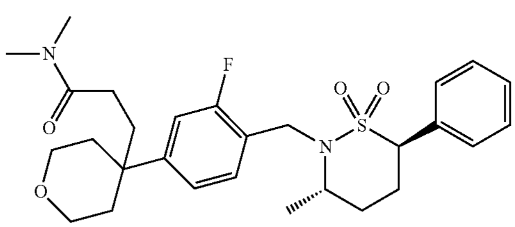 [SMILES: C[C@H]1CC[C@H](c2ccccc2)S(=O)(=O)N1Cc1ccc(C2(CCC(=O)N(C)C)CCOCC2)cc1F] | 3-[4-[3-fluoro-4-[[(3S,6R)-3-methyl-1,1-dioxo-6-phenyl-thiazinan-2-yl]methyl]phenyl]tetrahydropyran-4-yl]-N,N-dimethyl-propanamide | 0.0105 |
| 86 | 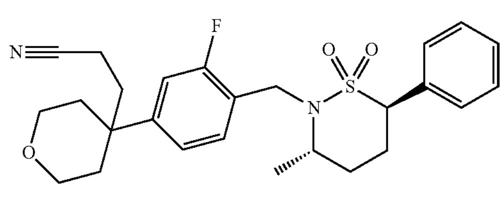 [SMILES: C[C@H]1CC[C@H](c2ccccc2)S(=O)(=O)N1Cc1ccc(C2(CCC#N)CCOCC2)cc1F] | 3-[4-[3-fluoro-4-[[(3S,6R)-3-methyl-1,1-dioxo-6-phenyl-thiazinan-2-yl]methyl]phenyl]tetrahydropyran-4-yl]propanenitrile | 0.0078 |
| 87 | 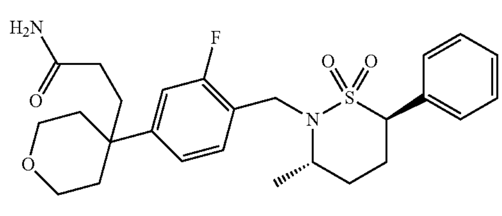 [SMILES: C[C@H]1CC[C@H](c2ccccc2)S(=O)(=O)N1Cc1ccc(C2(CCC(N)=O)CCOCC2)cc1F] | 3-[4-[3-fluoro-4-[[(3S,6R)-3-methyl-1,1-dioxo-6-phenyl-thiazinan-2-yl]methyl]phenyl]tetrahydropyran-4-yl]propanamide | 0.0088 |

TABLE 4-continued

| | Structure | name | IC$_{50}$ |
|---|---|---|---|
| 88 | 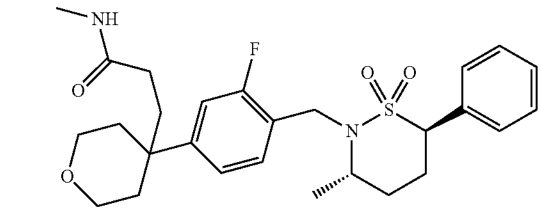 [SMILES: CNC(=O)CCC1(c2ccc(CN3[C@@H](C)CC[C@H](c4ccccc4)S3(=O)=O)c(F)c2)CCOCC1] | 3-[4-[3-fluoro-4-[[(3S,6R)-3-methyl-1,1-dioxo-6-phenyl-thiazinan-2-yl]methyl]phenyl]tetrahydropyran-4-yl]-N-methyl-propanamide | 0.0148 |
| 89 | 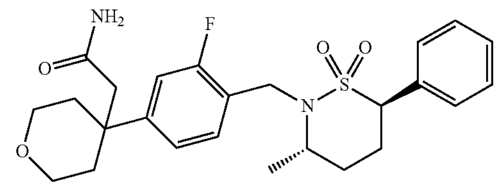 [SMILES: C[C@H]1CC[C@H](c2ccccc2)S(=O)(=O)N1Cc1ccc(C2(CC(N)=O)CCOCC2)cc1F] | 2-[4-[3-fluoro-4-[[(3S,6R)-3-methyl-1,1-dioxo-6-phenyl-thiazinan-2-yl]methyl]phenyl]tetrahydropyran-4-yl]acetamide | 0.376 |
| 90 | 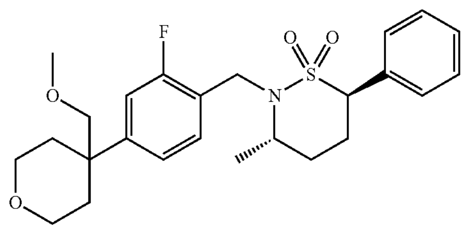 [SMILES: COCC1(c2ccc(CN3[C@@H](C)CC[C@H](c4ccccc4)S3(=O)=O)c(F)c2)CCOCC1] | (3S,6R)-2-[[2-fluoro-4-[4-(methoxymethyl)tetrahydropyran-4-yl]phenyl]methyl]-3-methyl-6-phenyl-thiazinane 1,1-dioxide | 0.067 |
| 91 | 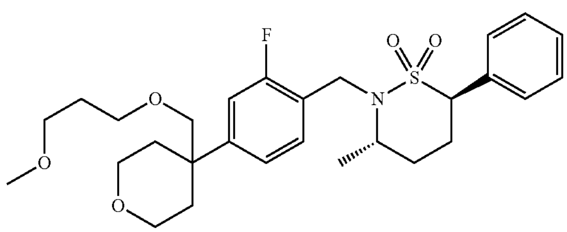 [SMILES: COCCCOCC1(c2ccc(CN3[C@@H](C)CC[C@H](c4ccccc4)S3(=O)=O)c(F)c2)CCOCC1] | (3S,6R)-2-[[2-fluoro-4-[4-(3-methoxypropoxymethyl)tetrahydro-pyran-4-yl]phenyl]methyl]-3-methyl-6-phenyl-thiazinane 1,1-dioxide | 0.103 |
| 92 | 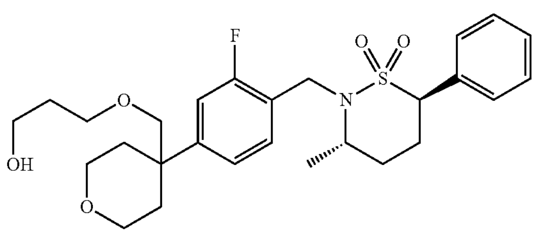 [SMILES: C[C@H]1CC[C@H](c2ccccc2)S(=O)(=O)N1Cc1ccc(C2(COCCCO)CCOCC2)cc1F] | 3-[[4-[3-fluoro-4[[(3S,6R)-3-methyl-1,1-dioxo-6-phenyl-thiazinan-2-yl]methyl]phenyl]tetrahydropyran-4-yl]methoxy]propan-1-ol | 0.0758 |
| 93 | 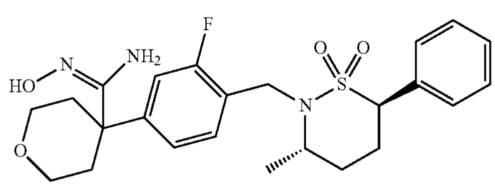 [SMILES: C[C@H]1CC[C@H](c2ccccc2)S(=O)(=O)N1Cc1ccc(C2(/C(N)=N\O)CCOCC2)cc1F] | 4-[3-fluoro-4-[[(3S,6R)-3-methyl-1,1-dioxo-6-phenyl-thiazinan-2-yl]methyl]phenyl]-N'-hydroxy-tetrahydropyran-4-carboxamidine | 0.0378 |
| 94 | 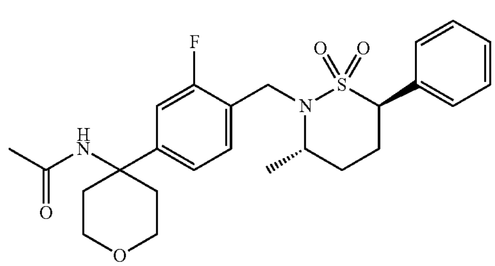 [SMILES: CC(=O)NC1(c2ccc(CN3[C@@H](C)CC[C@H](c4ccccc4)S3(=O)=O)c(F)c2)CCOCC1] | N-[4-[3-fluoro-4-[[(3S,6R)-3-methyl-1,1-dioxo-6-phenyl-thiazinan-2-yl]methyl]phenyl]tetrahydropyran-4-yl]acetamide | 0.0932 |

TABLE 4-continued

| | Structure | name | IC$_{50}$ |
|---|---|---|---|
| 95 | 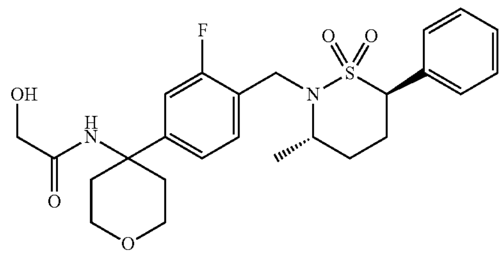 [SMILES: C[C@H]1CC[C@H](c2ccccc2)S(=O)(=O)N1Cc1ccc(C2(NC(=O)CO)CCOCC2)cc1F] | N-[4-[3-fluoro-4-[[(3S,6R)-3-methyl-1,1-dioxo-6-phenyl-thiazinan-2-yl]methyl]phenyl]tetrahydropyran-4-yl]-2-hydroxy-acetamide | 0.122 |
| 96 | 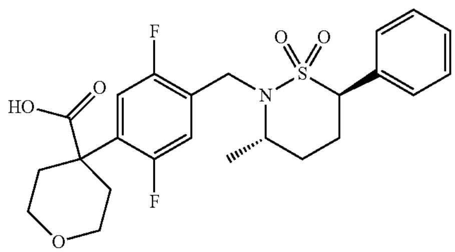 [SMILES: C[C@H]1CC[C@H](c2ccccc2)S(=O)(=O)N1Cc1cc(F)c(C2(C(=O)O)CCOCC2)cc1F] | 4-[2,5-difluoro-4-[[(3S,6R)-3-methyl-1,1-dioxo-6-phenyl-thiazinan-2-yl]methyl]phenyl]tetrahydropyran-4-carboxylic acid | 0.214 |
| 97 | 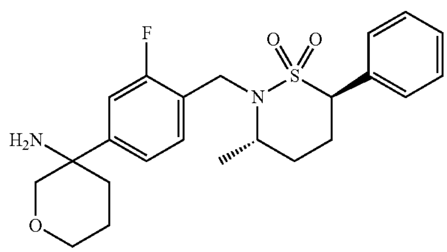 [SMILES: C[C@H]1CC[C@H](c2ccccc2)S(=O)(=O)N1Cc1ccc(C2(N)CCCOC2)cc1F] | 4-[3-fluoro-4-[[(3S,6R)-3-methyl-1,1-dioxo-6-phenyl-thiazinan-2-yl]methyl]phenyl]tetrahydropyran-4-amine | 0.892 |
| 98 | 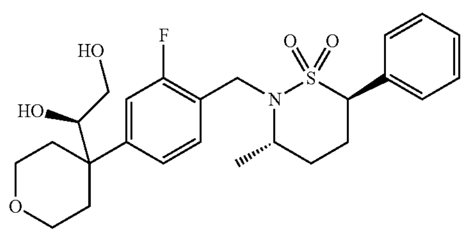 [SMILES: C[C@H]1CC[C@H](c2ccccc2)S(=O)(=O)N1Cc1ccc(C2([C@@H](O)CO)CCOCC2)cc1F] | (1R)-1-[4-[3-fluoro-4-[[(3S,6R)-3-methyl-1,1-dioxo-6-phenyl-thiazinan-2-yl]methyl]phenyl]tetrahydropyran-4-yl]ethane-1,2-diol | 0.063 |
| 99 | 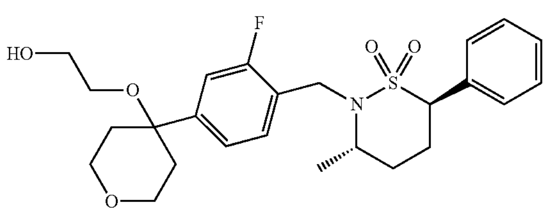 [SMILES: C[C@H]1CC[C@H](c2ccccc2)S(=O)(=O)N1Cc1ccc(C2(OCCO)CCOCC2)cc1F] | 2-[4-[3-fluoro-4-[[(3S,6R)-3-methyl-1,1-dioxo-6-phenyl-thiazinan-2-yl]methyl]phenyl]tetrahydropyran-4-yl]oxyethanol | 0.0664 |
| 100 | 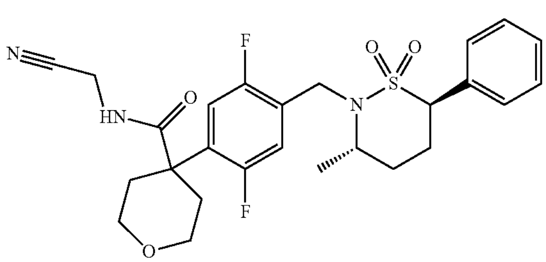 [SMILES: C[C@H]1CC[C@H](c2ccccc2)S(=O)(=O)N1Cc1cc(F)c(C2(C(=O)NCC#N)CCOCC2)cc1F] | N-(cyanomethyl)-4[2,5-difluoro-4-[[(3S,6R)-3-methyl-1,1-dioxo-6-phenyl-thiazinan-2-yl]methyl]phenyl]tetrahydropyran-4-carboxamide | 0.031 |

TABLE 4-continued

| | Structure | name | IC$_{50}$ |
|---|---|---|---|
| 101 | 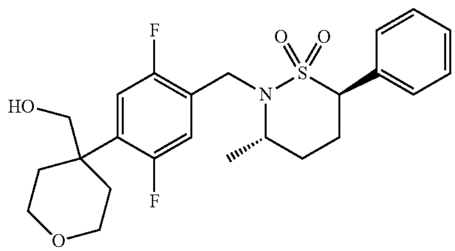 [SMILES: C[C@H]1CC[C@H](c2ccccc2)S(=O)(=O)N1Cc1cc(F)c(C2(CO)CCOCC2)cc1F] | [4-[2,5-difluoro-4-[[(3S,6R)-3-methyl-1,1-dioxo-6-phenyl-thiazinan-2-yl]methyl]phenyl]tetrahydropyran-4-yl]methanol | 0.0090 |
| 102 | 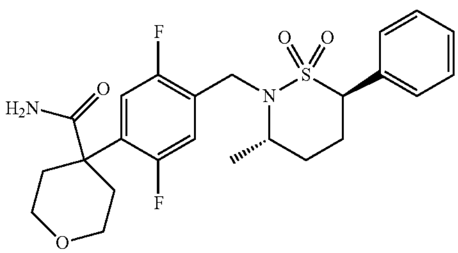 [SMILES: C[C@H]1CC[C@H](c2ccccc2)S(=O)(=O)N1Cc1cc(F)c(C2(C(N)=O)CCOCC2)cc1F] | 4-[2,5-difluoro-4-[[(3S,6R)-3-methyl-1,1-dioxo-6-phenyl-thiazinan-2-yl]methyl]phenyl]tetrahydropyran-4-carboxamide | 0.0378 |
| 103 | 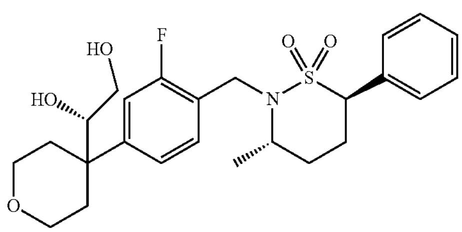 [SMILES: C[C@H]1CC[C@H](c2ccccc2)S(=O)(=O)N1Cc1ccc(C2([C@H](O)CO)CCOCC2)cc1F] | (1S)-1-[4-[3-fluoro-4-[[(3S,6R)-3-methyl-1,1-dioxo-6-phenyl-thiazinan-2-yl]methyl]phenyl]tetrahydropyran-4-yl]ethane-1,2-diol | 0.0689 |
| 104 | 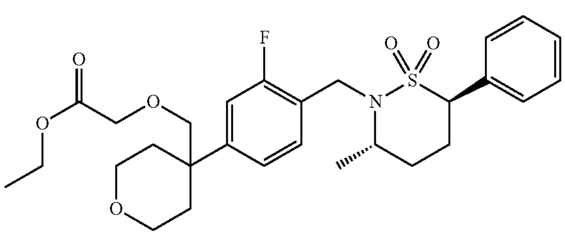 [SMILES: CCOC(=O)COCC1(c2ccc(CN3[C@@H](C)CC[C@H](c4ccccc4)S3(=O)=O)c(F)c2)CCOCC1] | ethyl 2-[[4-[3-fluoro-4-[[(3S,6R)-3-methyl-1,1-dioxo-6-phenyl-thiazinan-2-yl]methyl]phenyl]tetrahydropyran-4-yl]methoxy]acetate | 0.0238 |
| 105 | 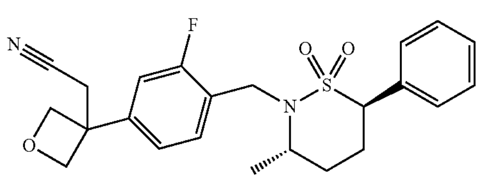 [SMILES: C[C@H]1CC[C@H](c2ccccc2)S(=O)(=O)N1Cc1ccc(C2(CC#N)COC2)cc1F] | 2-[3-[3-fluoro-4-[[(3S,6R)-3-methyl-1,1-dioxo-6-phenyl-thiazinan-2-yl]methyl]phenyl]oxetan-3-yl]acetonitrile | 0.0749 |
| 106 | 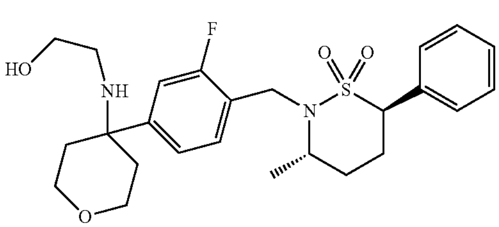 [SMILES: C[C@H]1CC[C@H](c2ccccc2)S(=O)(=O)N1Cc1ccc(C2(NCCO)CCOCC2)cc1F] | 2-[[4-[3-fluoro-4-[[(3S,6R)-3-methyl-1,1-dioxo-6-phenyl-thiazinan-2-yl]methyl]phenyl]tetrahydropyran-4-yl]amino]ethanol | 0.137 |

TABLE 4-continued

| | Structure | name | IC$_{50}$ |
|---|---|---|---|
| 107 | 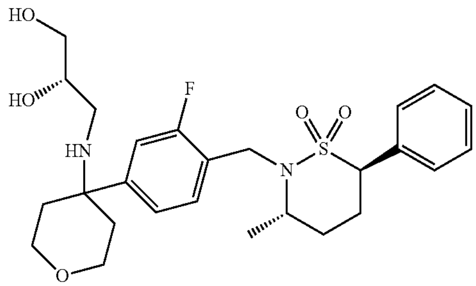 [SMILES: C[C@H]1CC[C@H](c2ccccc2)S(=O)(=O)N1Cc1ccc(C2(NC[C@H](O)CO)CCOCC2)cc1F] | (2S)-3-[[4-[3-fluoro-4-[[(3S,6R)-3-methyl-1,1-dioxo-6-phenyl-thiazinan-2-yl]methyl]phenyl]tetrahydropyran-4-yl]amino]propane-1,2-diol | 0.0226 |
| 108 | 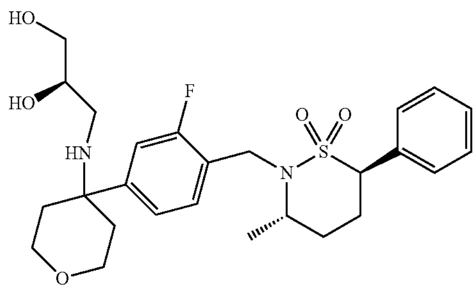 [SMILES: C[C@H]1CC[C@H](c2ccccc2)S(=O)(=O)N1Cc1ccc(C2(NC[C@@H](O)CO)CCOCC2)cc1F] | (2R)-3-[[4-[3-fluoro-4-[[(3S,6R)-3-methyl-1,1-dioxo-6-phenyl-thiazinan-2-yl]methyl]phenyl]tetrahydropyran-4-yl]amino]propane-1,2-diol | 0.0504 |
| 109 | 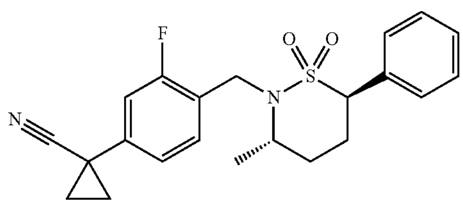 [SMILES: C[C@H]1CC[C@H](c2ccccc2)S(=O)(=O)N1Cc1ccc(C2(C#N)CC2)cc1F] | 1-[3-fluoro-4-[[(3S,6R)-3-methyl-1,1-dioxo-6-phenyl-thiazinan-2-yl]methyl]phenyl]cyclopropanecarbonitrile | 0.116 |
| 110 | 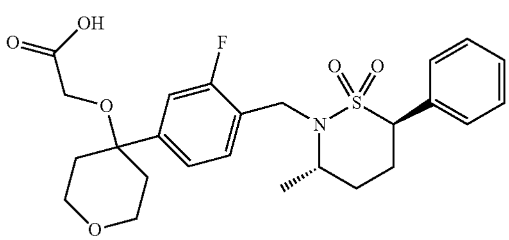 [SMILES: C[C@H]1CC[C@H](c2ccccc2)S(=O)(=O)N1Cc1ccc(C2(OCC(=O)O)CCOCC2)cc1F] | 2-[4-[3-fluoro-4-[[(3S,6R)-3-methyl-1,1-dioxo-6-phenyl-thiazinan-2-yl]methyl]phenyl]tetrahydropyran-4-yl]oxyacetic acid | 0.0629 |
| 111 | 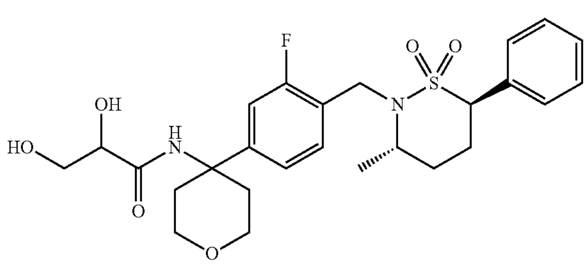 [SMILES: C[C@H]1CC[C@H](c2ccccc2)S(=O)(=O)N1Cc1ccc(C2(NC(=O)C(O)CO)CCOCC2)cc1F] | N-[4-[3-fluoro-4-[[(3S,6R)-3-methyl-1,1-dioxo-6-phenyl-thiazinan-2-yl]methyl]phenyl]tetrahydropyran-4-yl]-2,3-dihydroxy-propanamide | 0.138 |
| 112 | 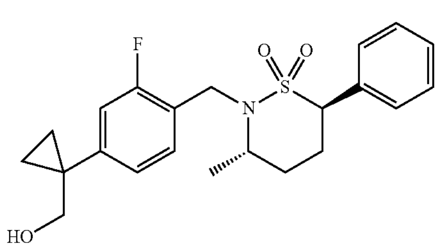 [SMILES: C[C@H]1CC[C@H](c2ccccc2)S(=O)(=O)N1Cc1ccc(C2(CO)CC2)cc1F] | [1-[3-fluoro-4-[[(3S,6R)-3-methyl-1,1-dioxo-6-phenyl-thiazinan-2-yl]methyl]phenyl]cyclopropyl]methanol | 0.206 |

TABLE 4-continued

| | Structure | name | IC$_{50}$ |
|---|---|---|---|
| 113 | 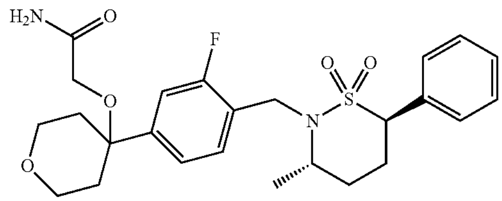 [SMILES: C[C@H]1CC[C@H](c2ccccc2)S(=O)(=O)N1Cc1ccc(C2(OCC(N)=O)CCOCC2)cc1F] | 2-[4-[3-fluoro-4-[[(3S,6R)-3-methyl-1,1-dioxo-6-phenyl-thiazinan-2-yl]methyl]phenyl]tetrahydropyran-4-yl]oxyacetamide | 0.0050 |
| 114 | 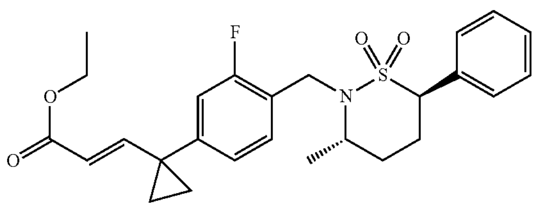 [SMILES: CCOC(=O)/C=C/C1(c2ccc(CN3[C@@H](C)CC[C@H](c4ccccc4)S3(=O)=O)c(F)c2)CC1] | ethyl (E)-3-[1-[3-fluoro-4-[[(3S,6R)-3-methyl-1,1-dioxo-6-phenyl-thiazinan-2-yl]methyl]phenyl]cyclopropyl]prop-2-enoate | 0.0536 |
| 115 | 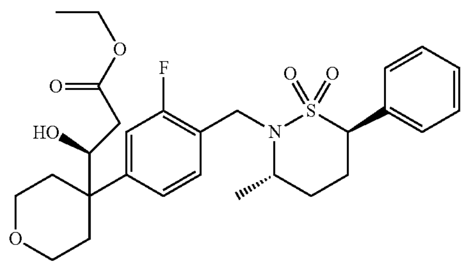 [SMILES: CCOC(=O)C[C@H](O)C1(c2ccc(CN3[C@@H](C)CC[C@H](c4ccccc4)S3(=O)=O)c(F)c2)CCOCC1] | ethyl (3S)-3-[4-[3-fluoro-4-[[(3S,6R)-3-methyl-1,1-dioxo-6-phenyl-thiazinan-2-yl]methyl]phenyl]tetrahydropyran-4-yl]-3-hydroxy-propanoate | 0.0395 |
| 116 | 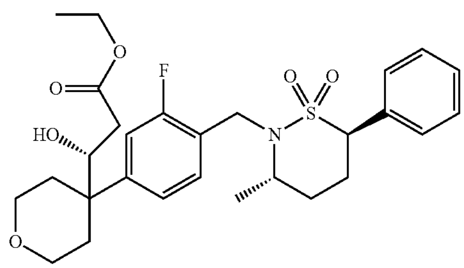 [SMILES: CCOC(=O)C[C@@H](O)C1(c2ccc(CN3[C@@H](C)CC[C@H](c4ccccc4)S3(=O)=O)c(F)c2)CCOCC1] | ethyl (3R)-3-[4-[3-fluoro-4-[[(3S,6R)-3-methyl-1,1-dioxo-6-phenyl-thiazinan-2-yl]methyl]phenyl]tetrahydropyran-4-yl]-3-hydroxy-propanoate | 0.0122 |
| 117 | 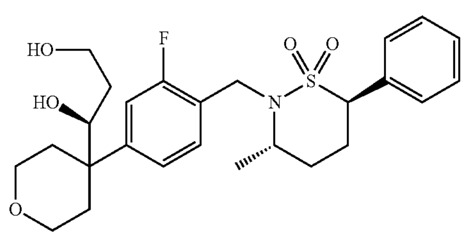 [SMILES: C[C@H]1CC[C@H](c2ccccc2)S(=O)(=O)N1Cc1ccc(C2([C@@H](O)CCO)CCOCC2)cc1F] | (1S)-1-[4-[3-fluoro-4-[[(3S,6R)-3-methyl-1,1-dioxo-6-phenyl-thiazinan-2-yl]methyl]phenyl]tetrahydropyran-4-yl]propane-1,3-diol | 0.0352 |
| 118 | 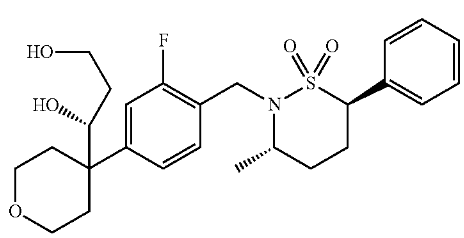 [SMILES: C[C@H]1CC[C@H](c2ccccc2)S(=O)(=O)N1Cc1ccc(C2([C@H](O)CCO)CCOCC2)cc1F] | (1R)-1-[4-[3-fluoro-4-[[(3S,6R)-3-methyl-1,1-dioxo-6-phenyl-thiazinan-2-yl]methyl]phenyl]tetrahydropyran-4-yl]propane-1,3-diol | 0.0166 |

TABLE 4-continued

| | Structure | name | IC$_{50}$ |
|---|---|---|---|
| 119 | 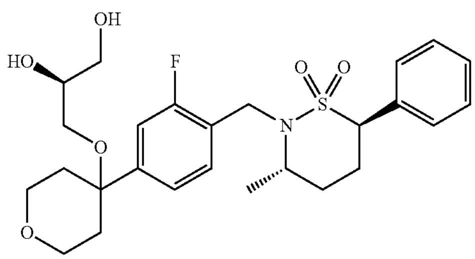 [SMILES: C[C@H]1CC[C@H](c2ccccc2)S(=O)(=O)N1Cc1ccc(C2(OC[C@@H](O)CO)CCOCC2)cc1F] | (2S)-3-[4-[3-fluoro-4-[[(3S,6R)-3-methyl-1,1-dioxo-6-phenyl-thiazinan-2-yl]methyl]phenyl]tetrahydropyran-4-yl]oxypropane-1,2-diol | 0.0274 |
| 120 | 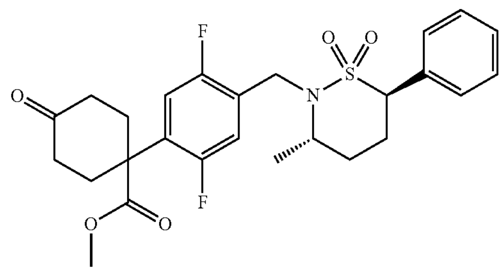 [SMILES: COC(=O)C1(c2cc(F)c(CN3[C@@H](C)CC[C@H](c4ccccc4)S3(=O)=O)cc2F)CCC(=O)CC1] | methyl 1-[2,5-difluoro-4-[[(3S,6R)-3-methyl-1,1-dioxo-6-phenyl-thiazinan-2-yl]methyl]phenyl]-4-oxo-cyclohexanecarboxylate | 0.0061 |
| 121 | 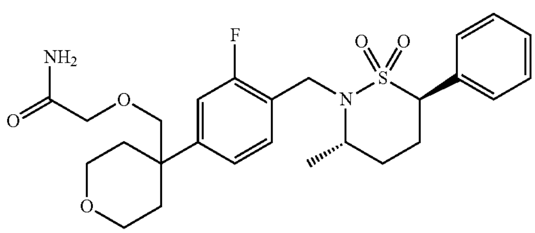 [SMILES: C[C@H]1CC[C@H](c2ccccc2)S(=O)(=O)N1Cc1ccc(C2(COCC(N)=O)CCOCC2)cc1F] | 2-[[4-[3-fluoro-4-[[(3S,6R)-3-methyl-1,1-dioxo-6-phenyl-thiazinan-2-yl]methyl]phenyl]tetrahydropyran-4-yl]methoxy]acetamide | 0.016 |
| 122 | 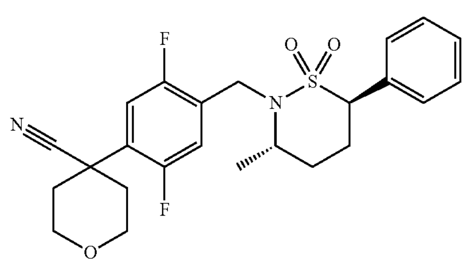 [SMILES: C[C@H]1CC[C@H](c2ccccc2)S(=O)(=O)N1Cc1cc(F)c(C2(C#N)CCOCC2)cc1F] | 4-[2,5-difluoro-4-[[(3S,6R)-3-methyl-1,1-dioxo-6-phenyl-thiazinan-2-yl]methyl]phenyl]tetrahydropyran-4-carbonitrile | 0.0268 |
| 123 | 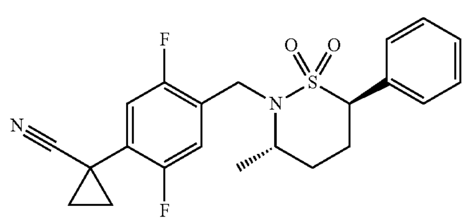 [SMILES: C[C@H]1CC[C@H](c2ccccc2)S(=O)(=O)N1Cc1cc(F)c(C2(C#N)CC2)cc1F] | 1-[2,5-difluoro-4-[[(3S,6R)-3-methyl-1,1-dioxo-6-phenyl-thiazinan-2-yl]methyl]phenyl]cyclopropanecarbonitrile | 0.0227 |
| 124 | 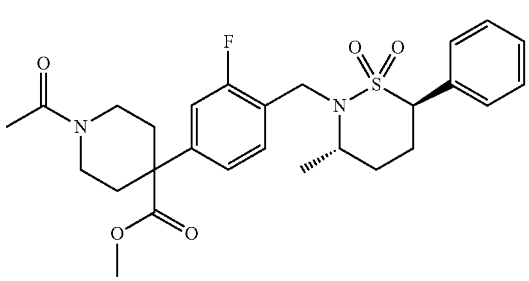 [SMILES: COC(=O)C1(c2ccc(CN3[C@@H](C)CC[C@H](c4ccccc4)S3(=O)=O)c(F)c2)CCN(C(C)=O)CC1] | methyl 1-acetyl-4-[3-fluoro-4-[[(3S,6R)-3-methyl-1,1-dioxo-6-phenyl-thiazinan-2-yl]methyl]phenyl]piperidine-4-carboxylate | 0.013 |

TABLE 4-continued

| | Structure | name | IC$_{50}$ |
|---|---|---|---|
| 125 | 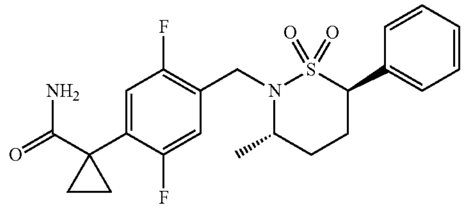 [SMILES: C[C@H]1CC[C@H](c2ccccc2)S(=O)(=O)N1Cc1cc(F)c(C2(C(N)=O)CC2)cc1F] | 1-[2,5-difluoro-4-[[(3S,6R)-3-methyl-1,1-dioxo-6-phenyl-thiazinan-2-yl]methyl]phenyl]cyclopropane-carboxamide | 0.346 |
| 126 | 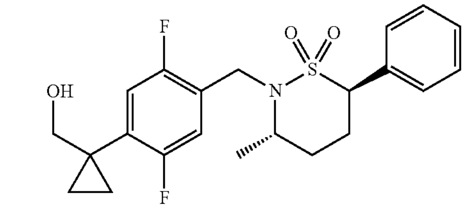 [SMILES: C[C@H]1CC[C@H](c2ccccc2)S(=O)(=O)N1Cc1cc(F)c(C2(CO)CC2)cc1F] | [1-[2,5-difluoro-4-[[(3S,6R)-3-methyl-1,1-dioxo-6-phenyl-thiazinan-2-yl]methyl]phenyl]cyclopropyl]methanol | 0.0499 |
| 127 | 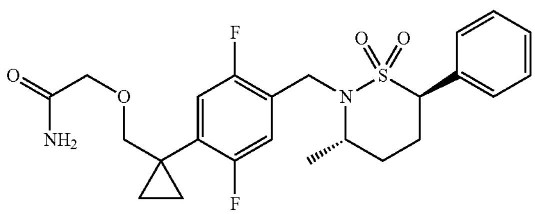 [SMILES: C[C@H]1CC[C@H](c2ccccc2)S(=O)(=O)N1Cc1cc(F)c(C2(COCC(N)=O)CC2)cc1F] | 2-[[1-[2,5-difluoro-4-[[(3S,6R)-3-methyl-1,1-dioxo-6-phenyl-thiazinan-2-yl]methyl]phenyl]cyclopropyl]methoxy]acetamide | 0.020 |
| 128 | 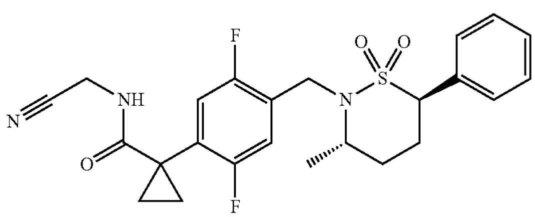 [SMILES: C[C@H]1CC[C@H](c2ccccc2)S(=O)(=O)N1Cc1cc(F)c(C2(C(=O)NCC#N)CC2)cc1F] | N-(cyanomethyl)-1-[2,5-difluoro-4-[[(3S,6R)-3-methyl-1,1-dioxo-6-phenyl-thiazinan-2-yl]methyl]phenyl]cyclopropane-carboxamide | 0.39 |
| 129 | 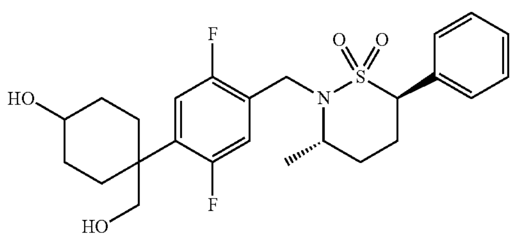 [SMILES: C[C@H]1CC[C@H](c2ccccc2)S(=O)(=O)N1Cc1cc(F)c(C2(CO)CCC(O)CC2)cc1F] | 4-[2,5-difluoro-4-[[(3S,6R)-3-methyl-1,1-dioxo-6-phenyl-thiazinan-2-yl]methyl]phenyl]-4-(hydroxymethyl)cyclohexanol | 0.0081 |
| 130 | 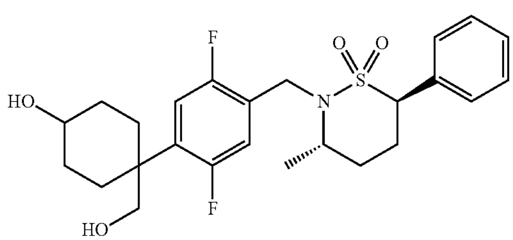 [SMILES: C[C@H]1CC[C@H](c2ccccc2)S(=O)(=O)N1Cc1cc(F)c(C2(CO)CCC(O)CC2)cc1F] | 4-[2,5-difluoro-4-[[(3S,6R)-3-methyl-1,1-dioxo-6-phenyl-thiazinan-2-yl]methyl]phenyl]-4-(hydroxymethyl)cyclohexanol | 0.0347 |
| 131 | 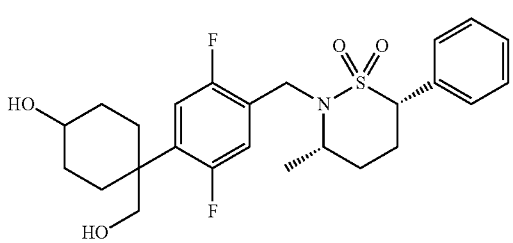 [SMILES: C[C@H]1CC[C@@H](c2ccccc2)S(=O)(=O)N1Cc1cc(F)c(C2(CO)CCC(O)CC2)cc1F] | 4-[2,5-difluoro-4-[[3S,6S)-3-methyl-1,1-dioxo-6-phenyl-thiazinan-2-yl]methyl]phenyl]-4-(hydroxymethyl)cyclohexanol | 0.0728 |

TABLE 4-continued

| | Structure | name | IC$_{50}$ |
|---|---|---|---|
| 132 | 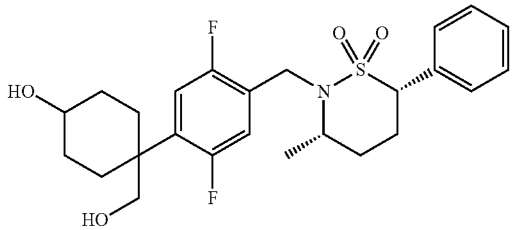 [SMILES: C[C@H]1CC[C@@H](c2ccccc2)S(=O)(=O)N1Cc1cc(F)c(C2(CO)CCC(O)CC2)cc1F] | 4-[2,5-difluoro-4-[[3S,6S)-3-methyl-1,1-dioxo-6-phenyl-thiazinan-2-yl]methyl]phenyl]-4-(hydroxymethyl)cyclohexanol | 0.24 |
| 133 | 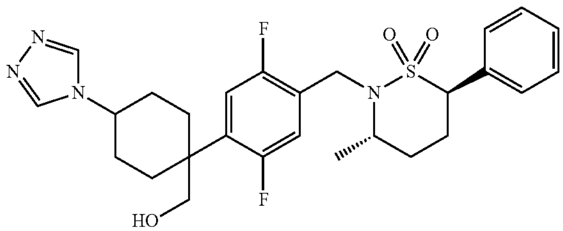 [SMILES: C[C@H]1CC[C@H](c2ccccc2)S(=O)(=O)N1Cc1cc(F)c(C2(CO)CCC(n3cnnc3)CC2)cc1F] | [1-[2,5-difluoro-4-[[(3S,6R)-3-methyl-1,1-dioxo-6-phenyl-thiazinan-2-yl]methyl]phenyl]-4-(1,2,4-triazol-4-yl)cyclohexyl]methanol | 0.0052 |
| 134 | 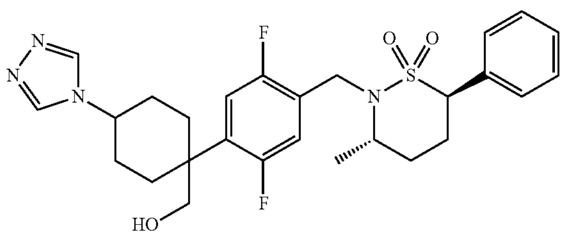 [SMILES: C[C@H]1CC[C@H](c2ccccc2)S(=O)(=O)N1Cc1cc(F)c(C2(CO)CCC(n3cnnc3)CC2)cc1F] | [1-[2,5-difluoro-4-[[(3S,6R)-3-methyl-1,1-dioxo-6-phenyl-thiazinan-2-yl]methyl]phenyl]-4-(1,2,4-triazol-4-yl)cyclohexyl]methanol | 0.0879 |
| 135 | 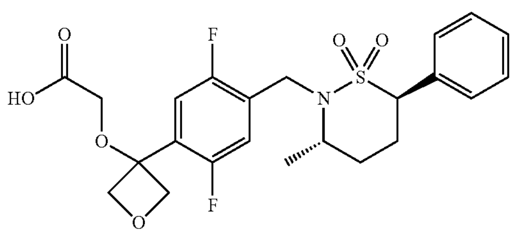 | 2-[3-[2,5-difluoro-4-[[(3S,6R)-3-methyl-1,1-dioxo-6-phenyl-thiazinan-2-yl]methyl]phenyl]oxetan-3-yl]oxyacetic acid | 0.0272 |
| 136 | 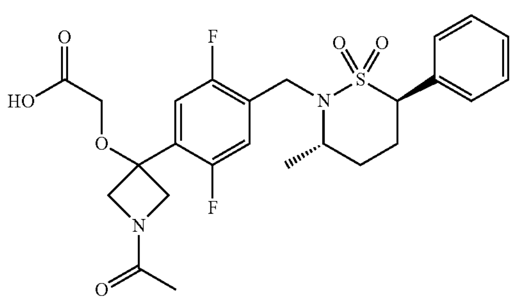 [SMILES: CC(=O)N1CC(OCC(=O)O)(c2cc(F)c(CN3[C@@H](C)CC[C@H](c4ccccc4)S3(=O)=O)cc2F)C1] | 2-[1-acetyl-3-[2,5-difluoro-4-[[(3S,6R)-3-methyl-1,1-dioxo-6-phenyl-thiazinan-2-yl]methyl]phenyl]azetidin-3-yl]oxyacetic acid | 0.0172 |
| 137 | 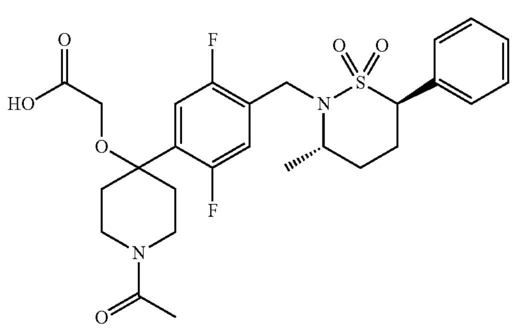 [SMILES: CC(=O)N1CCC(OCC(=O)O)(c2cc(F)c(CN3[C@@H](C)CC[C@H](c4ccccc4)S3(=O)=O)cc2F)CC1] | 2-[[1-acetyl-4-[2,5-difluoro-4-[[(3S,6R)-3-methyl-1,1-dioxo-6-phenyl-thiazinan-2-yl]methyl]phenyl]-4-piperidyl]oxy]acetic acid | 0.0179 |

TABLE 4-continued

| | Structure | name | IC$_{50}$ |
|---|---|---|---|
| 138 | 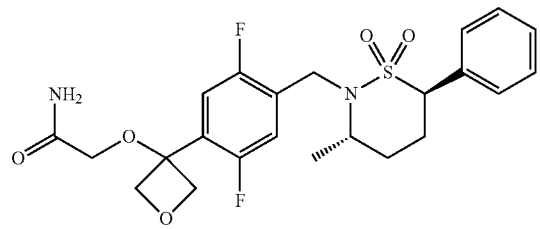 [SMILES: C[C@H]1CC[C@H](c2ccccc2)S(=O)(=O)N1Cc1cc(F)c(C2(OCC(N)=O)COC2)cc1F] | 2-[3-[2,5-difluoro-4-[[(3S,6R)-3-methyl-1,1-dioxo-6-phenyl-thiazinan-2-yl]methyl]phenyl]oxetan-3-yl]oxyacetamide | 0.0026 |
| 139 | 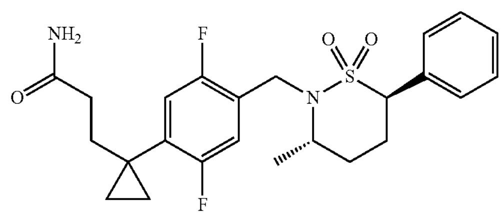 [SMILES: C[C@H]1CC[C@H](c2ccccc2)S(=O)(=O)N1Cc1cc(F)c(C2(CCC(N)=O)CC2)cc1F] | 3-[1-[2,5-difluoro-4-[[(3S,6R)-3-methyl-1,1-dioxo-6-phenyl-thiazinan-2-yl]methyl]phenyl]cyclopropyl]propanamide | 0.0237 |
| 140 | 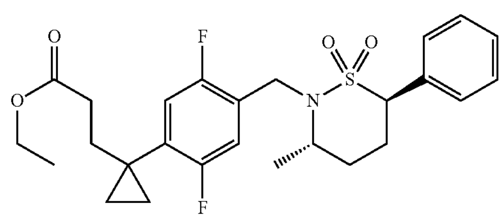 [SMILES: CCOC(=O)CCC1(c2cc(F)c(CN3[C@@H](C)CC[C@H](c4ccccc4)S3(=O)=O)cc2F)CC1] | ethyl 3-[1-[2,5-difluoro-4-[[(3S,6R)-3-methyl-1,1-dioxo-6-phenyl-thiazinan-2-yl]methyl]phenyl]cyclopropyl]propanoate | 0.0457 |
| 141 | 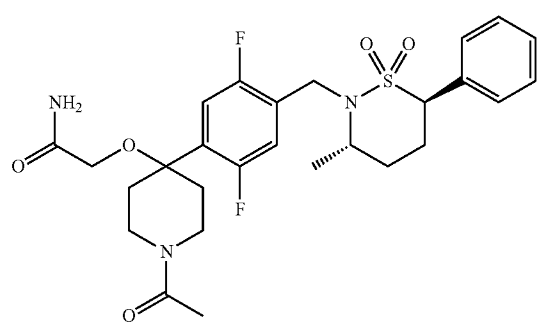 [SMILES: CC(=O)N1CCC(OCC(N)=O)(c2cc(F)c(CN3[C@@H](C)CC[C@H](c4ccccc4)S3(=O)=O)cc2F)CC1] | 2-[[1-acetyl-4-[2,5-difluoro-4-[[(3S,6R)-3-methyl-1,1-dioxo-6-phenyl-thiazinan-2-yl]methyl]phenyl]-4-piperidyl]oxy]acetamide | 0.026 |
| 142 | 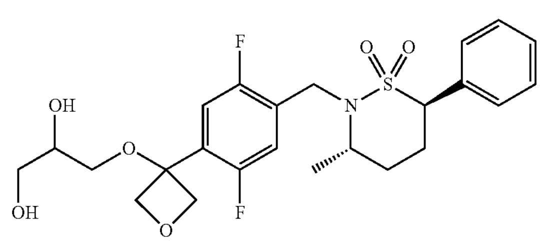 [SMILES: C[C@H]1CC[C@H](c2ccccc2)S(=O)(=O)N1Cc1cc(F)c(C2(OCC(O)CO)COC2)cc1F] | 3-[3-[2,5-difluoro-4-[[(3S,6R)-3-methyl-1,1-dioxo-6-phenyl-thiazinan-2-yl]methyl]phenyl]oxetan-3-yl]oxypropane-1,2-diol | 0.0206 |
| 143 | 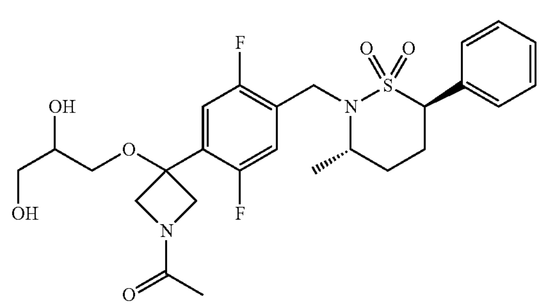 [SMILES: CC(=O)N1CC(OCC(O)CO)(c2cc(F)c(CN3[C@@H](C)CC[C@H](c4ccccc4)S3(=O)=O)cc2F)C1] | 1-[3-[2,5-difluoro-4-[[(3S,6R)-3-methyl-1,1-dioxo-6-phenyl-thiazinan-2-yl]methyl]phenyl]-3-(2,3-dihydroxypropoxy)azetidin-1-yl]ethanone | 0.0298 |

TABLE 4-continued

| | Structure | name | IC$_{50}$ |
|---|---|---|---|
| 144 | 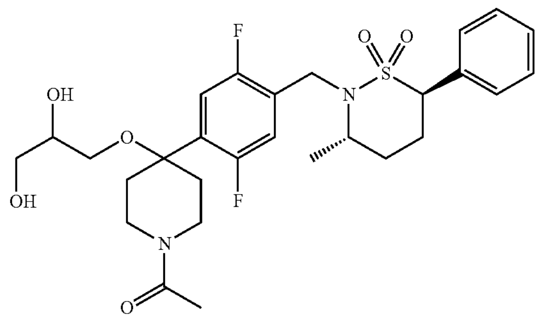 [SMILES: CC(=O)N1CCC(OCC(O)CO)(c2cc(F)c(CN3[C@@H](C)CC[C@H](c4ccccc4)S3(=O)=O)cc2F)CC1] | 1-[4-[2,5-difluoro-4-[[(3S,6R)-3-methyl-1,1-dioxo-6-phenyl-thiazinan-2-yl]methyl]phenyl]-4-(2,3-dihydroxypropoxy)-1-piperidyl]ethanone | 0.0216 |
| 145 | 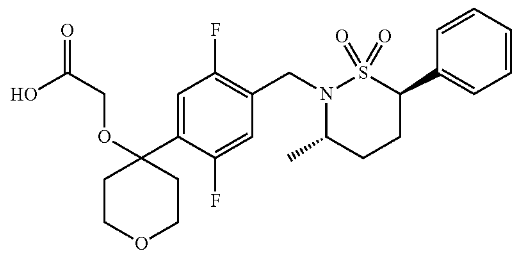 [SMILES: C[C@H]1CC[C@H](c2ccccc2)S(=O)(=O)N1Cc1cc(F)c(C2(OCC(=O)O)CCOCC2)cc1F] | 2-[4-[2,5-difluoro-4-[[(3S,6R)-3-methyl-1,1-dioxo-6-phenyl-thiazinan-2-yl]methyl]phenyl]tetrahydropyran-4-yl]oxyacetic acid | 0.0143 |
| 146 | 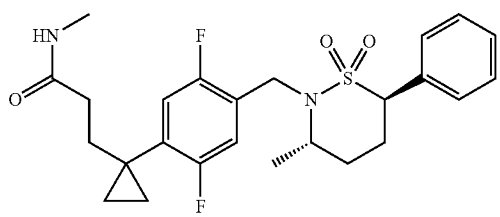 [SMILES: CNC(=O)CCC1(c2cc(F)c(CN3[C@@H](C)CC[C@H](c4ccccc4)S3(=O)=O)cc2F)CC1] | 3-[1-[2,5-difluoro-4-[[(3S,6R)-3-methyl-1,1-dioxo-6-phenyl-thiazinan-2-yl]methyl]phenyl]cyclopropyl]-N-methyl-propanamide | 0.0327 |
| 147 | 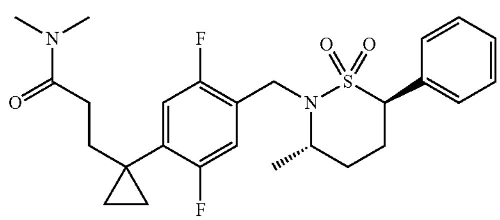 [SMILES: C[C@H]1CC[C@H](c2ccccc2)S(=O)(=O)N1Cc1cc(F)c(C2(CCC(=O)N(C)C)CC2)cc1F] | 3-[1-[2,5-difluoro-4-[[(3S,6R)-3-methyl-1,1-dioxo-6-phenyl-thiazinan-2-yl]methyl]phenyl]cyclopropyl]-N,N-dimethyl-propanamide | 0.0325 |
| 148 | 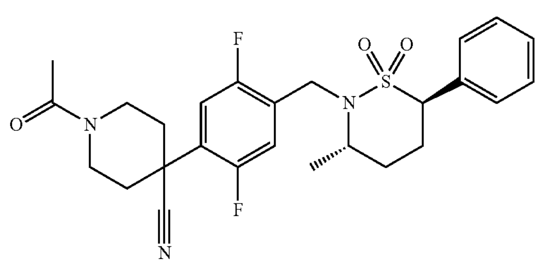 [SMILES: CC(=O)N1CCC(C#N)(c2cc(F)c(CN3[C@@H](C)CC[C@H](c4ccccc4)S3(=O)=O)cc2F)CC1] | 1-acetyl-4-[2,5-difluoro-4-[[(3S,6R)-3-methyl-1,1-dioxo-6-phenyl-thiazinan-2-yl]methyl]phenyl]piperidine-4-carbonitrile | 0.0145 |
| 149 | 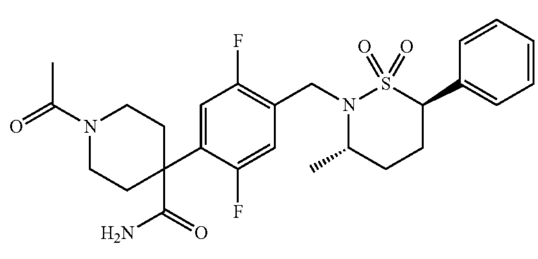 [SMILES: CC(=O)N1CCC(C(N)=O)(c2cc(F)c(CN3[C@@H](C)CC[C@H](c4ccccc4)S3(=O)=O)cc2F)CC1] | 1-acetyl-4-[2,5-difluoro-4-[[(3S,6R)-3-methyl-1,1-dioxo-6-phenyl-thiazinan-2-yl]methyl]phenyl]piperidine-4-carboxamide | 0.0114 |

TABLE 4-continued

| | Structure | name | IC$_{50}$ |
|---|---|---|---|
| 150 | 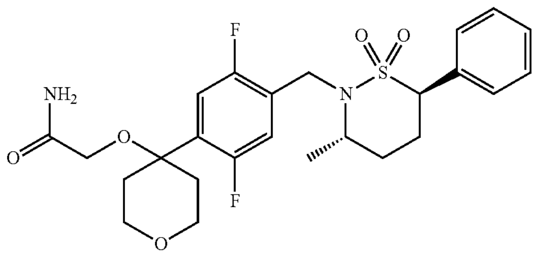 [SMILES: C[C@H]1CC[C@H](c2ccccc2)S(=O)(=O)N1Cc1cc(F)c(C2(OCC(N)=O)CCOCC2)cc1F] | 2-[4-[2,5-difluoro-4-[[(3S,6R)-3-methyl-1,1-dioxo-6-phenyl-thiazinan-2-yl]methyl]phenyl]tetrahydropyran-4-yl]oxyacetamide | 0.0061 |
| 151 | 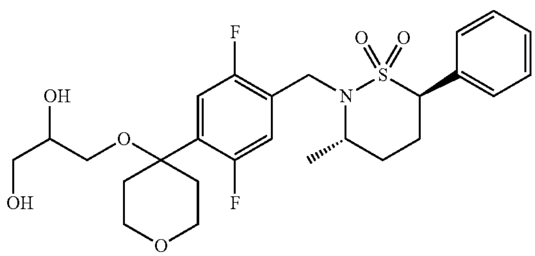 [SMILES: C[C@H]1CC[C@H](c2ccccc2)S(=O)(=O)N1Cc1cc(F)c(C2(OCC(O)CO)CCOCC2)cc1F] | 3-[4-[2,5-difluoro-4-[[(3S,6R)-3-methyl-1,1-dioxo-6-phenyl-thiazinan-2-yl]methyl]phenyl]tetrahydropyran-4-yl]oxypropane-1,2-diol | 0.0078 |
| 152 | 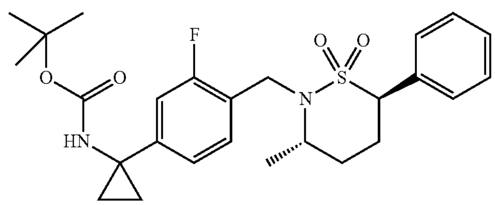 [SMILES: C[C@H]1CC[C@H](c2ccccc2)S(=O)(=O)N1Cc1ccc(C2(NC(=O)OC(C)(C)C)CC2)cc1F] | tert-butyl N-[1-[3-fluoro-4-[[(3S,6R)-3-methyl-1,1-dioxo-6-phenyl-thiazinan-2-yl]methyl]phenyl]cyclopropyl]carbamate | 0.227 |
| 153 | 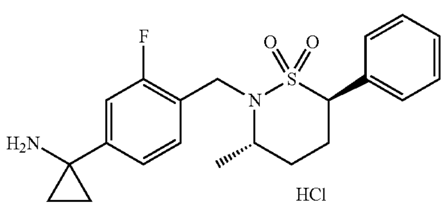 [SMILES: C[C@H]1CC[C@H](c2ccccc2)S(=O)(=O)N1Cc1ccc(C2(N)CC2)cc1F ; Cl] | 1-[3-fluoro-4-[[(3S,6R)-3-methyl-1,1-dioxo-6-phenyl-thiazinan-2-yl]methyl]phenyl]cyclopropanamine; hydrochloride | 0.572 |
| 154 | 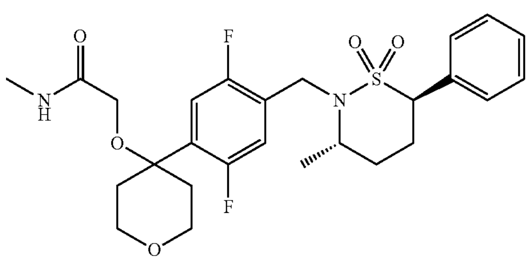 [SMILES: CNC(=O)COC1(c2cc(F)c(CN3[C@@H](C)CC[C@H](c4ccccc4)S3(=O)=O)cc2F)CCOCC1] | 2-[4-[2,5-difluoro-4-[[(3S,6R)-3-methyl-1,1-dioxo-6-phenyl-thiazinan-2-yl]methyl]phenyl]tetrahydropyran-4-yl]oxy-N-methyl-acetamide | 0.0057 |
| 155 | 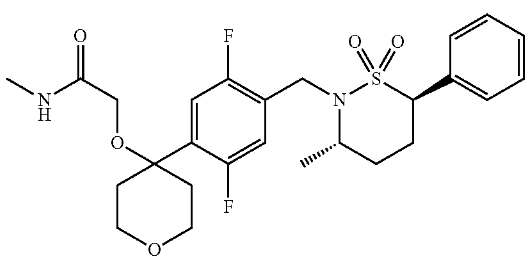 [SMILES: CNC(=O)COC1(c2cc(F)c(CN3[C@@H](C)CC[C@H](c4ccccc4)S3(=O)=O)cc2F)CCOCC1] | 2-[4-[2,5-difluoro-4-[[(3S,6R)-3-methyl-1,1-dioxo-6-phenyl-thiazinan-2-yl]methyl]phenyl]tetrahydropyran-4-yl]oxy-N,N-dimethyl-acetamide | 0.0386 |

TABLE 4-continued

| | Structure | name | IC$_{50}$ |
|---|---|---|---|
| 156 | 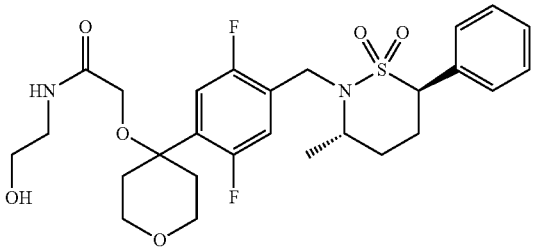 [SMILES: C[C@H]1CC[C@H](c2ccccc2)S(=O)(=O)N1Cc1cc(F)c(C2(OCC(=O)NCCO)CCOCC2)cc1F] | 2-[4-[2,5-difluoro-4-[[(3S,6R)-3-methyl-1,1-dioxo-6-phenyl-thiazinan-2-yl]methyl]phenyl]tetrahydropyran-4-yl]oxy-N-(2-hydroxyethyl)acetamide | 0.0152 |
| 157 | 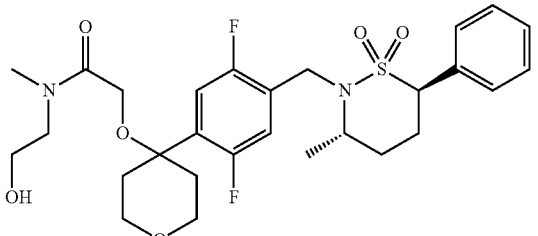 | 2-[4-[2,5-difluoro-4-[[(3S,6R)-3-methyl-1,1-dioxo-6-phenyl-thiazinan-2-yl]methyl]phenyl]tetrahydropyran-4-yl]oxy-N-(2-hydroxyethyl)-N-methyl-acetamide | 0.0472 |
| 158 | 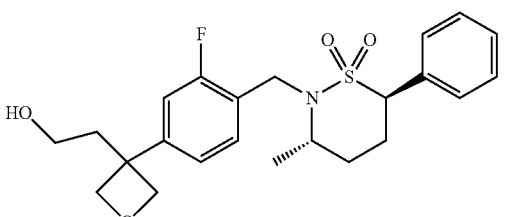 | 2-[3-[3-fluoro-4-[(3S,6R)-3-methyl-1,1-dioxo-6-phenyl-thiazinan-2-yl]methyl]phenyl]oxetan-3-yl]ethanol | 0.0603 |
| 159 | 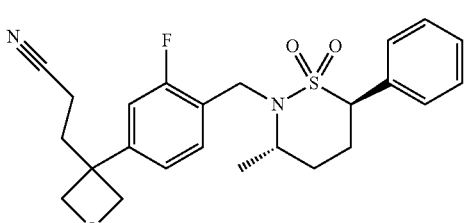 | 3-[3-[3-fluoro-4-[(3S,6R)-3-methyl-1,1-dioxo-6-phenyl-thiazinan-2-yl]methyl]phenyl]oxetan-3-yl]propanenitrile | 0.0771 |
| 160 | 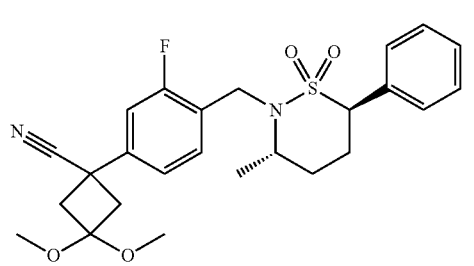 [SMILES: COC1(OC)CC(C#N)(c2ccc(CN3[C@@H](C)CC[C@H](c4ccccc4)S3(=O)=O)c(F)c2)C1] | 1-[3-fluoro-4-[[(3S,6R)-3-methyl-1,1-dioxo-6-phenyl-thiazinan-2-yl]methyl]phenyl]-3,3-dimethoxy-cyclobutanecarbonitrile | 0.0145 |
| 161 | 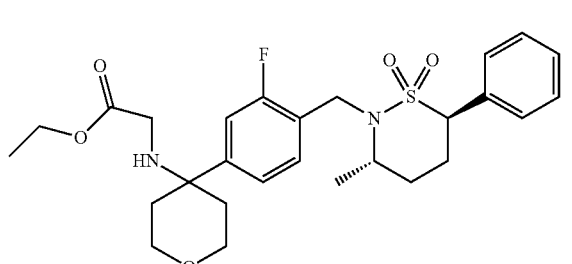 | ethyl 2-[[4-[3-fluoro-4-[[(3S,6R)-3-methyl-1,1-dioxo-6-phenyl-thiazinan-2-yl]methyl]phenyl]tetrahydropyran-4-yl]amino]acetate | 0.0295 |

| | Structure | name | IC$_{50}$ |
|---|---|---|---|
| 162 | 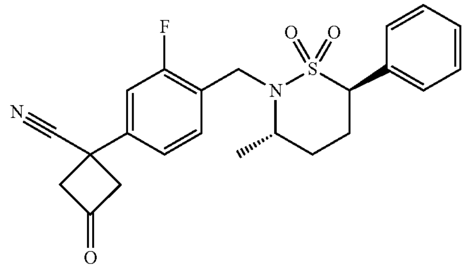 [SMILES: C[C@H]1CC[C@H](c2ccccc2)S(=O)(=O)N1Cc1ccc(C2(C#N)CC(=O)C2)cc1F] | 1-[3-fluoro-4-[[(3S,6R)-3-methyl-1,1-dioxo-6-phenyl-thiazinan-2-yl]methyl]phenyl]-3-oxo-cyclobutanecarbonitrile | 0.0639 |
| 163 | 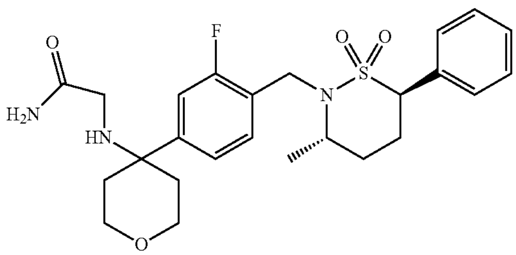 [SMILES: C[C@H]1CC[C@H](c2ccccc2)S(=O)(=O)N1Cc1ccc(C2(NCC(N)=O)CCOCC2)cc1F] | 2-[[4-[3-fluoro-4-[[(3S,6R)-3-methyl-1,1-dioxo-6-phenyl-thiazinan-2-yl]methyl]phenyl]tetrahydropyran-4-yl]amino]acetamide | 0.0032 |
| 164 | 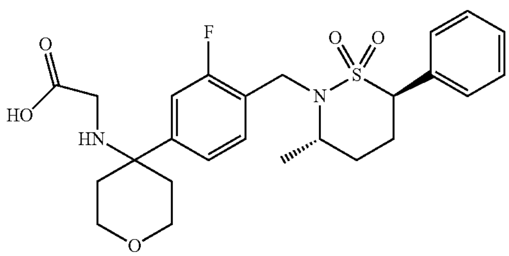 [SMILES: C[C@H]1CC[C@H](c2ccccc2)S(=O)(=O)N1Cc1ccc(C2(NCC(=O)O)CCOCC2)cc1F] | 2-[[4-[3-fluoro-4-[[(3S,6R)-3-methyl-1,1-dioxo-6-phenyl-thiazinan-2-yl]methyl]phenyl]tetrahydropyran-4-yl]amino]acetic acid | 0.112 |
| 165 | 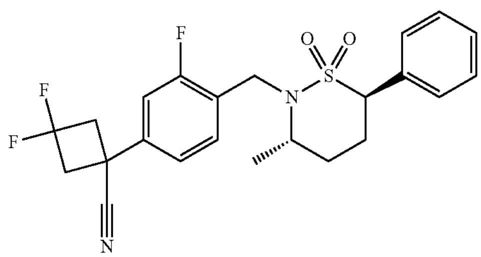 [SMILES: C[C@H]1CC[C@H](c2ccccc2)S(=O)(=O)N1Cc1ccc(C2(C#N)CC(F)(F)C2)cc1F] | 3,3-difluoro-1-[3-fluoro-4-[[(3S,6R)-3-methyl-1,1-dioxo-6-phenyl-thiazinan-2-yl]methyl]phenyl]cyclobutanecarbonitrile | 0.0522 |
| 166 | 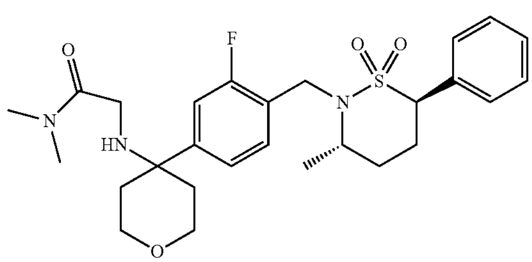 [SMILES: C[C@H]1CC[C@H](c2ccccc2)S(=O)(=O)N1Cc1ccc(C2(NCC(=O)N(C)C)CCOCC2)cc1F] | 2-[[4-[3-fluoro-4-[[(3S,6R)-3-methyl-1,1-dioxo-6-phenyl-thiazinan-2-yl]methyl]phenyl]tetrahydropyran-4-yl]amino]-N,N-dimethyl-acetamide | 0.0276 |
| 167 | 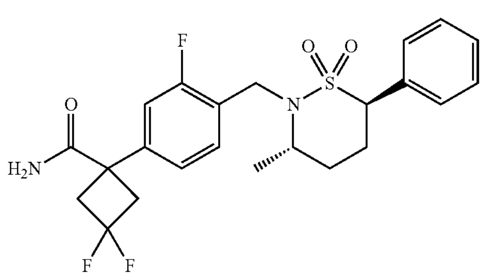 [SMILES: C[C@H]1CC[C@H](c2ccccc2)S(=O)(=O)N1Cc1ccc(C2(C(N)=O)CC(F)(F)C2)cc1F] | 3,3-difluoro-1-[3-fluoro-4-[[(3S,6R)-3-methyl-1,1-dioxo-6-phenyl-thiazinan-2-yl]methyl]phenyl]cyclobutanecarboxamide | 0.0111 |

TABLE 4-continued

| | Structure | name | IC$_{50}$ |
|---|---|---|---|
| 168 | 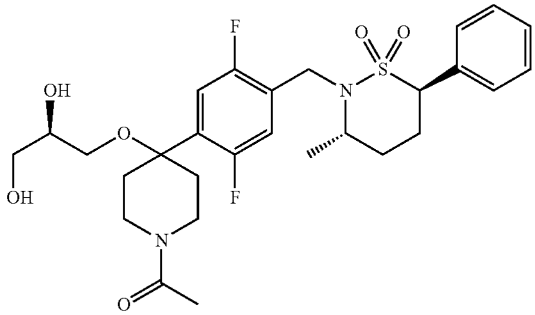 [SMILES: CC(=O)N1CCC(OC[C@H](O)CO)(c2cc(F)c(CN3[C@@H](C)CC[C@H](c4ccccc4)S3(=O)=O)cc2F)CC1] | 1-[4-[2,5-difluoro-4-[[(3S,6R)-3-methyl-1,1-dioxo-6-phenyl-thiazinan-2-yl]methyl]phenyl]-4-[(2S)-2,3-dihydroxypropoxy]-1-piperidyl]ethanone | 0.0355 |
| 169 | 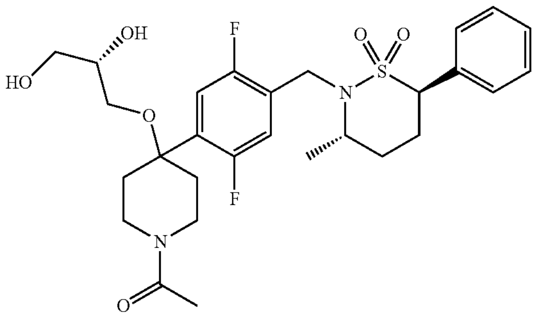 [SMILES: CC(=O)N1CCC(OC[C@@H](O)CO)(c2cc(F)c(CN3[C@@H](C)CC[C@H](c4ccccc4)S3(=O)=O)cc2F)CC1] | 1-[4-[2,5-difluoro-4-[[(3S,6R)-3-methyl-1,1-dioxo-6-phenyl-thiazinan-2-yl]methyl]phenyl]-4-[(2R)-2,3-dihydroxypropoxy]-1-piperidyl]ethanone | 0.0208 |
| 170 | 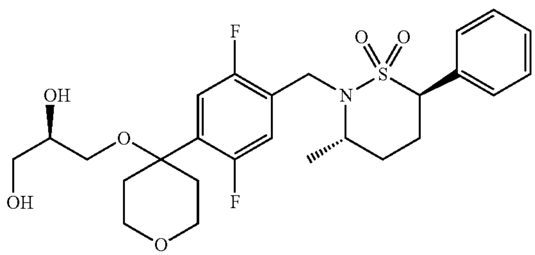 [SMILES: C[C@H]1CC[C@H](c2ccccc2)S(=O)(=O)N1Cc1cc(F)c(C2(OC[C@H](O)CO)CCOCC2)cc1F] | (2S)-3-[4-[2,5-difluoro-4-[[(3S,6R)-3-methyl-1,1-dioxo-6-phenyl-thiazinan-2-yl]methyl]phenyl]tetrahydropyran-4-yl]oxypropane-1,2-diol | 0.0117 |
| 171 | 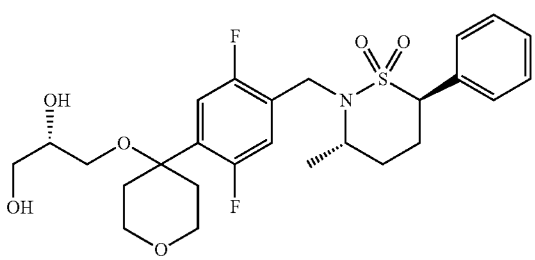 [SMILES: C[C@H]1CC[C@H](c2ccccc2)S(=O)(=O)N1Cc1cc(F)c(C2(OC[C@@H](O)CO)CCOCC2)cc1F] | (2R)-3-[4-[2,5-difluoro-4-[[(3S,6R)-3-methyl-1,1-dioxo-6-phenyl-thiazinan-2-yl]methyl]phenyl]tetrahydropyran-4-yl]oxypropane-1,2-diol | 0.0116 |
| 172 | 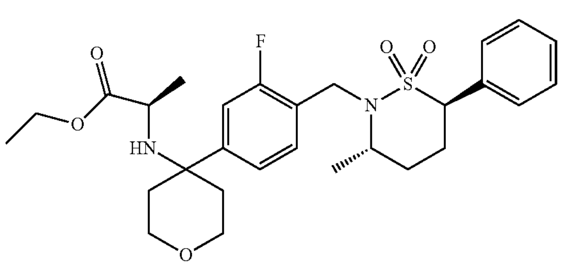 [SMILES: CCOC(=O)[C@@H](C)NC1(c2ccc(CN3[C@@H](C)CC[C@H](c4ccccc4)S3(=O)=O)c(F)c2)CCOCC1] | ethyl (2R)-2-[[4-[3-fluoro-4-[[(3S,6R)-3-methyl-1,1-dioxo-6-phenyl-thiazinan-2-yl]methyl]phenyl]tetrahydropyran-4-yl]amino]propanoate | 0.12 |

TABLE 4-continued

| | Structure | name | IC$_{50}$ |
|---|---|---|---|
| 173 | 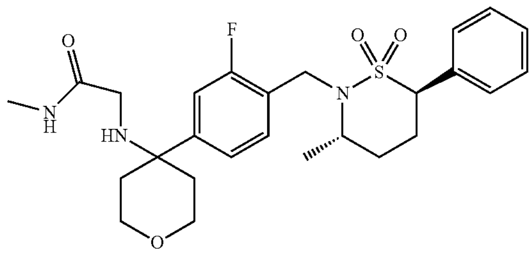 [SMILES: CNC(=O)CNC1(c2ccc(CN3[C@@H](C)CC[C@H](c4ccccc4)S3(=O)=O)c(F)c2)CCOCC1] | 2-[[4-[3-fluoro-4-[[(3S,6R)-3-methyl-1,1-dioxo-6-phenyl-thiazinan-2-yl]methyl]phenyl]tetrahydropyran-4-yl]amino]-N-methyl-acetamide | 0.0331 |
| 174 | 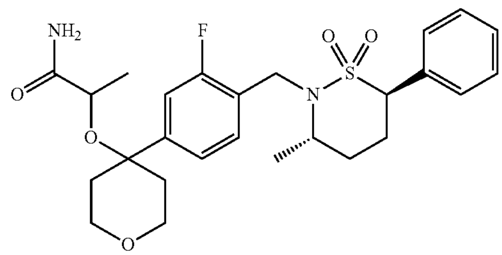 [SMILES: CC(OC1(c2ccc(CN3[C@@H](C)CC[C@H](c4ccccc4)S3(=O)=O)c(F)c2)CCOCC1)C(N)=O] | 2-[4-[3-fluoro-4-[[(3S,6R)-3-methyl-1,1-dioxo-6-phenyl-thiazinan-2-yl]methyl]phenyl]tetrahydropyran-4-yl]oxypropanamide | 0.0379 |
| 175 | 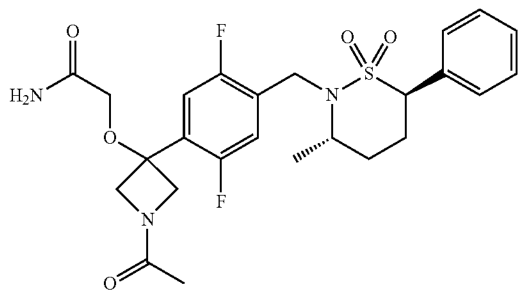 [SMILES: CC(=O)N1CC(OCC(N)=O)(c2cc(F)c(CN3[C@@H](C)CC[C@H](c4ccccc4)S3(=O)=O)cc2F)C1] | 2-[1-acetyl-3-[2,5-difluoro-4-[[(3S,6R)-3-methyl-1,1-dioxo-6-phenyl-thiazinan-2-yl]methyl]phenyl]azetidin-3-yl]oxyacetamide | 0.0049 |
| 176 | 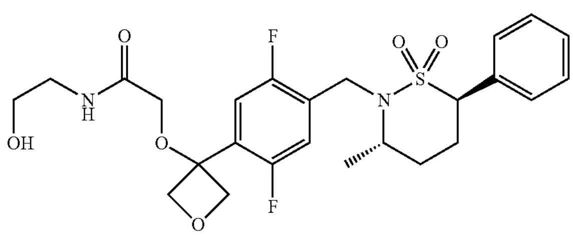 [SMILES: C[C@H]1CC[C@H](c2ccccc2)S(=O)(=O)N1Cc1cc(F)c(C2(OCC(=O)NCCO)COC2)cc1F] | 2-[3-[2,5-difluoro-4-[[(3S,6R)-3-methyl-1,1-dioxo-6-phenyl-thiazinan-2-yl]methyl]phenyl]oxetan-3-yl]oxy-N-(2-hydroxyethyl)acetamide | 0.0025 |
| 177 | 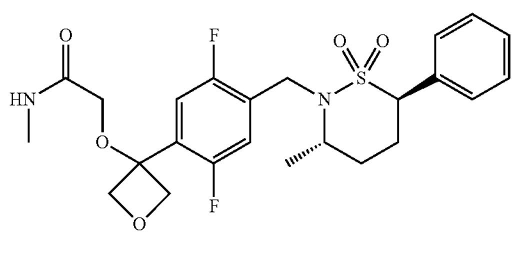 [SMILES: CNC(=O)COC1(c2cc(F)c(CN3[C@@H](C)CC[C@H](c4ccccc4)S3(=O)=O)cc2F)COC1] | 2-[3-[2,5-difluoro-4-[[(3S,6R)-3-methyl-1,1-dioxo-6-phenyl-thiazinan-2-yl]methyl]phenyl]oxetan-3-yl]oxy-N-methyl-acetamide | 0.00435 |
| 178 | 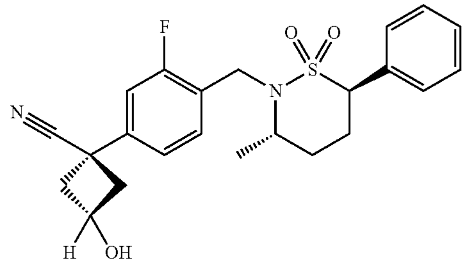 [SMILES: C[C@H]1CC[C@H](c2ccccc2)S(=O)(=O)N1Cc1ccc([C@]2(C#N)C[C@H](O)C2)cc1F] | 1-[3-fluoro-4-[[(3S,6R)-3-methyl-1,1-dioxo-6-phenyl-thiazinan-2-yl]methyl]phenyl]-3-hydroxy-cyclobutanecarbonitrile | 0.0441 |

TABLE 4-continued

| | Structure | name | IC$_{50}$ |
|---|---|---|---|
| 179 | 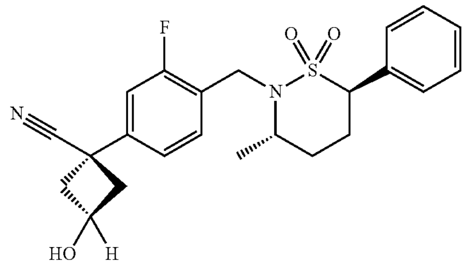 [SMILES: C[C@H]1CC[C@H](c2ccccc2)S(=O)(=O)N1Cc1ccc([C@]2(C#N)C[C@@H](O)C2)cc1F] | 1-[3-fluoro-4-[[(3S,6R)-3-methyl-1,1 dioxo-6-phenyl-thiazinan-2-yl]methyl]phenyl]-3-hydroxy-cyclobutanecarbonitrile | 0.159 |
| 180 | 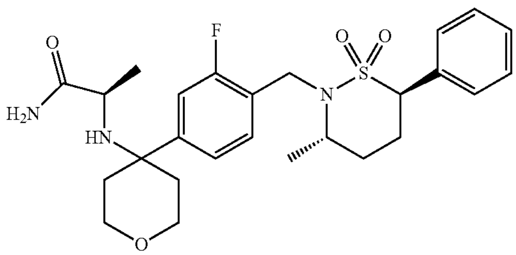 [SMILES: C[C@@H](NC1(c2ccc(CN3[C@@H](C)CC[C@H](c4ccccc4)S3(=O)=O)c(F)c2)CCOCC1)C(N)=O] | (2R)-2-[[4-[3-fluoro-4-[[(3S,6R)-3-methyl-1,1-dioxo-6-phenyl-thiazinan-2-yl]methyl]phenyl]tetrahydropyran-4-yl]amino]propanamide | 0.0067 |
| 181 | 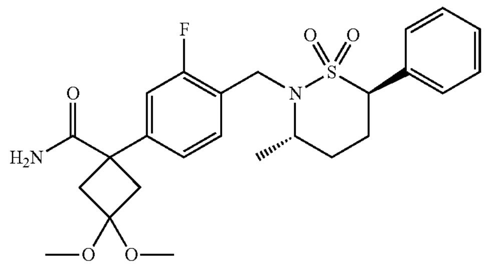 [SMILES: COC1(OC)CC(C(N)=O)(c2ccc(CN3[C@@H](C)CC[C@H](c4ccccc4)S3(=O)=O)c(F)c2)C1] | 1-[3-fluoro-4-[[(3S,6R)-3-methyl-1,1-dioxo-6-phenyl-thiazinan-2-yl]methyl]phenyl]-3,3-dimethoxy-cyclobutanecarboxamide | 0.0237 |
| 182 | 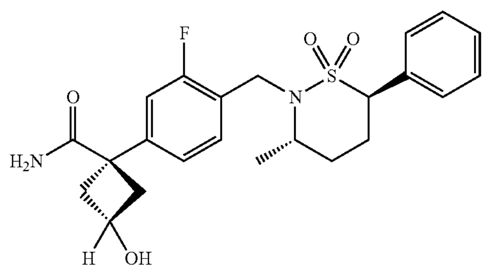 [SMILES: C[C@H]1CC[C@H](c2ccccc2)S(=O)(=O)N1Cc1ccc([C@]2(C(N)=O)C[C@H](O)C2)cc1F] | 1-[3-fluoro-4-[[(3S,6R)-3-methyl-1,1-dioxo-6-phenyl-thiazinan-2-yl]methyl]phenyl]-3-hydroxy-cyclobutanecarboxamide | 0.0373 |
| 183 | 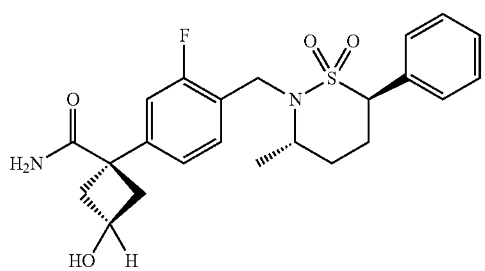 [SMILES: C[C@H]1CC[C@H](c2ccccc2)S(=O)(=O)N1Cc1ccc([C@]2(C(N)=O)C[C@@H](O)C2)cc1F] | 1-[3-fluoro-4-[[(3S,6R)-3-methyl-1,1-dioxo-6-phenyl-thiazinan-2-yl]methyl]phenyl]-3-hydroxy-cyclobutanecarboxamide | 0.0552 |
| 184 | 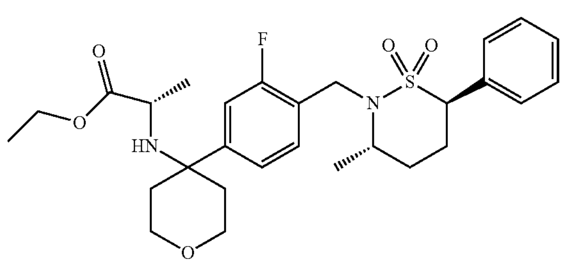 [SMILES: CCOC(=O)[C@H](C)NC1(c2ccc(CN3[C@@H](C)CC[C@H](c4ccccc4)S3(=O)=O)c(F)c2)CCOCC1] | ethyl (2S)-2-[[4-[3-fluoro-4-[[(3S,6R)-3-methyl-1,1-dioxo-6-phenyl-thiazinan-2-yl]methyl]phenyl]tetrahydropyran-4-yl]amino]propanoate | 0.0409 |

TABLE 4-continued

| | Structure | name | IC$_{50}$ |
|---|---|---|---|
| 185 | 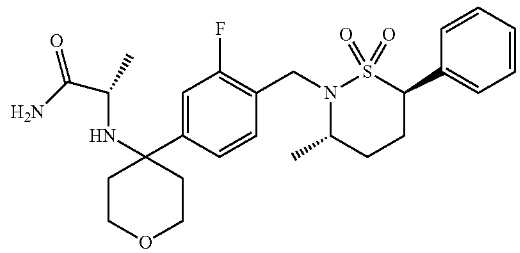 [SMILES: C[C@H](NC1(c2ccc(CN3[C@@H](C)CC[C@H](c4ccccc4)S3(=O)=O)c(F)c2)CCOCC1)C(N)=O] | (2S)-2-[[4-[3-fluoro-4-[[(3S,6R)-3-methyl-1,1-dioxo-6-phenyl-thiazinan-2-yl]methyl]phenyl]tetrahydropyran-4-yl]amino]propanamide | 0.102 |
| 186 | 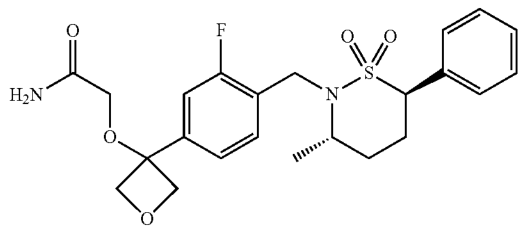 [SMILES: C[C@H]1CC[C@H](c2ccccc2)S(=O)(=O)N1Cc1ccc(C2(OCC(N)=O)COC2)cc1F] | 2-[3-[3-fluoro-4-[[(3S,6R)-3-methyl-1,1-dioxo-6-phenyl-thiazinan-2-yl]methyl]phenyl]oxetan-3-yl]oxyacetamide | 0.008 |
| 187 | 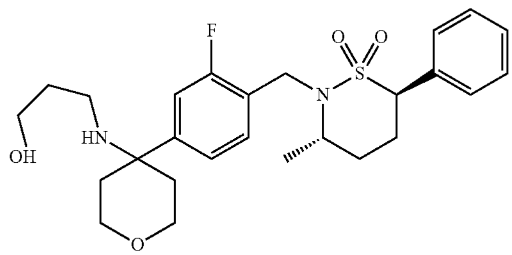 [SMILES: C[C@H]1CC[C@H](c2ccccc2)S(=O)(=O)N1Cc1ccc(C2(NCCCO)CCOCC2)cc1F] | 3-[[4-[3-fluoro-4-[[(3S,6R)-3-methyl-1,1-dioxo-6-phenyl-thiazinan-2-yl]methyl]phenyl]tetrahydropyran-4-yl]amino]propan-1-ol | 0.074 |
| 188 | 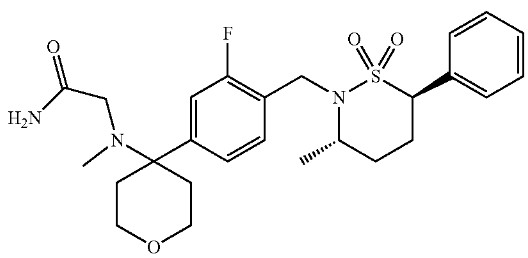 [SMILES: C[C@H]1CC[C@H](c2ccccc2)S(=O)(=O)N1Cc1ccc(C2(N(C)CC(N)=O)CCOCC2)cc1F] | 2-[[4-[3-fluoro-4-[[(3S,6R)-3-methyl-1,1-dioxo-6-phenyl-thiazinan-2-yl]methyl]phenyl]tetrahydropyran-4-yl]-methyl-amino]acetamide | 0.024 |
| 189 | 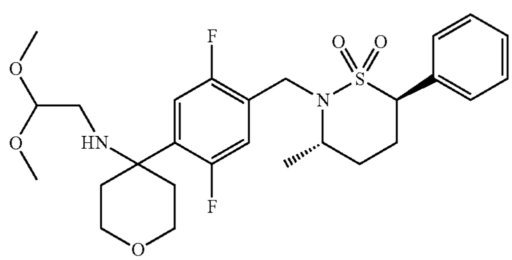 [SMILES: COC(CNC1(c2cc(F)c(CN3[C@@H](C)CC[C@H](c4ccccc4)S3(=O)=O)cc2F)CCOCC1)OC] | 4-[2,5-difluoro-4-[[(3S,6R)-3-methyl-1,1-dioxo-6-phenyl-thiazinan-2-yl]methyl]phenyl]-N-(2,2-dimethoxyethyl)tetrahydropyran-4-amine | 0.071 |
| 190 | 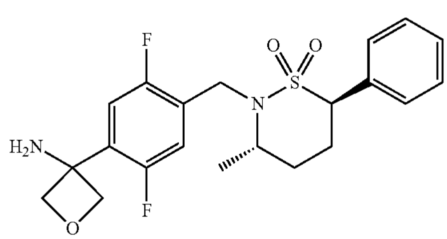 [SMILES: C[C@H]1CC[C@H](c2ccccc2)S(=O)(=O)N1Cc1cc(F)c(C2(N)COC2)cc1F] | 3-[2,5-difluoro-4-[[(3S,6R)-3-methyl-1,1-dioxo-6-phenyl-thiazinan-2-yl]methyl]phenyl]oxetan-3-amine | 0.0715 |

| | Structure | name | IC$_{50}$ |
|---|---|---|---|
| 191 | 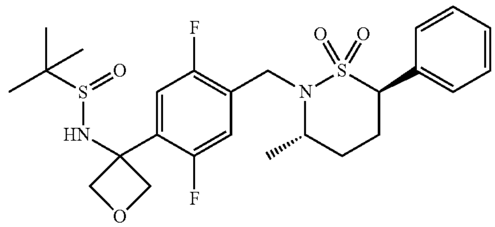 [SMILES: C[C@H]1CC[C@H](c2ccccc2)S(=O)(=O)N1Cc1cc(F)c(C2(NS(=O)C(C)(C)C)COC2)cc1F] | N-[3-[2,5-difluoro-4-[[(3S,6R)-3-methyl-1,1-dioxo-6-phenyl-thiazinan-2-yl]methyl]phenyl]oxetan-3-yl]-2-methyl-propane-2-sulfinamide | 0.0553 |
| 192 | 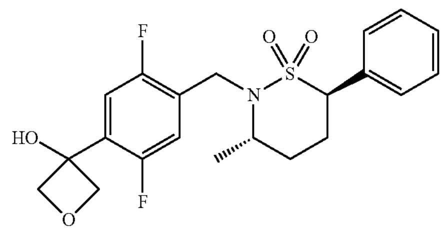 [SMILES: C[C@H]1CC[C@H](c2ccccc2)S(=O)(=O)N1Cc1cc(F)c(C2(O)COC2)cc1F] | 3-[2,5-difluoro-4-[[(3S,6R)-3-methyl-1,1-dioxo-6-phenyl-thiazinan-2-yl]methyl]phenyl]oxetan-3-ol | 0.00265 |
| 193 | 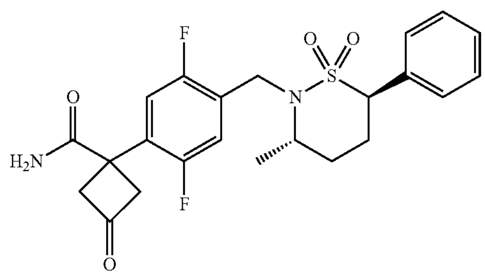 [SMILES: C[C@H]1CC[C@H](c2ccccc2)S(=O)(=O)N1Cc1cc(F)c(C2(C(N)=O)CC(=O)C2)cc1F] | 1-[2,5-difluoro-4-[[(3S,6R)-3-methyl-1,1-dioxo-6-phenyl-thiazinan-2-yl]methyl]phenyl]-3-oxo-cyclobutanecarboxamide | 0.00807 |
| 194 | 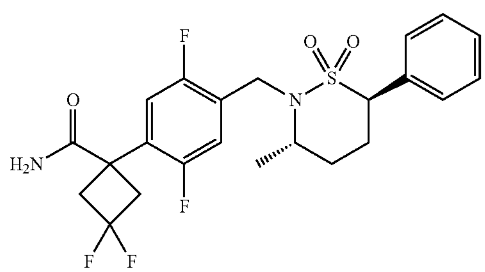 [SMILES: C[C@H]1CC[C@H](c2ccccc2)S(=O)(=O)N1Cc1cc(F)c(C2(C(N)=O)CC(F)(F)C2)cc1F] | 1-[2,5-difluoro-4-[[(3S,6R)-3-methyl-1,1-dioxo-6-phenyl-thiazinan-2-yl]methyl]phenyl]-3,3-difluoro-cyclobutanecarboxamide | 0.00305 |
| 195 | 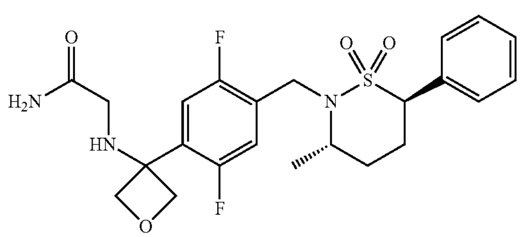 [SMILES: C[C@H]1CC[C@H](c2ccccc2)S(=O)(=O)N1Cc1cc(F)c(C2(NCC(N)=O)COC2)cc1F] | 2-[[3-[2,5-difluoro-4-[[(3S,6R)-3-methyl-1,1-dioxo-6-phenyl-thiazinan-yl]methyl]phenyl]oxetan-3-yl]amino]acetamide | 0.035 |
| 196 | 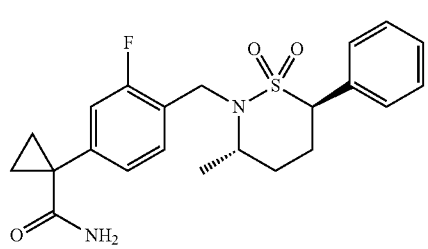 [SMILES: C[C@H]1CC[C@H](c2ccccc2)S(=O)(=O)N1Cc1ccc(C2(C(N)=O)CC2)cc1F] | 1-[3-fluoro-4-[[(3S,6R)-3-methyl-1,1-dioxo-6-phenyl-thiazinan-2-yl]methyl]phenyl]cyclopropanecarboxamide | 1.08 |

Table 4

Proton NMR values for selected compounds of Table 4 are provided below, with the Compound numbers below corresponding to the numbering in Table 4.

Compound 2 ¹H NMR (400 MHz, DMSO) δ 7.49-7.43 (m, 2H), 7.43-7.33 (m, 4H), 6.86-6.78 (m, 2H), 4.53-4.39 (m, 2H), 4.36-4.26 (m, 1H), 4.20-4.03 (m, 1H), 3.81-3.71 (s, 2H), 3.71-3.60 (m, 2H), 3.60-3.50 (m, 2H), 2.46-2.34 (m, 1H), 2.15-2.04 (m, 1H), 1.91-1.73 (m, 1H), 1.70-1.55 (m, 3H), 1.39-1.26 (m, 2H), 1.15-1.02 (m, 6H).

Compound 4 ¹H NMR (400 MHz, DMSO) δ 7.50-7.44 (m, 2H), 7.44-7.34 (m, 4H), 6.87-6.81 (m, 2H), 4.52-4.41 (m, 2H), 4.36-4.28 (m, 1H), 4.17-4.06 (m, 3H), 3.71-3.62 (m, 4H), 3.56-3.48 (s, 2H), 3.04-2.96 (s, 3H), 2.47-2.37 (m, 1H), 2.13-2.05 (m, 1H), 1.88-1.75 (m, 3H), 1.74-1.60 (m, 3H), 1.12-1.05 (d, J=6.9 Hz, 3H).

Compound 9 ¹H NMR (400 MHz, DMSO-$d_6$): δ 7.23-7.48 (8H, m), 5.22 (1H, s), 4.54 (2H, m), 4.34 (2H, m), 4.13 (1H, dd, J=11.96, 6.88 Hz), 3.69 (1H, d, J=13.22 Hz), 3.41 (1H, t, J=12.83 Hz), 2.89 (1H, t, J=12.46 Hz), 2.43 (2H, dd, J=14.64, 13.17 Hz), 2.10 (2H, dd, J=13.93, 3.80 Hz), 2.02 (3H, s), 1.52-1.95 (4H, m), 1.09 (3H, d, J=6.90 Hz)

Compound 12—¹H NMR (400 MHz, DMSO-$d_6$): δ 8.50 (s, 2H); 7.41-7.43 (m, 9H); 4.36-4.38 (m, 5H); 3.54 (s, 3H); 2.43 (m, 3H); 2.09 (t, J=13.2 Hz, 5H); 1.66-1.79 (m, 4H); 1.09 (d, J=6.9 Hz, 3H).

Compound 17 ¹H NMR (400 MHz, DMSO-$d_6$): δ 8.62 (s, 2H); 7.40-7.41 (m, 9H); 4.29-4.31 (m, 5H); 3.67 (s, 3H); 2.64 (d, J=9.2 Hz, 2H); 2.44 (dd, J=13.2, 3.5 Hz, 1H); 2.10-2.17 (m, 3H); 1.71-1.75 (m, 6H); 1.09 (d, J=6.9 Hz, 3H)

Compound 18 ¹H NMR (400 MHz, DMSO-$d_6$): δ 7.35-7.36 (6H, m), 7.10 (1H, dd, J=12.15, 6.11 Hz), 5.23 (1H, s), 4.49-4.51 (1H, m), 4.33-4.35 (2H, m), 4.08 (1H, dd, J=11.95, 6.92 Hz), 3.83 (4H, dd, J=6.36, 3.80 Hz), 2.38-2.40 (1H, m), 2.18 (2H, t, J=13.19 Hz), 2.05 (1H, dd, J=13.88, 3.86 Hz), 1.88 (2H, t, J=12.98 Hz), 1.72-1.77 (1H, m), 1.51-1.58 (5H, m), 1.07 (3H, d, J=6.88 Hz), −0.05 (1H, s).

Compound 20 ¹H NMR (400 MHz, CHCl$_3$-d): δ 8.27 (2H, s), 7.76 (1H, t, J=8.07 Hz), 7.15-7.48 (7H, s), 4.49-4.51 (2H, m), 4.28 (1H, m), 4.18 (1H, m), 4.00 (1H, m), 2.68 (3H, m), 2.30-2.36 (5H, m), 2.01 (2H, d, J=16.80 Hz), 1.77-1.79 (2H, m), 1.15 (3H, d, J=6.91 Hz)

Compound 21 ¹H NMR (400 MHz, DMSO-$d_6$): δ 7.58 (t, J=8.2 Hz, 1H); 7.37-7.39 (m, 7H); 4.52-4.55 (m, 2H); 4.39 (d, J=17.7 Hz, 1H); 4.14 (dd, J=12.0, 6.9 Hz, 1H); 3.92 (t, J=2.5 Hz, 4H); 2.43-2.45 (m, 1H); 2.19 (d, J=13.2 Hz, 2H); 2.04-2.07 (m, 3H); 1.82-1.88 (m, 5H); 1.66 (d, J=14.2 Hz, 1H); 1.10 (d, J=6.9 Hz, 3H)

Compound 22 ¹H NMR (400 MHz, DMSO-$d_6$): δ 7.58 (t, J=8.2 Hz, 1H); 7.37-7.39 (m, 7H); 4.52-4.55 (m, 2H); 4.39 (d, J=17.7 Hz, 1H); 4.14 (dd, J=12.0, 6.9 Hz, 1H); 3.92 (t, J=2.5 Hz, 4H); 2.43-2.45 (m, 1H); 2.19 (d, J=13.2 Hz, 2H); 2.04-2.07 (m, 3H); 1.82-1.88 (m, 5H); 1.66 (d, J=14.2 Hz, 1H); 1.10 (d, J=6.9 Hz, 3H)

Compound 23 ¹H NMR (400 MHz, DMSO-$d_6$): δ 7.54-7.56 (m, 1H); 7.39-7.40 (m, 7H); 4.81 (t, J=4.1 Hz, 1H); 4.51-4.53 (m, 2H); 4.38 (d, J=17.7 Hz, 1H); 4.13 (d, J=9.3 Hz, 1H); 3.49-3.58 (m, 2H); 2.38 (d, J=42.0 Hz, 1H); 2.10 (d, J=13.3 Hz, 3H); 1.94 (t, J=12.0 Hz, 4H); 1.57-1.62 (m, 3H); 1.40 (d, J=7.1 Hz, 1H); 1.10 (d, J=6.9 Hz, 2H).

Compound 25 ¹H NMR (400 MHz, CHCl$_3$-d): δ 8.20 (2H, s), 7.68 (1H, t, J=8.15 Hz), 7.45-7.47 (2H, m), 7.37-7.39 (3H, m), 7.17 (1H, dd, J=8.20, 1.86 Hz), 7.06 (1H, dd, J=11.79, 1.86 Hz), 5.47 (1H, br s), 5.30 (1H, br s), 4.56 (1H, d, J=17.09 Hz), 4.41 (1H, d, J=17.06 Hz), 4.28-4.30 (1H, m), 4.04-4.06 (2H, m), 2.58-2.63 (3H, m), 2.16-2.24 (5H, m), 1.76-1.80 (4H, m), 1.16 (3H, d, J=6.90 Hz).

Compound 26 ¹H NMR (400 MHz, CHCl$_3$-d): δ 8.24 (2H, s), 7.69 (1H, t, J=8.24 Hz), 7.45-7.46 (2H, m), 7.37 (3H, d, J=6.76 Hz), 7.17 (1H, dd, J=8.24, 1.84 Hz), 7.03 (1H, dd, J=12.32, 1.84 Hz), 4.53 (1H, d), 4.44 (1H, d), 4.40, 4.26 (1H, m), 4.09 (1H, t, J=4.32 Hz), 4.00 (1H, dd, J=12.88, 3.57 Hz), 3.77 (2H, d, J=6.17 Hz), 2.64 (1H, m), 2.31 (1H, s), 2.27 (1H, s), 2.22-2.24 (1H, m), 2.15 (1H, d, J=6.38 Hz), 2.12 (1H, d, J=4.77 Hz), 2.00 (2H, d, J=12.23 Hz), 1.79-1.83 (2H, m), 1.77 (3H, d, J=6.97 Hz), 1.27-1.29 (2H, m), 1.16 (3H, d, J=6.91 Hz).

Compound 27 ¹H NMR (400 MHz, DMSO-$d_6$): δ 7.43 (dd, J=7.5, 1.8 Hz, 2H); 7.33-7.34 (m, 7H); 4.42-4.44 (m, 2H); 4.26-4.28 (m, 1H); 4.06 (dd, J=11.9, 6.8 Hz, 1H); 3.78 (dt, J=11.9, 3.7 Hz, 2H); 3.58 (s, 3H); 3.38 (t, J=11.3 Hz, 2H); 2.33-2.37 (m, 3H); 2.06-2.08 (m, 1H); 1.80-1.84 (m, 3H); 1.62 (dd, J=14.2, 3.1 Hz, 1H); 1.03-1.04 (m, 3H).

Compound 29 ¹H NMR (400 MHz, DMSO-$d_6$): δ 7.42-7.45 (m, 2H); 7.34-7.36 (m, 7H); 4.37-4.39 (m, 4H); 3.76 (d, J=11.5 Hz, 2H); 3.43 (t, J=11.9 Hz, 4H); 2.31-2.37 (m, 2H); 2.05-2.10 (m, 1H); 1.67-1.73 (m, 4H); 1.33 (d, J=7.1 Hz, 1H); 1.06 (d, J=6.9 Hz, 2H).

Compound 30 ¹H NMR (400 MHz, DMSO-$d_6$) δ 7.42-7.43 (m, 9H); 4.52 (d, J=17.1 Hz, 1H); 4.41 (dd, J=12.7, 3.5 Hz, 1H); 4.32 (d, J=17.1 Hz, 1H); 4.08 (dd, J=12.0, 6.9 Hz, 1H); 3.98 (dd, J=11.9, 3.5 Hz, 2H); 3.63 (td, J=11.6, 2.8 Hz, 2H); 2.40 (td, J=13.2, 3.7 Hz, 1H); 2.03-2.07 (m, 5H); 1.77-1.81 (m, 1H); 1.62-1.66 (m, 3H); 1.06 (d, J=6.9 Hz, 3H).

Compound 31 ¹H NMR (400 MHz, DMSO-$d_6$): δ 7.40-7.42 (m, 5H); 7.32 (s, 4H); 7.14 (s, 1H); 6.94 (s, 1H); 4.48 (d, J=17.0 Hz, 1H); 4.39 (dd, J=12.7, 3.6 Hz, 1H); 4.26 (d, J=17.0 Hz, 1H); 4.06 (dd, J=11.9, 6.9 Hz, 1H); 3.71 (d, J=11.4 Hz, 2H); 3.44 (t, J=11.0 Hz, 2H); 2.39-2.43 (m, 3H); 2.07 (dd, J=13.9, 3.8 Hz, 1H); 1.76 (t, J=12.6 Hz, 3H); 1.62 (d, J=14.2 Hz, 1H); 1.06 (d, J=6.9 Hz, 3H)

Compound 32 ¹H NMR (400 MHz, DMSO-$d_6$ δ 7.37-7.39 (m, 9H); 4.60 (t, J=5.4 Hz, 1H); 4.51 (d, J=16.9 Hz, 1H); 4.41 (dd, J=12.6, 3.6 Hz, 1H); 4.28 (d, J=16.9 Hz, 1H); 4.06-4.10 (m, 1H); 3.65-3.69 (m, 2H); 3.35 (d, J=6.3 Hz, 4H); 2.42-2.44 (m, 1H); 2.10 (dd, J=13.9, 3.9 Hz, 1H); 1.84-1.89 (m, 5H); 1.65 (d, J=14.1 Hz, 1H); 1.10 (d, J=6.9 Hz, 1H)

Compound 35 ¹H NMR (400 MHz, DMSO-$d_6$): δ 7.46 (dd, J=7.5, 1.8 Hz, 2H); 7.39 (d, J=8.0 Hz, 5H); 7.21 (d, J=8.2 Hz, 2H); 4.52 (d, J=16.8 Hz, 1H); 4.41 (dd, J=12.6, 3.6 Hz, 1H); 4.29 (d, J=16.9 Hz, 1H); 4.05-4.08 (m, 1H); 3.74 (d, J=11.3 Hz, 2H); 3.59 (t, J=11.2 Hz, 2H); 2.63 (br s, 6 H); 2.40-2.43 (m, 1H); 2.10-2.14 (m, 3H); 1.82-1.89 (m, 3H); 1.63-1.67 (m, 1H); 1.06 (d, J=6.9 Hz, 3H)

Compound 36 ¹H NMR (400 MHz, DMSO-$d_6$): δ 8.63 (2H, s), 7.42-7.44 (6H, m), 7.22 (1H, dd, J=11.92, 6.06 Hz), 5.46 (1H, s), 4.50-4.52 (3H, m), 4.32 (1H, br s), 3.65 (1H, t, J=6.60 Hz), 2.74 (1H, d, J=13.34 Hz), 2.0-2.23 (5H, t, J=9.11 Hz), 1.93 (2H, s), 1.77 (2H, d, J=8.89 Hz), 1.65 (1H, d, J=14.03 Hz), 1.41 (3H, d, J=7.11 Hz).

Compound 37 ¹H NMR (400 MHz, DMSO-$d_6$): δ 8.63 (2H, s), 7.33-7.49 (6H, m), 7.20 (1H, dd, J=11.92, 6.06 Hz), 5.43 (1H, s), 4.56 (1H, m), 4.43 (2H, dd, J=15 Hz), 4.30 (1H, br s), 4.12 (1H, m), 3.65 (1H, t, J=6.60 Hz), 2.44 (1H, m), 2.10-2.18 (4H, m), 1.92 (2H, s), 1.74-1.83 (2H, m), 1.66 (1H, m), 1.13 (3H, d, J=7.11 Hz).

Compound 40 ¹H NMR (400 MHz, DMSO-$d_6$): δ 7.36-7.37 (m, 9H); 4.43-4.45 (m, 3H); 4.28 (d, J=17.0 Hz, 1H); 4.07-4.12 (m, 1H); 3.69-3.74 (m, 3H); 3.42-3.47 (m, 3H);

2.54-2.55 (m, 2H); 2.40-2.43 (m, 2H); 2.10 (dd, J=14.2, 3.8 Hz, 1H); 1.77-1.85 (m, 3H); 1.36-1.40 (m, 1H); 1.10 (d, J=6.9 Hz, 3H).

Compound 41 $^1$H NMR (400 MHz, DMSO-d$_6$): δ 7.30-7.49 (8H, m), 5.76 (1H, s), 4.47-4.49 (2H, m), 3.61 (2H, m), 3.58 (1H, d, J=6.88 Hz), 3.35 (1H, m), 3.04 (1H, d, J=13.47 Hz), 2.75 (2H, m), 2.40 (2H, m), 2.37 (1H, s), 2.17 (1H, m), 2.08 (1H, d, J=3.38 Hz), 2.01 (1H, d, J=14.53 Hz), 1.63 (1H, d, J=14.04 Hz), 1.39 (3H, d, J=7.13 Hz).

Compound 42 $^1$H NMR (400 MHz, DMSO-d$_6$): δ 7.38-7.40 (8H, m), 5.73 (1H, s), 4.53 (1H, m), 4.52 (1H, d, J=17.57 Hz), 4.37 (1H, d, J=17.57 Hz) 4.15 (1H, s), 4.11 (1H, s), 3.33 (2H, m), 3.03 (2H, m), 2.39 (2H, m), 2.10 (1H, m), 1.99 (2H, m), 1.81 (1H, m), 1.66 (1H, m), 1.10 (3H, d, J=6.90 Hz).

Compound 79 $^1$H NMR (400 MHz, DMSO-d$_6$) □□ 7.49-7.33 (6H, m), 7.18-7.09 (2H, m), 4.52-4.45 (2H, m), 4.35 (1H, d, J=17.5 Hz), 4.14-4.04 (1H, m), 3.89 (2H, q, J=7.1 Hz), 3.66-3.61 (2H, m), 3.33 (2H, dd, J=9.6, 9.6 Hz), 2.45-2.35 (1H, m), 2.11-1.98 (3H, m), 1.85-1.70 (8H, m), 1.09-1.04 (6H, m)

Compound 81 $^1$H NMR (400 MHz, DMSO-d$_6$) □ 7.47-7.43 (3H, m), 7.40-7.33 (3H, m), 7.15 (1H, m), 7.08 (1H, m), 4.50 (3H, m), 4.35 (1H, d, J=17.7 Hz), 4.24 (1H, t, J=5.3 Hz), 4.13-4.05 (1H, m), 3.63 (2H, m), 3.35 (1H, m), 3.18 (2H, m), 2.41 (1H, m), 2.10-1.95 (4H, m), 1.86-1.60 (4H, m), 1.53 (3H, m), 1.07 (3H, d, J=6.7 Hz)

Compound 86 $^1$H NMR (400 MHz, DMSO-d$_6$) □□ 7.51-7.34 (6H, m), 7.20-7.12 (2H, m), 4.52-4.45 (2H, m), 4.35 (1H, d, J=17.4 Hz), 4.13-4.05 (2H, m), 3.67-3.63 (2H, m), 3.38-3.30 (2H, m), 2.44-2.37 (2H, m), 2.12-1.63 (9H, m), 1.06 (3H, d, J=6.8 Hz)

Compound 87 (400 MHz, DMSO-d$_6$) □□ 7.47 (3H, m), 7.38 (3H, m), 7.13 (3H, m), 6.60 (1H, br s), 4.50 (2H, m), 4.37 (1H, d, J=17.0 Hz), 4.11 (1H, m), 3.67 (2H, m), 3.38 (2H, m), 2.43 (1H, dt, J=6.9, 16.1 Hz), 2.10 (1H, m), 2.02 (2H, m), 1.84-1.58 (8H, m), 1.08 (3H, d, J=6.7 Hz).

Compound 101 $^1$H NMR (400 MHz, DMSO-d$_6$) δ 7.50-7.44 (m, 2H), 7.44-7.33 (m, 3H), 7.21-7.08 (m, 2H), 4.72 (t, J=5.6 Hz, 1H), 4.60-4.46 (m, 2H), 4.36 (d, J=17.8 Hz, 1H), 4.20-4.06 (m, 1H), 3.75-3.65 (m, 2H), 3.57 (d, J=5.6 Hz, 2H), 3.47-3.34 (m, 2H), 2.48-2.37 (m, 1H), 2.16-2.01 (m, 3H), 1.88-1.75 (m, 3H), 1.73-1.62 (m, 1H), 1.13 (d, J=6.8 Hz, 3H).

Compound 113 $^1$H NMR (400 MHz, DMSO-d$_6$) □ 7.51 (1H, dd, J=8.2, 8.2 Hz), 7.45 (2H, dd, J=1.5, 8.0 Hz), 7.42-7.34 (3H, m), 7.35-7.27 (4H, m), 4.55-4.49 (2H, m), 4.38 (1H, d, J=17.6 Hz), 4.16-4.06 (1H, m), 3.78-3.64 (4H, m), 3.36 (2H, s), 2.47-2.37 (1H, m), 2.13-1.78 (6H, m), 1.65 (1H, dd, J=2.1, 14.2 Hz), 1.09 (3H, d, J=6.9 Hz).

Compound 120 $^1$H NMR (400 MHz, DMSO-d$_6$) δ 7.49-7.45 (m, 2H), 7.42-7.35 (m, 4H), 7.23 (dd, J=11.9, 6.3 Hz, 1H), 4.60-4.49 (m, 2H), 4.38 (d, J=17.9 Hz, 1H), 4.17-4.06 (m, 1H), 3.66 (s, 3H), 2.58-2.54 (m, 2H), 2.46-2.41 (m, 2H), 2.32-2.22 (m, 5H), 2.13-2.05 (m, 1H), 1.83-1.73 (m, 1H), 1.70-1.62 (m, 1H), 1.13 (d, J=6.8 Hz, 3H).

Compound 129 $^1$H NMR (400 MHz, DMSO-d$_6$) δ 7.49-7.43 (m, 2H), 7.43-7.34 (m, 3H), 7.10 (ddd, J=18.6, 12.7, 6.5 Hz, 2H), 4.61-4.40 (m, 4H), 4.34 (d, J=17.7 Hz, 1H), 4.18-4.06 (m, 1H), 3.63-3.50 (m, 3H), 2.43-2.37 (m, 1H), 2.16-2.04 (m, 1H), 2.03-1.92 (m, 2H), 1.85-1.64 (m, 4H), 1.56-1.44 (m, 4H), 1.11 (d, J=6.8 Hz, 3H).

Compound 133 $^1$H NMR (400 MHz, DMSO-d$_6$) δ 8.65 (s, 2H), 7.50-7.44 (m, 2H), 7.44-7.33 (m, 3H), 7.21-7.10 (m, 2H), 4.64 (t, J=5.3 Hz, 1H), 4.59-4.46 (m, 2H), 4.36 (d, J=17.7 Hz, 1H), 4.26-4.07 (m, 2H), 3.87 (d, J=5.3 Hz, 2H), 2.47-2.39 (m, 1H), 2.28-2.18 (m, 2H), 2.16-2.05 (m, 1H), 2.05-1.88 (m, 4H), 1.85-1.65 (m, 4H), 1.13 (d, J=6.9 Hz, 3H).

Compound 135 $^1$H NMR (400 MHz, DMSO-d$_6$) □ 12.61 (1H, br. s), 7.46-7.33 (6H, m), 7.24 (1H, dd, J=6.1, 10.7 Hz), 4.88 (2H, d, J=7.7 Hz), 4.77 (2H, d, J=8.0 Hz), 4.56-4.48 (2H, m), 4.36 (1H, d, J=18.0 Hz), 4.15-4.07 (1H, m), 3.79 (2H, s), 2.45-2.39 (1H, m), 2.12-2.03 (1H, m), 1.85-1.72 (1H, m), 1.68-1.60 (1H, m), 1.09 (3H, d, J=6.5 Hz).

Compound 136 $^1$H NMR (400 MHz, DMSO-d$_6$) □ 12.68 (1H, s), 7.45-7.34 (6H, m), 7.25 (1H, dd, J=6.2, 10.9 Hz), 4.57-4.47 (3H, m), 4.41-4.33 (2H, m), 4.19 (1H, d, J=10.9 Hz), 4.12-4.04 (2H, m), 3.79 (2H, d, J=5.7 Hz), 2.45-2.37 (1H, m), 2.12-2.03 (1H, m), 1.83-1.72 (4H, m), 1.68-1.60 (1H, m), 1.08 (3H, d, J=6.2 Hz).

Compound 138 $^1$H NMR (400 MHz, DMSO-d$_6$) δ 7.46-7.43 (2H, m), 7.41-7.32 (4H, m), 7.30-7.24 (2H, m), 7.18 (1H, s), 4.89 (2H, d, J=7.4 Hz), 4.80 (2H, d, J=8.1 Hz), 4.58-4.50 (2H, m), 4.38 (1H, d, J=17.5 Hz), 4.15-4.10 (1H, m), 3.58 (2H, s), 2.45-2.36 (1H, m), 2.12-2.04 (1H, m), 1.85-1.73 (1H, m), 1.69-1.61 (1H, m), 1.10 (3H, d, J=7.1 Hz).

Compound 150 $^1$H NMR (400 MHz, DMSO-d$_6$) □ 7.46-7.15 (7H, m), 4.58-4.48 (1H, m), 4.37 (1H, d, J=17.8 Hz), 4.17-4.06 (1H, m), 3.80-3.63 (6H, m), 3.47 (2H, s), 2.46-2.37 (1H, m), 2.14-1.98 (6H, m), 1.85-1.73 (1H, m), 1.65 (1H, dd, J=2.1, 14.1 Hz), 1.11 (3H, d, J=6.9 Hz).

Compound 151 $^1$H NMR (400 MHz, DMSO-d$_6$) □ 7.45-7.25 (6H, m), 7.18 (1H, dd, J=6.3, 12.4 Hz), 4.67 (1H, d, J=4.2 Hz), 4.57-4.41 (3H, m), 4.34 (1H, d, J=17.7 Hz), 4.23 (1H, d, J=12.7 Hz), 4.12-4.05 (1H, m), 3.64 (1H, dd, J=1.6, 11.6 Hz), 3.57 (1H, d, J=4.4 Hz), 3.14-2.96 (2H, m), 2.87 (1H, dd, J=11.0, 20.3 Hz), 2.44-2.35 (1H, m), 2.13-2.04 (3H, m), 1.98 (3H, s), 1.95-1.71 (3H, m), 1.68-1.61 (1H, m), 1.08 (3H, d, J=6.8 Hz)

Compound 154 $^1$H NMR (400 MHz, DMSO-d$_6$) □ 7.65 (1H, q, J=5.2 Hz), 7.45-7.41 (2H, m), 7.40-7.32 (3H, m), 7.26-7.17 (2H, m), 4.56-4.46 (2H, m), 4.35 (1H, d, J=17.9 Hz), 4.15-4.05 (1H, m), 3.80-3.61 (4H, m), 3.49 (2H, s), 2.62 (3H, d, J=4.7 Hz), 2.45-2.37 (1H, m), 2.14-1.95 (5H, m), 1.84-1.71 (1H, m), 1.69-1.59 (1H, m), 1.09 (3H, d, J=7.0 Hz).

Compound $^1$H NMR (400 MHz, DMSO-d$_6$) □ 7.46-7.43 (2H, m), 7.41-7.24 (5H, m), 7.23-7.16 (2H, m), 4.56-4.47 (2H, m), 4.34 (1H, d, J=18.0 Hz), 4.14-4.06 (1H, m), 3.63 (2H, s), 2.46-2.35 (1H, m), 2.12-2.04 (1H, m), 1.83-1.74 (1H, m), 1.68-1.62 (1H, m), 1.53 (6H, s), 1.10 (3H, d, J=6.7 Hz).

Compound 163 $^1$H NMR (400 MHz, DMSO-d$_6$) □ 7.44 (3H, m), 7.40-7.33 (3H, m), 7.26-7.19 (3H, m), 7.01-6.96 (1H, m), 4.52-4.45 (2H, m), 4.34 (1H, d, J=17.5 Hz), 4.15-4.05 (1H, m), 3.85-3.77 (2H, m), 3.54 (2H, tt, J=3.9, 3.8 Hz), 2.62-2.56 (2H, m), 2.45-2.35 (1H, m), 2.11-2.04 (1H, m), 1.90-1.71 (6H, m), 1.63 (1H, dd, J=2.0, 14.1 Hz), 1.06 (3H, d, J=6.7 Hz).

Compound 175 $^1$H NMR (400 MHz, DMSO-d$_6$) □ 7.47-7.16 (9H, m), 4.58-4.48 (3H, m), 4.45-4.35 (2H, m), 4.23-4.05 (3H, m), 3.56 (2H, d, J=5.1 Hz), 2.45-2.37 (1H, m), 2.12-2.04 (1H, m), 1.83-1.73 (4H, m), 1.68-1.60 (1H, m), 1.10 (3H, d, J=6.3 Hz).

Compound 176 $^1$H NMR (400 MHz, DMSO-d$_6$) □ 7.60 (1H, t, J=5.9 Hz), 7.46-7.41 (2H, m), 7.41-7.34 (4H, m), 7.27 (1H, dd, J=6.0, 11.0 Hz), 4.90 (2H, d, J=7.5 Hz), 4.81 (2H, d, J=7.5 Hz), 4.66 (1H, t, J=5.4 Hz), 4.58-4.49 (2H, m), 4.38 (1H, d, J=17.8 Hz), 4.15-4.05 (1H, m), 3.64 (2H, s), 3.35 (2H, q, J=5.9 Hz), 3.09 (2H, q, J=5.9 Hz), 2.44-2.36

(1H, m), 2.12-2.04 (1H, m), 1.83-1.72 (1H, m), 1.69-1.61 (1H, m), 1.10 (3H, d, J=7.5 Hz).

Compound 177 $^1$H NMR (400 MHz, DMSO-d$_6$) □ 7.71-7.63 (1H, m), 7.46-7.32 (6H, m), 7.26 (1H, dd, J=5.8, 10.9 Hz), 4.89 (2H, d, J=8.2 Hz), 4.80 (2H, d, J=8.5 Hz), 4.58-4.48 (2H, m), 4.37 (1H, d, J=18.0 Hz), 4.13-4.05 (1H, m), 3.61 (2H, s), 2.54 (3H, d, J=4.4 Hz), 2.45-2.36 (1H, m), 2.12-2.04 (1H, m), 1.83-1.72 (1H, m), 1.68-1.61 (1H, m), 1.09 (3H, d, J=7.3 Hz).

Compound 180 $^1$H NMR (400 MHz, DMSO-d$_6$) □□ 7.47-7.43 (3H, m), 7.41-7.35 (4H, m), 7.28-7.20 (3H, m), 6.81 (1H, br d, J=2.3 Hz), 4.50 (2H, m), 4.36 (1H, d, J=16.6 Hz), 4.15-4.06 (1H, m), 3.87-3.78 (2H, m), 3.55-3.41 (3H, m), 2.66-2.55 (1H, m), 2.42 (1H, m), 2.09 (1H, m), 1.93 (1H, m), 1.86-1.60 (4H, m), 1.07 (3H, d, J=6.9 Hz), 0.87 (3H, d, J=6.4 Hz)

Compound 186 $^1$H NMR (400 MHz, DMSO-d$_6$) □ 7.56 (1H, t, J=8.0 Hz), 7.46-7.43 (2H, m), 7.41-7.32 (7H, m), 4.82 (2H, d, J=7.5 Hz), 4.72 (2H, dd, J=2.0, 7.5 Hz), 4.57-4.49 (2H, m), 4.38 (1H, d, J=17.7 Hz), 4.17-4.06 (1H, m), 3.56 (2H, s), 2.45-2.36 (1H, m), 2.10-2.06 (1H, m), 1.85-1.75 (1H, m), 1.68-1.60 (1H, m), 1.08 (1H, d, J=6.6 Hz).

Example 24 In Vitro RORc Ligand Binding Assay

This assay was used to determine a compound's potency in inhibiting activity of RORc by determining, Ki$_{app}$, IC$_{50}$, or percent inhibition values. Consumables used in this Example are shown in Table 5 below.

TABLE 5

| Consumable | Supplier and product code |
| --- | --- |
| GFB Unifilter plates | Perkin Elmer 6005177 |
| 3-[(3-Cholamidopropyl)dimethylammonio]-1-propanesulfonate (CHAPS) | Sigma C5070 |
| 96-well polypropylene U-bottom assay plate | Nunc 267245 |
| HEPES buffer, 1M | Sigma H3375 |
| Magnesium chloride (MgCl$_2$) | Sigma M8266 |
| D,L-Dithiothreitol (DTT) | Sigma D0632 |
| Sodium chloride (NaCl) | Sigma 71382 |
| Bovine serum albumin (BSA) | Sigma A7030 [lyophilized powder, ≥98% (agarose gel electrophoresis), Essentially fatty acid free, essentially globulin free] |
| 25-hydroxycholesterol | Sigma H1015 |
| 25-[26,27-$^3$H]hydroxycholesterol | Perkin Elmer NET674250UC American Radiolabeled Chemicals ART0766 |
| RORc ligand binding domain | Genentech (e.g., PUR 28048), expressed in E. coli |
| Plate seals | Perkin Elmer 6005185 |
| Microscint 0 | Perkin Elmer 6013611 |

Filter Plate Preparation

On day of the assay, 100 uL of 0.05% CHAPS (in deionized H$_2$O) was added to all wells of the GFB Unifilter plate and allowed soak for 1 h. A wash buffer of 50 mM HEPES (pH 7.4), 150 mM NaCl, and 5 mM MgCl$_2$ was prepared to wash the filter plate. To prepare an assay buffer, BSA was added to the wash buffer to reach 0.01% and DTT was added to reach 1 mM.

Compounds

For IC$_{50}$ mode, 10 mM compound stocks were serially diluted in DMSO with DMSO to give 20× required final concentration in DMSO (15 uL compound+30 uL DMSO). The 20× compound stocks were diluted in DMSO with Assay Buffer 4-fold to reach 5× the final test concentration in 25% DMSO (10 uL compound+30 uL Assay Buffer). Solutions were mixed by aspiration several times with a pipette set on 50 uL volume. For the assay, 10 uL of 5× compound stock solutions in 25% DMSO were added to the assay plate in duplicate.

For two point screening, 10 mM stock compound solutions were diluted in DMSO to obtain 200 uM (20× the high test concentration) and then diluted 10-fold further to reach 20 uM (20× the low test concentration). The 20× stocks were diluted 4-fold with Assay Buffer (10 uL compound+30 uL Assay Buffer) to reach 5× the test concentrations (50 uM and 5 uM) and 10 uL were added to two assay plates for the duplicate wells. With each concentration tested on 2 plates, each set of 80 compounds used 4 assay plates (1 uM and 10 uM, with n=2).

Nonspecific Binding (NSB) Samples, Total Binding (TB) Samples and No Receptor (No R) Samples 25-hydroxycholesterol (1 uM) was used to determine the level of NSB signal is prepared in DMSO as for compounds above, then diluted in Assay Buffer to give a final concentration of 5 uM. For 25-hydroxycholesterol in 25% DMSO/75% Assay Buffer; 10 uL per well was used for NSB samples. Wells for Total Binding and No Receptor sample determination contained 10 uL of 25% DMSO/75% Assay Buffer per well.

Radioligand 25-[$^3$H]hydroxycholesterol) Preparation

25-[$^3$H]hydroxycholesterol was dilute in Assay Buffer to obtain 15 nM and vortex to mix. Add 20 uL to all wells to reach 6 nM final in the assay.

Receptor Preparation

The optimal concentration for RORc receptor was found to be 0.6 ug/mL. Stock receptor solution was diluted in assay buffer to obtain 1.5 ug/mL in Assay Buffer. 20 uL was added to all wells. For No R samples, 20 uL Assay Buffer was substituted for receptor solution.

Sample Addition to Plates and Incubation

Assay plates were 96-well polypropylene V-bottom plates. 10 uL of 5× compound in 25% DMSO/75% Assay Buffer was added to Test wells. 10 uL of 25% DMSO/75% Assay Buffer was added to Total Binding or No Receptor wells. 10 uL of 5 uM 25-hydroxycholesterol in 25% DMSO/75% Assay Buffer was added to NSB wells. 20 uL of 15 nM 25-[$^3$H]hydroxycholesterol prepared in Assay Buffer was added to all wells. 20 uL of 1.5 ug/mL RORc receptor was added to wells (or 40 uL Assay Buffer to No R wells). Following addition to the wells, the plates were incubated 3 h at 25° C.

Filtration

Using a Packard Filtermate Harvester, the filter plate were washed 4 times following transfer of the incubated samples. Plates were dry-filtered completely (2 h at 50° C. or overnight at room temperature). 50 uL Microscint 0 was added to all wells and read on Topcount protocol Inverted.

Final Concentrations

Final concentrations were as follows: 50 mM HEPES buffer (pH 7.4); 150 mM NaCl; 1 mM DTT; 5 mM MgCl$_2$; 0.01% BSA; 5% DMSO; 0.6 ug/mL RORc receptor; 6 nM 25-[$^3$H]hydroxycholesterol. For NSB wells, 1 uM 25-hydroxycholesterol was also present.

Example 25: RORc Coactivator Peptide Binding Assay

Assays were carried out in 16-microL reaction volumes in black 384 Plus F Proxiplates (Perkin-Elmer 6008269). All assay components except test ligand were mixed in coregulator buffer D (Invitrogen PV4420) containing 5 mM DTT and added to the plate at twice their final concentrations in a volume of 8 microL. Test ligands at 2× the final concentration were then added to the wells in 8 □L of coregulator buffer D containing 5 mM DTT and 4% DMSO. Final incubations contained 1× coregulator buffer D, 5 mM DTT, test ligand, 2% DMSO, 50 nM biotinyl-CPSSHSSLTERKH-KILHRLLQEGSPS (American Peptide Company; Vista, Calif.), 2 nM Europium anti-GST (Cisbio 61GSTKLB), 12.5 nM streptavidin-D2 (Cisbio 610SADAB), 50 mM KF, and 10 nM of bacterially-expressed human RORc ligand binding domain protein containing an N-terminal 6×His-GST-tag and residues 262-507 of Accession NP_005051. Ten test ligand concentrations were tested in duplicate. After the reaction plates were incubated for 3 h in the dark at room temperature (22-23° C.), the plate was read on an EnVision plate reader (PerkinElmer) following the Europium/D2 HTRF protocol (ex 320, em 615 and 665, 100 □s lag time, 100 flashes, 500 s window). The time-resolved FRET signal at 665 nm was divided by that at 615 nm to generate the signal ratio of each well. The signal ratio of wells containing RORc and peptide but no test ligand were averaged and set to 0% Effect while the signal ratios of the blank wells containing coactivator peptide but no RORc were averaged and set to −100% Effect. RORc exhibits a basal (constitutive) signal in this assay and test ligands can increase or decrease the signal ratio relative to this basal signal level. RORc agonists increase the signal ratio in this assay and result in a positive % Effect value. Inverse agonists decrease the signal ratio, and result in a negative % Effect value. The $EC_{50}$ value is the concentration of test compound that provides half-maximal effect (increased or decreased assay signal) and is calculated by Genedata Screener® software (Genedata; Basel, Switzerland) using the following equation:

$$\% \text{ Effect} = S_0 + \{(S_{inf} - S_0)/[1 + (10^{\log EC_{50}}/10^c)^n]\}$$

where $S_0$ equals the activity level at zero concentration of test compound, $S_{inf}$ is the activity level at infinite concentration of test compound, $EC_{50}$ is the concentration at which the activity reaches 50% of the maximal effect, c is the concentration in logarithmic units corresponding to the values on the x-axis of the dose-response curve plot, and n is the Hill coefficient (the slope of the curve at the $EC_{50}$).

Example 26: Arthritis Mouse Model 8 to 10-week old male DBA/1 (DBA/1OlaHsd, Harlan Laboratories) mice are housed in a specific pathogen free (SPF) animal facility. Arthritis is induced by two injections of collagen subcutaneously in the base of the tail. The initial injection (on day 0) uses bovine type II collagen (2 mg/ml from Chondrex, Redmond, Wash.) emulsified in equal volume of CFA containing 4 mg/ml of *M. tuberculosis* (Chondrex). The CII booster injection on Day 29 is emulsified in incomplete Freund's adjuvant (IFA). Each animal receives 0.1 ml of emulsion by subcutaneous/intradermal injection in the tail 2 to 3 cm from the body of the mouse. The booster injection site is in the vicinity of but different from the initial injection site and closer to the body of the animal. OR-1050 was formulated in HRC-6 as above. On weekdays, the animals receive two doses (a.m. and p.m.) of HRC-6 or 50 mg/kg OR-1050 p.o. (2.5 mls/kg). On weekends, a single dose of 100 mg/kg is administered (5 mls/kg).

The mice were observed daily for clinical symptoms of CIA based on the following qualitative scale. Each paw was examined individually and scored. Grade 0, normal; grade 1, mild but definite redness and swelling of the ankle or wrist, or apparent redness and swelling limited to individual digits, regardless of the number of affected digits; grade 2, moderate redness and swelling of ankle or wrist; grade 3, severe redness and swelling of the entire paw including digits; grade 4, maximally inflamed limb with involvement of multiple joints. To estimate cumulative disease severity for each animal, an area under the curve score is calculated for each animal by totaling the sum of the daily hind paw measurements between days 24 and 48.

Example 27: Muscular Sclerosis Mouse Model I

Experiments are conducted on female mice aged 4-6 weeks belong to the C57BL/6 strain weighing 17-20 g. Experimental autoimmune encephalomyelitis (EAE) is actively induced using 95% pure synthetic myelin oligodendrocyte glycoprotein peptide 35-55 ($MOG_{35-55}$) (Invitrogen). Each mouse is anesthetized and receives 200 ug of $MOG_{35-55}$ peptide and 15 ug of Saponin extract from Quilija bark emulsified in 100 uL of phosphate-buffered saline. A 25 uL volume is injected subcutaneously over four flank areas. Mice are also intraperitoneally injected with 200 ng of pertussis toxin in 200 uL of PBS. A second, identical injection of pertussis toxin is given after 48 h.

A compound of the invention is administered at selected doses. Control animals receive 25 uL of DMSO. Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hind limbs); 2, unilateral partial hind limb paralysis; 2.5, bilateral hind limb paralysis; 3, complete bilateral hindlimb paralysis; 3.5, complete hindlimb paralysis and unilateral forelimb paralysis; 4, total paralysis of hind limbs and forelimbs (Eugster et al., Eur J Immunol 2001, 31, 2302-2312).

Inflammation and demyelination may be assessed by histology on sections from the CNS of EAE mice. Mice are sacrificed after 30 or 60 days and whole spinal cords are removed and placed in 0.32M sucrose solution at 4° C. overnight. Tissues are prepared and sectioned. Luxol fast blue stain is used to observe areas of demyelination. Haematoxylin and eosin staining is used to highlight areas of inflammation by darkly staining the nuclei of mononuclear cells. Immune cells stained with H&E are counted in a blinded manner under a light microscope. Sections are separated into gray and white matter and each sector is counted manually before being combined to give a total for the section. T cells are immunolabeled with anti-CD3+ monoclonal antibody. After washing, sections are incubated with goat anti-rat HRP secondary antibody. Sections are then washed and counterstained with methyl green. Splenocytes isolated from mice at 30 and 60 days post-immunization are treated with lysis buffer to remove red blood cells. Cells are then re-suspended in PBS and counted. Cells at a density of about $3 \times 10^6$ cells/mL are incubated overnight with 20 ug/mL of MOG peptide. Supernatants from stimulated cells are assayed for IFNgamma protein levels using an appropriate mouse IFN-gamma immunoassay system.

Example 28: Muscular Sclerosis Mouse Model II

In this model, female rodents are anesthetized with isoflurane and injected with Freund's Incomplete Adjuvant containing 1 mg/mL neuronal antigen (e.g. myelin basic protein, myelin oligodendrocyte glycoprotein, proteolipid protein) and 4 mg/mL *mycobacterium tuberculosis* at two sites on the back on day 0 of this study. A compound of interest is then dosed daily in a sub-cutaneous, intra-peritoneally, or oral manner from day 0 until the end of study at an efficacious dose. Daily observations of degree of paralysis are taken as measures of efficacy.

Example 29: Psoriasis Mouse Model I

The severe, combined immunodeficient (SCID) mouse model can be used to evaluate the efficacy of compounds for treating psoriasis in humans (Boehncke, Ernst Schering Res Found Workshop 2005, 50, 213-34; and Bhagavathula et al., J Pharmacol Expt'l Therapeutics 2008, 324(3), 938-947). Briefly, SCID mice are used as tissue recipients. One biopsy for each normal or psoriatic volunteer (human) is transplanted onto the dorsal surface of a recipient mouse. Treatment is initiated 1 to 2 weeks after transplantation. Animals with the human skin transplants are divided into treatment groups. Animals are treated twice daily for 14 days. At the end of treatment, animals are photographed and then euthanized. The transplanted human tissue along with the surrounding mouse skin is surgically removed and fixed in 10% formalin and samples obtained for microscopy. Epidermal thickness is measured. Tissue sections are stained with an antibody to the proliferation-associated antigen Ki-67 and with an anti-human $CD3.^{+}$ monoclonal antibody to detect human T lymphocytes in the transplanted tissue. Sections are also probed with antibodies to c-myc and beta-catenin. A positive response to treatment is reflected by a reduction in the average epiderma thickness of the psoriatic skin transplants. A positive response is also associated with reduced expression of Ki-67 in keratinocytes.

Example 30: Psoriasis Mouse Model II

Using the Imidquimod model of skin inflammation (Fits et al, Journal of Immunology, 2009, 182: 5836-5845), 10-12 week old BALB/c, Il17c+/+ or Il17c−/−, or Il17re+/+ or Il17re−/− mice were administered 50 mg Aldara cream (5% Imidquimod in Graceway, 3M) in the shaved back and right ear daily for 5 days. Clinical scoring and ear thickness measurements were performed daily. Scoring was based upon the manifestation of psoriatic symptoms, such as erythema, scaling and thickness: 0, No disease. 1, Very mild erythema with very mild thickening and scaling involving a small area. 2, Mild erythema with mild thickening and scaling involving a small area. 3, Moderate erythema with moderate thickening and scaling (irregular and patchy) involving a small area (<25%). 4, Severe erythema with marked thickening and scaling (irregular and patchy) involving a moderate area (25-50%). 5, Severe erythema with marked thickening and scaling (irregular and patchy) involving a large area (>50%). Ear and back tissue were harvested on day 5 for histological evaluation. Efficacy of compounds is compared in the imiquimod (IMQ) mouse model of psoriasis. Balb/c mice (10 males/group) received daily topical IMQ (5% cream) on shaved back and right ear for 5 days as described above. Animals received oral dose of a representative compound or DMF (45 or 90 mg-eq MMF/kg twice daily) or vehicle from Day −5 to Day +5. Erythema score is the primary outcome measure. The Erythema score values of the compounds tested at an oral dose of 90 mg-eq MMF/kg BID for 10 days in male Balb/C mice are set forth in Table 3, below. The data shows that the compounds of the disclosure are equipotent to DMF.

Example 31: Irritable Bowel Disease Mouse Model I

Effectiveness in treatment of inflammatory bowel disease may be evaluated as described by Jurjus et al., J Pharmaocol Toxicol Methods 2004, 50, 81-92; Villegas et al., Int'l Immunopharmacol 2003, 3, 1731-1741; and Murakami et al., Biochemical Pharmacol 2003, 66, 1253-1261. Briefly, female ICR mice are divided into treatment groups which are given either water (control), 5% DSS in tap water is given at the beginning of the experiment to induce colitis, or various concentrations of test compound. After administering test compound for 1 week, 5% DSS in tap water is also administered to the groups receiving test compound for 1 week. At the end of the experiment, all mice are sacrificed and the large intestine is removed. Colonic mucosa samples are obtained and homogenized. Proinflammatory mediators (e.g., IL-1alpha, IL-1beta, TNFalpha, PGE2, and PGF2alpha.) and protein concentrations are quantified. Each excised large intestine is histologically examined and the damage to the colon scored.

Example 32: Chronic Obstructive Pulmonary Disease Mouse Model

The cigarette smoke model of Martorana et al., Am J Respir Crit Care Med 2005, 172, 848-835; and Cavarra et al., Am J Respir Crit Care Med 2001, 164, 886-890 can be used for assessing efficacy in treating emphysema. Briefly, six-week old C57Bl/6J male mice are exposed either to room air or to the smoke of five cigarettes for 20 minutes. For the acute study, mice are divided into three groups of 40 animals each. These groups are then divided into four subgroups of 10 mice each as follows: (1) no treatment/air-exposed; (2) no treatment/smoke-exposed; (3) a first dose of test compound plus smoke-exposed; and (4) a second dose of test compound. In the first group, trolox equivalent antioxidant capacity is assessed at the end of the exposure in bronchoalveolar lavage fluid. In the second group, cytokines and chemokines are determined in bronchoalveolar lavage fluid using a commercial cytokine panel at 4 hours; and in the third group bronchoalveolar lavage fluid cell count is assessed at 24 hours.

In a chronic study, the mice are exposed to either room air or to the smoke of three cigarettes/day, for 5 days/week, for 7 months. Five groups of animals are used: (1) no treatment/air-exposed; (2) a first dose of a test compound plus air-exposed; (3) no treatment/smoke-exposed; (4) a second dose of the test compound plus smoke-exposed; and (5) the first dose of the test compound plus smoke exposed. Seven months after chronic exposure to room air or cigarette smoke, 5 to 12 animals from each group are sacrificed and the lungs fixed intratracheally with formalin. Lung volume is measured by water displacement. Lungs are stained. Assessment of emphysema includes mean linear intercept and internal surface area. The volume density of macrophages, marked immunohistochemically with anti-mouse Mac-3 monoclonal antibodies is determined by point counting. A mouse is considered to have goblet cell metaplasia when at least one or more midsize bronchi/lung showed a positive periodic acid-Schiff staining for the determination of desmosine, fresh lungs are homogenized, processed, and analyzed by high-pressure liquid chromatography.

Example 33: Asthma Mouse Model

A single inhaled allergen challenge can induce an acute increase in airway responsiveness in some individuals and animal models. However, repeated allergen inhalations have demonstrated more pronounced, consistent, and prolonged increases in airway responsiveness. This mouse model of long-term repeated inhalations of allergen has been used to study the long term effect of allergic diseases in the lung, and to delineate the cells, mechanisms, molecules, and mediators involved in the induction of airway hyperresponsiveness of lung in humans.

Crystalline OVA is obtained from Pierce Chem. Co. (Rockford, Ill.) aluminum potassium sulfate (alum) from Sigma Chem. Co. (St. Louis, Mo.), pyrogen-free distilled water from Baxter, Healthcare Corporation (Deerfield, Ill.), 0.9% sodium chloride (normal saline) from Lymphomed (Deerfield, Ill.) and Trappsol™ HPB-L100 (aqueous hydroxypropylbeta cyclodextrin; 45 wt/vol % aqueous solution) from Cyclodextrin Technologies Development, Inc. (Gainesville, Fla.). The OVA (500 ug/ml in normal saline) is mixed with equal volumes of 10% (wt/vol) alum in distilled water. The mixture (pH 6.5 using 10N NaOH) after incubation for 60 minutes at room temperature is centrifuged at 750 g for 5 minutes; the pellet resuspended to the original volume in distilled water and used within one hour. The selective 5-lipoxtgenase inhibitor, Zileuton (N-[1-benzo[b]thien-2-ylethyl]-N-hydroxyurea; J. Pharmacol Exp Ther. 1991; 256: 929-937) is dissolved in Trappsol™ Histatek, Inc. (Seattle, Wash.) to provide the mast cell degranulation inhibitor, f-Met-Leu-Phe-Phe ("HK-X").

Female BALB/c Once (6-8 wk of age) receive an i.p. injection of 0.2 ml (100 ug) of OVA with alum on the different protocols of Standard (J. Exp Med. 1996; 184: 1483-1494). Mice are anesthetized with 0.2 ml i.p. of ketamine (0.44 mg/ml)/xylazine (6.3 mg/ml) in normal saline before receiving an intranasal (i.n.) dose of 100 ug OVA in 0.05 ml normal saline and an i.n. dose of 50 ug OVA in 0.05 ml normal saline separately on different days. Two control groups are used: the first group receives normal saline with alum i.p. and normal saline without alum i.n.; and the second group receives OVA with alum i.p., OVA without alum i.n., and normal saline, alone.

The trachea and left lung (the right lung may be used for bronchoalveolar lavage ("BAL") as described below) are obtained and fixed in 10% neutral formaldehyde solution at room temperature for about 15 h. After being embedded in paraffin, the tissues are cut into 5-um sections and processed with the different staining or immunolabling further. Discombe's eosinophil staining is used for counting the cell numbers with the counterstain of methylene blue. The eosinophil number per unit airway area (2,200 um²) is determined by morphometry (J. Pathol. 1992; 166: 395-404; Am Rev Respir Dis. 1993; 147:448-456). Fibrosis is identified with the Masson's trichrome staining. Airway mucus iss identified by the following staining method: methylene blue, hematoxylin and eosin, mucicarmine, alcian blue, and alcian blue/periodic acid-Schiff (PAS) reaction (Troyer, H., "Carbohydrates" in Principles and Techniques of Histochemistry, Little, Brown and Company, Boston, Mass., 1980: 89-121; Sheehan, D. C., et al., "Carbohydrates" in Theory and Practice of Histotechnology, Battle Press, Columbus, Ohio, 1980: 159-179) Mucin is stained with mucicarmine solution; metanil yellow counterstain is employed. Acidic mucin and sulfated mucosubstances are stained with alcian blue, pH 2.5; nuclear fast red counterstain is used. Neutral and acidic mucosubstances are identified by alcian blue, pH 2.5, and PAS reaction. The degree of mucus plugging of the airways (0.5-0.8 mm in diameter) is also assessed by morphometry. The percent occlusion of airway diameter by mucus iss classified on a semiquantitative scale from 0 to 4+. The histologic and morphometric analyses may be performed by individuals blinded to the protocol design.

On day 28, 24 hours after the last i.n. administration of either normal saline or OVA, pulmonary mechanics to intravenous infusion of methacholine may be determined in mice in vivo by a plethysmographic method as previously described (10, 1958; 192: 364-368; J. Appl. Physiol. 1988; 64: 2318-2323; J. Exp. Med. 1996; 184: 1483-1494).

After tying off the left lung at the mainstem bronchus, the right lung may be lavaged three times with 0.4 ml of normal saline. Bronchoalveolar lavage (BAL) fluid cells from a 0.05-ml aliquot of the pooled sample are counted using a hemocytometer and the remaining fluid centrifuged at 4° C. for 10 minutes at 200 g. The supernatant may be stored at 70.degree. C. until eicosanoid analysis is performed. After resuspension of the cell pellet in normal saline containing 10% bovine serum albumin ("BSA"), BAL cell smears are made on glass slides. To stain eosinophils, dried slides are stained with Discombe's diluting fluid (0.05% aqueous eosin and 5% acetone (vol/vol) in distilled water; J. Exp. Med. 1970; 131: 1271-1287) for 5-8 minutes, rinsed with water for 0.5 minutes, and counterstained with 0.07% methylene blue for 2 minutes.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I

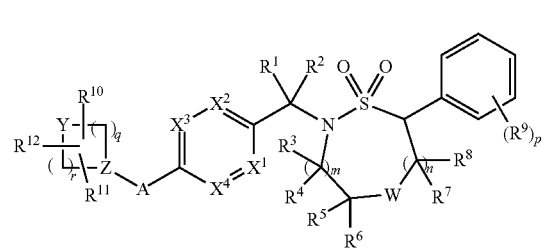

or a pharmaceutically acceptable salt thereof,
wherein:
  m is 0 or 1;
  n is 0 or 1;
  p is from 0 to 3;
  q is 0, 1 or 2;
  r is from 1 to 3;
  A is:
    a bond;
  W is:
    —$CR^bR^c$—;
  Y is:
    —O—; or
    —$CR^fR^g$—;

Z is: CR$^m$;
R$^1$, R$^2$, R$^3$, R$^4$, R$^5$, R$^6$, R$^7$ and R$^8$ each independently is:
 hydrogen; or C$_{1-6}$alkyl which may be unsubstituted or substituted one or more times with halo;
R$^9$ is
 halo;
R$^{10}$ is:
 hydrogen;
 halo; or
 C$_{1-6}$alkyl which may be unsubstituted or substituted one or more times with halo or oxo;
R$^{11}$ is:
 hydrogen;
 halo; or
 C$_{1-6}$alkyl which may be unsubstituted or substituted one or more times with halo or oxo;
R$^{12}$ is:
 hydrogen;
 halo; or
 C$_{1-6}$alkyl which may be unsubstituted or substituted one or more times with halo or oxo;
R$^{13}$ is:
 hydrogen; or
 C$_{1-6}$alkyl which may be unsubstituted or substituted one or more times with halo;
R$^b$, and R$^c$ each independently is:
 hydrogen; or
  C$_{1-6}$alkyl which may be unsubstituted or substituted one or more times with halo;
each R$^e$ is independently:
 hydrogen;
 C$_{1-6}$alkyl;
 halo;
 C$_{1-6}$alkoxy; or
 cyano;
  wherein the C$_{1-6}$alkyl moieties may be unsubstituted or substituted one or more times with halo, hydroxy or C$_{1-6}$alkoxy;
R$^f$ is:
 hydrogen;
 halo;
 C$_{1-6}$alkoxy; or
 C$_{1-6}$alkyl which may be unsubstituted or substituted one or more times with halo, hydroxy, or C$_{1-6}$alkoxy;
R$^g$ is:
 hydrogen;
 C$_{1-6}$alkyl;
 C$_{3-6}$cycloalkyl;
 C$_{3-6}$cycloalkenyl;
 C$_{3-6}$cycloalkyl-C$_{1-6}$alkyl;
 halo;
 C$_{1-6}$alkyl-carbonyl;
 C$_{3-6}$cycloalkyl-carbonyl;
 C$_{3-6}$cycloalkyl-C$_{1-6}$alkyl-carbonyl;
 cyano-C$_{1-6}$alkyl-carbonyl;
 hydroxy-C$_{1-6}$alkyl-carbonyl;
 C$_{1-6}$alkoxy-C$_{1-6}$alkyl-carbonyl;
 carboxy;
 N-cyano-aminocarbonyl;
 N-cyano-N—C$_{1-6}$alkyl-aminocarbonyl;
 N—C$_{1-6}$alkyl-acetimidamidyl;
 N,N'-di-C$_{1-6}$alkyl-acetimidamidyl;
 N'-cyano-N—C$_{1-6}$alkyl-acetimidamidyl;
 N'-hydroxy-acetimidamidyl;
 N'—C$_{1-6}$alkoxy-acetimidamidyl;
 N'-hydroxy-N—C$_{1-6}$alkyl-acetimidamidyl;
 N'—C$_{1-6}$alkoxy-N—C$_{1-6}$alkyl-acetimidamidyl;
 2-nitro-1-N—C$_{1-6}$alkylamino-vinyl; formyl;
 C$_{1-6}$alkyl-sulfonyl;
 C$_{3-6}$cycloalkyl-sulfonyl;
 C$_{3-6}$cycloalkyl-C$_{1-6}$alkyl-sulfonyl;
 C$_{1-6}$alkyl-sulfonyl-C$_{1-6}$alkyl;
 aminocarbonyl;
 carbonylamino;
 N-hydroxy-aminocarbonyl;
 N—C$_{1-6}$alkoxy-aminocarbonyl;
 N—C$_{1-6}$alkyl-aminocarbonyl;
 aminocarbonyl-C$_{1-6}$alkyl;
 N—C$_{1-6}$alkyl-aminocarbonyl-C$_{1-6}$alkyl;
 N,N-di-C$_{1-6}$alkyl-aminocarbonyl-C$_{1-6}$alkyl;
 C$_{1-6}$alkoxy-carbonyl;
 N-hydroxy-N—C$_{1-6}$alkyl-aminocarbonyl;
 N—C$_{1-6}$alkoxy-N—C$_{1-6}$alkyl-aminocarbonyl;
 N,N-di-C$_{1-6}$alkyl-aminocarbonyl;
 aminosulfonyl;
 N—C$_{1-6}$alkyl-aminosulfonyl;
 N,N-di-C$_{1-6}$alkyl-aminosulfonyl;
 cyano;
 C$_{1-6}$alkoxy;
 C$_{1-6}$alkyl-sulfonylamino;
 N—C$_{1-6}$alkyl-sulfonylaminocarbonyl;
 N—(C$_{1-6}$alkyl-sulfonyl)-N—C$_{1-6}$alkyl-aminocarbonyl;
 N—(C$_{1-6}$alkyl-sulfonyl)-amino-C$_{1-6}$alkyl; amino;
 N—C$_{1-6}$alkyl-amino;
 N,N-di-C$_{1-6}$alkyl-amino;
 halo-C$_{1-6}$alkyl;
 phenyl;
 heterocyclyl;
 heteroaryl;
 C$_{1-6}$alkyl-carbonylamino;
 carbonylamino; or
 hydroxy;
  wherein the C$_{1-6}$alkyl moieties may be unsubstituted or substituted one or more times with halo; and
  wherein the phenyl, heterocyclyl, heteroaryl, C$_{3-6}$cycloalkyl, C$_{3-6}$cycloalkenyl and C$_{3-6}$cycloalkyl-C$_{1-6}$ alkyl moieties may be unsubstituted or substituted one or more times with R$^i$;
or R$^f$ and R$^g$ together may form oxo;
R$^m$ is: C$_{1-6}$alkyl;
 hydroxy;
 halo;
 hydroxy-C$_{1-6}$alkyl;
 C$_{1-6}$alkylsulfonyl-C$_{1-6}$alkyl;
 cyano;
 C$_{1-6}$alkylsulfonyl-amino-
 C$_{1-6}$alkylsulfinyl-amino-
 cyano-C$_{1-6}$alkyl;
 cyano-C$_{2-6}$alkenyl;
 amino-C$_{1-6}$alkyl;
 C$_{1-6}$alkoxy-C$_{1-6}$alkyl;
 C$_{1-6}$alkoxy-C$_{1-6}$alkoxy-C$_{1-6}$alkyl;
 hydroxy-C$_{1-6}$alkoxy;
 hydroxy-C$_{1-6}$alkoxy-C$_{1-6}$alkyl;
 hydroxy-C$_{1-6}$alkyl-amino;
 C$_{1-6}$alkoxy-C$_{1-6}$alkyl-amino;
 N-hydroxy-carboxamidinyl;
 C$_{1-6}$alkoxy-carbonyl-C$_{2-6}$alkenyl;
 amino;
 N—C$_{1-6}$alkylamino N,N-di-$C_{1-6}$alkylamino;
—$(CHR^t)_u$—C(O)—$NR^pR^q$;
—$(CHR^s)_u$—O—$(CHR^s)_v$—C(O)—$NR^pR^q$;
—$(CHR^s)_u$—$NR^a$—$(CHR^s)_v$—C(O)—$NR^pR^q$,
$(CHR^t)_u$—C(O)—$R^u$;
—$(CHR^s)_u$—O—$(CHR^s)_v$—C(O)—$R^u$; or
$(CHR^s)_u$—$NR^a$—$(CHR^s)_v$—C(O)—$R^u$;
u is from 0 to 2;
v is from 0 to 2;
each $R^n$ is independently:
  hydrogen; or
  $C_{1-6}$alkyl;
$R^p$ is:
  hydrogen; or
  $C_{1-6}$alkyl;
$R^q$ is:
  hydrogen;
  $C_{1-6}$alkyl;
  hydroxy-$C_{1-6}$alkyl;
  N—($C_{1-6}$alkylcarbonyl)-amino-$C_{1-6}$alkyl;
  $C_{1-6}$alkylsulfonyl-$C_{1-6}$alkyl;
  amino-$C_{1-6}$alkyl;
  N—$C_{1-6}$alkylamino-$C_{1-6}$alkyl;
  N,N-di-$C_{1-6}$alkylamino-$C_{1-6}$alkyl;
  N,N-di-$C_{1-6}$alkylaminocarbonyl-$C_{1-6}$alkyl;
  cyano-$C_{1-6}$alkyl;
  carboxy-$C_{1-6}$alkyl;
  aminocarbonyl-$C_{1-6}$alkyl;
  N—$C_{1-6}$alkylaminocarbonyl-$C_{1-6}$alkyl;
  N,N-di-$C_{1-6}$alkyl aminocarbonyl-$C_{1-6}$alkyl;
  $C_{1-6}$alkylsulfonyl-$C_{1-6}$alkyl; or
  $C_{1-6}$alkoxy-$C_{1-6}$alkyl;
each $R^s$ is independently:
  hydrogen; or
  $C_{1-6}$alkyl;
each $R^t$ is independently:
  hydrogen;
  $C_{1-6}$alkyl;
  halo; or
  hydroxy; and
$R^u$ is: $C_{1-6}$alkyl;
  $C_{1-6}$alkoxy;
  hydroxy;
  hydroxy-$C_{1-6}$alkyl.

2. The compound of claim 1, wherein $R^1$, $R^2$, $R^4$, $R^5$, $R^6$, $R^7$, $R^8$, $R^{13}$, $R^b$ and $R^c$ are hydrogen.

3. The compound of claim 1, wherein p is 0.

4. The compound of claim 1, wherein m is 1.

5. The compound of claim 1, wherein n is 0.

6. The compound of claim 1, wherein Y is —O—.

7. The compound of claim 1, wherein each $R^e$ is independently: hydrogen; or halo.

8. The compound of claim 1, wherein $R^m$ is selected from:

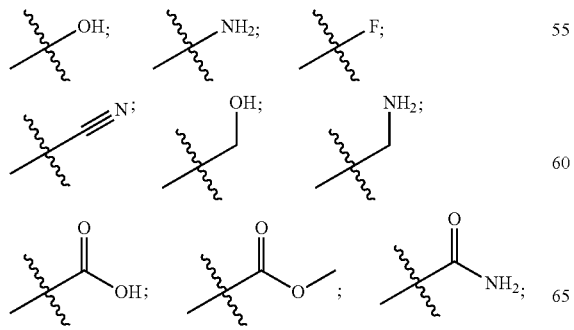

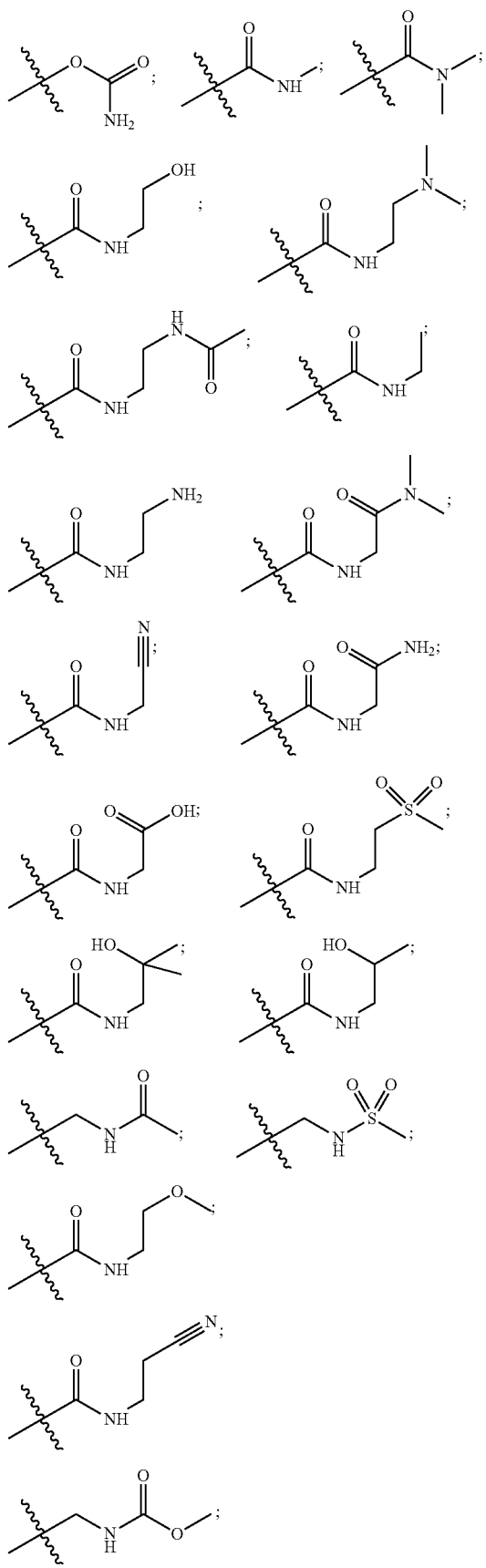

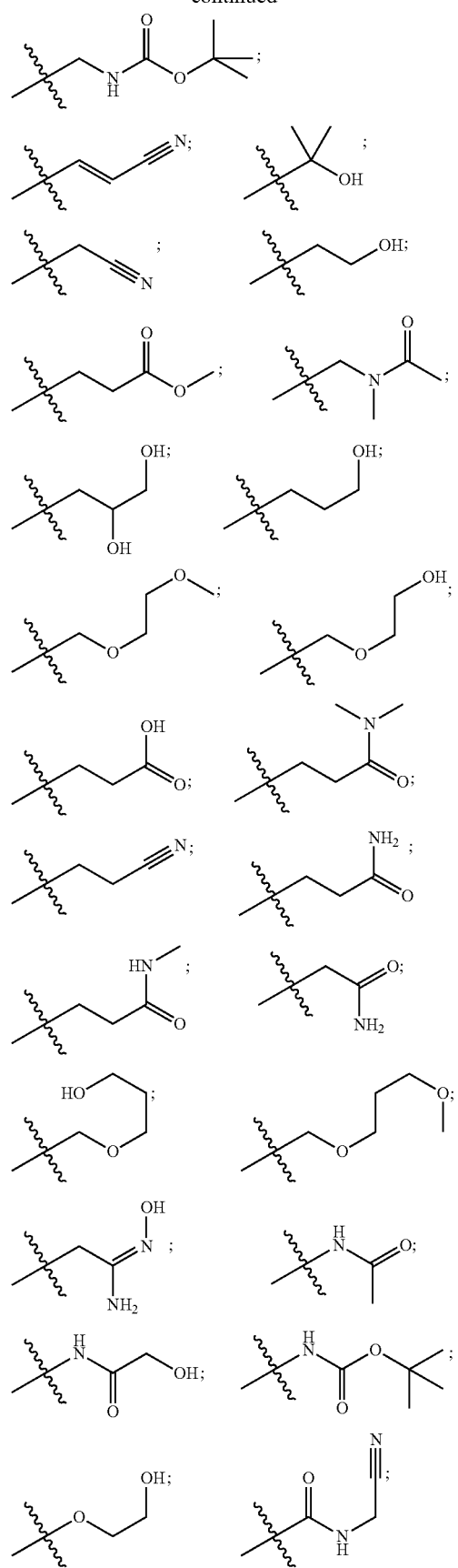
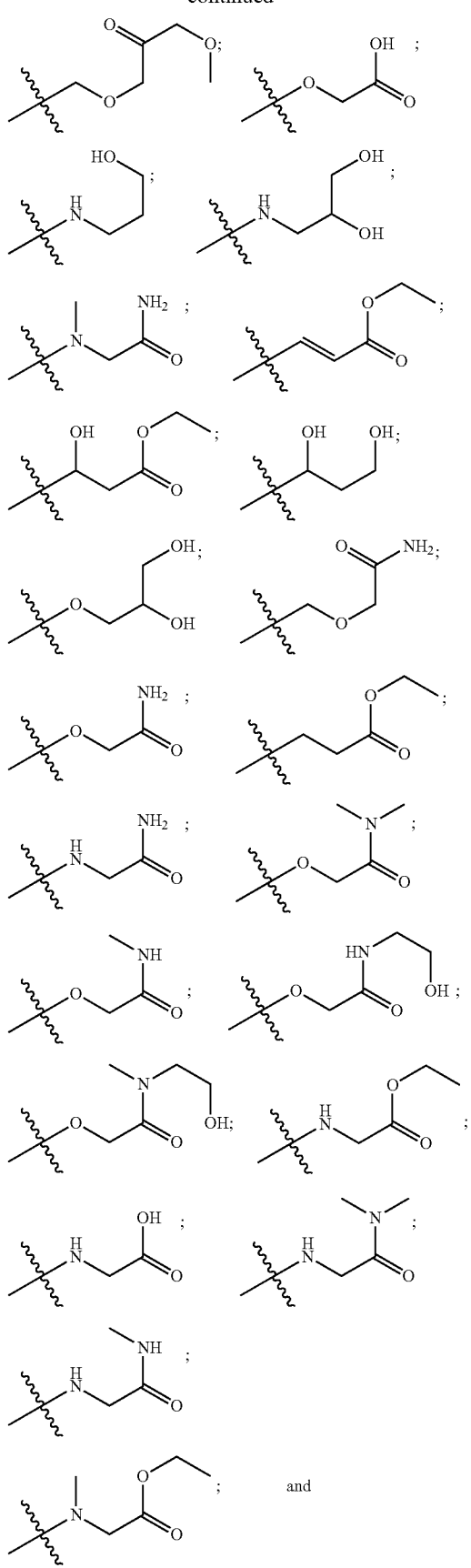

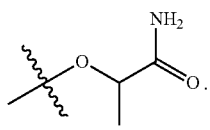

9. The compound of claim 1, wherein the compound is of formula VII

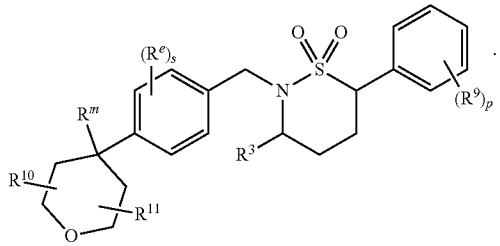

10. A composition comprising:
(a) a pharmaceutically acceptable carrier; and
(b) a compound of claim 1.

11. The compound of claim 1, wherein the compound is of formula IV:

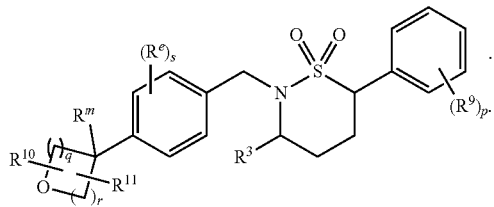

12. The compound of claim 11, wherein q and r are 1.

13. The compound of claim 1, wherein the compound is of formula V:

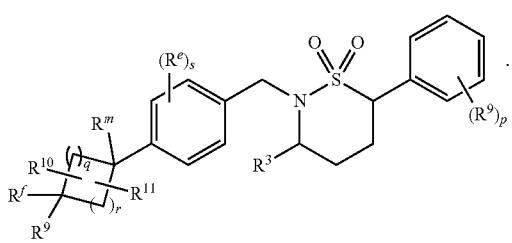

14. The compound of claim 13, wherein q and r are 1.

15. A compound selected from:

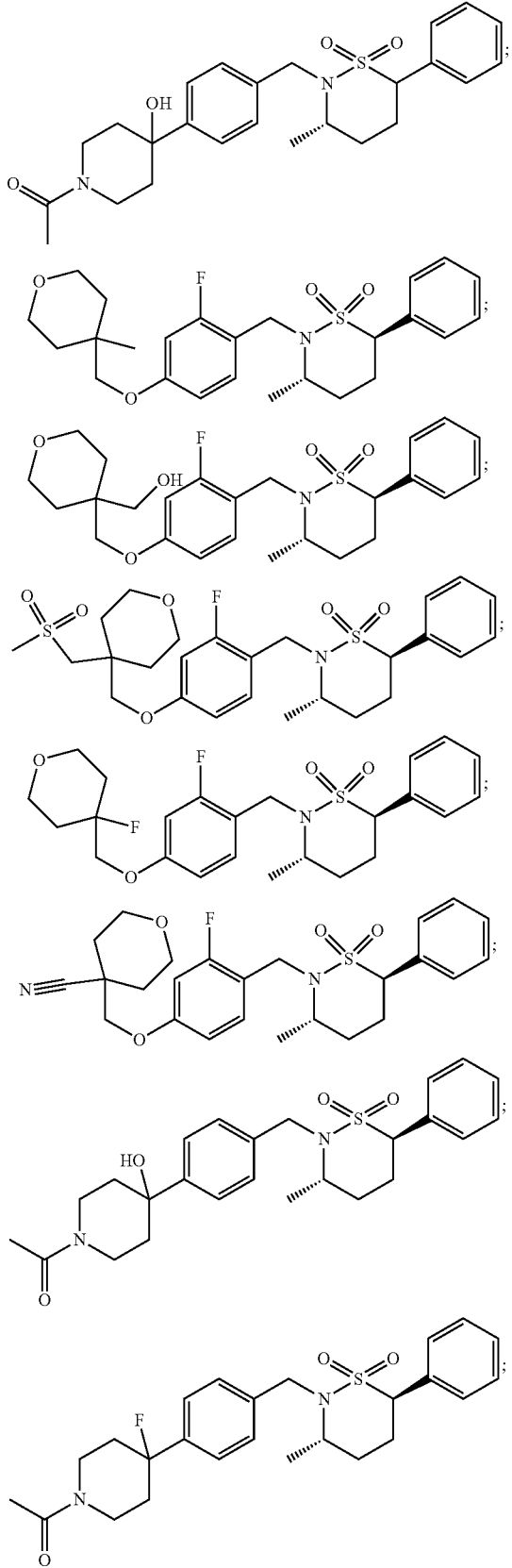

181
-continued
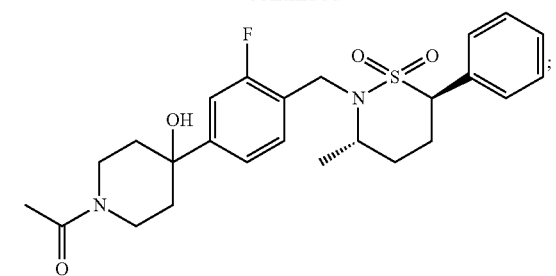
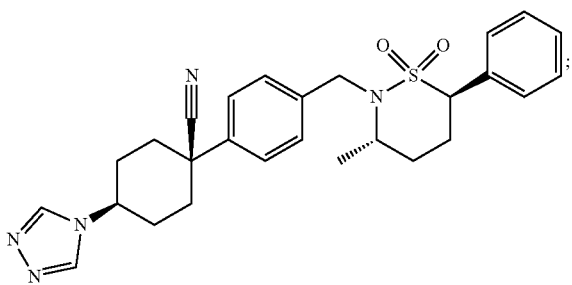
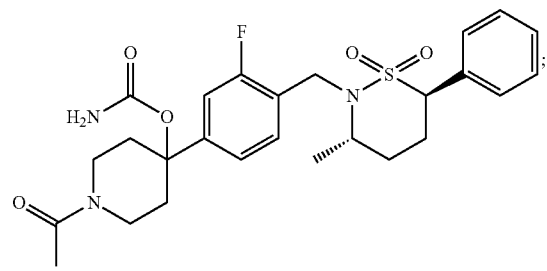
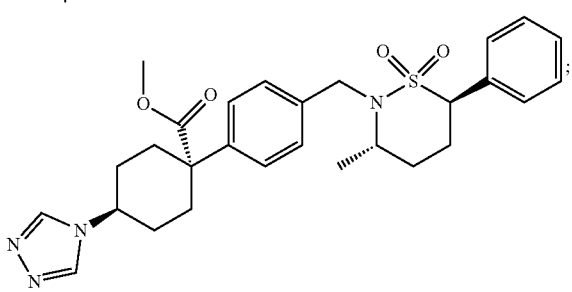
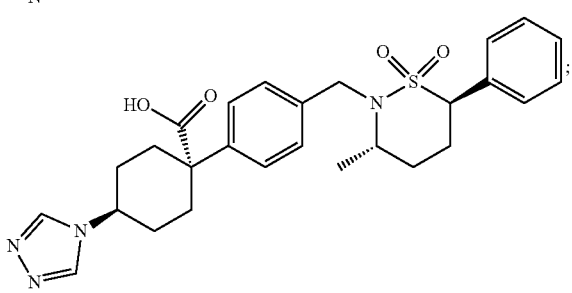
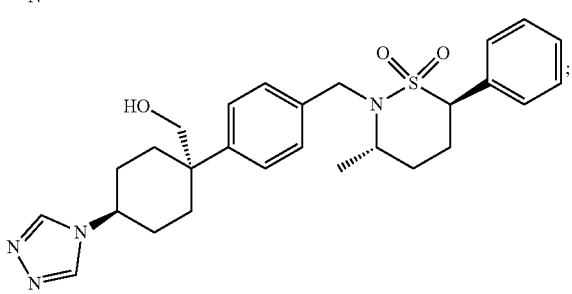
182
-continued
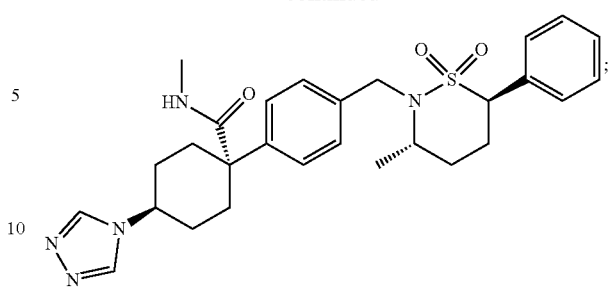
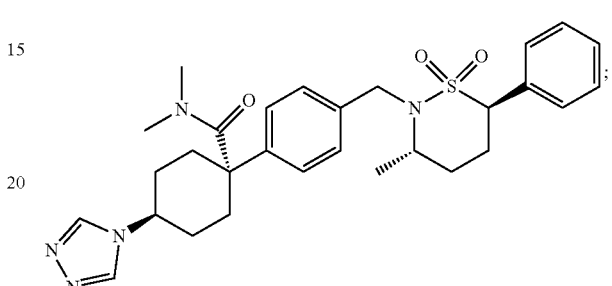
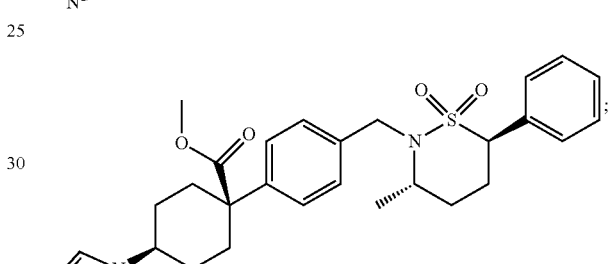
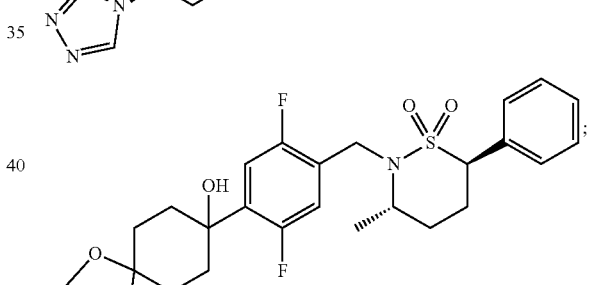
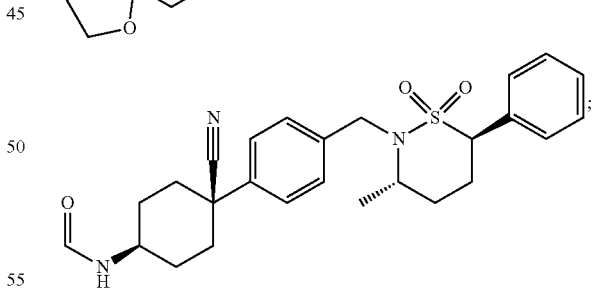
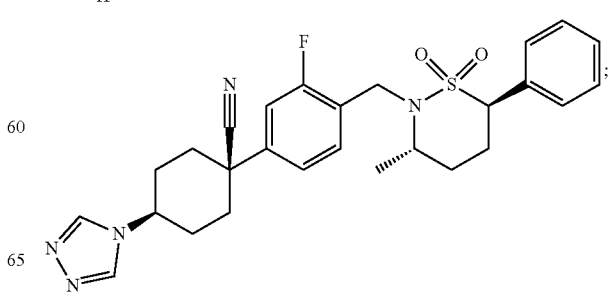

183
-continued
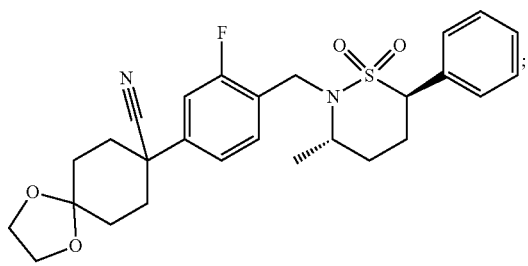
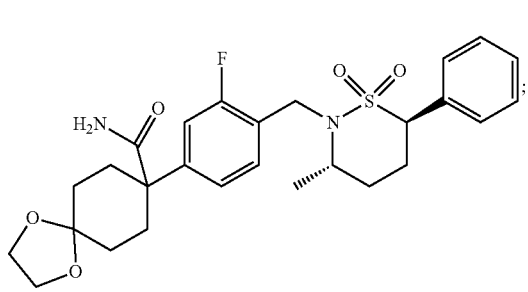
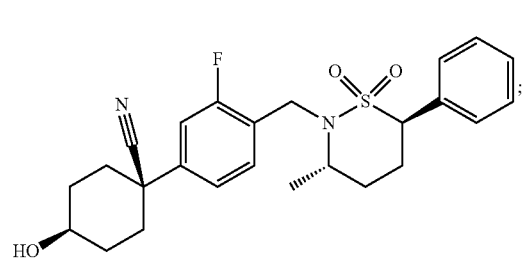
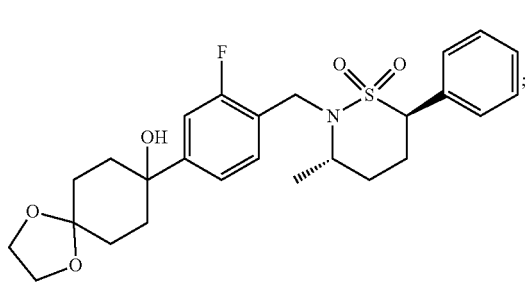
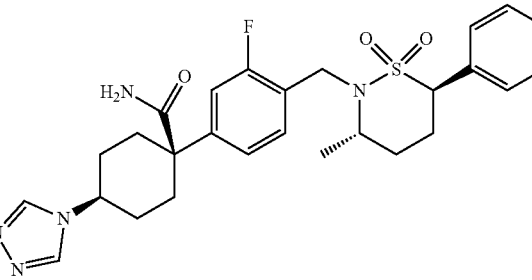
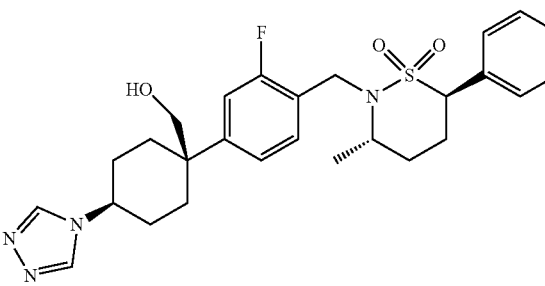
184
-continued
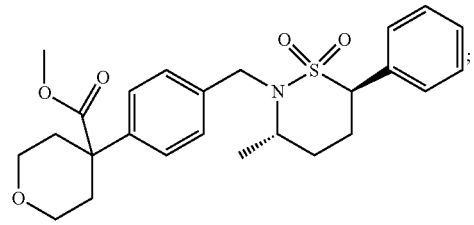
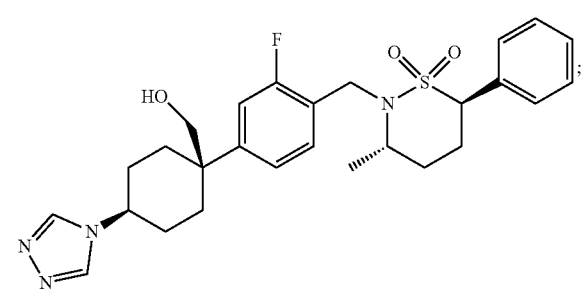
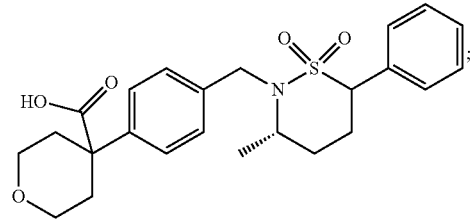
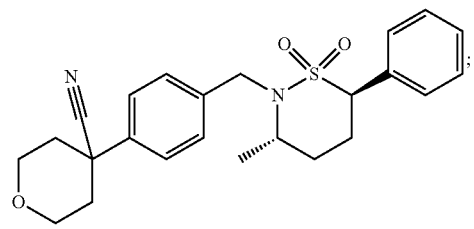
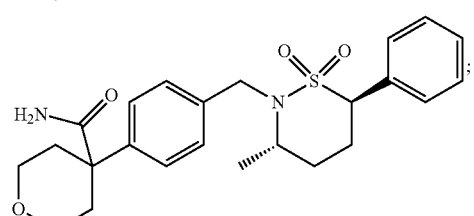
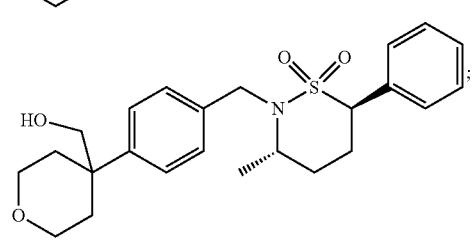
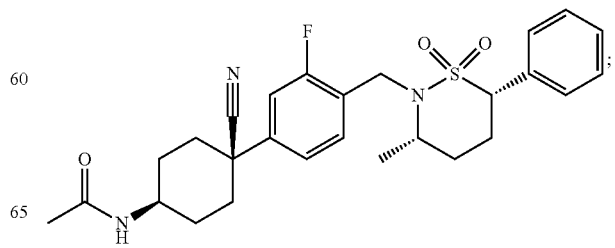

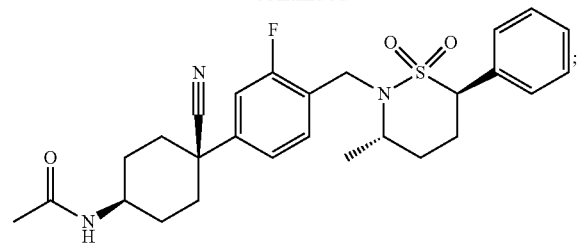
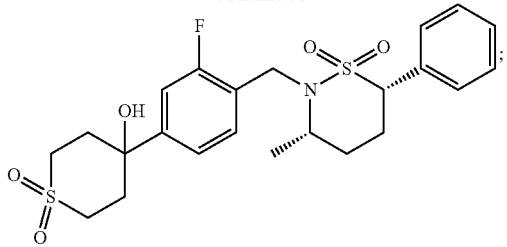
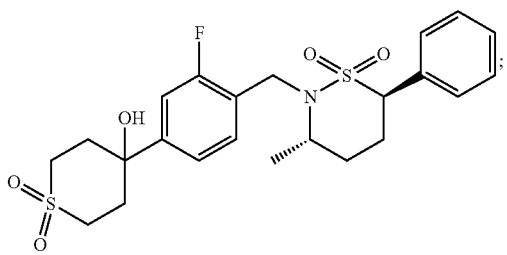
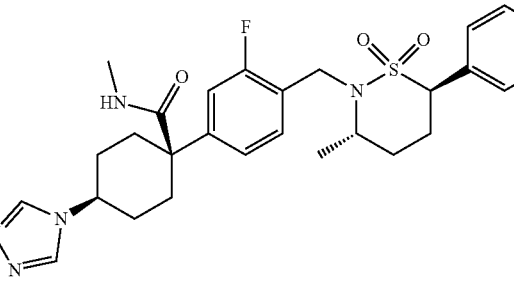
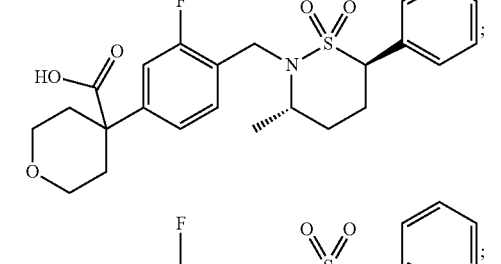
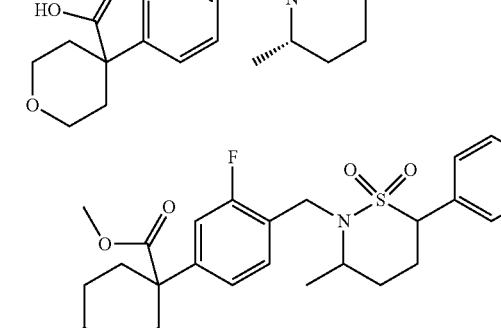
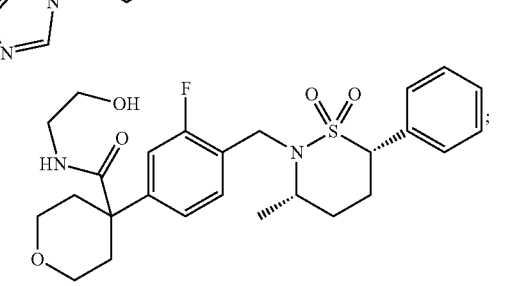

187
-continued
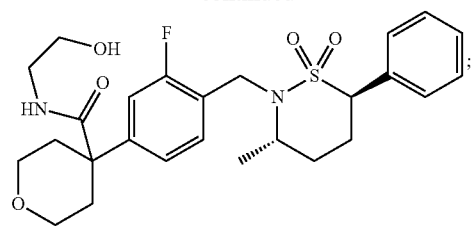
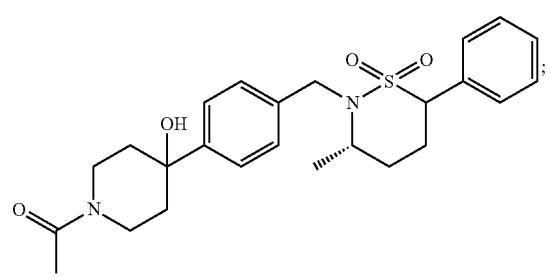
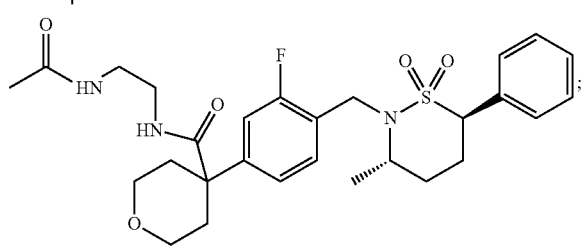
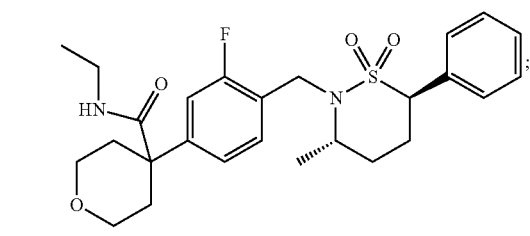
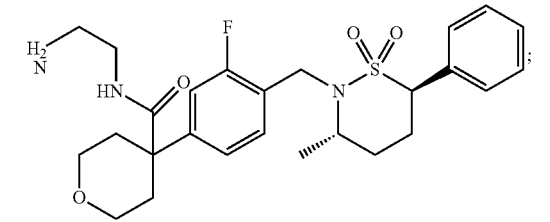
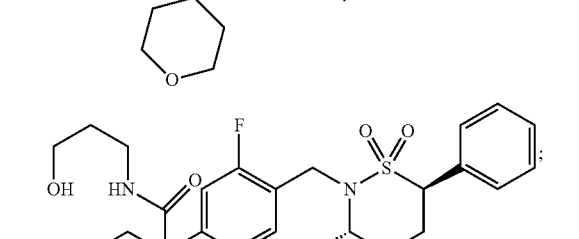
188
-continued
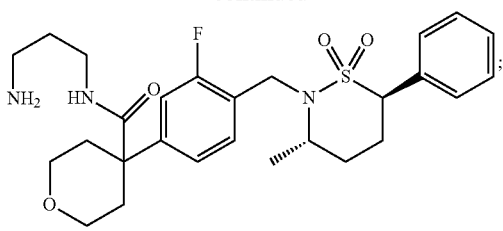
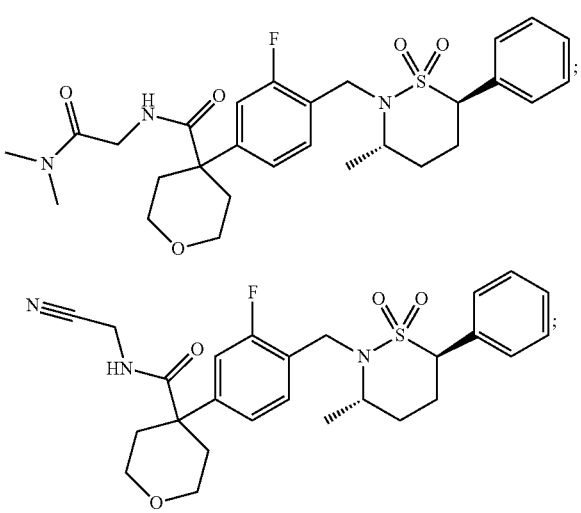
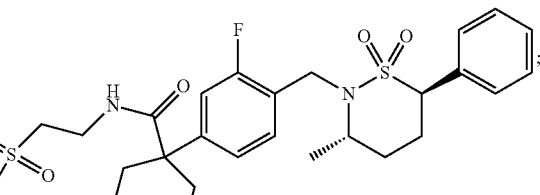
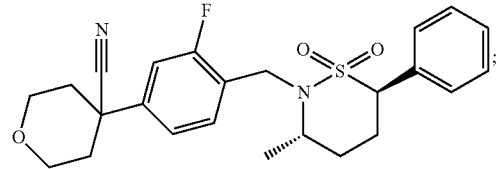

189
-continued
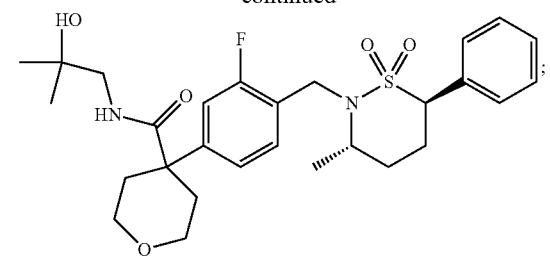
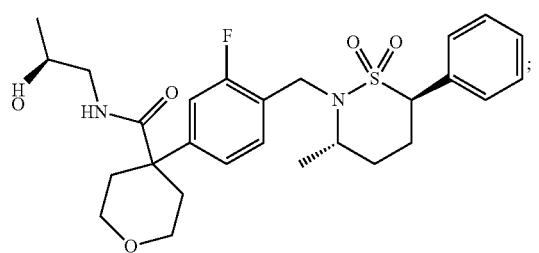
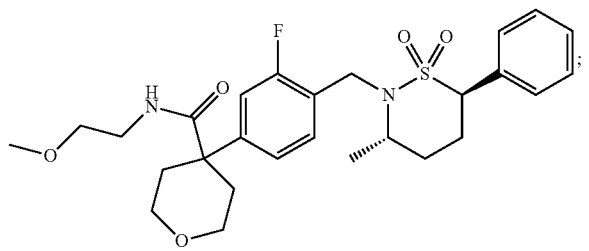
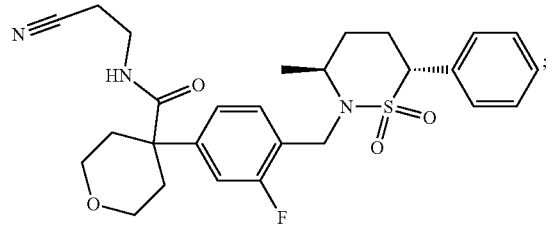
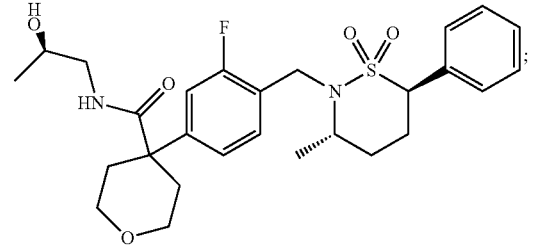
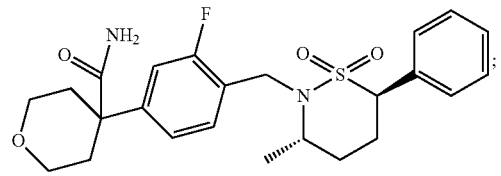
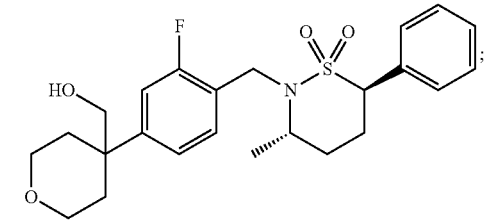
190
-continued
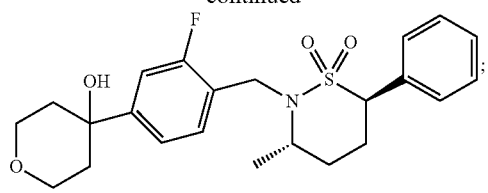
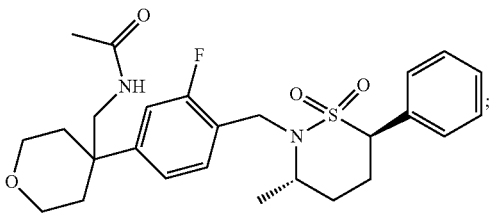
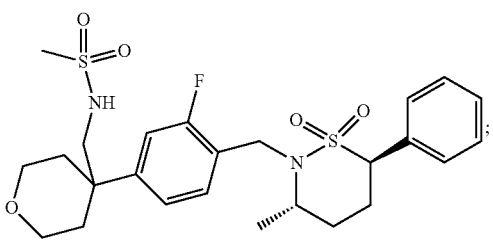
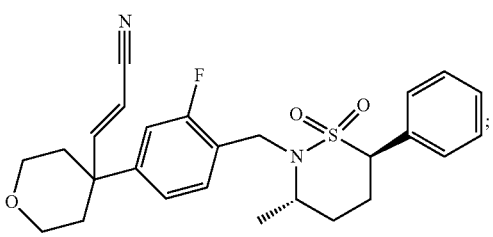
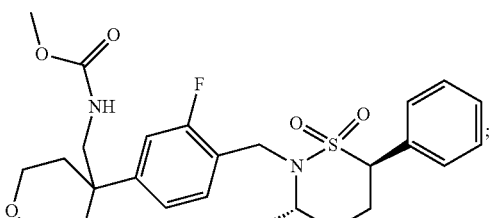
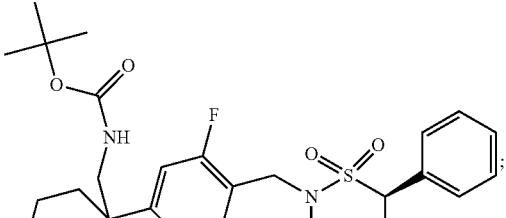
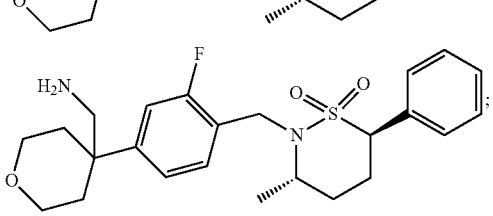

191
-continued
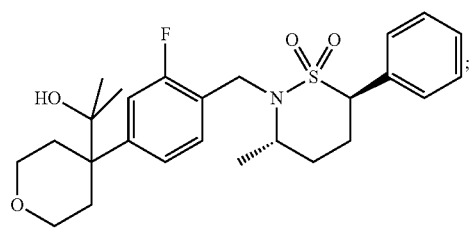
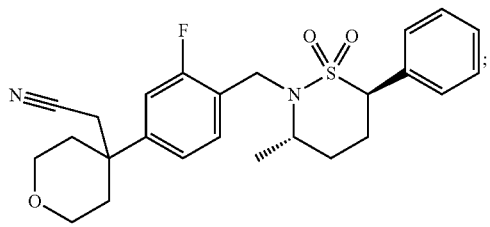
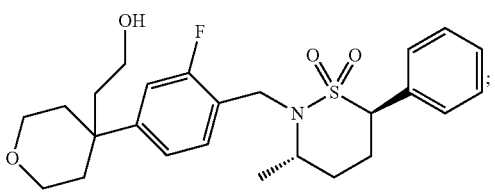
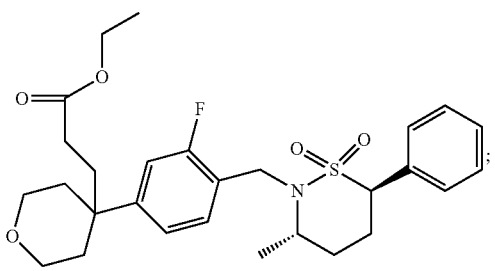
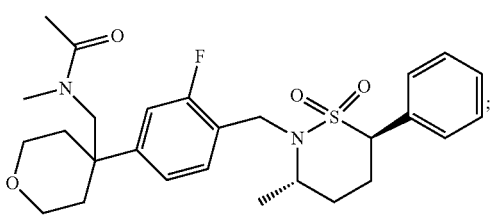
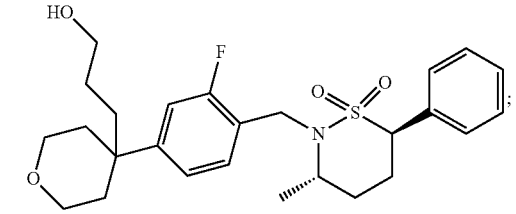
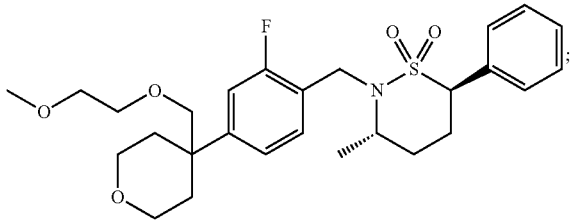
192
-continued
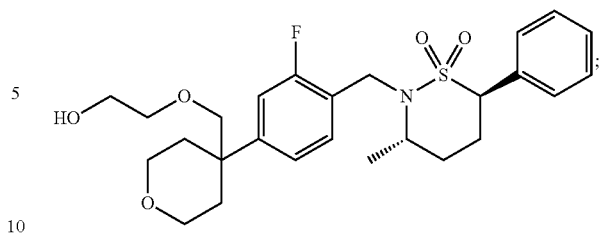
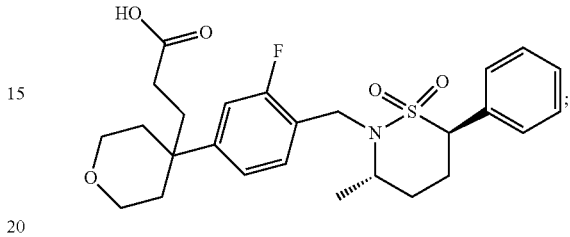
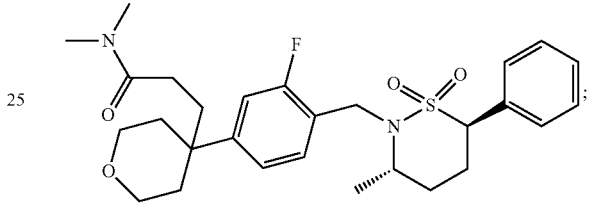
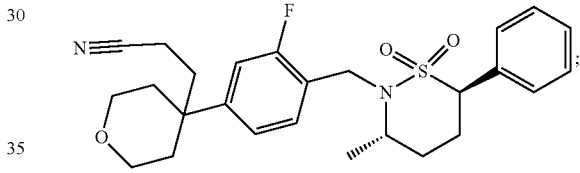
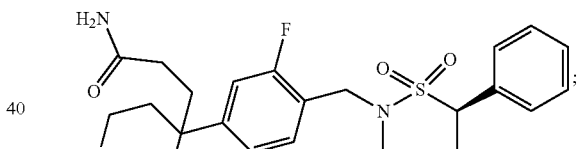
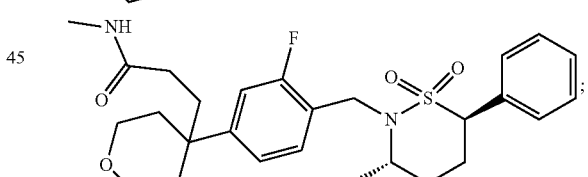
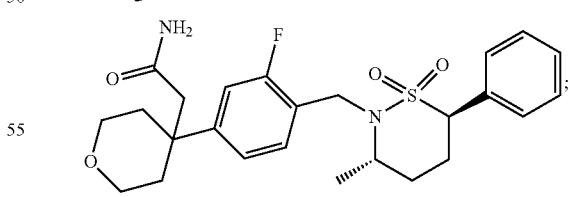
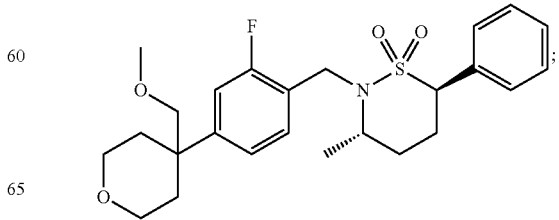

193
-continued
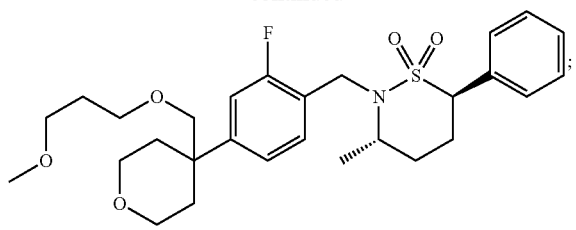
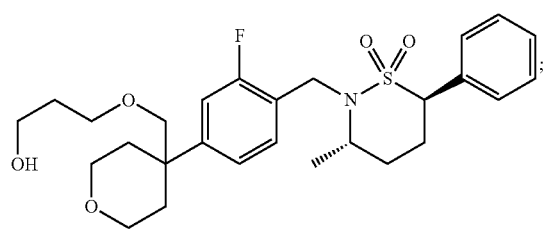
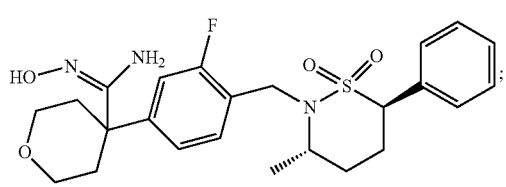
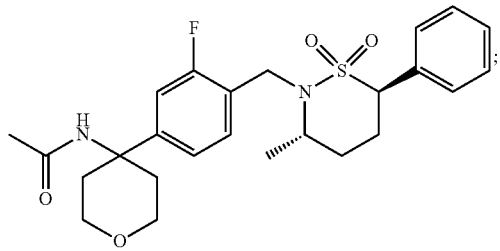
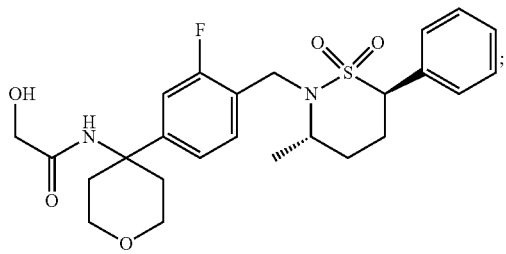
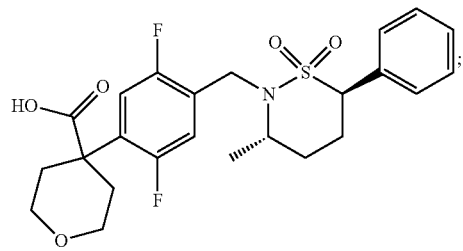
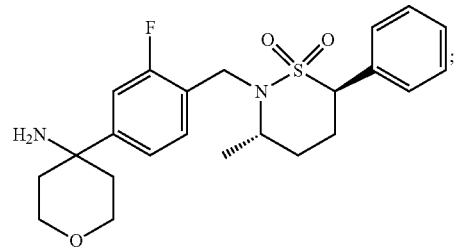
194
-continued
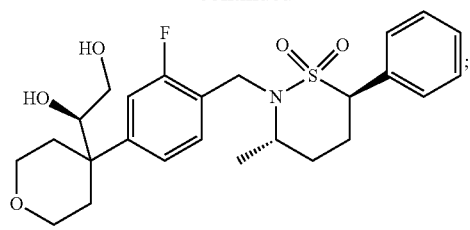
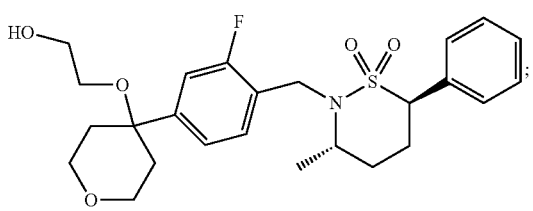
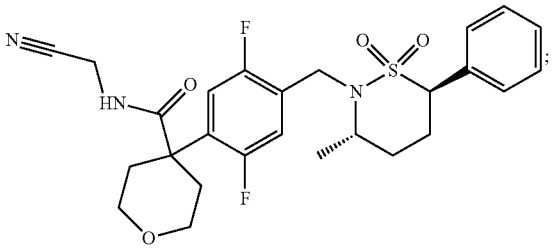
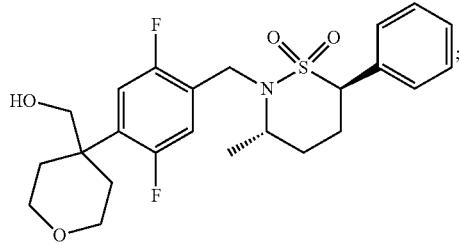
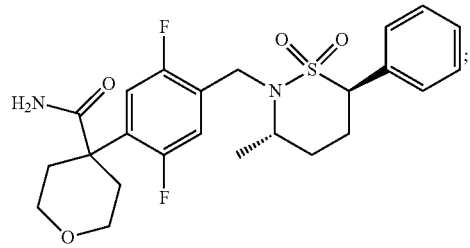
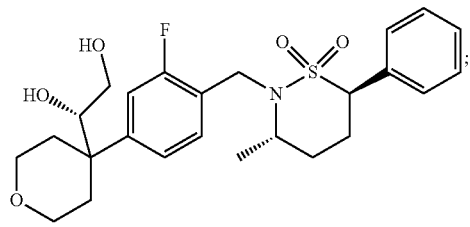
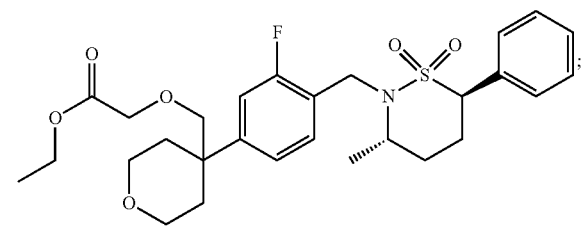

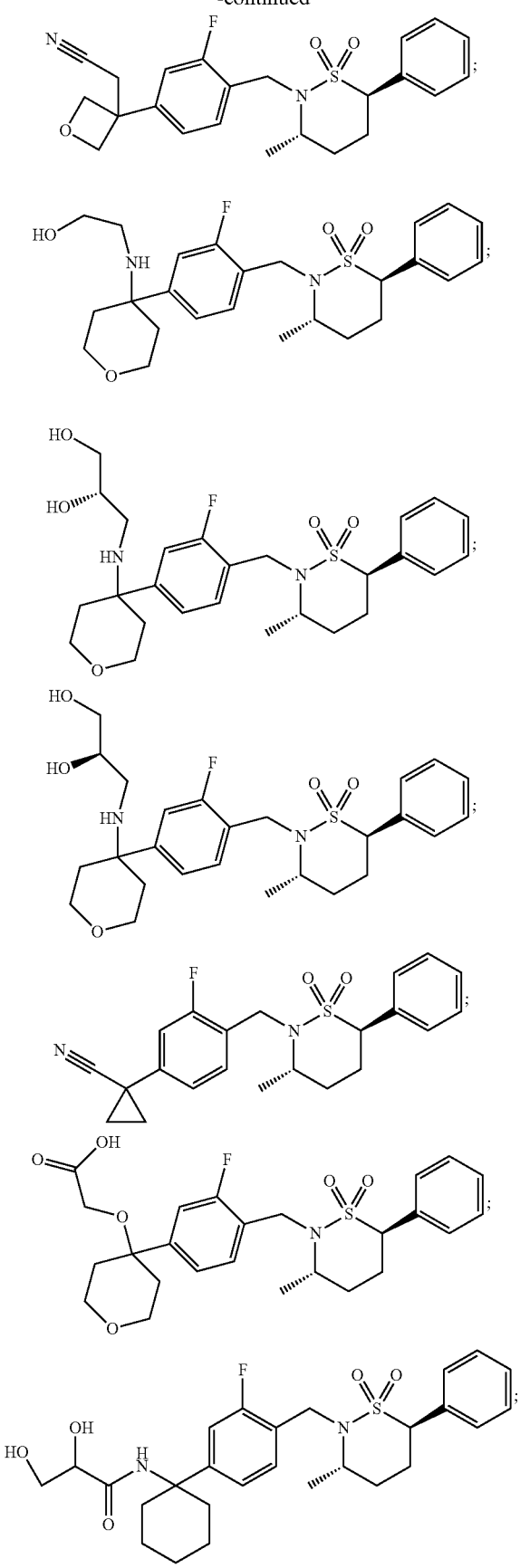
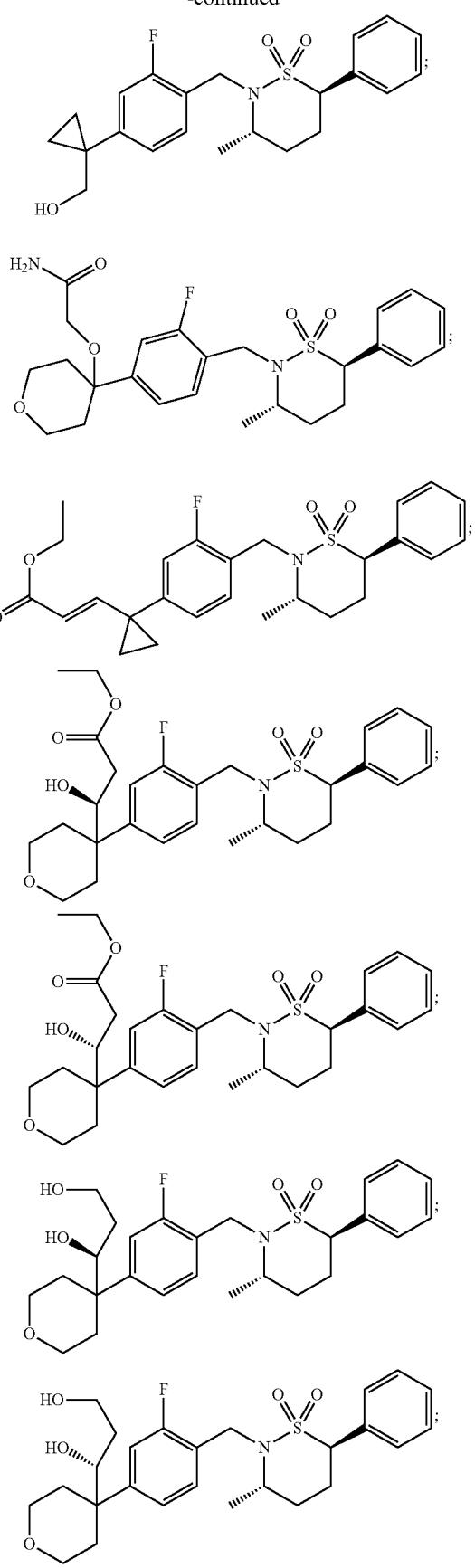

197
-continued
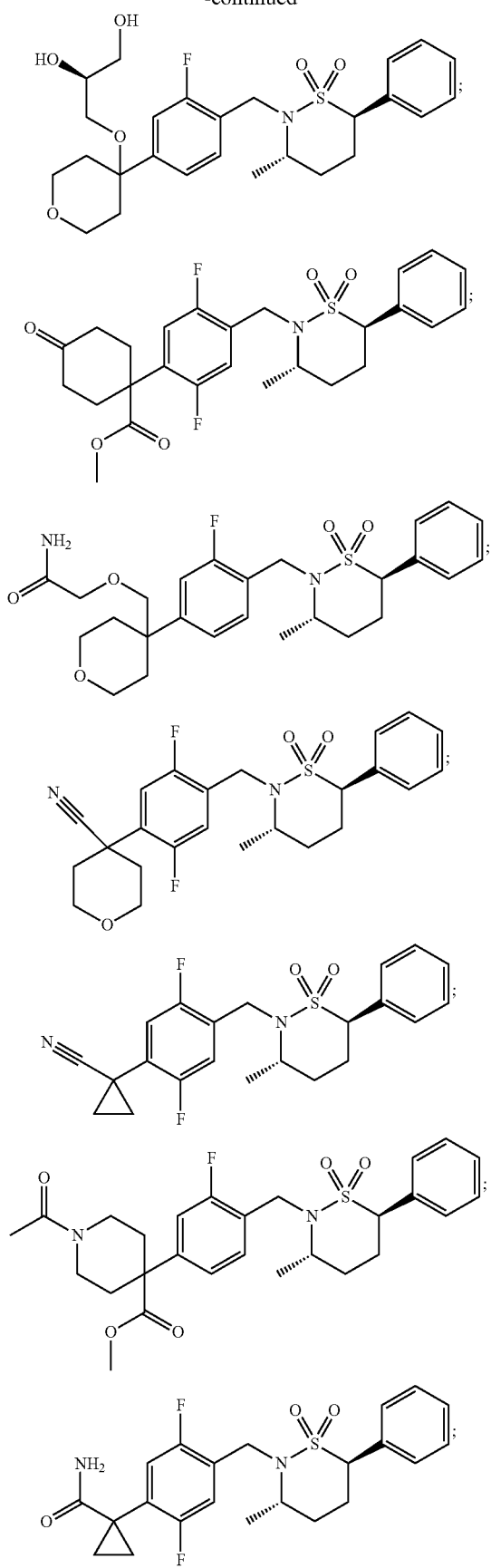
198
-continued
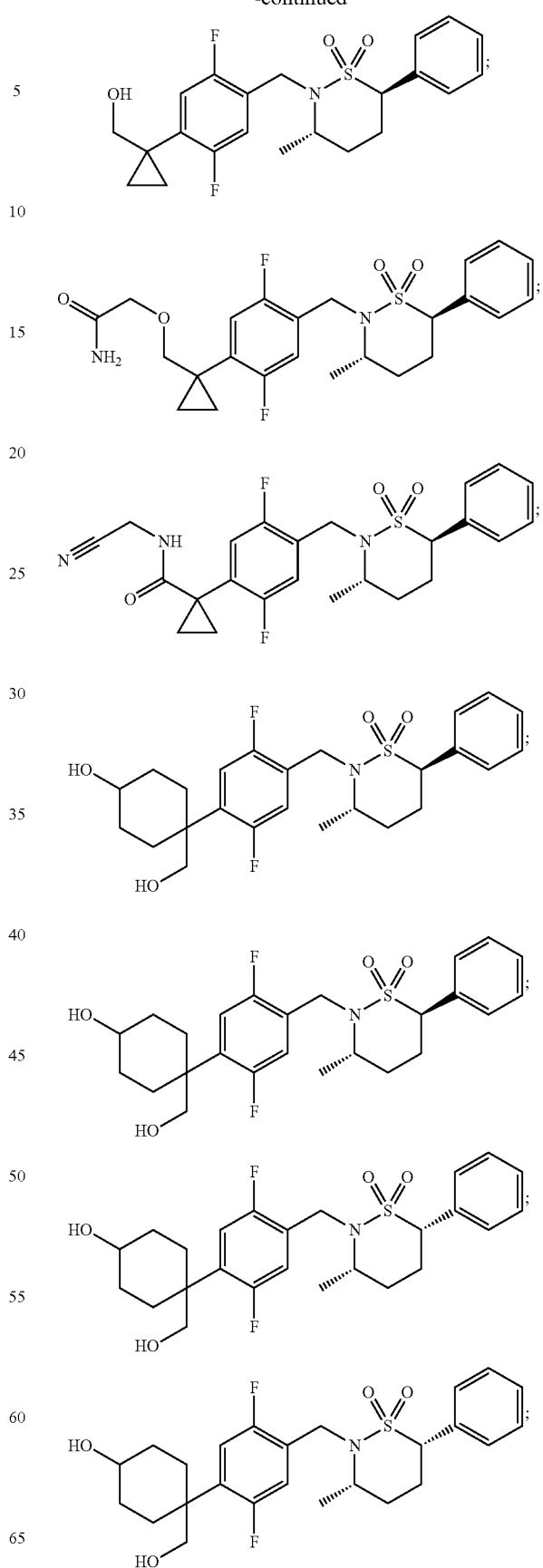

199
-continued
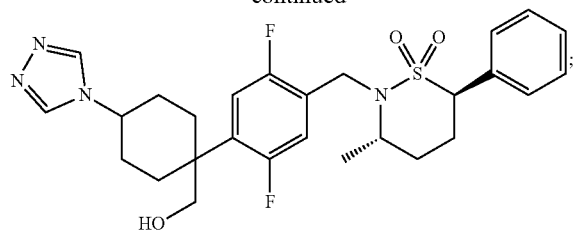
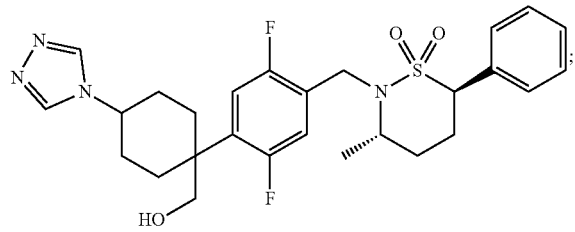
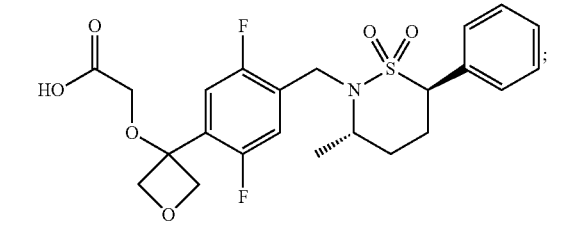
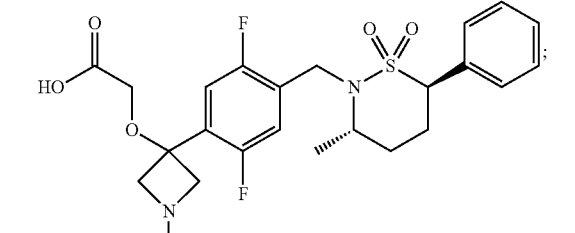
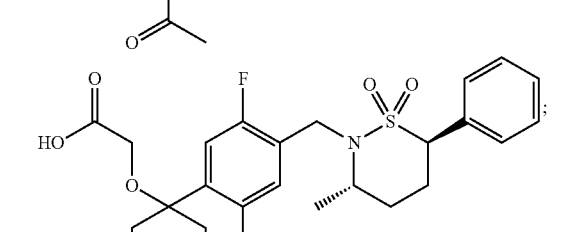
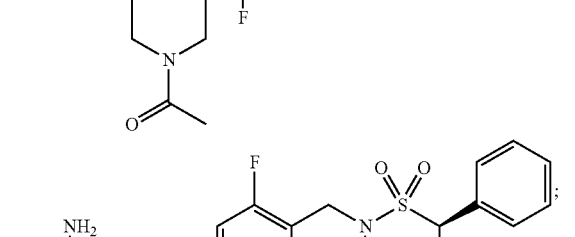
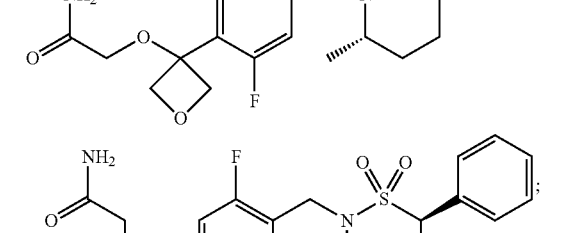
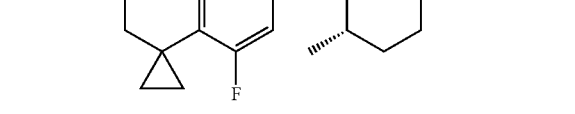
200
-continued
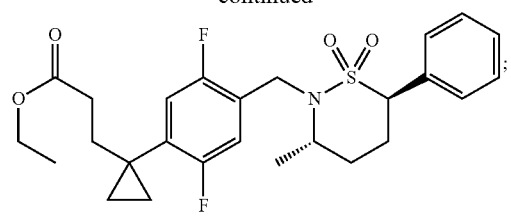
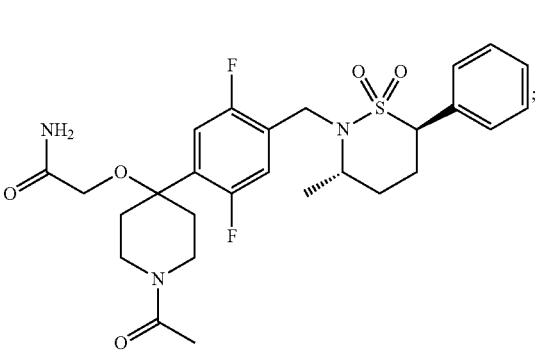
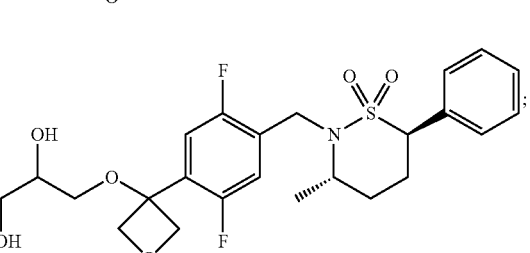
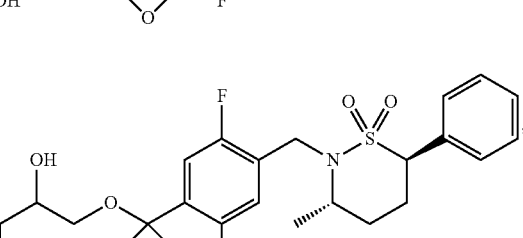
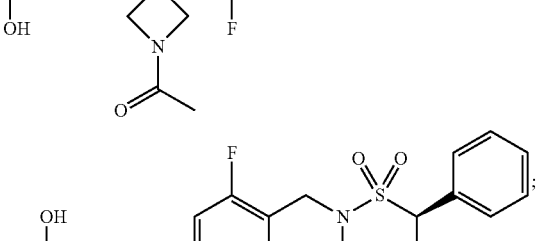
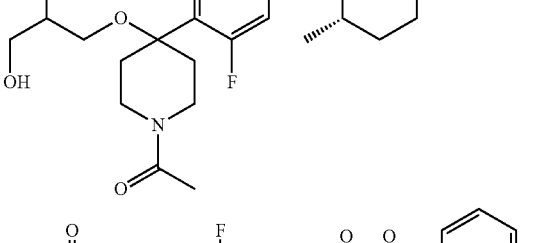
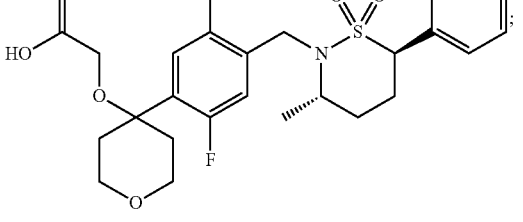

201
-continued
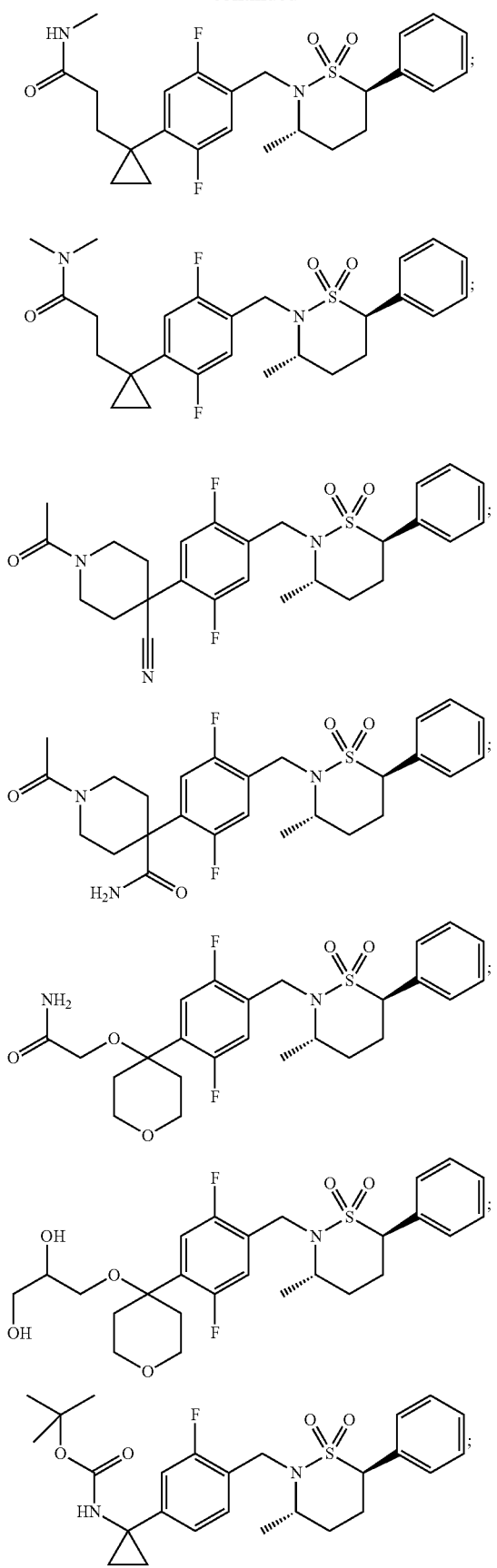
202
-continued
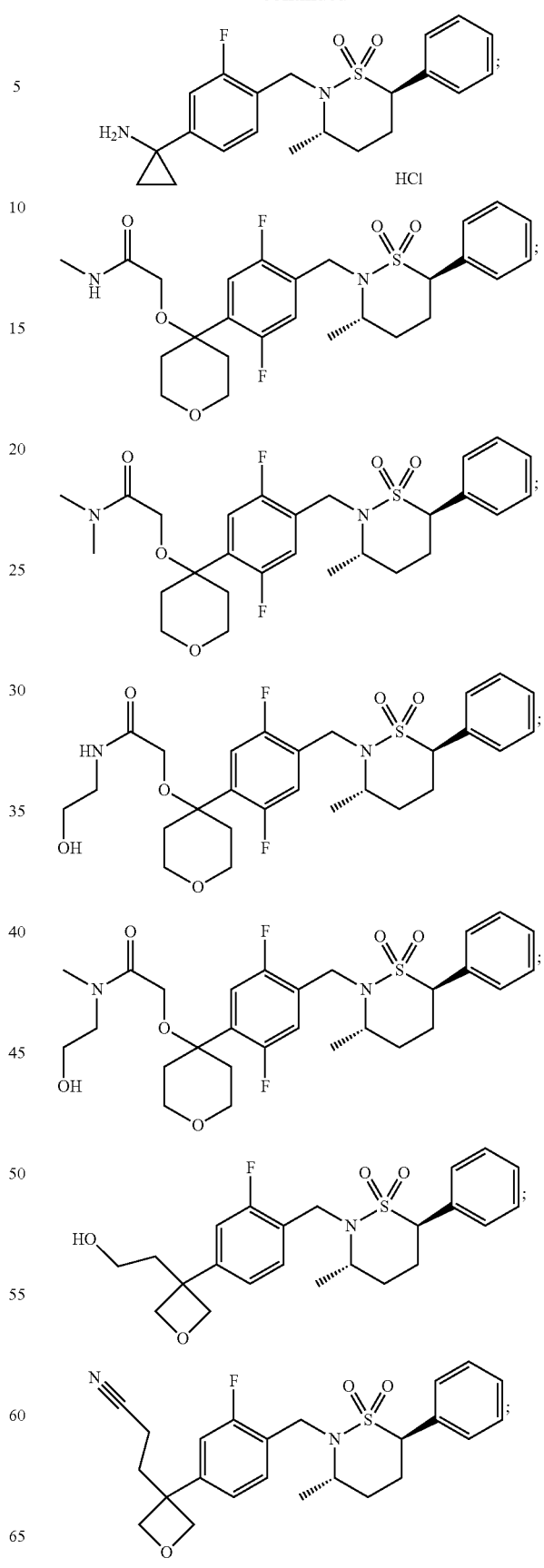

203
-continued
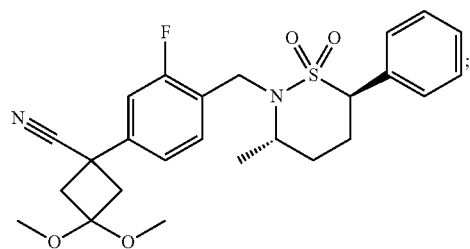
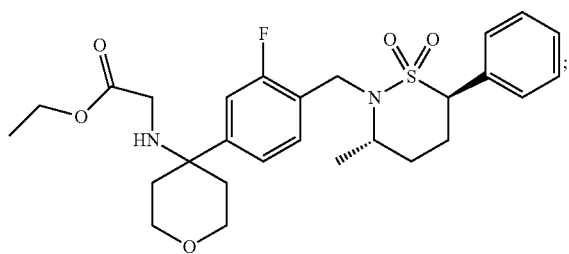
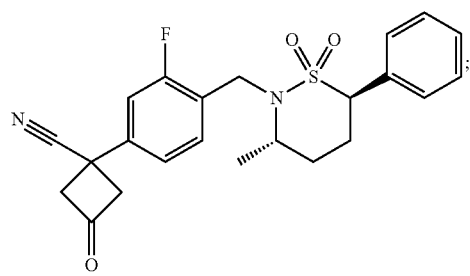
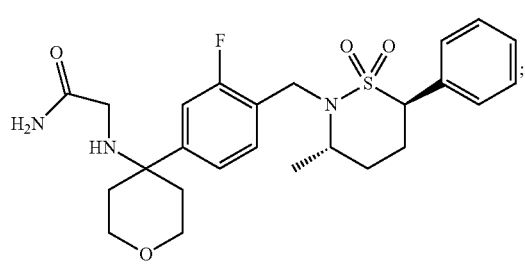
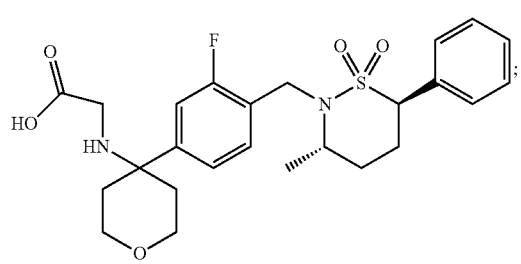
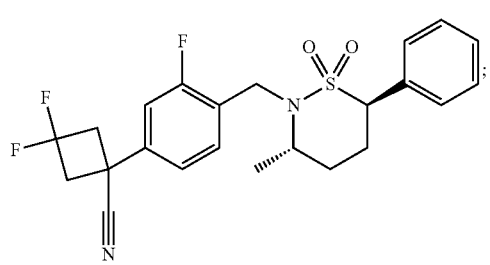
204
-continued
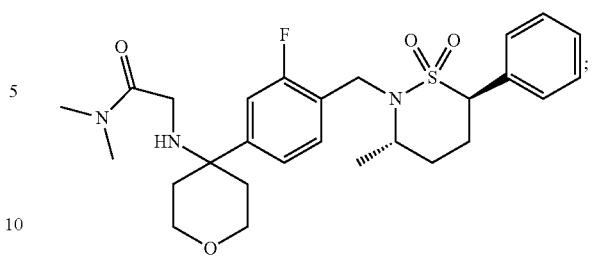
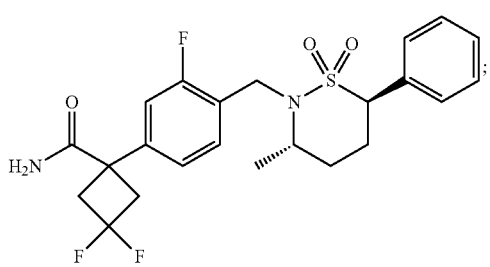
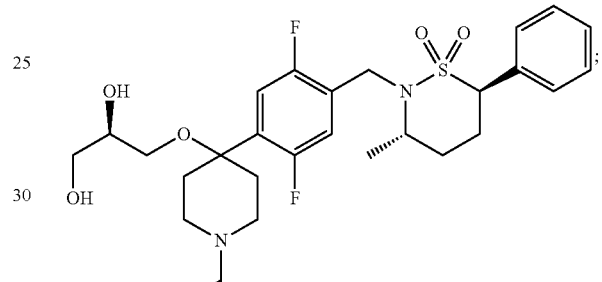
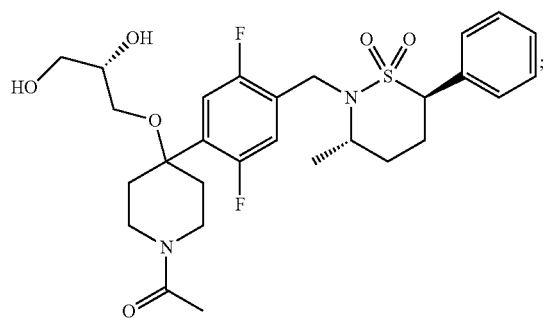
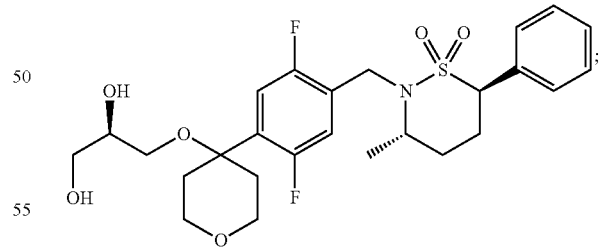
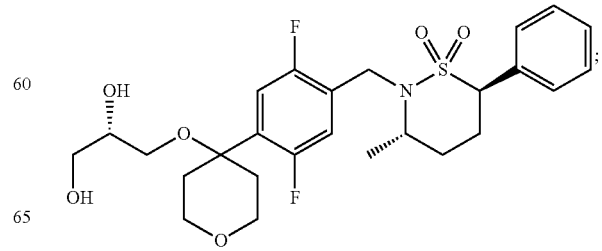

205
-continued
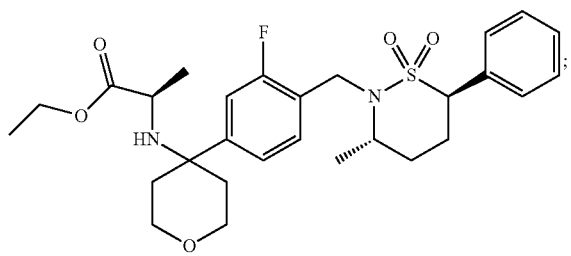
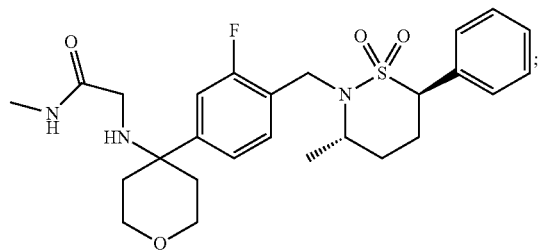
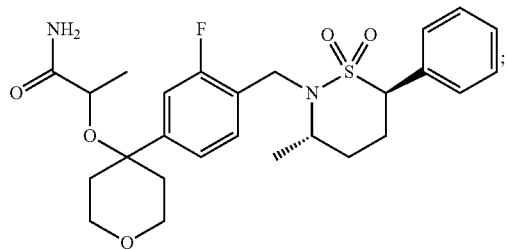
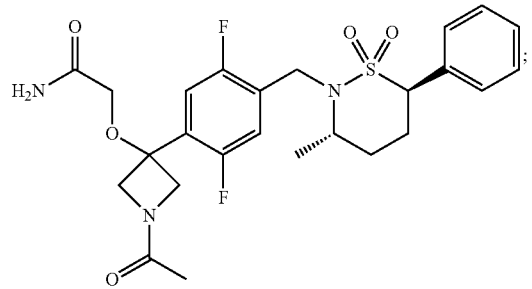
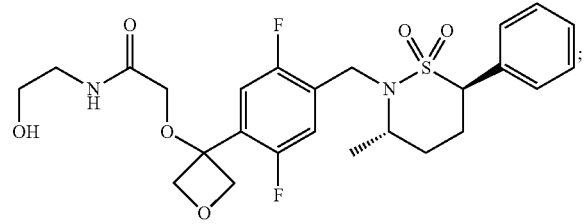
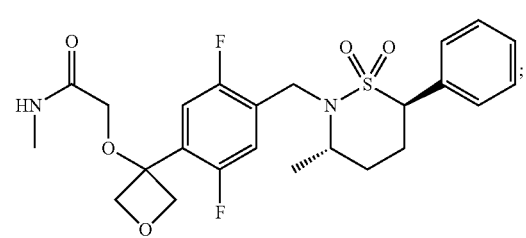
206
-continued
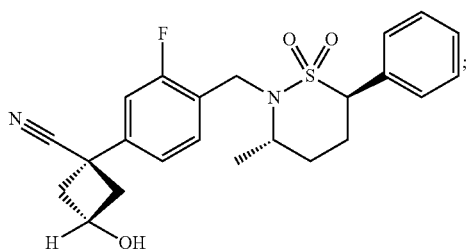
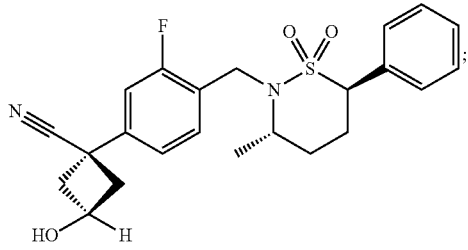
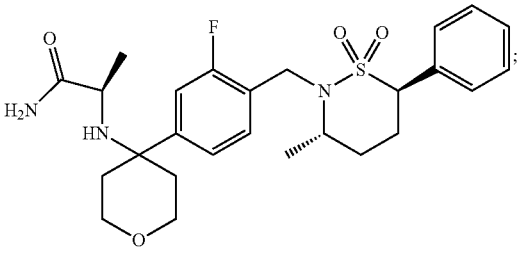
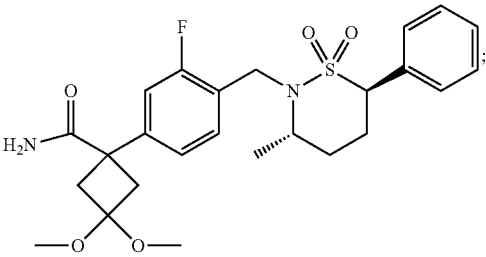
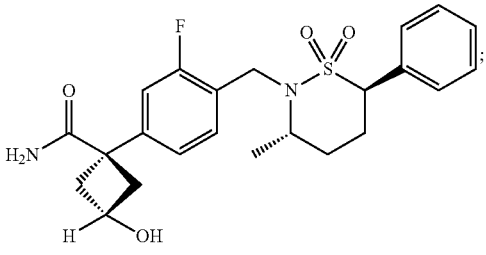
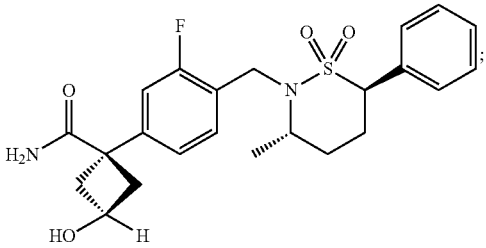

207
-continued
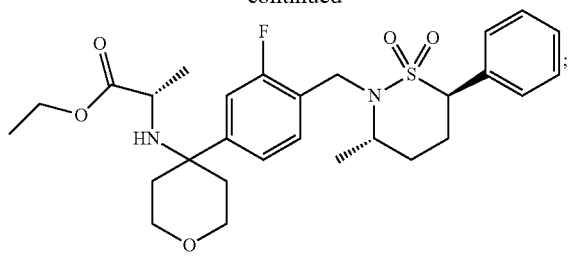
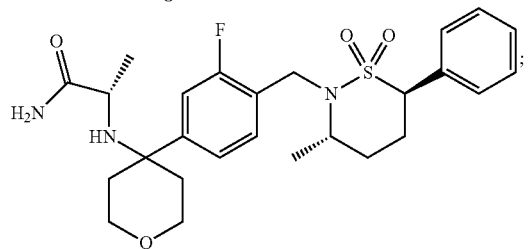
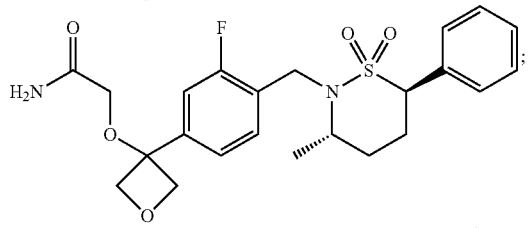
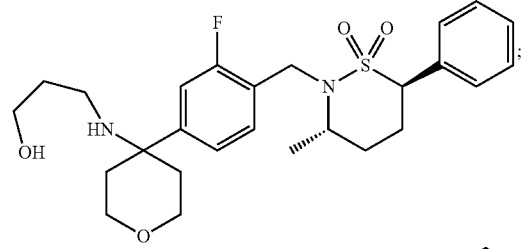
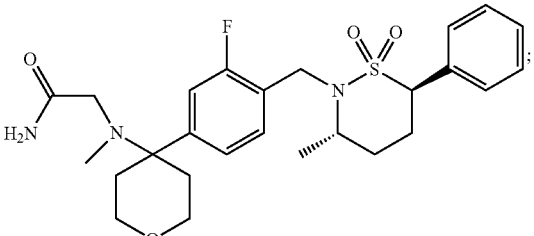
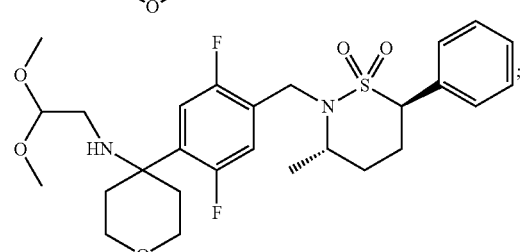
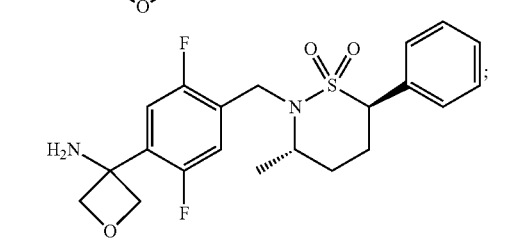
208
-continued
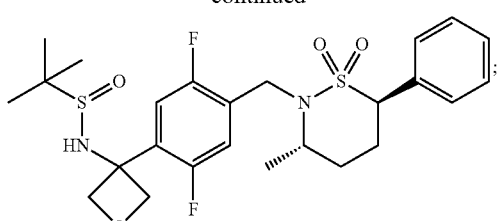
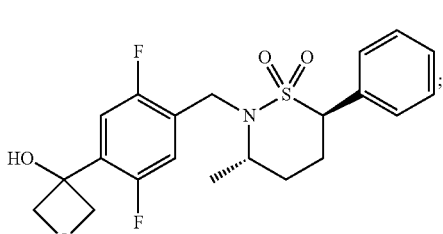
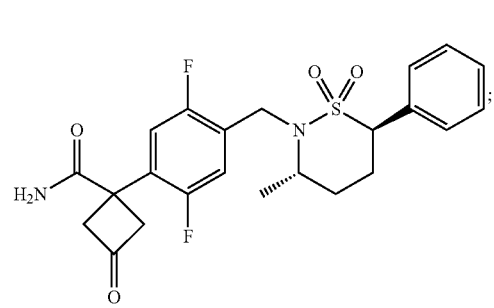
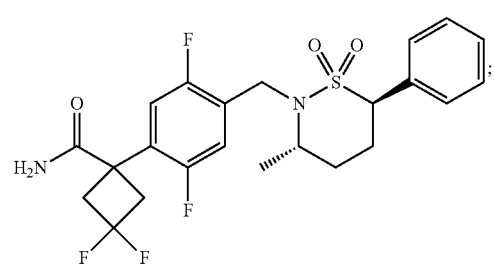
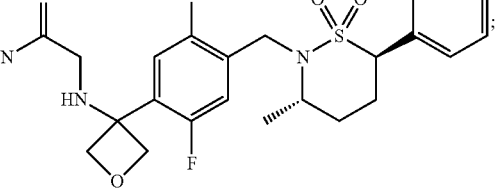
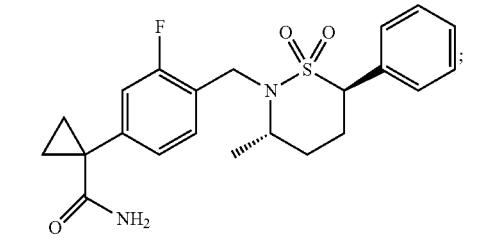
or a pharmaceutically acceptable salt thereof.
* * * * *